United States Patent
Ishikawa et al.

(10) Patent No.: US 8,829,035 B2
(45) Date of Patent: Sep. 9, 2014

(54) AGENT FOR TREATMENT OR PREVENTION OF DISEASES ASSOCIATED WITH ACTIVITY OF NEUROTROPHIC FACTORS

(75) Inventors: Junichi Ishikawa, Osaka (JP); Koichi Saito, Osaka (JP); Norihisa Ohe, Nara (JP); Kentaro Kobayashi, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/322,888

(22) PCT Filed: May 28, 2010

(86) PCT No.: PCT/JP2010/003622
§ 371 (c)(1),
(2), (4) Date: Nov. 28, 2011

(87) PCT Pub. No.: WO2010/137349
PCT Pub. Date: Dec. 2, 2010

(65) Prior Publication Data
US 2012/0115856 A1    May 10, 2012

(30) Foreign Application Priority Data
May 29, 2009  (JP) .................. 2009-131333

(51) Int. Cl.
| | | |
|---|---|---|
| *A61K 31/428* | (2006.01) | |
| *A61K 31/423* | (2006.01) | |
| *C07D 417/02* | (2006.01) | |
| *C07D 263/54* | (2006.01) | |
| *A61K 31/4184* | (2006.01) | |
| *C07D 417/04* | (2006.01) | |
| *C07D 409/14* | (2006.01) | |
| *A61K 31/4439* | (2006.01) | |
| *A61K 31/454* | (2006.01) | |
| *C07D 413/14* | (2006.01) | |
| *C07D 413/04* | (2006.01) | |
| *C07D 417/14* | (2006.01) | |
| *C07D 405/14* | (2006.01) | |

(52) U.S. Cl.
CPC .......... *A61K 31/4184* (2013.01); *C07D 417/04* (2013.01); *C07D 409/14* (2013.01); *A61K 31/423* (2013.01); *A61K 31/4439* (2013.01); *A61K 31/454* (2013.01); *A61K 31/428* (2013.01); *C07D 413/14* (2013.01); *C07D 413/04* (2013.01); *C07D 417/14* (2013.01); *C07D 405/14* (2013.01)
USPC ............ 514/367; 514/375; 548/159; 548/235

(58) Field of Classification Search
USPC ............................ 514/367, 375; 548/159, 235
See application file for complete search history.

(56) References Cited

U.S. PATENT DOCUMENTS

| | | |
|---|---|---|
| 5,385,925 A | 1/1995 | Narr et al. |
| 5,563,147 A | 10/1996 | Gilmore et al. |
| 5,587,393 A | 12/1996 | Narr et al. |
| 5,684,029 A | 11/1997 | Narr et al. |
| 6,696,437 B1 | 2/2004 | Lubisch et al. |
| 2009/0156613 A1 | 6/2009 | Kindrachuk et al. |

FOREIGN PATENT DOCUMENTS

| | | | |
|---|---|---|---|
| CN | 1623992 | * 6/2005 | ........... C07D 413/04 |
| DE | 1 063 028 B | 8/1959 | |
| DE | 199 20 936 A1 | 11/2000 | |
| EP | 0 468 470 A1 | 1/1992 | |
| JP | 4-253966 A | 9/1992 | |
| JP | 8-81464 A | 3/1996 | |
| JP | 2002-544199 A | 12/2002 | |
| JP | 2007-282501 A | 11/2007 | |

(Continued)

OTHER PUBLICATIONS

"Stroke," Google Health; Accessed Nov. 6, 2010 <https://health.google.com/health/ref/Stroke#Treatment>.*

(Continued)

*Primary Examiner* — Samantha Shterengarts
(74) *Attorney, Agent, or Firm* — Birch, Stewart, Kolasch & Birch, LLP

(57) ABSTRACT

A compound depicted by the formula below, or a pharmaceutically acceptable salt or solvate thereof.

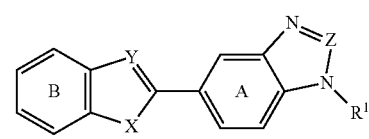

(I)

Figure 1:
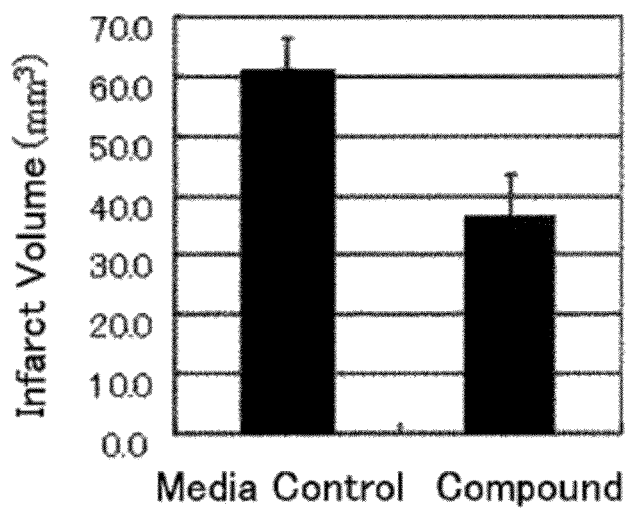

wherein, $R^1$ represents (1) a $C_{3-6}$ alkyl group, (2) a $C_{1-6}$ alkyl group substituted with one or more substituent group(s) selected from those consisting a halogen atom, etc., (3) a $C_{3-10}$ non-aromatic cyclic hydrocarbon group or a 5- to 6-membered non-aromatic heterocyclic group which respectively is optionally substituted with one or more substituent group(s) selected from those consisting an oxo group, etc., (4) an aromatic cyclic hydrocarbon group substituted with one or more substituent selected from the group consisting halogen atom and $C_{1-4}$ alkoxy group; X represents NH, O, or S; Y represents CH or N; Z represents N or a C—$R^2$; $R^2$ represents (1) hydrogen atom, (2) a $C_{1-6}$ alkyl group, a $C_{2-6}$ alkenyl group or a $C_{2-6}$ alkynyl group that respectively is optionally substituted with one or more substituent group(s) selected from among those consisting (a) a halogen atom, etc., or (3) a $C_{5-6}$ non-aromatic cyclic hydrocarbon group or a 5- to 6-membered non-aromatic heterocyclic group optionally substituted; ring A represents a benzene ring optionally substituted; ring B represents a benzene ring optionally substituted.

12 Claims, 1 Drawing Sheet

(56) References Cited

FOREIGN PATENT DOCUMENTS

| JP | 2007-282502 A | 11/2007 |
|---|---|---|
| JP | 2010-47517 A | 3/2010 |
| WO | WO 00/66206 A1 | 11/2000 |
| WO | WO 01/00213 A1 | 1/2001 |
| WO | WO 2007/115408 A1 | 10/2007 |
| WO | WO 2008/073451 A2 | 6/2008 |
| WO | WO 2008/153701 A1 | 12/2008 |
| WO | WO 2009/079001 A1 | 6/2009 |

OTHER PUBLICATIONS

Antonio R. Damasio, Alzheimer's Disease and Related Dementias, Cecil Textbook of Medicine, 20th edition (1996), vol. 2, pp. 1992-1996.*

FDA mulls drug to slow late-stage Alzheimer's [online], [retrieved on Sep. 23, 2003]. Retrieved from the Internet, URL: http://www.cnn.com/2003/HEALTH/conditions/09/24/alzheimers.drug.ap/indez.html, pp. 1 and 2.*

Dafang Wu, "Neuroprotection in Experimental Stroke with Targeted Neurotrophins", The Journal of the American Society for Experimental NeuroTherapeutics, vol. 2, Jan. 2005, pp. 120-128.

Furukawa et al., "Neuronal Protection by Neurotrophic Factors", Current Medicine Japan (saishin igaku), 1999, pp. 1730-1736.

International Search Report, dated Jun. 22, 2010 in PCT/JP2010/003622.

Koji Abe, "Gene therapy with GNDF", Studies on Intervention Periods for Stroke (Revised 2nd Ed) vol. 1—From the hyperacute phase to prevention, 2006, pp. 649-654.

Morgan et al., "Role of ion flux in the control of c-fos expression", Nature, vol. 322, Aug. 7, 1986, pp. 552-555.

Semkova et al., "Neuroprotection mediated via neurotrophic factors and induction of neurotrophic factors", Brain Research Reviews 30, 1999, pp. 176-188.

Sofroniew et al., "Nerve Growth Factor Signaling, Neuroprotection, and Neural Repair", Annual Review Neuroscience, vol. 24, 2001, pp. 1217-1281.

Tabakman et al., "Interactions between the cells of the immune and nervous system: neurotrophins as neuroprotection mediators in CNS injury", Progress in Brain Research, vol. 146, 2004, pp. 387-401.

Extended European Search Report issued Apr. 17, 2012, in European Patent Application No. 1078039.0.

Office Action issued Jun. 17, 2014, in Japanese Patent Application No. 2010-123614.

Urainskii Khimicheskii Zhurnal (1964), vol. 30, No. 1, pp. 80-82.

* cited by examiner

AGENT FOR TREATMENT OR PREVENTION OF DISEASES ASSOCIATED WITH ACTIVITY OF NEUROTROPHIC FACTORS

TECHNICAL FIELD

The present invention relates to agents for the treatment or prevention of diseases associated with activity of neurotrophic factors.

BACKGROUND ART

Neurotrophic factors such as BDNF, NGF, and the like are proteins that play an important role in the differentiation of cells in the central and peripheral nervous systems, in maintaining function and in the formation of synapses, and in regeneration and repair during injuries, and they are known to be effective in therapies such as for neurodegenerative diseases, diabetic neuropathy, amyotrophic lateral sclerosis, multiple sclerosis, cerebral ischemic disease, Alzheimer's disease, Parkinson's disease, Huntington's chorea, depression, peripheral neuropathy due to cancer chemotherapy, and the like (Non-patent Documents 2, 3, 4, and 5). Nevertheless, neurotrophic factors are macromolecular proteins whose molecular weight number is over than 10000, and since it is known that there are limitations and safety problems when such macromolecular proteins are used as therapeutic agents (Non-patent Documents 6 and 7), there is a desperate need for small-molecular-weight compounds that potentiate the effects of neurotrophic factors with few undesired side effects.

At the same time, it is known that the expression of some types of transcriptional regulatory factors are controlled by neurotrophic factors (see Non-patent Document 1), and NXF is known to be one of the transcriptional regulatory factors the expression of which is controlled by neurotrophic factors (see Non-patent Document 1).

In addition, since more severe glutamate-induced neuronal toxicity appear in NXF deficient mice, it is known that NXF holds an important role in neuroprotective action (see Non-patent Document 2).

By the way, Patent Document 3 discloses compounds represented by the generic structure:

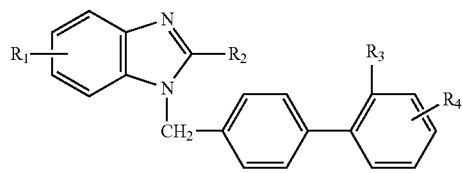

Moreover, Patent Document 4 discloses compounds represented by the generic structure:

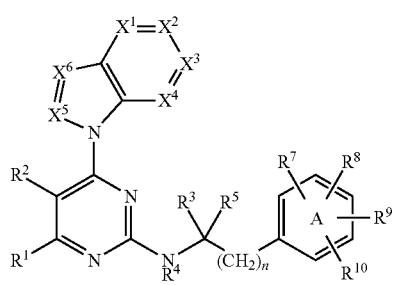

In addition, in Patent Document 5 discloses compounds represented by the generic structure:

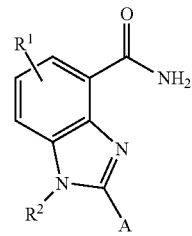

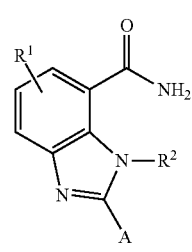

Additionally, in Patent Document 6 discloses compounds represented by the generic structure:

(I)

R—[benzimidazole]—$R^1$, $R^2$, $R^3$, $R^4$

PRIOR ART LITERATURE

Patent Literature

Patent Document 1: Japanese Published Unexamined Patent Application No. 2007-282502
Patent Document 2: Japanese Published Unexamined Patent Application No. 2007-282501
Patent Document 3: EP 468470 Specification
Patent Document 4: WO 01/00213
Patent Document 5: DE 19920936 Laid-open Publication, Specification
Patent Document 6: WO 2008/153701

Non-Patent Literature

Non-patent Document 1: Nature 1986 322 552-555
Non-patent Document 2: The Journal of the American Society for Experimental NeuroTherapeutics 2005 2 120-128
Non-patent Document 3: Annual Review of Neuroscience 2001 24 1217-1281
Non-patent Document 4: Brain Research Reviews 1999 30 176-188
Non-patent Document 5: Progress in Brain Research 2004 146 387-401
Non-patent Document 6: Current Medicine Japan (saishin igaku) 1999 54(7) 88-94
Non-patent Document 7: Studies on Intervention Periods for Stroke (Revised $2^{nd}$ Ed) Vol. 1—From the hyperacute phase to prevention 2006, pp 649-654

SUMMARY OF THE INVENTION

Problem to be Solved by the Invention

As stated above, there is a desperate need for small-molecular-weight compounds that potentiate the activity of neurotrophic factors with few undesired effects.

Means to Solve the Problem

Using the induction of NXF expression as an indicator, a search for compounds that potentiate the activity of neurotrophic factors by present inventors resulted in compounds depicted in the formula:

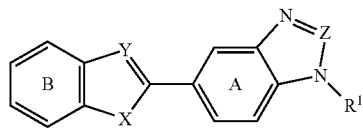

(I)

wherein, Z represents N or C—$R^2$,
X represents N—$R^3$, O, or S,
Y represents C—$R^4$, or N,
$R^1$ represents a hydrogen atom, optionally substituted acyclic hydrocarbon group, or optionally substituted cyclic group,
$R^2$ represents a hydrogen atom, optionally substituted acyclic hydrocarbon group, or optionally substituted cyclic group,
$R^3$ represents a hydrogen atom, or substituent group,
$R^4$ represents a hydrogen atom, or substituent group,
Ring A represents an optionally substituted benzene ring, and
Ring B represents an optionally substituted benzene ring, pharmaceutically acceptable salt or solvate thereof (when referred to as compound (I) in the present specification, moreover when referred to a compound of the present invention) that potentiates the activity of neurotrophic factors, and discovered that it have neuroprotective action, thus accomplishing the present invention.

The present invention also provides the following [1] through [13].

[1] A compound depicted by the formula:

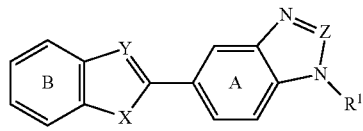

(I)

wherein, $R^1$ represents:
(1) a $C_{3-6}$ alkyl group,
(2) a $C_{1-6}$ alkyl group substituted with one or more substituent group(s) selected from those consisting:
  (a) a halogen atom,
  (b) a $R^a$—O—,
  (c) a $R^a$—O—CO—,
  (d) a $R^a$—O—CO—$NR^a$—,
  (e) a $R^a$—O—CO—$C_2H_4$—CO—NH—
  (f) a $R^a$—S—,
  (g) a $R^a$—$SO_2$—,
  (h) a $R^a$—CO—O—,
  (i) a $R^a$—CO—$NR^a$—,
  (j) a $R^a$—$NR^a$—,
  (k) a $R^a$—$NR^a$—CS—$NR^a$—,
  (l) a 5- to 6-membered ring group,
  (m) a carboxy group,
  (n) a hydroxy group,
  (o) an amino group,
  (p) a heterocyclic-carbonyl group,
  (q) a HO—CO—$C_2H_4$—CO—NH—
(wherein, each $R^a$ is the same or different, and represents an optionally halogen-substituted $C_{1-6}$ alkyl group), or
(3) a $C_{3-10}$ non-aromatic cyclic hydrocarbon group or a 5- to 6-membered non-aromatic heterocyclic group which respectively is optionally substituted with one or more substituent group(s) selected from those consisting:
  (a) an oxo group, and
  (b) a $C_{1-4}$ alkoxycarbonyl group,
or,
(4) an aromatic cyclic hydrocarbon group substituted with one or more substituent selected from the group consisting halogen atom and $C_{1-4}$ alkoxy group,
X represents NH, O, or S,
Y represents CH or N,
Z represents N or a C—$R^2$,
$R^2$ represents:
(1) a hydrogen atom,
(2) a $C_{1-6}$ alkyl group, a $C_{2-6}$ alkenyl group or a $C_{2-6}$ alkynyl group that respectively is optionally substituted with one or more substituent group(s) selected from among those consisting:
  (a) a halogen atom,
  (b) a $R^b$—O—,
  (c) a $R^b$—O—CO—,
  (d) a $R^b$—O—CO—$NR^b$—,
  (e) a $R^b$—S—,
  (f) a $R^b$—$SO_2$—,
  (g) a $R^b$—CO—O—,
  (h) a $R^b$—CO—$NR^b$—,
  (i) a $R^b$—$NR^b$—,
  (j) a $R^b$—CO—$NR^b$—$R^b$—$S(O)_n$—,
  (k) a phenyl group,
  (l) a 5- to 6-membered saturated heterocyclic group,
  (m) a hydroxy group, and
  (n) an amino group
(wherein, each $R^b$ is the same or different, and represents a hydrogen atom or $C_{1-6}$ alkyl group optionally substituted with one or more halogens, and n represents an integer from 0 to 2), or,
(3) a $C_{5-6}$ non-aromatic cyclic hydrocarbon group or a 5- to 6-membered non-aromatic heterocyclic group optionally substituted with one or more substituent group(s) selected from the group consisting:
  (a) a halogen atom,
  (b) a $R^c$—O—,
  (c) a $R^c$—O—CO—, and
  (d) a $R^c$—CO—$NR^c$—,
(wherein, each $R^c$ is the same or different, and represents a hydrogen atom or $C_{1-6}$ alkyl group),
ring A represents a benzene ring optionally substituted with one or more substituent group(s) selected from the group consisting:
  (a) a halogen atom,
  (b) a hydroxy group,
  (c) a carboxy group,
  (d) a cyano group,
  (e) a sulfamoyl group,
  (f) a monoalkylamide group, (g) a dialkylamide group,
(h) an alkyl group optionally substituted with a halogen atom,
(i) a nitro group, and
(j) an aryloxy group,
ring B represents a benzene ring optionally substituted with one or more substituent group(s) selected from the group consisting:
(a) a halogen atom,
(b) a hydroxy group,
(c) a carboxy group,
(d) a cyano group,
(e) a sulfamoyl group,
(f) a monoalkylamide group,
(g) a dialkylamide group,
(h) an amide group,
(i) an ester group,
(j) an alkyl group optionally substituted with a halogen atom,
(k) a nitro group, and
(l) an aryloxy group,
or a pharmaceutically acceptable salt or solvate thereof.
[2] The compound according to [1], wherein Z is a C—$R^2$, and Y is N.
[3] The compound according to [1], wherein $R^1$ is a 5- to 6-membered non-aromatic heterocyclic group.
[4] The compound according to [1], wherein $R^2$ is a $C_{1-6}$ alkyl group.
[5] The compound according to [1], wherein Z is a C—$R^2$, Y is N, $R^1$ is a 5- to 6-membered non-aromatic heterocyclic group, and $R^2$ is a $C_{1-6}$ alkyl group.
[6] A pharmaceutical composition comprising the compound of [1].
[7] The pharmaceutical composition according to [6], wherein the composition is an agent for the prevention or treatment of a disease that is associated with neurotrophic factor activity, or an agent that promotes a physiotherapeutic effect.
[8] The pharmaceutical composition according to [7], wherein the agent for the prevention or treatment of a disease that is associated with neurotrophic factor activity or the agent that promotes the physiotherapeutic effect is an agent for the prevention or treatment of cerebral ischemic disease or diabetic neuropathy.
[9] An agent for the prevention or treatment of a disease that is associated with neurotrophic factor activity, or an agent that promotes a physiotherapeutic effect comprising a compound depicted in the formula:

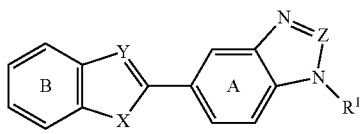

(I)

wherein, Z represents N or a C—$R^2$,
X represents a N—$R^3$, O, or S,
Y represents a C—$R^4$ or N,
$R^1$ represents a hydrogen atom, an optionally substituted acyclic hydrocarbon group, or an optionally substituted cyclic group,
$R^2$ represents a hydrogen atom, an optionally substituted acyclic hydrocarbon group, or an optionally substituted cyclic group,
$R^3$ represents a hydrogen atom or a substituent group,
$R^4$ represents a hydrogen atom or a substituent group,
ring A represents an optionally substituted benzene ring,
ring B represents an optionally substituted benzene ring,
or a pharmaceutically acceptable salt or solvate thereof as an active ingredient.
[10] The agent according to [9], wherein ring A is a benzene ring optionally substituted with one or more substituent group(s) selected from the group consisting:
(a) a halogen atom,
(b) a hydroxy group,
(c) a carboxy group,
(d) a cyano group,
(e) a sulfamoyl group,
(f) a monoalkylamide group,
(g) a dialkylamide group,
(h) an alkyl group optionally substituted with a halogen atom,
(i) a nitro group, and
(j) an aryloxy group
ring B is a benzene ring optionally substituted with one or more substituent group(s) selected from the group consisting:
(a) a halogen atom,
(b) a hydroxy group,
(c) a carboxy group,
(d) a cyano group,
(e) a sulfamoyl group,
(f) a monoalkylamide group,
(g) a dialkylamide group,
(h) an amide group,
(i) an ester group,
(j) an alkyl group optionally substituted with a halogen atom,
(k) a nitro group, and
(l) an aryloxy group,
Z is N or a C—$R^2$,
X is NH, O, or S,
Y is CH or N,
$R^1$ is
(1) a hydrogen atom,
(2) a $C_{1-6}$ alkyl group,
(3) a $C_{1-6}$ alkyl group substituted with one or more substituent group(s) selected from those consisting:
(a) a halogen atom,
(b) a $R^a$—O—,
(c) a $R^a$—O—CO—,
(d) a $R^a$—O—CO—$NR^a$—,
(e) a $R^a$—O—CO—$C_2H_4$—CO—NH—
(f) a $R^a$—S—,
(g) a $R^a$—$SO_2$—,
(h) a $R^a$—CO—O—,
(i) a $R^a$—CO—$NR^a$—,
(j) a $R^a$—$NR^a$—,
(k) a $R^a$—$NR^a$—CS—$NR^a$—,
(l) a 5- to 6-membered ring group,
(m) a carboxy group,
(n) a hydroxy group,
(o) an amino group,
(p) a heterocyclic carbonyl group,
(q) a HO—CO—$C_2H_4$—CO—NH—
(wherein, each $R^a$ is the same or different, and represents an optionally halogen-substituted $C_{1-6}$ alkyl group),
(4) a $C_{3-10}$ non-aromatic cyclic hydrocarbon group or a 5- to 6-membered non-aromatic heterocyclic group which may respectively be optionally substituted with one or more substituent group(s) selected from the group consisting:

(a) an oxo group,
(b) a $C_{1-4}$ alkoxycarbonyl group, and
(c) a hydroxy group,
or,
(5) an aromatic cyclic hydrocarbon group optionally substituted with one or more substituent selected from the group consisting a halogen atom and a $C_{1-4}$ alkoxy group,
$R^2$ represents
(1) a hydrogen atom,
(2) a $C_{1-6}$ alkyl group, a $C_{2-6}$ alkenyl group or a $C_{2-6}$ alkynyl group that respectively is optionally substituted with one or more substituent group(s) selected from the group consisting:
 (a) a halogen atom,
 (b) a $R^b$—O—,
 (c) a $R^b$—O—CO—,
 (d) a $R^b$—O—CO—$NR^b$—,
 (e) a $R^b$—S—,
 (f) a $R^b$—$SO_2$—,
 (g) a $R^b$—CO—O—,
 (h) a $R^b$—CO—$NR^b$—,
 (i) a $R^b$—$NR^b$—,
 (j) a $R^b$—CO—$NR^b$—$R^b$—$S(O)_n$—,
 (k) a phenyl group,
 (l) a 5- to 6-membered saturated heterocyclic group,
 (m) a hydroxy group, and
 (n) an amino group,
(wherein, each $R^b$ is the same or different, and represents a hydrogen atom or a $C_{1-6}$ alkyl group optionally substituted with one or more halogens, and n represents an integer from 0 to 2),
or,
(3) a $C_{5-6}$ non-aromatic cyclic hydrocarbon group or a 5- to 6-membered non-aromatic heterocyclic group optionally substituted with one or more substituent group(s) selected from the group consisting:
 (a) a halogen atom,
 (b) a $R^c$—O—,
 (c) a $R^c$—O—CO—, and
 (d) a $R^c$—CO—$NR^c$—,
(wherein, each $R^c$ is the same or different, and represents a hydrogen atom or a $C_{1-6}$ alkyl group),
or,
(4) a phenyl group optionally substituted with one or more substituent group(s) selected from the group consisting:
 (a) a halogen atom,
 (b) a $R^c$—O—,
 (c) a $R^c$—O—CO—, and
 (d) a $R^c$—CO—$NR^c$—,
(wherein, each $R^c$ is the same or different, and represents a hydrogen atom or a $C_{1-6}$ alkyl group),
or,
$R^1$ and $R^2$ taken together with adjacent N and C can form a 5- to 8-membered nitrogen-containing non-aromatic heterocyclic ring.
[11] The agent according to [9], wherein the agent is an agent for prevention or treatment of cerebral ischemic disease or diabetic neuropathy.
[12] A method for prevention or treatment of diseases that is associated with neurotrophic factor activity or a method to promote a physiotherapeutic effect comprising;
administrating an amount active of a compound depicted in the formula:

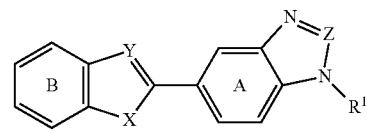

wherein, Z represents N or a C—$R^2$,
X represents a N—$R^3$, O, or S,
Y represents a C—$R^4$ or N,
$R^1$ represents a hydrogen atom, an optionally substituted acyclic hydrocarbon group, or an optionally substituted cyclic group,
$R^2$ represents a hydrogen atom, an optionally substituted acyclic hydrocarbon group, or an optionally substituted cyclic group,
$R^3$ represents a hydrogen atom or a substituent group,
$R^4$ represents a hydrogen atom or a substituent group,
ring A represents an optionally substituted benzene ring,
ring B represents an optionally substituted benzene ring,
or a pharmaceutically acceptable salt or solvate thereof to a mammal.
[13] Use of a compound depicted in the formula:

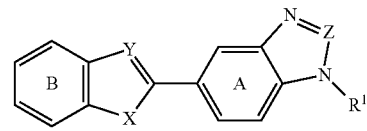

wherein, Z represents N or a C—$R^2$,
X represents a N—$R^3$, O, or S,
Y represents a C—$R^4$ or N,
$R^1$ represents a hydrogen atom, an optionally substituted acyclic hydrocarbon group, or an optionally substituted cyclic group,
$R^2$ represents a hydrogen atom, an optionally substituted acyclic hydrocarbon group, or an optionally substituted cyclic group,
$R^3$ represents a hydrogen atom or a substituent group,
$R^4$ represents a hydrogen atom or a substituent group,
ring A represents an optionally substituted benzene ring,
ring B represents an optionally substituted benzene ring,
or a pharmaceutically acceptable salt or solvate thereof for manufacture as an agent for prevention or treatment of diseases that are associated with neurotrophic factor activity, or an agent that promotes a physiotherapeutic effect.
In addition, the present invention also provides the following [1'] through [4'].
[1'] A compound depicted in the formula:

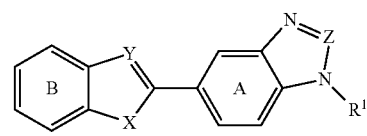

wherein, $R^1$ represents a hydrogen atom, an optionally substituted acyclic hydrocarbon group, or an optionally substituted cyclic group;

X represents a N—$R^3$ (wherein $R^3$ represents a hydrogen atom or a substituent group), O, or S;

Y represents a C—$R^4$ (wherein $R^4$ represents a hydrogen atom or a substituent group), or N;

Z represents N or a C—$R^2$ (wherein $R^2$ represents a hydrogen atom, an optionally substituted acyclic hydrocarbon group, or an optionally substituted cyclic group); and ring A and ring B independently represent an optionally substituted benzene ring, or a pharmaceutically acceptable salt or solvate, $R^1$ is not a group represented by the formula hereunder:

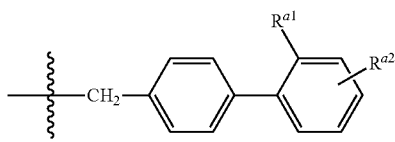

wherein, $R^{a1}$ represents a carboxy group, a cyano group, a 1H-tetrazolyl group, a 1-triphenylmethyl-tetrazolyl group, or an alkoxycarbonyl group, and $R^{a2}$ represents a hydrogen atom, a fluorine atom, a chlorine atom or a bromine atom, Furthermore, $R^1$ is not a group represented by the formula hereunder:

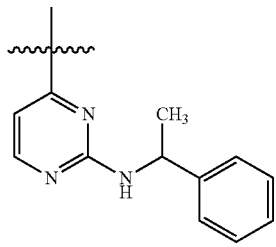 [SMILES: *c1ccnc(NC(C)c2ccccc2)n1]

or a pharmaceutically acceptable salt or solvate thereof.
(On addition that [2,5'-bi-1H-benzimidazole]-5-carboxylic acid, 1-butyl-1'-(3-phenylpropyl)-, methyl ester, [2,5'-bi-1H-benzimidazole]-5-carboxylic acid, 1-butyl-1'-(2-furanylmethyl)-, methyl ester, [2,5'-bi-1H-benzimidazole]-5-carboxylic acid, 1-butyl-1'-cyclopentyl)-, methyl ester, [2,5'-bi-1H-benzimidazole]-5-carboxylic acid, 1'-(2-furanylmethyl)-1-(1-methylethyl)-, methyl ester, [2,5'-bi-1H-benzimidazole]-5-carboxylic acid, 1'-[(4-methoxyphenyl)methyl]-1-(1-methylethyl)-, methyl ester, [2,5'-bi-1H-benzimidazole]-5-carboxylic acid, 1'-cyclopentyl-1-(2-furanylmethyl)-2'-phenyl-, methyl ester, [2,5'-bi-1H-benzimidazole]-5-carboxylic acid, 1'-cyclopentyl-1-(2-furanylmethyl)-2'-[4-(methylthio)phenyl]-, methyl ester, [2,5'-bi-1H-benzimidazole]-5-carboxylic acid, 2'-cyclohexyl-1'-cyclopentyl-1-(2-furanylmethyl)-, methyl ester, [2,5'-bi-1H-benzimidazole]-5-carboxylic acid, 1'-cyclopentyl-1-(2-furanylmethyl)-2'-(3-thienyl)-, methyl ester, [2,5'-bi-1H-benzimidazole]-5-carboxylic acid, 1'-cyclopentyl-2'-[4-(methylthio)phenyl]-1-[3-(4-morpholinyl)propyl]-, methyl ester, [2,5'-bi-1H-benzimidazole]-5-carboxylic acid, 2'-(4-chlorophenyl)-1'-cyclopentyl-1-[3-(4-morpholinyl)propyl]-, methyl ester, 2,5'-bi-1H-benzimidazole, 6-phenyl-1,1'-bis(phenylmethyl)-, 2,5':2',5''-ter-1H-benzimidazole, 6-phenyl-1,1',1''-tris(phenylmethyl)-, 2,5'-bi-1H-benzimidazole, 1,1',2'-tris(phenylmethyl)-, 2,5'-bi-1H-benzimidazole, 2'-(3-chlorophenyl)-1'-[(2,5-difluorophenyl)methyl]-1-(phenylmethyl), benzothiazole, 2-(2-methyl-1-phenyl-1H-benzimidazol-5-yl)-, 4-methylbenzene sulfonate (1:1), benzothiazole, 2-(2-methyl-1-phenyl-1H-benzimidazol-5-yl)-, benzoxazole, 2-(2-methyl-1-phenyl-1H-benzimidazol-5-yl)-, 2,5'-bi-1H-benzimidazole, 2'-methyl-1'-phenyl-, 2,5'-bi-1H-benzimidazole, 1-ethyl-2'-methyl-1'-phenyl-, benzoxazole, 2-(2-methyl-1-phenyl-1H-benzimidazol-5-yl)-, 4-methylbenzene sulfonate (1:1), [1,1'-biphenyl]-2-carboxylic acid, 4'-[(1,7'-dimethyl-2'-propyl[2,5'-bi-1H-benzimidazole]-1'-yl)methyl]-, 1,1-dimethylethyl ester, [1,1'-biphenyl]-2-carboxylic acid, 4'-[(1,7'-dimethyl-2'-propyl[2,5'-bi-1H-benzimidazole]-1'-yl)methyl]-, [2,5'-bi-1H-benzimidazole]-5-carboxylic acid, 1-cyclopentyl-1'-(1-methylethyl)-, methyl ester, [2,5'-bi-1H-benzimidazole]-5-carboxylic acid, 1-(2-methoxyethyl)-1'-(2-methylpropyl)-, methyl ester, [2,5'-bi-1H-benzimidazole]-5-carboxylic acid, 1'-(1-methylethyl)-1-(2-methylpropyl)-, methyl ester, [2,5'-bi-1H-benzimidazole]-5-carboxylic acid, 1-butyl-1-(2-methylpropyl)-, methyl ester, [2,5'-bi-1H-benzimidazole]-5-carboxylic acid, 1-(2-methoxyethyl)-1'-(1-methylethyl)-, methyl ester, phenol, 4-[1,1'-dimethyl-5-(4-methyl-1-piperazinyl)[2,5'-bi-1H-benzimidazole]-2'-yl]-, [2,5'-bi-1H-benzimidazole]-4,4',7,7'-tetraol, 2'-(3,4-dihydroxyphenyl)-1,1'-dimethyl-5-(4-methyl-1-piperazinyl)-, [2,5'-bi-1H-benzimidazole]-4,4',7,7'-tetraol, 2'-(4-hydroxyphenyl)-1,1'-dimethyl-5-(4-methyl-1-piperazinyl)-, 2,5'-bi-1H-benzimidazole, 4',7'-dimethoxy-2'-(methoxymethyl)-1'-methyl-6-(4-methyl-1-piperazinyl)-, [2,5'-bi-1H-benzimidazole]-2'-methanol, 4',7'-dimethoxy-1'-methyl-6-(4-methyl-1-piperazinyl)-, [2,5'-bi-1H-benzimidazole]-4',7'-diol, 2'-(hydroxymethyl)-1'-methyl-6-(4-methyl-1-piperazinyl)-, [2,5'-bi-1H-benzimidazole]-2'-methanol, 4',7'-dimethoxy-1'-methyl-6-(4-methyl-1-piperazinyl)-, 2'-acetate, 2,5'-bi-1H-benzimidazole, 2'-(chloromethyl)-4',7'-dimethoxy-1'-methyl-6-(4-methyl-1-piperazinyl)-, [2,5'-bi-1H-benzimidazole]-2'-methanol, 7'-hydroxy-4'-methoxy-1'-methyl-6-(4-methyl-1-piperazinyl)-, [2,5'-bi-1H-benzimidazole]-4',7'-diol, 2'-(chloromethyl)-1'-methyl-6-(4-methyl-1-piperazinyl)-, 2,5'-bi-1H-benzimidazole, 2'-methyl-1'-(1-methylethyl)-1-(phenylmethyl)-, 2,5'-bi-1H-benzimidazole, 2'-(3-chlorophenyl)-1-(phenylmethyl)-1'-[2-[(phenylmethyl)thio]ethyl]-, [2,5'-bi-1H-benzimidazole]-6-carboximidamide, 2'-(4-fluorophenyl)-1'-methyl-N-(1-methylethyl)-, 1H-benzimidazole-6-carboximidamide, 2-[4-[1'-butyl-6-[imino[(1-methylethyl)amino]methyl][2,5'-bi-1H-benzimidazole]-2'-yl]phenyl]-N-(1-methylethyl)-, [2,5'-bi-1H-benzimidazole]-5-carboxylic acid, 1-butyl-2'-(2-fluorophenyl)-1'-(1-methylethyl)-, methyl ester, [2,5'-bi-1H-benzimidazole]-5-carboxylic acid, 1-butyl-2'-cyclohexyl-1'-(1-methylethyl)-, methyl ester, [2,5'-bi-1H-benzimidazole]-5-carboxylic acid, 1-butyl-1'-(1-methylethyl)-2'-(3-thienyl)-, methyl ester, [2,5'-bi-1H-benzimidazole]-5-carboxylic acid, 1-butyl-1'-(1-methylethyl)-2'-(4-nitrophenyl)-, methyl ester, [2,5'-bi-1H-benzimidazole]-5-carboxylic acid, 1-butyl-1'-(1-methylethyl)-2'-phenyl-, methyl ester, [2,5'-bi-1H-benzimidazole]-5-carboxylic acid, 2'-(2-bromophenyl)-1-butyl-1'-(1-methylethyl)-, methyl ester, [2,5'-bi-1H-benzimidazole]-5-carboxylic acid, 1-butyl-1'-(1-methylethyl)-, methyl ester, benzoxazole, 2-(1,2-dimethyl-1H-benzimidazol-5-yl)-, benzoxazole, 2-(1-ethyl-2-methyl-1H-benzimidazol-5-yl)-, benzothiazole, 2-(1-ethyl-2-methyl-1H-benzimidazol-5-yl)-, and benzothiazole, 2-(1,2-dimethyl-1H-benzimidazol-5-yl)-, are excluded).

[2'] A compound according to [1'] wherein
R$^1$ is:
a) a C$_{1-6}$ acyclic hydrocarbon group optionally substituted with 6-membered ring group, or
b) a 6- to 10-membered ring group optionally substituted with one or more substituent group(s) selected from among a halogen atom, a C$_{1-4}$ alkoxy group, and a C$_{1-4}$ alkoxycarbonyl group,
  X is a N—R$^3$ (R$^3$ is hydrogen atom, or R$^a$—O—CO— (R$^a$ is a C$_{1-6}$ alkyl group)), O, or S,
  Y is CH or N,
  Z is N or a C—R$^2$,
  wherein, R$^2$ is:
a) a hydrogen atom
b) a C$_{1-6}$ alkyl group optionally substituted with one or more (preferably 1-3) substituent group(s) selected from among:
  (1) a halogen atom,
  (2) a R$^b$—O—,
  (3) a R$^b$—CO—,
  (4) a R$^b$—CO—O—, and
  (5) a R$^b$—NR$^b$—,
  wherein, each R$^b$ is the same or different, and represents a hydrogen atom or a C$_{1-6}$ alkyl group optionally substituted with one phenyl group),
or
c) a 5- to 6-membered ring group,
  ring A is a benzene ring, and
  ring B is a benzene ring optionally substituted with one or more substituent group(s) selected from among a halogen atom, a nitro group, a C$_{1-6}$ alkyl group, and an amino group).
[3'] An agent for prevention or treatment of diseases that are associated with neurotrophic factor activity, or an agent that promotes a physiotherapeutic effect, comprising a compound depicted by the formula:

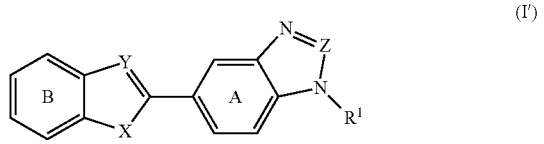

(I')

wherein, R$^1$ represents a hydrogen atom, an optionally substituted acyclic hydrocarbon group, or an optionally substituted cyclic group;
  X represents a N—R$^3$ (where R$^3$ represents a hydrogen atom or a substituent group), O, or S;
  Y represents a C—R$^4$ (where R$^4$ represents a hydrogen atom or a substituent group), or N;
  Z represents N or a C—R$^2$ (where R$^2$ represents a hydrogen atom, an optionally substituted acyclic hydrocarbon group, or an optionally substituted cyclic group); and
  ring A and ring B independently represent an optionally substituted benzene ring, or a pharmaceutically acceptable salt or solvate thereof as an active ingredient (when referred to below as a compound (I'). compound (I') is understood in the same manner as according to the explanation for the aforementioned compound (I)).
[4'] The agent according to [3'], wherein the agent is an agent for prevention or treatment of cerebral ischemic disease or diabetic neuropathy.

Effect of the Invention

It is possible according to the present invention to provide an effective low-molecular compound for the treatment, prevention, or the like of diseases that are associated with neurotrophic factor activity.

BRIEF EXPLANATION OF DIAGRAMS

Figure 2:
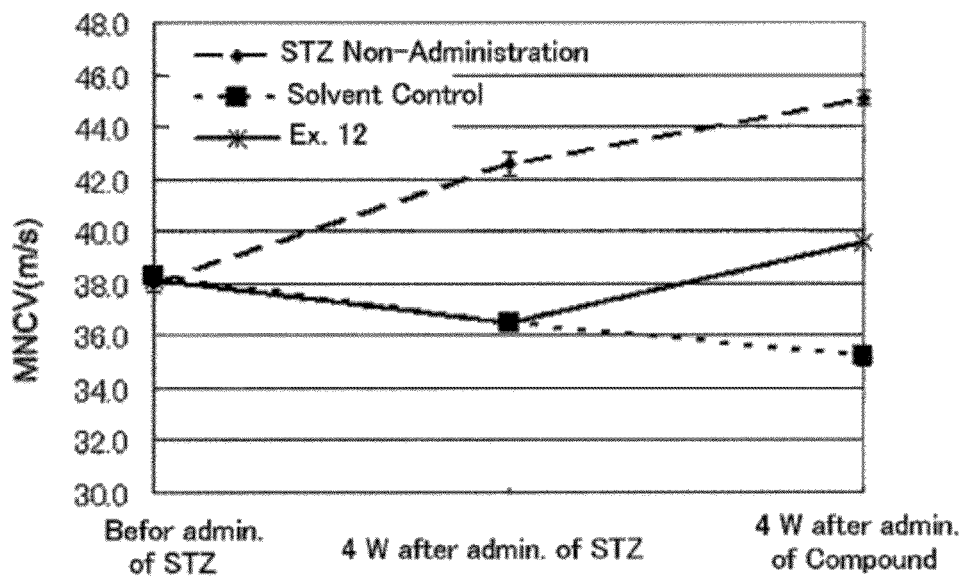

FIG. 1 is a graph that shows the infarct volume (Test Example 2).
FIG. 2 is a graph that shows the prolongation of latency of the motor nerve conduction velocity (MNCV) (Test Example 3).

MODES FOR IMPLEMENTING THE INVENTION

The present invention is explained in detail below.
Explanations of the terms used in the present specification are found below.
Examples of an "aryl (group)" that can be named include a C$_{6-14}$ aryl (group). Examples of the "C$_{6-14}$ aryl (group)" include phenyl, naphthyl, and anthryl.
Examples of a "heteroaryl (group)" that can be named include a 5- to 6-membered heteroaryl (group). Examples of a "5- to 6-membered heteroaryl (group)" that can be named include a 5- to 6-membered heteroaryl (group) that has 1-3 (preferably 1-2) heteroatoms selected from among oxygen atom, sulfur atom, and nitrogen atom as ring constituent atoms.
Examples of a "5- to 6-membered heteroaryl (group) that has 1-3 (preferably 1-2) heteroatoms selected from among oxygen atom, sulfur atom, and nitrogen atom as ring constituent atoms" that can be named include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 2-pyrazolyl, 3-pyrazolyl, 4-pyrazolyl), thiazolyl (e.g., 2-thiazolyl, 4-thiazolyl, 5-thiazolyl), isothiazolyl, oxazolyl (e.g., 2-oxazolyl, 4-oxazolyl, 5-oxazolyl), isoxazolyl, oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl, triazinyl, and the like.
Examples of a "cycloalkyl (group)" that can be named include a C$_{3-10}$ cycloalkyl (group).
Examples of the "C$_{3-10}$ cycloalkyl (group)" that can be named include cyclopropyl, cyclobutyl, cyclopentyl, cyclohexyl, cycloheptyl, cyclooctyl, cyclononyl, and cyclodecyl.
Examples of a "cycloalkenyl (group)" that can be named include a C$_{3-10}$ cycloalkenyl (group).
Examples of the "C$_{3-10}$ cycloalkenyl (group)" that can be named include cyclopropenyl, cyclobutenyl, cyclopentenyl, cyclohexenyl, cycloheptenyl, cyclooctenyl, cyclononenyl, and cyclodecenyl.
Examples of a "cycloalkadienyl (group)" that can be named include a C$_{4-10}$ cycloalkadienyl (group).
Examples of the "C$_{4-10}$ cycloalkadienyl (group)" that can be named include cyclobutadienyl, cyclopentadienyl, cyclohexadienyl, cycloheptadienyl, cyclooctadienyl, cyclononadienyl, and cyclodecadienyl.

Examples of a "non-aromatic heterocycle groups" that can be named include a 5- to 6-membered non-aromatic heterocycle group. Examples of the "5- to 6-membered non-aromatic heterocycle group" that can be named include a 5- to 6-membered non-aromatic heterocycle group that has 1-3 (preferably 1-2) heteroatoms selected from among oxygen atom, optionally oxidized sulfur atom, and nitrogen atom as ring constituent atoms.

Examples of the "5- to 6-membered non-aromatic heterocycle group that has 1-3 (preferably 1-2) heteroatoms selected from among oxygen atom, optionally oxidized sulfur atom, and nitrogen atom as ring constituent atoms" that can be named include:

pyrrolidinyl (e.g., 1-pyrrolidinyl, 2-pyrrolidinyl),
piperidinyl (e.g., piperidino, 2-piperidinyl, 3-piperidinyl, 4-piperidinyl),
morpholinyl (e.g., morpholino),
thiomorpholinyl (e.g., thiomorpholino),
piperazinyl (e.g., 2-piperazinyl, 2-piperazinyl, 3-piperazinyl),
hexamethyleneiminyl (e.g., hexamethyleneimin-1-yl),
oxazolidinyl (e.g., oxazolidin-2-yl),
thioxazolidinyl (e.g., thioxazolidin-2-yl),
imidazolidinyl (e.g., imidazolidin-2-yl, imidazolidin-3-yl),
oxazolinyl (e.g., oxazolin-2-yl),
thiazolinyl (e.g., thiazolin-2-yl),
imidazolinyl (e.g., imidazolin-2-yl, imidazolin-3-yl),
dioxolyl (e.g., 1,3-dioxol-4-yl), dioxolanyl (e.g., 1,3-dioxolan-4-yl),
dihydrooxadiazolyl (e.g., 4,5-dihydro-1,2,4-oxadiazol-3-yl),
pyranyl (e.g., 4-pyranyl),
tetrahydropyranyl (e.g., 2-tetrahydropyranyl, 3-tetrahydropyranyl, 4-tetrahydropyranyl),
thiopyranyl (e.g., 4-thiopyranyl),
tetrahydrothiopyranyl (e.g., 2-tetrahydrothiopyranyl, 3-tetrahydrothiopyranyl, 4-tetrahydrothiopyranyl),
1-oxidotetrahydrothiopyranyl (e.g., 1-oxidotetrahydrothiopyran-4-yl),
1,1-dioxidotetrahydrothiopyranyl (e.g., 1,1-dioxidotetrahydrothiopyran-4-yl),
tetrahydrofuryl (e.g., 2-tetrahydrofuran-3-yl, 3-tetrahydrofuran-2-yl),
pyrazolidinyl (e.g., pyrazolidin-1-yl, pyrazolidin-3-yl),
pyrazolinyl (e.g., pyrazolin-1-yl),
tetrahydropyrimidinyl (e.g., tetrahydropyrimidin-1-yl),
dihydrotriazolyl (e.g., 2,3-dihydro-1H-1,2,3-triazol-1-yl),
tetrahydrotriazolyl (e.g., 2,3,4,5-tetra-1H-1,2,3-triazol-1-yl),
dihydrooxazepinyl and the like.

Examples of an "alkyl (group)" that can be named include a $C_{1-6}$ alkyl (group). Examples of the "$C_{1-6}$ alkyl (group)" that can be named include methyl, ethyl, n-propyl, isopropyl, n-butyl, sec-butyl, tert-butyl, pentyl, and hexyl.

Examples of an "alkenyl (group)" that can be named include a $C_{2-6}$ alkenyl (group). Examples of the "$C_{2-6}$ alkenyl (group)" that can be named include vinyl, 2-propenyl, 3-methyl-2-butenyl, and 1,3-butadienyl.

Examples of the "alkynyl (group)" that can be named include a $C_{2-6}$ alkynyl (group). Examples of the "$C_{2-6}$ alkynyl (group)" that can be named include ethynyl, 2-propynyl, and 2-penten-4-ynyl.

Examples of the "alkylene (chain)" that can be named include a $C_{1-3}$ alkylene (chain). Examples of the "$C_{1-3}$ alkylene (chain)" that can be named include methylene, ethylene, and trimethylene.

Examples of a "halogen (atom)" that can be named include fluorine, chlorine, bromine, and iodine.

Examples of an "alkoxy (group)" that can be named include a $C_{1-6}$ alkoxy (group).

Examples of the "$C_{1-6}$ alkoxy (group)" that can be named include methoxy, ethoxy, n-propoxy, isopropoxy, n-butoxy, sec-butoxy, tert-butoxy, pentyloxy, and hexyloxy.

In other words, the $C_{1-6}$ alkoxy (group) is $R^a$—O— (where $R^a$ is a $C_{1-6}$ alkyl (group)).

Examples of "an alkoxycarbonyl (group)" that can be named include a $C_{1-6}$ alkoxycarbonyl (group).

Examples of the "$C_{1-6}$ alkoxycarbonyl (group)" that can be named include methoxycarbonyl, ethoxycarbonyl, n-propoxycarbonyl, isopropoxycarbonyl, n-butoxycarbonyl, sec-butoxycarbonyl, tert-butoxycarbonyl, n-pentyloxycarbonyl, and n-hexyloxycarbonyl group.

In other words, the $C_{1-6}$ alkoxycarbonyl (group) is $R^a$—O—CO— (where $R^a$ is a $C_{1-6}$ alkyl (group)).

Unless specifically stated otherwise, even when a portion of a single word in these terms is used, it will be used in the same manner as in these examples.

The symbols that are used in Formula (I) are explained below.

$R^1$ represents a hydrogen atom, optionally substituted acyclic hydrocarbon group, or optionally substituted cyclic group, Examples of what is represented by $R^1$ in those "acyclic hydrocarbon group" that is the "optionally substituted acyclic hydrocarbon group" that can be named include alkyl group, alkenyl group, and alkynyl group.

Examples of the "alkyl group" that can be named include the examples mentioned above.

Examples of the "alkenyl group" that can be named include the examples mentioned above.

Examples of the "alkynyl group" that can be named include the examples mentioned above.

Among these, the alkyl group is preferred, and the $C_{1-6}$ alkyl group is more preferred.

The "Acyclic hydrocarbon group" that is the "optionally substituted acyclic hydrocarbon group" represented by $R^1$ is an optionally substituted with one or more (preferably 1-3) substituent group(s).

Examples of the substituent group that can be named include
(1) halogen atom,
(2) nitro group,
(3) cyano group,
(4) $R^a$—CO—,
(5) $R^a$—CO—O—,
(6) $R^a$—CO—$NR^a$—,
(7) $R^a$—O—,
(8) $R^a$—O—CO—,
(9) $R^a$—O—CO—$NR^a$—,
(10) $R^a$—S—,
(11) $R^a$—SO—,
(12) $R^a$—SO_2—,
(13) $R^a$—$NR^a$—,
(14) $R^a$—S—$NR^a$—,
(15) $R^a$—SO—$NR^a$—,
(16) $R^a$—SO_2—$NR^a$—,
(17) $R^a$—$NR^a$—,
(18) $R^a$—$NR^a$—CO—,
(19) $R^a$—$NR^a$—CO—$NR^a$—,
(20) $R^a$—$NR^a$—S—,
(21) $R^a$—$NR^a$—SO—,
(22) $R^a$—$NR^a$—SO_2—,
(23) $R^a$—$NR^a$—S—$NR^a$—,
(24) $R^a$—$NR^a$—SO—$NR^a$—,
(25) $R^a$—$NR^a$—SO_2—$NR^a$—,

(26) optionally substituted cyclic group,
(27) $R^a$—O—CO—$C_2H_4$—CO—NH—, and
(28) $R^a$—$NR^a$—CS—$NR^a$-L-,
(wherein, each $R^a$ can be the same or different, and represents a hydrogen atom or a $C_{1-6}$ alkyl group optionally substituted with one or more (preferably 1-3) substituent group(s) selected from among halogen atom and phenyl group)

Examples of the "halogen atom" that can be named include the examples mentioned above.

Examples of the "$C_{1-6}$ alkyl group" that can be named include the examples mentioned above.

Examples of the "optionally substituted cyclic group" that can be named include the examples shown below, which are the same as the "optionally substituted cyclic group" represented by $R^1$.

Among the aforementioned substituent groups,
(a) halogen atom,
(b) $R^a$—O—,
(c) $R^a$—O—CO—,
(d) $R^a$—O—CO—$NR^a$—,
(e) $R^a$—O—CO—$C_2H_4$—CO—NH—
(f) $R^a$—S—,
(g) $R^a$—$SO_2$—,
(h) $R^a$—CO—O—,
(i) $R^a$—CO—$NR^a$—,
(j) $R^a$—$NR^a$—,
(k) $R^a$—$NR^a$—CS—$NR^a$—,
(l) 5- to 6-membered ring group,
(m) carboxyl group,
(n) hydroxyl group,
(o) amino group,
(p) heterocyclic-carbonyl group,
(q) HO—CO—$C_2H_4$—CO—NH—
(wherein, each $R^a$ can be the same or different, and represents an optionally halogen-substituted $C_{1-6}$ alkyl group)
are preferred, and
(a) halogen atom,
(b) $R^a$—O—,
(c) $R^a$—O—CO—,
(d) $R^a$—O—CO—$NR^a$—,
(e) $R^a$—O—CO—$C_2H_4$—CO—NH—
(f) $R^a$—CO—O—,
(g) $R^a$—CO—$NR^a$—,
(h) $R^a$—$NR^a$—,
(i) $R^a$—$NR^a$—CS—$NR^a$—,
j) 5- to 6-membered ring group,
(wherein, each $R^a$ can be the same or different, and represents a $C_{1-6}$ alkyl group optionally substituted with one or more halogen(s))
are more preferred.

In addition, the "acyclic hydrocarbon group" that is the "optionally substituted acyclic hydrocarbon group" represented by $R^1$ can also be unsubstituted, which is preferred.

Examples of the "cyclic group" that is the "optionally substituted cyclic group" represented by $R^1$ that can be named include a carbocyclic group such as an aryl group (aromatic carbocyclic group) and an non-aromatic cyclic hydrocarbon group (alicyclic hydrocarbon group) and the like; a heterocycle such as heteroaryl group (aromatic heterocyclic group) and a non-aromatic heterocyclic groups and the like; along with a condensed cyclic group comprised of the foregoing.

Examples of the "aryl group" that can be named include the examples mentioned above.

Examples of the "heteroaryl group" that can be named include the examples mentioned above.

Examples of the "non-aromatic cyclic hydrocarbon group" that can be named include a cycloalkyl group, cycloalkenyl group, and cycloalkadienyl group.

Examples of the "cycloalkyl group", "cycloalkenyl group", and "cycloalkadienyl group" that can be named include the corresponding examples mentioned above.

Examples of the "non-aromatic heterocyclic group" that can be named include the examples mentioned above. Preferred examples of the aforementioned cyclic group are a $C_{3-10}$ alicyclic hydrocarbon group such as a $C_{3-10}$ cycloalkyl, $C_{3-10}$ cycloalkenyl, $C_{4-10}$ cycloalkadienyl, or a 5- to 6-membered ring non-aromatic heterocyclic group.

The "cyclic group" that is the "optionally substituted cyclic group" represented by $R^1$ is optionally substituted with one or more (preferably 1-3) substituent groups.

Examples of the substituent group that can be named include
(1) halogen atom,
(2) nitro group,
(3) cyano group,
(4) $C_{1-6}$ alkyl group optionally substituted with one or more (preferably 1-3) halogen atom(s),
(5) $C_{2-6}$ alkenyl group optionally substituted with one or more (preferably 1-3) halogen atom(s),
(6) $C_{2-6}$ alkynyl group optionally substituted with one or more (preferably 1-3) halogen atom(s),
(7) $R^a$—CO-L-,
(8) $R^a$—CO—O-L-,
(9) $R^a$—CO—$NR^a$-L-,
(10) $R^a$—O-L-,
(11) $R^a$—O—CO-L-,
(12) $R^a$—O—CO—$NR^a$-L-,
(13) $R^a$—S-L-,
(14) $R^a$—SO-L-,
(15) $R^a$—$SO_2$-L-,
(16) $R^a$—$NR^a$-L-,
(17) $R^a$—S—$NR^a$-L-,
(18) $R^a$—SO—$NR^a$-L-,
(19) $R^a$—$SO_2$—$NR^a$-L-,
(20) $R^a$—$NR^a$-L-,
(21) $R^a$—$NR^a$—CO-L-,
(22) $R^a$—$NR^a$—CO—$NR^a$-L-,
(23) $R^a$—$NR^a$—S-L-,
(24) $R^a$—$NR^a$—SO-L-,
(25) $R^a$—$NR^a$—$SO_2$-L-,
(26) $R^a$—$NR^a$—S—$NR^a$-L-,
(27) $R^a$—$NR^a$—SO—$NR^a$-L-,
(28) $R^a$—$NR^a$—$SO_2$—$NR^a$-L-,
(29) $R^a$—O—CO—$C_2H_4$—CO—NH—, and
(30) $R^a$—$NR^a$—CS—$NR^a$-L-,
(wherein, each $R^a$ can be the same or different, and represents a hydrogen atom or a $C_{1-6}$ alkyl group optionally substituted with one or more (preferably 1-3) halogen atom(s), and L represents a bond or alkylene chain).

Examples of the "halogen atom", "$C_{1-6}$ alkyl group", "$C_{2-6}$ alkenyl group", "$C_{2-6}$ alkynyl group", and "alkylene chain" that can be named include the respective examples mentioned above.

Among the substituent groups for the aforementioned non-aromatic cyclic hydrocarbon groups (in particular, $C_{3-10}$ alicyclic hydrocarbon groups) and the aforementioned non-aromatic heterocyclic groups (in particular, 5- to 6-membered non-aromatic heterocyclic groups),
(a) oxo group,
(b) $C_{1-4}$ alkoxycarbonyl group, and
(c) hydroxyl group,
are preferred, and (a) oxo group, and
(b) $C_{1-4}$ alkoxycarbonyl group are more preferred.

In addition, among the substituent groups for the aforementioned aryl group (in particular, the phenyl group),
(a) halogen atom,
(b) $R^c$—O—,
(c) $R^c$—O—CO—,
(d) $R^c$—CO—$NR^c$—, (wherein, each $R^c$ can be the same or different, and represents a hydrogen atom or $C_{1-6}$ alkyl group) are preferred.

Examples of preferred $R^1$ include
(1) hydrogen atom,
(2) $C_{1-6}$ alkyl group,
(3) $C_{1-6}$ alkyl group optionally substituted with one or more substituent group(s) selected from those comprising:
(a) halogen atom,
(b) $R^a$—O—,
(c) $R^a$—O—CO—,
(d) $R^a$—O—CO—$NR^a$—,
(e) $R^a$—O—CO—$C_2H_4$—CO—NH—
(f) $R^a$—S—,
(g) $R^a$—$SO_2$—,
(h) $R^a$—CO—O—,
(i) $R^a$—CO—$NR^a$—,
(j) $R^a$—$NR^a$—,
(k) $R^a$—$NR^a$—CS—$NR^a$—,
(l) 5- to 6-membered ring group,
(m) carboxyl group,
(n) hydroxyl group,
(o) amino group,
(p) heterocyclic carbonyl,
(q) HO—CO—$C_2H_4$—CO—NH—

(wherein, each $R^a$ can be the same or different, and represents a $C_{1-6}$ alkyl group optionally substituted with halogen(s)),
(4) $C_{3-10}$ non-aromatic cyclic hydrocarbon group or 5- to 6-membered non-aromatic heterocyclic group respectively optionally substituted with one or more substituent group(s) selected from those comprising:
(a) oxo group,
(b) $C_{1-4}$ alkoxycarbonyl group, and
(c) hydroxyl group, or, (5) an aromatic cyclic hydrocarbon group optionally substituted with one or more substituent selected from those comprising halogen atom and $C_{1-4}$ alkoxy group, and more preferred examples are:
(1) $C_{3-6}$ alkyl group,
(2) $C_{1-6}$ alkyl group substituted with one or more substituent group(s) selected from those comprising:
(a) halogen atom,
(b) $R^a$—O—,
(c) $R^a$—O—CO—,
(d) $R^a$—O—CO—$NR^a$—,
(e) $R^a$—O—CO—$C_2H_4$—CO—NH—
(f) $R^a$—CO—O—,
(g) $R^a$—CO—$NR^a$—,
(h) $R^a$—$NR^a$—,
(i) $R^a$—$NR^a$—CS—$NR^a$—, and
(j) $C_{5-6}$ carbocyclic group (wherein, each $R^a$ can be the same or different, and represents a $C_{1-6}$ alkyl group optionally substituted with one or more halogen(s)),
(3) $C_{3-10}$ non-aromatic cyclic hydrocarbon group or 5- to 6-membered non-aromatic heterocyclic group which respectively can be optionally substituted with one or more substituent group(s) selected from those comprising:

(a) an oxo group, and
(b) $C_{1-4}$ alkoxycarbonyl group, or (4) an aromatic cyclic hydrocarbon group optionally substituted with one or more group selected from those comprising halogen atom and $C_{1-4}$ alkoxy group, and still further preferred examples are 5- to 6-membered non-aromatic heterocyclic groups.

Moreover, in another embodiment of the present invention, preferred examples of $R^1$ include:

a) $C_{1-6}$ acyclic hydrocarbon group optionally substituted with 6-membered ring group(s), or
b) 3- to 10-membered ring group optionally substituted with one or more substituent group(s) selected from those comprising:
(1) halogen atom,
(2) $C_{1-6}$ alkyl group optionally substituted with one or more (preferably 1-3) halogen atom(s),
(3) $C_{1-6}$ alkoxycarbonyl group optionally substituted with one or more (preferably 1-3) halogen atom(s), and more preferred examples are:

a) a $C_{1-6}$ acyclic hydrocarbon group optionally substituted with 6-membered ring group(s), or
b) 6- to 10-membered ring group optionally substituted with one or more (preferably 1-3) substituent group(s) selected from among a halogen atom, $C_{1-4}$ alkoxyl group, and $C_{1-4}$ alkoxycarbonyl groups, and still further preferred examples are:

a) $C_{1-4}$ alkyl groups optionally substituted with 6-membered ring group(s), or
b) 6-membered ring group optionally substituted with one or more (preferably 1-3) $C_{1-4}$ alkoxy group(s).

X represents N—$R^3$ (where $R^3$ represents a hydrogen atom or substituent group), O, or S.

$R^3$ represents a substituent group, for example,
(1) $C_{1-6}$ alkyl group optionally substituted with one or more (preferably 1-3) halogen atom(s),
(2) $C_{2-6}$ alkenyl group optionally substituted with one or more (preferably 1-3) halogen atom(s),
(3) $C_{2-6}$ alkynyl group optionally substituted with one or more (preferably 1-3) halogen atom(s),
(4) $R^a$—CO-L-,
(5) $R^a$—CO—O-L-,
(6) $R^a$—CO—$NR^a$-L-,
(7) $R^a$—O-L-,
(8) $R^a$—O—CO-L-,
(9) $R^a$—O—CO—$NR^a$-L-,
(10) $R^a$—S-L-,
(11) $R^a$—SO-L-,
(12) $R^a$—$SO_2$-L-,
(13) $R^a$—$NR^a$-L-,
(14) $R^a$—S—$NR^a$-L-,
(15) $R^a$—SO—$NR^a$-L-,
(16) $R^a$—$SO_2$—$NR^a$-L-,
(17) $R^a$—$NR^a$-L-,
(18) $R^a$—$NR^a$—CO-L-,
(19) $R^a$—$NR^a$—CO—$NR^a$-L-,
(20) $R^a$—$NR^a$—S-L-,
(21) $R^a$—$NR^a$—SO-L-,
(22) $R^a$—$NR^a$—$SO_2$-L-,
(23) $R^a$—$NR^a$—S—$NR^a$-L-,
(24) $R^a$—$NR^a$—SO—$NR^a$-L-, and
(25) $R^a$—$NR^a$—$SO_2$—$NR^a$-L-

(wherein, each $R^a$ can be the same or different, and represents a hydrogen atom or a $C_{1-6}$ alkyl group optionally substituted with one or more (preferably 1-3) halogen atom(s), and L represents a bond or alkylene chain).

Examples of the "halogen atom", "$C_{1-6}$ alkyl group", "$C_{2-6}$ alkenyl group", "$C_{2-6}$ alkynyl group", and "alkylene chain" that can be named include the respective examples mentioned above.

More preferred examples are where X is N—$R^3$ ($R^3$ is hydrogen atom, or $R^a$—O—CO— ($R^a$ is a $C_{1-6}$ alkyl group)), O, or S.

Still further preferred examples of X are NH, O, or S.

Y represents C—$R^4$ (where $R^4$ represents a hydrogen atom or substituent group), or N.

$R^4$ represents a substituent group, for example, (1) $C_{1-6}$ alkyl group optionally substituted with one or more (preferably 1-3) halogen atom(s),
(2) $C_{2-6}$ alkenyl group optionally substituted with one or more (preferably 1-3) halogen atom(s),
(3) $C_{2-6}$ alkynyl group optionally substituted with one or more (preferably 1-3) halogen atom(s),
(4) $R^a$—CO-L-,
(5) $R^a$—CO—O-L-,
(6) $R^a$—CO—$NR^a$-L-,
(7) $R^a$—O-L-,
(8) $R^a$—O—CO-L-,
(9) $R^a$—O—CO—$NR^a$-L-,
(10) $R^a$—S-L-,
(11) $R^a$—SO-L-,
(12) $R^a$—$SO_2$-L-,
(13) $R^a$—$NR^a$-L-,
(14) $R^a$—S—$NR^a$-L-,
(15) $R^a$—SO—$NR^a$-L-,
(16) $R^a$—$SO_2$—$NR^a$-L-,
(17) $R^a$—$NR^a$-L-,
(18) $R^a$—$NR^a$—CO-L-,
(19) $R^a$—$NR^a$—CO—$NR^a$-L-,
(20) $R^a$—$NR^a$—S-L-,
(21) $R^a$—$NR^a$—SO-L-,
(22) $R^a$—$NR^a$—$SO_2$-L-,
(23) $R^a$—$NR^a$—S—$NR^a$-L-,
(24) $R^a$—$NR^a$—SO—$NR^a$-L-, and
(25) $R^a$—$NR^a$—$SO_2$—$NR^a$-L-

(wherein, each $R^a$ can be the same or different, and represents a hydrogen atom or a $C_{1-6}$ alkyl group optionally substituted with one or more (preferably 1-3) halogen atom(s), and L represents a bond or alkylene chain).

Examples of the "halogen atom", "$C_{1-6}$ alkyl group", "$C_{2-6}$ alkenyl group", "$C_{2-6}$ alkynyl group", and "alkylene chain" that can be named include the respective examples mentioned above.

More preferred examples are where Y is CH or N.

Still further preferred examples are where Y is N.

Z represents N or C—$R^2$.

$R^2$ represents a hydrogen atom, optionally substituted acyclic hydrocarbon group, or optionally substituted cyclic group.

In the compound of the present invention, Z is preferably C—$R^2$.

Examples of what is represented by $R^1$ in those "acyclic hydrocarbon group" that is "optionally substituted acyclic hydrocarbon group" that can be named include alkyl group, alkenyl group, and alkynyl group.

Examples of the "alkyl group" are the examples mentioned above.

Examples of the "alkenyl group" are the examples mentioned above.

Examples of the "alkynyl group" that can be named include the examples mentioned above.

The "acyclic hydrocarbon group" that is the "optionally substituted acyclic hydrocarbon group" represented by $R^2$ is optionally substituted with one or more (preferably 1-3) substituent group.

Examples of the substituent groups that can be named include (1) halogen atom,
(2) nitro group,
(3) cyano group,
(4) $R^b$—CO—,
(5) $R^b$—CO—O—,
(6) $R^b$—CO—$NR^b$—,
(7) $R^b$—O—,
(8) $R^b$—O—CO—,
(9) $R^b$—O—CO—$NR^b$—,
(10) $R^b$—S—,
(11) $R^b$—SO—,
(12) $R^b$—$SO_2$—,
(13) $R^b$—$NR^b$—,
(14) $R^b$—S—$NR^b$—,
(15) $R^b$—SO—$NR^b$—,
(16) $R^b$—$SO_2$—$NR^b$—,
(17) $R^b$—$NR^b$—,
(18) $R^b$—$NR^b$—CO—,
(19) $R^b$—$NR^b$—CO—$NR^b$—,
(20) $R^b$—$NR^b$—S—,
(21) $R^b$—$NR^b$—SO—,
(22) $R^b$—$NR^b$—$SO_2$—,
(23) $R^b$—$NR^b$—S—$NR^b$—,
(24) $R^b$—$NR^b$—SO—$NR^b$—, and
(25) $R^b$—$NR^b$—$SO_2$—$NR^b$—, (wherein, each $R^b$ can be the same or different, and represents a hydrogen atom or a $C_{1-6}$ alkyl group optionally substituted with one or more (preferably 1-3) substituent group(s) selected from among halogen atom, and phenyl group)

Examples of the "halogen atom" that can be named include the examples mentioned above.

Examples of the "$C_{1-6}$ alkyl group" that can be named include the examples mentioned above.

Among the aforementioned substituent groups, for example (a) halogen atom,
(b) $R^b$—O—,
(c) $R^b$—O—CO—,
(d) $R^b$—O—CO—$NR^b$—,
(e) $R^b$—CO—O—,
(f) $R^b$—CO—$NR^b$—,
(g) $R^b$—$NR^b$—,
(h) $R^b$—CO—$NR^b$—$R^b$—$S(O)_n$—,
(i) phenyl group,
(j) 5- to 6-membered saturated heterocyclic group, and
(k) hydroxy group,
(l) amino group, (wherein, each $R^b$ can be the same or different, and represents a hydrogen atom or a $C_{1-6}$ alkyl group optionally substituted with one or more halogen(s), and n represents an integer from 0 to 2) are preferred, and (a) halogen atom,
(b) $R^b$—O—,
(c) $R^b$—O—CO—,
(d) $R^b$—O—CO—$NR^b$—, and
(e) $R^b$—CO—$NR^b$—,
(f) $R^b$—CO—$NR^b$—$R^b$—$S(O)_n$, (wherein, each $R^b$ can be the same or different, and represents a hydrogen atom or a $C_{1-6}$ alkyl group optionally substituted with one or more halogen(s), and n represents an integer from 0 to 2)
are more preferred.

The "optionally substituted cyclic group" represented by $R^2$ that can be named is the same as the "optionally substituted cyclic group" represented by $R^1$.

Preferred examples of $R^1$ include:
(1) hydrogen atom,
(2) a $C_{1-6}$ alkyl group, $C_{2-6}$ alkenyl group or $C_{2-6}$ alkynyl group optionally substituted respectively with one or more substituent group(s) selected from the group comprising:
   (a) halogen atom,
   (b) $R^b$—O—,
   (c) $R^b$—O—CO—,
   (d) $R^b$—O—CO—$NR^b$—,
   (e) $R^b$—S—,
   (f) $R^b$—$SO_2$—,
   (g) $R^b$—CO—O—,
   (h) $R^b$—CO—$NR^b$—,
   (i) $R^b$—$NR^b$—,
   (j) $R^b$—CO—$NR^b$—$R^b$—$S(O)_n$,
   (k) phenyl group,
   (l) 5- to 6-membered saturated heterocyclic group,
   (m) hydroxyl group, and
   (n) amino group (where in the formula, each $R^b$ can be the same or different, and represents a hydrogen atom or a $C_{1-6}$ alkyl group optionally substituted with one or more halogen(s), and n represents an integer from 0 to 2)
or,
(3) $C_{5-6}$ non-aromatic cyclic hydrocarbon group or a 5- to 6-membered non-aromatic heterocyclic group optionally substituted with one or more substituent group(s) selected from the group comprising:
   (a) halogen atom,
   (b) $R^c$—O—,
   (c) $R^c$—O—CO—, and
   (d) $R^c$—CO—$NR^c$—,
(wherein, each $R^c$ can be the same or different, and represents a hydrogen atom or a $C_{1-6}$ alkyl group)
(4) a phenyl group optionally substituted with one or more substituent group(s) selected from those comprising:
   (a) halogen atom,
   (b) $R^c$—O—,
   (c) $R^c$—O—CO—, and
   (d) $R^c$—CO—$NR^c$—,
(wherein, each $R^c$ can be the same or different, and represents a hydrogen atom or $C_{1-6}$ alkyl group)
and preferably,
(1) hydrogen atom,
(2) substituted $C_{1-6}$ alkyl group optionally substituted with one or more substituent group(s) selected from those comprising:
   (a) halogen atom,
   (b) $R^b$—O—,
   (c) $R^b$—O—CO—,
   (d) $R^b$—O—CO—$NR^b$—, and
   (e) $R^b$—CO—$NR^b$—,
   (f) $R^b$—CO—$NR^b$—$R^b$—$S(O)_n$,
(wherein, each $R^b$ can be the same or different, and represents a hydrogen atom or $C_{1-6}$ alkyl group optionally substituted with one or more halogen(s), and n represents an integer from 0 to 2),
or,
(3) $C_{5-6}$ non-aromatic cyclic hydrocarbon group or 5- to 6-membered non-aromatic heterocyclic group optionally substituted with one or more substituent group(s) selected from those comprising:
   (a) halogen atom,
   (b) $R^c$—O—,
   (c) $R^c$—O—CO—, and
   (d) $R^c$—CO—$NR^c$—,
(wherein, each $R^c$ can be the same or different, and represents a hydrogen atom or $C_{1-6}$ alkyl group)

Moreover, in another embodiment of the present invention, Z is preferably N, or C—$R^2$
$R^2$ is,
a) hydrogen atom,
b) $C_{1-6}$ alkyl group optionally substituted with one or more (preferably 1-3) substituent group(s) selected from among:
   (1) halogen atom,
   (2) $R^b$—O—,
   (3) $R^b$—O—CO—,
   (4) $R^b$—O—CO—$NR^b$—,
   (5) $R^b$—CO—,
   (6) $R^b$—CO—O—, and
   (7) $R^b$—$NR^b$—,
(wherein, each $R^b$ can be the same or different, and represents a hydrogen atom, or a $C_{1-6}$ alkyl group optionally substituted with one or more (preferably 1-3) substituent group(s) selected from among halogen atom, and phenyl group),
or,
c) 5- to 6-membered ring group optionally substituted with one or more (preferably 1) substituent group(s) selected from those comprising:
   (1) halogen atom,
   (2) $R^a$—O— (where in the formula, $R^a$ represents a $C_{1-6}$ alkyl group),
   (3) $R^a$—S-L- (where in the formula, $R^a$ represents a hydrogen atom or $C_{1-3}$ alkyl group, and L is a bond or a Cl_2 alkylene chain),
and preferably is, for example, N, or C—$R^2$
($R^2$ is:
a) hydrogen atom,
b) $C_{1-6}$ alkyl group optionally substituted with one or more (preferably 1-3) substituent group(s) selected from among:
   (1) halogen atom,
   (2) $R^b$—O—,
   (3) $R^b$—CO—,
   (4) $R^b$—CO—O—, and
   (5) $R^b$—$NR^b$—,
(wherein, each $R^b$ can be the same or different, and represents a hydrogen atom or $C_{1-6}$ alkyl group optionally substituted with one phenyl group),
or,
c) 5- to 6-membered ring group)

Ring A represents an optionally substituted benzene ring.
The "benzene ring" that is the "optionally substituted benzene ring" represented by ring A is optionally substituted with one or more (preferably 1-3) substituent group(s).

Examples of the substituent group that can be named are the same as the exemplified substituent groups for the "optionally substituted cyclic group" represented by $R^1$.

Among these, for example,
   (a) halogen atom,
   (b) hydroxyl group,
   (c) carboxyl group,
   (d) cyano group, (e) sulfamoyl group,
(f) monoalkylamide group,
(g) dialkylamide group,
(h) optional halogen atom substitutions,
(i) nitro group,
(j) aryloxy group
are preferred.

Ring A is, for example, preferably an unsubstituted benzene ring (specifically, excepting where

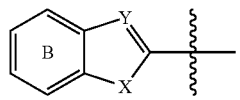

has no substituent).

Ring B represents an optionally substituted benzene ring.

The "benzene ring" that is the "optionally substituted benzene ring" represented by ring B is optionally substituted with one or more (preferably 1-3) substituent group(s).

Examples of the substituent groups that can be named are the same as the exemplified substituent groups for the "optionally substituted cyclic group" represented by $R^1$.

Among these, for example,
(a) halogen atom,
(b) hydroxyl group,
(c) carboxyl group,
(d) cyano group,
(e) sulfamoyl group,
(f) monoalkylamide group,
(g) dialkylamide group,
(h) amide group,
(i) alkoxycarbonyl group,
(j) alkyl group optionally substituted with halogen atoms,
(k) nitro group,
(l) aryloxy group
are preferred.

Ring B is preferably an unsubstituted benzene ring.

In another embodiment of the present invention, preferred examples of ring B include benzene ring group optionally substituted with one or more (preferably 1-3) substituent group(s) selected from those comprising:
(1) halogen atom,
(2) nitro group,
(3) $C_{1-6}$ alkyl group optionally substituted with one or more (preferably 1-3) halogen atom(s),
(4) $R^a$—O—CO-L-,
(5) $R^a$—$SO_2$—$NR^a$-L-, and
(6) $R^a$—$NR^a$-L-
(wherein, each $R^a$ can be the same or different, and is a hydrogen atom or a $C_{1-6}$ alkyl group optionally substituted with one or more (preferably 1-3) halogen atom(s), and L is a bond).

Preferred examples of ring B include benzene ring group optionally substituted with one or more (preferably 1-3) substituent group(s) selected from those comprising:
(1) halogen atom (preferably chlorine atom),
(2) nitro group,
(3) $C_{1-6}$ alkyl group (preferably methyl), and
(4) amino group.

Furthermore, from among the compound (I), preferably a compound depicted in the formula:

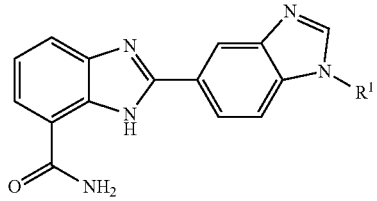

wherein, $R^1$ represents an optionally substituted alkyl group,
or a pharmaceutically acceptable salt or solvate thereof is excluded.

As the compound (I), two or more selected from the examples of the aforementioned preferred partial structures, the more preferred partial structures, and the still further preferred partial structures used in combination is more preferred.

The compound (I) is preferably, for example, a compound A below. Furthermore, the compound A is novel compound.
(Compound A)

The compound depicted in the formula:

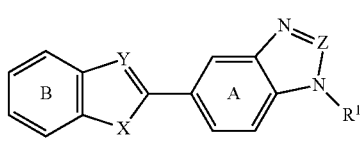

(I)

wherein, $R^1$ is
(1) $C_{3-6}$ alkyl group,
(2) $C_{1-6}$ alkyl group substituted with one or more substituent group(s) selected from those comprising:
(a) halogen atom,
(b) $R^a$—O—,
(c) $R^a$—O—CO—,
(d) $R^a$—O—CO—$NR^a$—,
(e) $R^a$—O—CO—$C_2H_4$—CO—NH—,
(f) $R^a$—S—,
(g) $R^a$—$SO_2$—,
(h) $R^a$—CO—O—,
(i) $R^a$—CO—$NR^a$—,
(j) $R^a$—$NR^a$—,
(k) $R^a$—$NR^a$—CS—$NR^a$—,
(l) 5- to 6-membered ring group,
(m) carboxyl group,
(n) hydroxyl group,
(o) amino group,
(p) heterocyclic carbonyl group,
(q) HO—CO—$C_2H_4$—CO—NH—
(wherein, each $R^a$ can be the same or different, and represents an optionally halogen-substituted $C_{1-6}$ alkyl group),
(3) respectively an $C_{3-10}$ non-aromatic cyclic hydrocarbon group or $C_{5-6}$ non-aromatic heterocyclic group optionally substituted with one or more substituent group(s) selected from those comprising:

(a) an oxo group, and
(b) $C_{1-4}$ alkoxycarbonyl group,
or,
(4) aromatic cyclic hydrocarbon group substituted with one or more substituent group(s) selected from those comprising halogen atom and $C_{1-4}$ alkoxyl group,
X represents NH, O, or S,
Y represents CH or N,
Z represents N or C—$R^2$,
$R^2$ represents
(1) hydrogen atom,
(2) $C_{1-6}$ alkyl group, $C_{2-6}$ alkenyl group or $C_{2-6}$ alkynyl group optionally substituted respectively with one or more substituent group(s) selected from those comprising:
    (a) halogen atom,
    (b) $R^b$—O—,
    (c) $R^b$—O—CO—,
    (d) $R^b$—O—CO—$NR^b$—,
    (e) $R^b$—S—,
    (f) $R^b$—$SO_2$—,
    (g) $R^b$—CO—O—,
    (h) $R^b$—CO—$NR^b$—,
    (i) $R^b$—$NR^b$—,
    (j) $R^b$—CO—$NR^b$—$R^b$—$S(O)_n$,
    (k) phenyl group,
    (l) 5- to 6-membered saturated heterocyclic group,
    (m) hydroxyl group, and
    (n) amino group,
(wherein, each $R^b$ can be the same or different, and represents a hydrogen atom or a $C_{1-6}$ alkyl group optionally substituted with one or more halogen(s), and n represents an integer from 0 to 2),
or,
(3) $C_{5-6}$ non-aromatic cyclic hydrocarbon group or a 5- to 6-membered non-aromatic heterocyclic group optionally substituted with one or more substituent group(s) selected from those comprising:
    (a) halogen atom,
    (b) $R^c$—O—,
    (c) $R^c$—O—CO—, and
    (d) $R^c$—CO—NRS—,
(wherein, each $R^c$ can be the same or different, and represents a hydrogen atom or a $C_{1-6}$ alkyl group),
ring A represents a benzene ring optionally substituted with one or more substituent group(s) selected from those comprising:
    (a) halogen atom,
    (b) hydroxyl group,
    (c) carboxyl group,
    (d) cyano group,
    (e) sulfamoyl group,
    (f) monoalkylamide group,
    (g) dialkylamide group,
    (h) alkyl group optionally substituted with a halogen atom,
    (i) nitro group, and
    (j) aryloxy group,
ring B represents a benzene ring optionally substituted with one or more substituent group(s) selected from those comprising:
    (a) halogen atom,
    (b) hydroxyl group,
    (c) carboxyl group,
    (d) cyano group,
    (e) sulfamoyl group,
    (f) monoalkylamide group,
    (g) dialkylamide group,
    (h) amide group,
    (i) alkoxycarbonyl group,
    (j) alkyl group optionally substituted with a halogen atom,
    (k) nitro group, and
    (l) aryloxy group,
pharmaceutically acceptable salt or solvate thereof.

In the compound A, preferably,
Z is C—$R^2$, and
Y is N.
In the compound A, preferably,
$R^1$ is a 5- to 6-membered non-aromatic heterocyclic group.
In the compound A, preferably,
$R^2$ is $C_{1-6}$ alkyl group.
In the compound A, preferably,
Z is C—$R^2$,
Y is N,
$R^1$ is a 5- to 6-membered non-aromatic heterocyclic group, and
$R^2$ is $C_{1-6}$ alkyl group.

Moreover, as the compound (I'), preferably,
$R^1$ is
a) $C_{1-6}$ acyclic hydrocarbon groups optionally substituted with 6-membered ring group(s), or,
b) 6- to 10-membered ring group optionally substituted with one or more substituent group(s) selected from among a halogen atom, one or more $C_{1-4}$ alkoxyl group(s), and $C_{1-4}$ alkoxycarbonyl group(s),
X is N—$R^3$ ($R^3$ is hydrogen atom, or $R^a$—O—CO— ($R^a$ is a $C_{1-6}$ alkyl group)), O, or S,
Y is CH or N,
Z is N or C—$R^2$,
(wherein, $R^2$ is
a) hydrogen atom,
b) $C_{1-6}$ alkyl group optionally substituted with one or more (preferably 1-3) substituent group(s) selected from among:
    (1) halogen atom,
    (2) $R^b$—O—,
    (3) $R^b$—CO—,
    (4) $R^b$—CO—O—, and
    (5) $R^b$—$NR^b$—,
(wherein, each $R^b$ can be the same or different, and represents a hydrogen atom or a $C_{1-6}$ alkyl group optionally substituted with one phenyl group),
or,
c) 5- to 6-membered ring group,
ring A is (unsubstituted) benzene ring, and
ring B is a benzene ring optionally substituted with one or more (preferably 1-3) substituent group(s) selected from among a halogen atom, $C_{1-6}$ alkyl group, nitro group, and amino group.

The compound (I) can be pharmaceutically acceptable salt. Examples of such salts that can be named include a metal salt, ammonium salt, salt with an organic base, salt with an inorganic base, salt with an organic acid, salt of a basic or acidic amino acid, or the like. Suitable examples of the metal salt that can be named include alkali metal salts such as sodium salts, potassium salts, and the like; alkaline earth metal salts such as calcium salts, magnesium salts, barium salts, and the like; aluminum salts, and the like. Suitable examples of salts with the organic base that can be named include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, and the like. Suitable examples of salts with the inorganic acid that can be named include salts with hydrochloric acid, hydrobromic acid, nitric acid, sulfuric acid, phosphoric acid, and the like. Suitable examples of salts with the organic acid that can be named include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, and the like. Suitable examples of salts with the basic amino acid that can be named include salts with arginine, lysine, ornithine, and the like, and suitable examples of salts with acidic amino acid that can be named include salts with aspartic acid, glutamic acid, and the like. Among these, the pharmaceutically acceptable salt is preferred. When there are an acidic functional group in the compound, examples thereof include inorganic salts such as alkali metal salts (for example, lithium salts, sodium salts, potassium salts, and the like), alkaline earth metal salts (for example, magnesium salts, calcium salts, barium salts, and the like), ammonium salts and the like, or when there are a basic functional group in the compound, examples thereof include salts with the inorganic acid such as hydrochloric acid, hydrobromic acid, nitric acid, sulfuric acid, phosphoric acid, and the like, or salts with the organic acid such as acetic acid, phthalic acid, fumaric acid, oxalic acid, tartaric acid, maleic acid, citric acid, succinic acid, methanesulfonic acid, p-toluenesulfonic acid, and the like.

When tautomers of the compound (I) are possible, the stable configuration is taken as the preferred one, although the present invention is not limited to these and other isomers are not excluded from being within the scope of the present invention.

Moreover, when isomers such as optical isomers, stereoisomers, positional isomers, rotational isomers, and the like are possible for the compound (I), all of these isomers and mixtures of these isomers are within the scope of the present invention. They are comprised by the compounds of present invention. Furthermore, when optical isomers of the compound (I) can exist, optical isomers separated from a racemic mixture are also within the scope of the present invention.

The compound (I) is also within the scope of the present invention whether are crystalline or amorphous.

The compound (I) that is labeled or substituted with an isotope ($^{2}H$, $^{3}H$, $^{14}C$, $^{35}S$, $^{125}I$, and the like) is also within the scope of the present invention.

The compound (I) can also be a solvate (for example, hydrates) or non-solvate.

The manufacturing methods for the compound (I) are described below.

Unless specifically stated to the contrary, the symbols used for the compounds in reaction equations have the same meaning as described above. Furthermore, the compounds in the equations include the case when salts are formed, so that examples of such salts are likewise named, for example, as a salt of the compound (I). In addition, the compounds obtained in each of the processes, either as reaction solutions as is or as crude materials, can be used in the succeeding reaction, but they can be isolated from the reaction mixture according to conventional methods using means that are well-known in their own right, for example, they can be easily purified using separation means such as extraction, concentration, neutralization, filtration, distillation, recrystallization, distillation, chromatography, and the like. In addition, when the compound in the equations can be obtained commercially, the commercial products can be used as is.

Unless specifically stated to the contrary, room temperature in this specification is approximately 10° C. to approximately 35° C.

The compound (I), for example, can be manufactured using the methods depicted in the following schemes, or by methods that conform thereto.

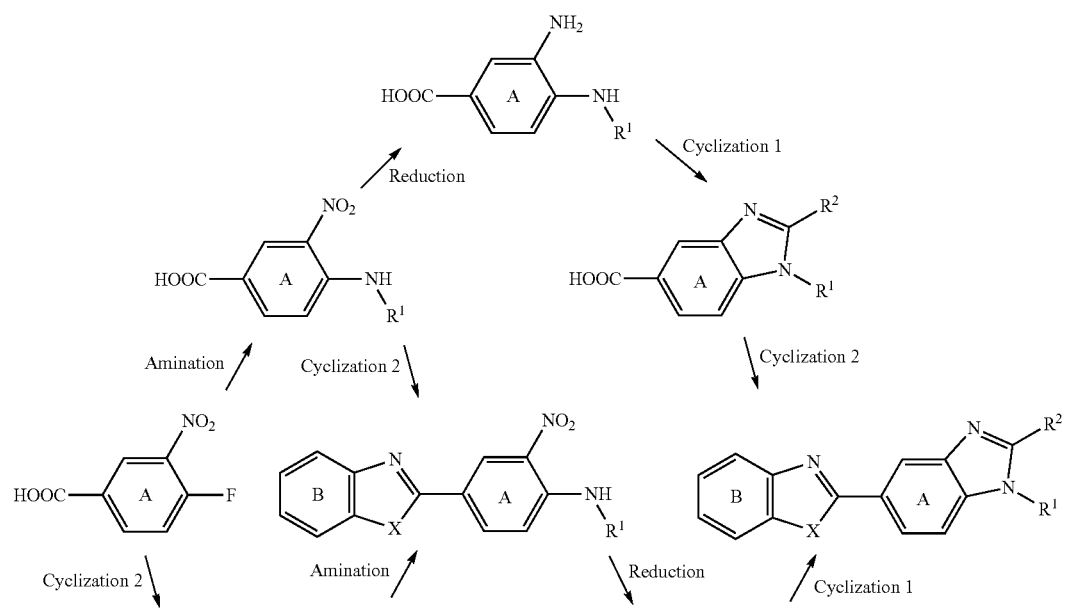

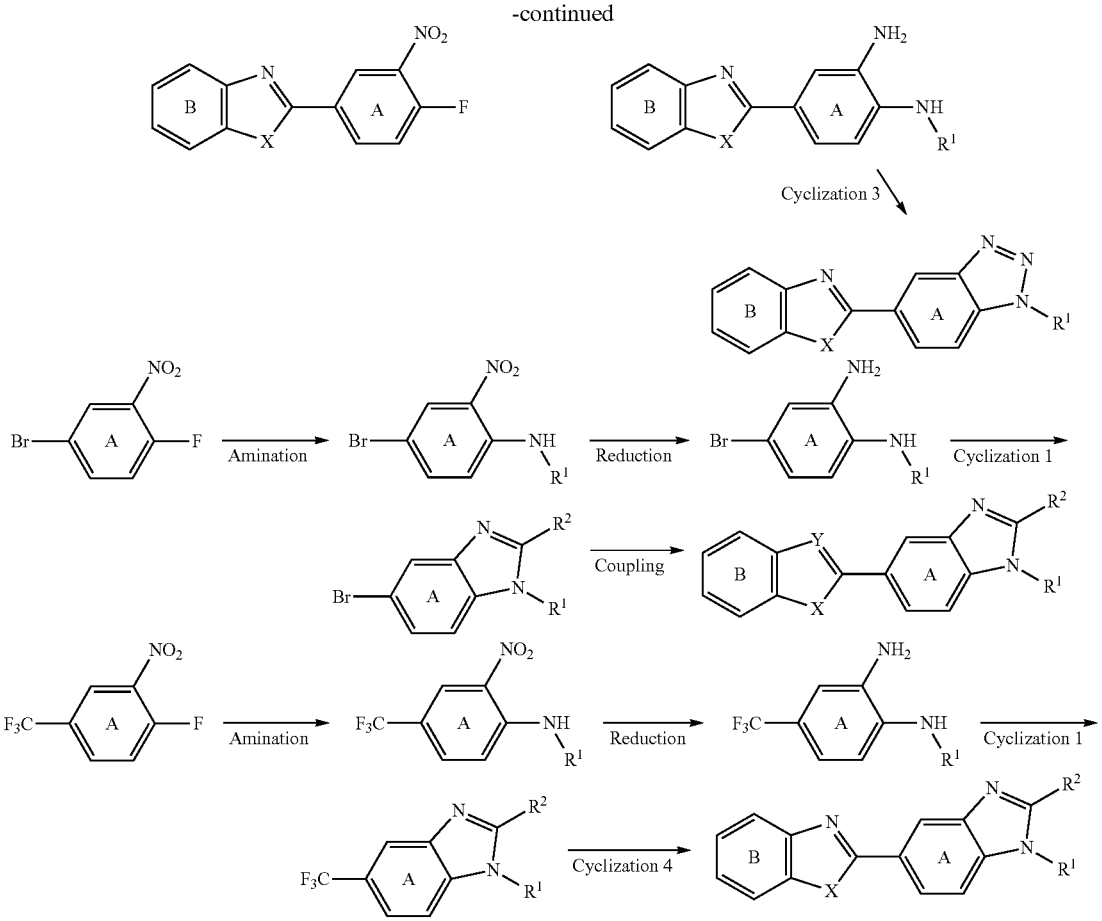

The reactions of the processes in the scheme shown above are described in detail below. The compound represented by Formula (I) of the present invention or salt thereof can be manufactured through combinations of such reactions.

[Amination]

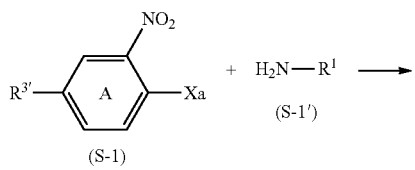

The compound (S-1) as represented by the generic formula

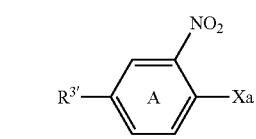

(where R[3'] represents:
carboxyl group,
halogen atom, trihalomethyl group, or a group represented as the generic formula:

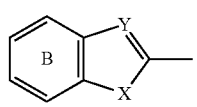

Xa represents a leaving group,
X, Y, ring A, and ring B are as given above),
and a compound (S-1') as represented by generic formula

(where R[1] is as given above)
and its salt are caused to react to manufacture the compound (S-2) as represented by the generic formula

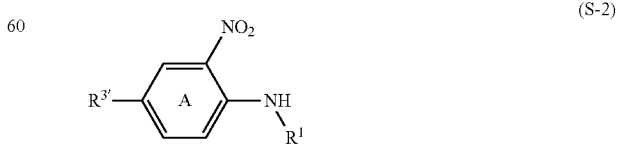

(where R[1], R[3'], and ring A are as given above).

Examples of the leaving group represented by Xa that can be named include, halogen atom; optionally substituted alkylsulfonyloxy group (for example, methanesulfonyloxy group, ethanesulfonyloxy group, and optionally halogen atom-substituted alkylsulfonyloxy groups such as trifluoromethanesulfonyloxy group); and optionally substituted arylsulfonyloxy group (for example, benzenesulfonyloxy group, p-toluenesulfonyloxy group, and 2-nitrobenzenesulfonyloxy group), in particular halogen atom is preferred.

In the present reactions, the range of reaction temperatures is from usual room temperature to reflux temperature, and the range of reaction times is from normally a moment to approximately 24 hours.

The amount of the compound (S-1') used with respect to 1 mole of the compound (S-1) is usually 1 to 2 moles, preferably 1 to 1.5 moles.

Examples of the base used that can be named include carbonates such as sodium carbonate, sodium hydrogen carbonate, potassium carbonate, cesium carbonate, potassium phosphate, and the like; hydroxides such as sodium hydroxide, potassium hydroxide, and the like; organic amines such as morpholine, piperidine, pyridine, trimethylamine, triethylamine, diisopropylethylamine, 4-dimethylaminopyridine, and the like. The amount of these used with respect to 1 mole of the compound (S-1) is usually 1 to 2 moles, preferably 1 to 1.5 moles.

Examples of solvents used include water; alcoholic solvents such as methanol, ethanol, and the like; ethereal solvents such as tetrahydrofuran, dioxane, and the like; aromatic hydrocarbon solvents such as benzene, toluene, xylene, and the like; aprotic solvents such as acetonitrile, dimethylformamide, dimethylsulfoxide, N-methylpyrrolidone, and the like; halogenated hydrocarbons such as chloroform, and the like, or solvent mixtures of these, or the like, and the abovementioned organic amines can be used as solvents for the compound (S-1').

[Reduction]

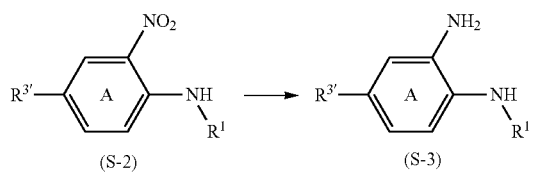

The compound (S-2) represented by the generic formula

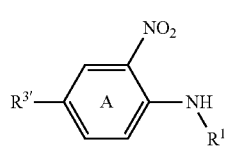

(where $R^1$, $R^{3'}$, and ring A are as given above) is subjected to a catalytic reduction method or a metal reduction agent to manufacture the compound (S-3) represented by the generic formula

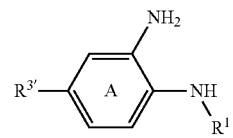

(where $R^1$, $R^{3'}$, and ring A are as given above).

The catalytic reduction method can be carried out by effecting the reaction under 1 to 5 atmospheres of hydrogen, or depending on the case with ammonium formate used to replace hydrogen, in the presence of a metal catalyst, at a temperature within the range of approximately 0° C. to the boiling point of the solvent used, and for a reaction time of from 10 minutes to 48 hours.

Examples of metal catalysts that can be named include palladium-carbon, palladium hydroxide-carbon, rhodium-carbon, Raney nickel, platinum oxide and the like, and the amount used depends on the compound (S-2). Usually it is 0.01 to 100 wt %, preferably 0.1 to 50 wt %.

Examples of the solvent that can be named include alcoholic solvents such as methanol, ethanol, 2-propanol; ethereal solvents such as tetrahydrofuran and the like; ester solvents such as ethyl acetate and the like; polar aprotic solvents such as N,N-dimethylformamide and the like, as well as solvent mixtures thereof, or the like.

When metal reducing agents are used, the reaction is effected at a temperature within the range of approximately 0° C. to the boiling point of the solvent used, and for a reaction time of from 10 minutes to 48 hours.

Examples of metal reducing agents that can be named include tin(II) chloride, titanium(III) trichloride, and the like, and the amount used in proportion to 1 mole of the compound (S-2) is usually 1 to 20 moles, preferably 1 to 5 moles.

Examples of the solvent that can be named include water; dilute hydrochloric acid; acetic acid; alcoholic solvents such as methanol, ethanol, 2-propanol and the like; ethereal solvents such as tetrahydrofuran, 1,2-dimethoxyethane, and the like; ester solvents such as ethyl acetate and the like; polar aprotic solvents such as acetone, acetonitrile, N,N-dimethylformamide, and the like, as well as solvent mixtures thereof, or the like.

[Cyclization 1]

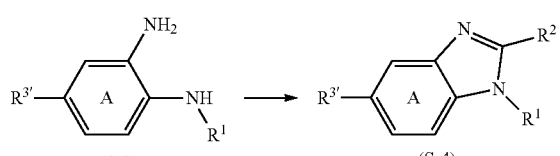

Cyclization 1 is carried out by methods well known to one skilled in the art, such as a method that uses acid chloride compound, a method that uses carboxylic acid compound, a method that uses aldehyde compound, a method that uses triacetal compound, and the like.

When an acid chloride compound is used, for example, it can be carried out according to the method described in Zhurnal Obshchei Khimii 1962 32(5) 1581-86 (Engl. Transl. Ver., pp 1565-1569).

Specifically, for example, the compound (S-3) represented by the generic formula

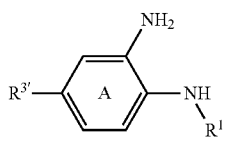

(where $R^1$, $R^{3'}$, and ring A are as given above)
and the acid chloride compound represented as

(where $R^2$ is as given above)
are caused to react to manufacture the compound (S-4) as represented by the generic formula

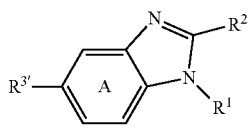

(where $R^1$, $R^2$, $R^{3'}$, and ring A are as given above)

In the present reactions, the range of reaction temperatures is from usual room temperature to reflux temperature, and the range of reaction times is from normally a moment to approximately 24 hours.

The amount of the acid chloride compound used with respect to 1 mole of the compound (S-3) is usually 1 to 5 moles, preferably 1 tot moles.

Examples of the solvent that can be named include ethereal solvents such as tetrahydrofuran, 1,2-dimethoxyethane, and the like; ester solvents such as ethyl acetate and the like; polar aprotic solvents such as acetone, acetonitrile, N,N-dimethylformamide and the like, as well as solvent mixtures thereof, or the like.

Meanwhile, when a carboxylic acid compound is used, for example, it can be carried out according to the method described in Zhurnal Obshchei Khimii 1962 32(5) 1581-86 (Engl. Transl. Ver., pp 1565-1569).

Specifically, for example, the compound (S-3) represented by the generic formula

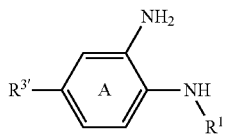

(where $R^1$, $R^{3'}$, and ring A are as given above)
and the carboxylic acid compound represented by the generic formula

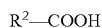

(where $R^2$ is as given above)
are caused to react to manufacture the compound (S-4) represented by the generic formula

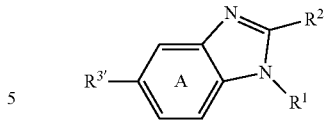

(where $R^1$, $R^2$, $R^{3'}$, and ring A are as given above)

In the present reactions, the range of reaction temperatures is from usual room temperature to reflux temperature, and the range of reaction times is from normally a moment to approximately 24 hours.

The amount of the carboxylic acid compound used with respect to 1 mole of the compound (S-3) is usually 1 to 5 moles, preferably 1 to 2 moles.

As the dehydrative condensing agent, lower aliphatic acid anhydrides such as acetic anhydride, propionic anhydride, and the like; organic sulfonic acids such as methanesulfonic acid, para-toluenesulfonic acid, and the like; and inorganic acids such as phosphorous oxychloride, phosphorus trichloride, phosphorus pentoxide, sulfuric acid, polyphosphoric acid, boric acid, and the like, can be used.

Examples of solvents to use include ethereal solvents such as tetrahydrofuran, dioxane, and the like; aromatic hydrocarbon solvents such as benzene, toluene, xylene, and the like; as well as solvent mixtures thereof, or the like, and the solvents described above for the carboxylic acid method can also be used.

In addition, when an aldehyde compound is used, for example, it can be carried out according to the method described in Synthesis 2003 (11) 1683-1692.

Specifically, for example, the compound (S-3) represented by the generic formula

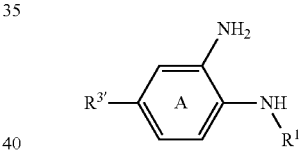

(where $R^1$, $R^{3'}$, and ring A are as given above)
and the aldehyde compound represented by the generic formula

(where $R^2$ is as described above)
are caused to react to manufacture the compound (S-4) represented by the generic formula

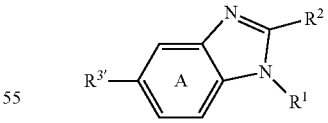

(where $R^1$, $R^2$, $R^{3'}$, and ring A are as given above)

In the present reactions, the range of reaction temperatures is from usual room temperature to reflux temperature, and the range of reaction times is from normally a moment to approximately 24 hours.

The amount of the aldehyde compound used with respect to 1 mole of the compound (S-3) is usually 1 to 5 moles, preferably 1 to 2 moles.

Examples of oxidizing agents that can be named include m-chloroperbenzoic acid, 2,3-dichloro-5,6-dicyano-1,4-benzoquinone (DDQ), oxone, benzofuroxan, potassium permanganate, hydrogen peroxide, peracetic acid, tert-butyl hydroperoxide, and the like, and usually 0.1 to 5 moles, preferably 0.5 to 2 moles, is used with respect to 1 mole of the compound (S-3).

Examples of solvents used include water; alcoholic solvents such as methanol, ethanol, and the like; ethereal solvents such as tetrahydrofuran, dioxane, and the like; aromatic hydrocarbon solvents such as benzene, toluene, xylene, and the like; aprotic solvents such as acetonitrile, dimethylformamide, dimethylsulfoxide, N-methylpyrrolidone, and the like; halogenated hydrocarbons such as chloroform, and the like, or solvent mixtures thereof, or the like.

In addition, when a triacetal compound is used, for example, it can be carried out according to the method described in Synthesis 2008 (3) 387-394.

Specifically, for example, the compound (S-3) represented by the generic formula

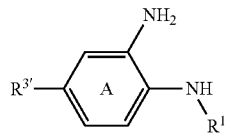

(where $R^1$, $R^{3'}$, and ring A are as given above)

and the triacetal compound represented by the generic formula

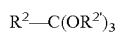

(where $R^2$ is as described above, and $R^{2'}$ represents an alkyl chain)

are caused to react to manufacture the compound (S-4) as represented by the generic formula

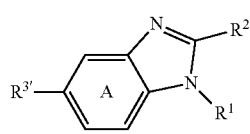

(where $R^1$, $R^2$, $R^{3'}$, and ring A are as given above)

In the present reactions, the range of reaction temperatures is from usual room temperature to reflux temperature, and the range of reaction times is from normally a moment to approximately 24 hours.

The amount of the triacetal compound used with respect to 1 mole of the compound (S-3) is usually 1 to 10 moles, preferably 1 to 5 moles.

A catalytic amount of acid can also be added to the reaction system. Examples of the type of acid to be used that can be named include inorganic acids such as hydrochloric acid, hydrobromic acid, nitric acid, sulfuric acid, and the like, or organic acids such as acetic acid, trifluoroacetic acid, methanesulfonic acid, p-toluenesulfonic acid, and the like.

Examples of solvents used include alcoholic solvents such as methanol, ethanol, and the like; ethereal solvents such as tetrahydrofuran, dioxane, and the like; aromatic hydrocarbon solvents such as benzene, toluene, xylene, and the like; aprotic solvents such as acetonitrile, dimethylformamide, dimethylsulfoxide, N-methylpyrrolidone, and the like; halogenated hydrocarbons such as chloroform, and the like, or solvent mixtures thereof, or the like. The solvents described above for the triacetal method can also be used.

Moreover, when an imidate compound is used, for example, it can be carried out according to the method described in Japanese Published Unexamined Patent Application No. H4-308580 (1992).

Specifically, for example, the compound (S-3) represented by the generic formula

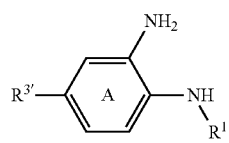

(where $R^1$, $R^{3'}$, and ring A are as given above)

and the imidate compound represented by the generic formula

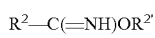

(where $R^2$ and $R^{2'}$ are as given above)

are caused to react to manufacture the compound (S-4) as represented by the generic formula

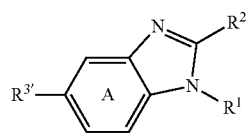

(where $R^1$, $R^2$, $R^{3'}$, and ring A are as given above)

In the present reactions, the range of reaction temperatures is from usual room temperature to reflux temperature, and the range of reaction times is from normally a moment to approximately 24 hours.

The amount of the imidate compound used with respect to 1 mole of the compound (S-3) is usually 1 to 5 moles, preferably 1 to 2 moles.

Examples of solvents used include alcoholic solvents such as methanol, ethanol, and the like; ethereal solvents such as tetrahydrofuran, dioxane, and the like; aromatic hydrocarbon solvents such as benzene, toluene, xylene, and the like; aprotic solvents such as acetonitrile, dimethylformamide, dimethylsulfoxide, N-methylpyrrolidone, and the like; halogenated hydrocarbons such as chloroform, and the like, or solvent mixtures thereof, or the like.

[Cyclization 2]

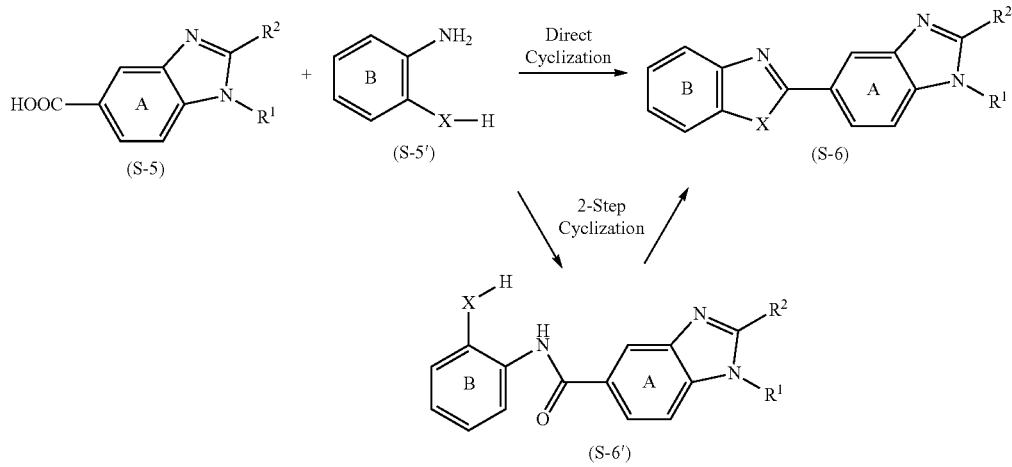

Cyclization 2 (specifically, direct cyclization or a 2-step cyclization) can be carried out by methods that are well known to one skilled in the art.

Direct cyclization, for example, can be carried out according to the method described in Zhurnal Obshchei Khimii 1962 32(5) 1581-86 (Engl. Transl. Ver.: pp 1565-1569), and the product can be manufactured by the same method as in Cyclization 1 when a carboxylic acid was used.

Specifically, for example, the compound (S-5) represented by the generic formula

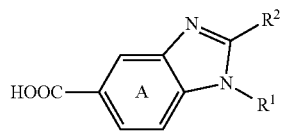

(where $R^1$, $R^2$, and ring A are as given above)
and the compound (S-5') as represented by the generic formula

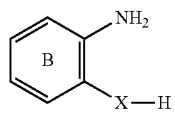

(where X and ring B are as given above)
are caused to react to manufacture the compound (S-6) as represented by the generic formula

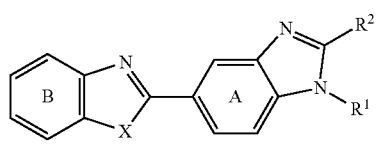

(where $R^1$, $R^2$, X, ring A, and ring B are as given above)

In the present reactions, the range of reaction temperatures is from usual room temperature to reflux temperature, and the range of reaction times is from normally a moment to approximately 24 hours.

The amount of the compound (S-5') used with respect to 1 mole of the compound (S-5) is usually 1 to 5 moles, preferably 1 to 2 moles.

As the dehydrative condensing agent, lower aliphatic acid anhydrides such as acetic anhydride, propionic anhydride, and the like; organic sulfonic acids such as methanesulfonic acid, para-toluenesulfonic acid, and the like; and inorganic acids such as phosphorous oxychloride, phosphorus trichloride, phosphorus pentoxide, sulfuric acid, polyphosphoric acid, boric acid, and the like, can be used.

Examples of solvents to use include ethereal solvents such as tetrahydrofuran, dioxane, and the like; aromatic hydrocarbon solvents such as benzene, toluene, xylene, and the like; as well as mixtures thereof, and the solvents described above for use with dehydrative condensing agents can also be used.

The 2-step cyclization, for example, can be carried out according to the methods described Journal of Medicinal Chemistry 1988 31(9) 1778-85 or Bioorganic & Medicinal Chemistry 2004 12(1) 17-21.

Specifically, for example, the compound (S-5) represented by the generic formula

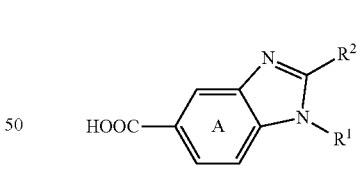

(where $R^1$, $R^2$, and ring A are as given above)
and the compound (S-5') as represented by the generic formula

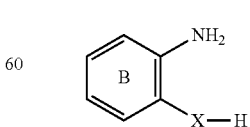

(where X and ring B are as given above)
are used to synthesize the compounds (S-6') as represented by the generic formula

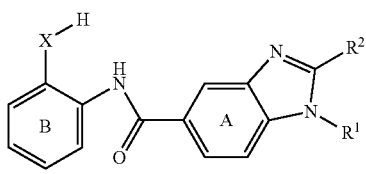

(where $R^1$, $R^2$, X, ring A, and ring B are as given above)

which is transformed to manufacture the compound (S-6) as represented by the generic formula

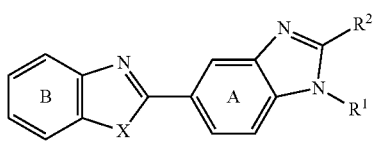

(where $R^1$, $R^2$, X, ring A, and ring B are as given above)

The first step is the reaction using a condensing agent or acid halogenating agent.

When a condensing agent is used, the range of reaction temperatures is from usual room temperature to reflux temperature, and the range of reaction times is from normally a moment to approximately 24 hours.

The amount of the compound (S-5') used with respect to 1 mole of the compound (S-5) is usually 1 to 2 moles, preferably 1 to 1.5 moles.

Examples of condensing agents that can be named include Bop (1H-1,2,3-benzotriazol-1-yloxy-tris(dimethylamino) phosphonium hexafluorophosphate), WSC (1-ethyl-3-(3-dimethylaminopropyl)carbodiimide hydrochloride), DCC (N,N-dicyclohexylcarbodiimide), CDI (carbonyl diimidazole), diethylphosphoryl cyanide, and the like. The amount of condensing agent used with respect to 1 mole of the compound (S-5) is usually 1 to 2 moles, preferably 1 to 1.5 moles.

Moreover, if necessary, with respect to the compound (S-5), from 1 equivalent to an excess of an organic base, for example triethylamine, can also be added.

Examples of solvents that can be named include halogenated hydrocarbons such as, for example, dichloromethane, chloroform, and the like, sulfoxides such as, for example, dimethyl sulfoxide, and the like, esters such as, for example, ethyl acetate, and the like, ethers such as, for example, tetrahydrofuran, 1,4-dioxane, and the like, amides such as, for example, N,N-dimethylformamide, N,N-dimethylacetamide, and the like.

When an acid halogenating agent is used, the range of reaction temperatures is from usual room temperature to reflux temperature, and the range of reaction times is from normally a moment to approximately 24 hours.

The amount of the compound (S-5') used with respect to 1 mole of the compound (S-5) is usually 1 to 2 moles, preferably 1 to 1.5 moles.

Examples of acid halogenating agents that can be named include thionyl chloride, oxalyl chloride, phosphorus trichloride, phosphorus pentachloride, and the like. The amount of acid halogenating agent used with respect to 1 mole of the compound (S-5) is usually 1 to 10 moles, preferably 1 to 1.5 moles.

A catalytic amount of N,N-dimethylformamide can also be added to the reaction system.

Examples of solvents that can be named include halogenated hydrocarbons such as, for example, dichloromethane, chloroform, and the like, sulfoxides such as, for example, dimethyl sulfoxide, and the like, esters such as, for example, ethyl acetate, and the like, ethers such as, for example, tetrahydrofuran, 1,4-dioxane, and the like, amides such as, for example, N,N-dimethylformamide, N,N-dimethylacetamide, and the like, aromatic hydrocarbons such as, for example, benzene, toluene, and the like.

The second step is the reaction using a dehydrative condensing agent.

The range of reaction temperatures is from usual room temperature to reflux temperature, and the range of reaction times is from normally a moment to approximately 48 hours.

As the dehydrative condensing agent, lower aliphatic acid anhydrides such as acetic anhydride, propionic anhydride, and the like; organic sulfonic acids such as methanesulfonic acid, para-toluenesulfonic acid, and the like; and inorganic acids such as phosphorous oxychloride, phosphorus trichloride, phosphorus pentoxide, sulfuric acid, polyphosphoric acid, boric acid, and the like, can be used.

Examples of solvents to use include ethereal solvents such as tetrahydrofuran, dioxane, and the like; aromatic hydrocarbon solvents such as benzene, toluene, xylene, and the like; as well as mixtures thereof, and the solvents described above for use with dehydrative condensing agents can also be used.

[Cyclization 3]

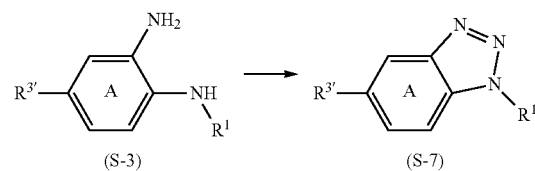

Cyclization 3 can be carried out using methods that are well known to one skilled in the art (for example, the method described in WO 2005/82901).

Specifically, for example, the compound (S-3) as represented by the generic formula

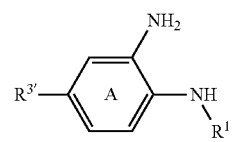

(where $R^1$, $R^{3'}$, and ring A are as given above)
is caused to react with a nitrosating agent to manufacture the compound (S-7) as represented by the generic formula

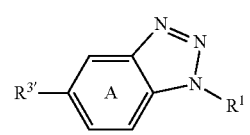

(where $R^1$, $R^{3'}$, and ring A are as given above)

In the present reactions, the range of reaction temperatures is from usual room temperature to reflux temperature, and the range of reaction times is from normally a moment to approximately 24 hours.

As the nitrosating agent, alkali metal nitrites such as sodium nitrite, or organic nitrite compounds such as methyl nitrite or isoamyl nitrite, and the amount used with respect to 1 mole of the compound (S-3) is normally 1 to 5 moles, preferably 1 to 2 moles.

As the solvent, combinations of water and acid are used. Examples of the acid that can be named include inorganic acids such as hydrochloric acid or sulfuric acid, and organic acids such as acetic acid.

[Cyclization 4]

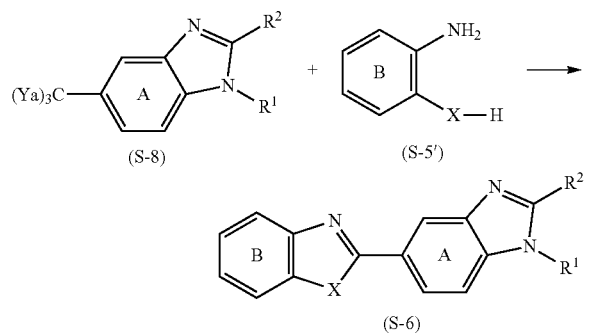

Cyclization 4 can be carried out using methods that are well known to one skilled in the art (for example, the method described in Synthetic Communications 1998 28(22) 4123-4135).

Specifically, for example, the compound (S-8) as represented by the generic formula

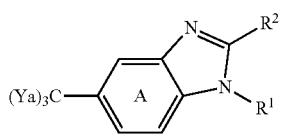

(where Ya represents a halogen atom, and $R^1$, $R^2$, and ring A are as given above) is caused to react with the compound (S-5') as represented by the generic formula

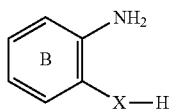

(where X and ring B are as given above) to manufacture the compound (S-6) as represented by the generic formula

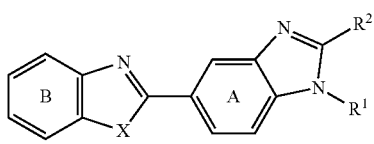

(where $R^1$, $R^2$, X, ring A, and ring B are as given above)

In the present reactions, the range of reaction temperatures is from usual room temperature to reflux temperature, and the range of reaction times is from normally a moment to approximately 24 hours.

The amount of the compound (S-5') used with respect to 1 mole of the compound (S-8) is usually 1 to 2 moles, preferably 1 to 1.5 moles.

As the dehydrative condensing agent, lower aliphatic acid anhydrides such as acetic anhydride, propionic anhydride, and the like; organic sulfonic acids such as methanesulfonic acid, para-toluenesulfonic acid, and the like; and inorganic acids such as phosphorous oxychloride, phosphorus trichloride, phosphorus pentoxide, sulfuric acid, polyphosphoric acid, boric acid, and the like, can be used.

Examples of solvents to use include ethereal solvents such as tetrahydrofuran, dioxane, and the like; aromatic hydrocarbon solvents such as benzene, toluene, xylene, and the like; as well as mixtures thereof, and the solvents described above for use with dehydrative condensing agents can also be used.

[Coupling]

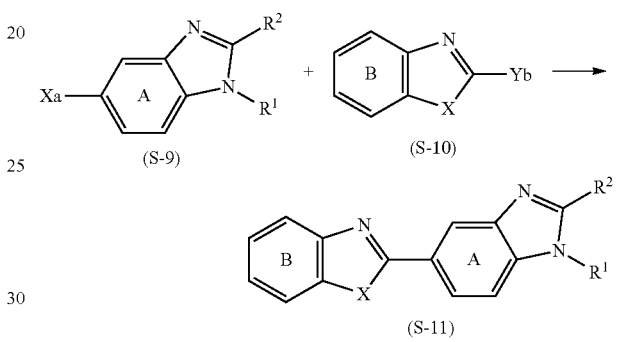

Coupling can be carried out using methods that are well known to one skilled in the art (for example, the methods described in "Strategic Applications of Named Reactions in Organic Synthesis" translated into Japanese by Kiyoshi Tomioka, publ. Kagaku Dojin, Aug. 15, 2006. pp 258-259: Kumada Cross-Coupling reaction; pp 310-311: Negishi Cross-Coupling reaction; pp 440-441: Stille-Kelly coupling reaction; pp 448-449: Suzuki-Miyaura coupling reaction).

Specifically, for example, the compound (S-9) as represented by the generic formula

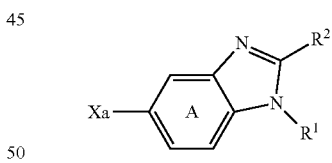

(where $R^1$, $R^2$, Xa, and ring A are as given above) is caused to react with the compound (5-10) as represented by the generic formula

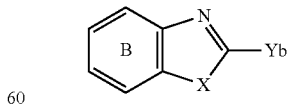

(where Yb is boric acid ($B(OH)_2$) or its esters, organotins (for example $SnBu_4$ (tetrabutyltin), or the like), or other metals (e.g., magnesium, lead, and the like) that form suitable organometallic compounds, and X and ring B are as given above) to manufacture the compound (S-11) as represented by the generic formula

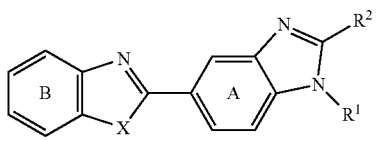

(where $R^1$, $R^2$, X, ring A, and ring B are as given above).

These reactions can be carried out in the presence of transition metal catalysts, or depending on the case, in the presence of ligands, bases, additives, or the like, at temperatures within the range of from approximately 20° C. up to the boiling point of the solvent used, and reaction times for from 10 minutes to 48 hours.

The amount of the compound (S-10) used with respect to 1 mole of the compound (S-9) is usually 1 to 20 moles, preferably 1 to 5 moles.

Examples of transition metal catalysts that can be named include palladium (II) acetate, palladium (II) chloride, tetrakis(triphenylphosphine)palladium (0), bis(triphenylphosphine)palladium (II) chloride, tris(dibenzylideneacetone)dipalladium (0), or [1,1'-bis(diphenylphosphino)ferrocene] dichloropalladium (II), and the like. The amount of the transition metal catalyst used with respect to 1 mole of the compound (S-10) is usually 0.0001 to 1 moles, preferably 0.001 to 1 moles.

Examples of ligands that can be named include triphenylphosphine, tri-o-tolylphosphine, tri-tert-butylphosphine, tri-2-furylphosphine, tri-cyclohexylphosphine, triphenylarsine, 1,1'-bis(diphenylphosphino)ferrocene (dppf), and the like. The amount of the ligand used with respect to 1 mole of the compound (S-9) is usually 0.0001 to 4 moles, preferably 0.001 to 4 moles.

Examples of the base that can be named include organic bases such as triethylamine, diisopropylethylamine, inorganic bases such as sodium carbonate, sodium hydrogen carbonate, potassium carbonate, cesium carbonate, potassium phosphate, and the like. The amount of the base used with respect to 1 mole of the compound (S-9) is usually 1 to 10 moles, preferably 1 to 4 moles.

Examples of additives that can be named include inorganic salts such as lithium chloride, cesium fluoride, copper (I) iodide, copper (I) bromide, and the like.

Examples of solvents that can be named include water, acetonitrile, chloroform, dichloromethane, and the like; examples of solvents that can be named include, for example, water; alcoholic solvents such as methanol, ethanol, and the like; ethereal solvents such as tetrahydrofuran, dioxane, and the like; aromatic hydrocarbon solvents such as benzene, toluene, xylene, and the like; aprotic solvents such as acetonitrile, dimethylformamide, dimethylsulfoxide, N-methylpyrrolidone, and the like; halogenated hydrocarbons such as chloroform, and the like, or mixtures thereof.

(Other Synthesis Methods)

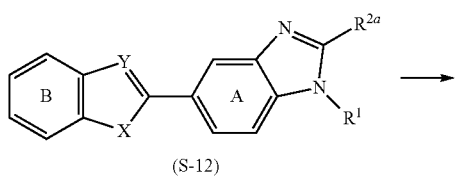

(S-12)

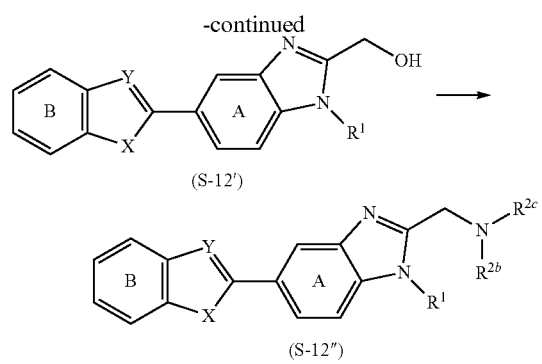

(S-12')

(S-12'')

According to methods well known to those skilled in the art (for example, methods described in WO 03/053344), the compound (S-12) as represented by the generic structure

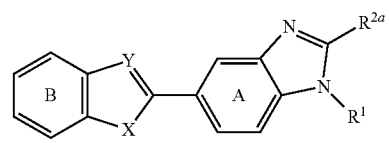

(where $R^{2a}$ represents an alkylcarbonyloxymethyl group or benzyloxymethyl group, and $R^1$, $R^2$, X, Y, ring A, and ring B are as given above)
is used to synthesize the compound (S-12') as represented by the generic formula

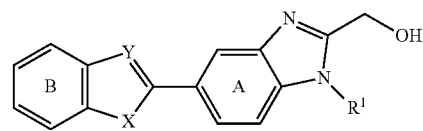

(where $R^1$, X, Y, ring A, and ring B are as given above)
which is further transformed to manufacture the compound (S-12'') as represented by the generic formula

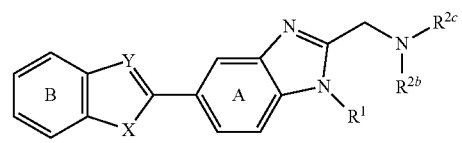

(where $R^{2b}$ and $R^{2c}$ represent hydrogen atom or optionally substituted carbon atom, and $R^1$, X, Y, ring A, and ring B are as given above)

In the first step, the manufacturing method is to use hydrolysis when $R^{2a}$ is an alkylcarbonyloxymethyl group, and to use a catalytic reduction method when $R^{2a}$ is a benzyloxymethyl group.

When $R^{2a}$ is an alkylcarbonyloxymethyl group, the range of reaction temperatures is from usual room temperature to reflux temperature, and the range of reaction times is from normally a moment to approximately 24 hours.

Examples of the type of alkali to be used that can be named include hydroxide compounds such as lithium hydroxide, sodium hydroxide, and the like, and the amount used with respect to 1 mole of the compound (S-12) is usually 1 to 10 moles, preferably 1 to 3 moles.

The solvents used are, for example, water, or alcoholic solvents such as, for example, methanol or ethanol; sulfoxides such as, for example, dimethyl sulfoxide; ethereal solvents such as, for example, tetrahydrofuran, 1,4-dioxane, and the like; amide solvents such as, for example, N,N-dimethylformamide, N,N-dimethylacetamide, and the like, as well as solvent mixtures thereof, or the like.

When $R^{2a}$ is a benzyloxymethyl group, the reaction can be effected under 1 to 5 atmospheres of hydrogen, or depending on the case with ammonium formate used to replace hydrogen, in the presence of a metal catalyst, at a temperature within the range of approximately 0° C. to the boiling point of the solvent used, and for a reaction time of from 10 minutes to 48 hours.

Examples of metal catalysts that can be named include palladium-carbon, palladium hydroxide-carbon, rhodium-carbon, Raney nickel, platinum oxide and the like, and the amount used depends on the compound (S-12). Usually it is 0.01 to 100 wt %, preferably 0.1 to 10 wt %.

Examples of the solvent that can be named include alcoholic solvents such as methanol, ethanol, 2-propanol; ethereal solvents such as tetrahydrofuran and the like; ester solvents such as ethyl acetate and the like; polar aprotic solvents such as N,N-dimethylformamide and the like, as well as mixtures thereof.

The second step is the reaction using an acid halogenating agent.

The range of reaction temperatures is from normally room temperature to reflux temperature, and the range of reaction times is from normally a moment to approximately 48 hours.

The amount of the compound (S-12') used with respect to 1 mole of the carboxylic acid compound is usually 1 to 2 moles, preferably 1 to 1.5 moles.

Examples of acid halogenating agents that can be named include thionyl chloride, oxalyl chloride, phosphorus trichloride, phosphorus pentachloride, and the like. The amount of acid halogenating agent used with respect to 1 mole of the compound (S-12') is usually 1 to 10 moles, preferably 1 to 1.5 moles.

A catalytic amount of N,N-dimethylformamide can also be added to the reaction system.

Examples of solvents that can be named include halogenated hydrocarbons such as, for example, dichloromethane, chloroform, and the like, sulfoxides such as, for example, dimethyl sulfoxide, and the like, esters such as, for example, ethyl acetate, and the like, ethers such as, for example, tetrahydrofuran, 1,4-dioxane, and the like, amides such as, for example, N,N-dimethylformamide, N,N-dimethylacetamide, and the like, aromatic hydrocarbons such as, for example, benzene, toluene, and the like.

Manufacturing methods for the compound (I) have been described above, but the compound (I) synthesized according to such manufacturing methods can be isolated from the reaction mixture and purified according to methods well known to those skilled in the art, such as rotary extraction, concentration, solvent extraction, fractional distillation, crystallization, recrystallization, column chromatography, and the like.

Moreover, when the compound (I) are obtained in their free state, if so intended, they can be converted into the above-described salts using known methods themselves or methods conforming thereto; conversely, when the compound (I) is obtained as a salt, it can be converted into its free state or, if so intended, to other salt using known methods themselves or methods conforming thereto.

For example, purified compound (I) can be caused to react with, for example, inorganic acids such as hydrochloric acid, hydrobromic acid, phosphoric acid, sulfuric acid, and the like, or organic acids such as acetic acid, citric acid, succinic acid, tartaric acid, fumaric acid, maleic acid, methanesulfonic acid, p-toluenesulfonic acid, and the like, and a pharmaceutically acceptable acid addition salt can easily be obtained.

In addition, purified compound (I) can be caused to react with, for example, an inorganic or organic metal salt such as lithium hydroxide, lithium methylate, sodium hydride, sodium carbonate, sodium hydroxide, sodium methylate, potassium hydride, potassium carbonate, potassium hydroxide, potassium t-butylate, and a pharmaceutically acceptable metal salt can easily be obtained.

The compound of the present invention can be provided in any form suitable for the intended administration. Suitable forms include a pharmaceutically (that is, physiologically) acceptable salt as well as a pre-drug form and a pro-drug form of the compound of the present invention. Such pre-drug form and pro-drug form also fall within the scope of the present invention.

The compound of the present invention has the action of potentiating the activity of neurotrophic factors, thereby, in particular, having the action of inducting expression of the NXF gene that plays an important role in neuroprotection.

Consequently, the compound of the present invention can be used for the prevention or treatment of diseases that are associated with neurotrophic factor activity.

Moreover, the compound of the present invention can be used as an agent that promotes physiotherapeutic effects for the recovery of body function.

In this specification, the meaning of "disease" includes disorders and their symptoms.

In addition, in this specification, the meaning of "treatment" includes the alleviation of symptoms.

Diseases that are associated with neurotrophic factor activity include the central neurodegenerative diseases, spinal degenerative diseases, retinal degenerative diseases, peripheral nerve degenerative diseases, and other diseases named below.

Examples of central neurodegenerative diseases that can be named include: neurodegenerative diseases (for example, Alzheimer's disease, Parkinson's disease, Huntington's chorea, Down's syndrome, and the like), cerebral ischemic disease (stroke, cerebral infarction, transient ischemic attacks, subarachnoid hemorrhage, ischemic encephalopathy, cerebral infarction (lacunar infarction, atherothrombotic brain infarction, cardiogenic cerebral infarction, hemorrhagic cerebral infarction, and other types of infarction), and the like), traumatic brain injury, leukoencephalopathy, and multiple sclerosis.

Examples of spinal degenerative diseases that can be named include: amyotrophic lateral sclerosis (ALS), spinal cord injury, spinal cord disorders due to various factors, spinal progressive muscular atrophy, and degenerative SCD.

Examples of retinal degenerative diseases that can be named include: age-related macular degeneration (AMD), diabetic retinopathy, retinitis pigmentosa, hypertensive retinopathy, and glaucoma.

Examples of peripheral nerve degenerative diseases that can be named include: diabetic neuropathy, peripheral nerve injury, traumatic peripheral neuropathy, peripheral nerve damage due to toxins and other toxic substances, peripheral nerve damage due to cancer chemotherapy, Guillain-Barre syndrome, peripheral nerve damage due to vitamin deficiencies, amyloid peripheral neuropathy, ischemic peripheral neuropathy, peripheral nerve damage associated with malignant tumors, uremic peripheral neuropathy, peripheral nerve damage due to physical factors, Charcot-Marie-Tooth disease, alcohol-related peripheral neuropathy, autonomic nerve anomalies (asymptomatic hypoglycemia, gastric paresis, neuropathic diarrhea or constipation, erectile dysfunction, orthostatic hypotension, arrhythmia, heart failure, painless myocardial infarction, dyshidrosis, neurogenic bladder, and the like), bladder function disorders (for example, uninhibited bladder, reflex bladder, automatic bladder, sensory paralytic bladder, motor paralytic bladder, and the like).

Examples of other diseases that can be named include: depression, schizophrenia, seizures, autism, periodontal disease, diabetes, diabetic cardiomyopathy, diabetic foot, inflammatory bowel disease (for example, ulcerative colitis, Crohn's disease, and the like), behavior problems associated with dementia (for example, wandering, aggressive behavior, and the like), anxiety, pain, deafness, osteopathy (for example, osteoporosis, and the like), arthritic disorders (for example, Charcot's arthropathy, osteoarthritis, rheumatism, and the like), and Hirschsprung's disease.

Among these, the compound of the present invention is suitable for use in cerebral ischemic disease or diabetic neuropathy.

The compound of the present invention can be administered, directly or as a formulated composition (for example, pharmaceutical compositions) in mixture with a pharmaceutically acceptable carrier, orally or non-orally in mammals such as humans for the prevention or treatment of diseases that are associated with neurotrophic factor activity due to its low toxicity. "Non-orally" includes administration by intravenous, intramuscular, subcutaneous, intraorgan, intranasal, percutaneous, eye drops, intracranial, intrarectal, intravaginal, intra-abdominal, or the like route.

Composition of the present invention contain, for example, one or more types of the compound (I) of the present invention, and a pharmaceutically acceptable carrier, filler, and/or excipient.

Depending on formulations, the composition of the present invention can be manufactured by well-known methods from mixture of the compound of the present invention with a pharmaceutically acceptable carrier, filler, and/or excipient (for example, a pharmaceutical excipient, food additive, cosmetic additive), and the like.

The pharmaceutically acceptable carrier, filler, and/or excipient, and the like used with the composition of the present invention can be suitably selected according to the specific application of the aforementioned composition. Moreover, the formulation of the composition can be, for example, various solid or liquid formulation or the like, depending on the specific application.

Examples of specific formulation that can be named, when using a pharmaceutical composition of the present invention or a compound of the present invention as a pharmaceutical product, include oral agents such as powder, finely granule, granule, tablet, syrup, capsule, suspension, emulsion, extract, pill, and the like, non-oral agents such as injectable, external use agent, ointment, percutaneously absorbed agent (agent for external use on the skin), suppository, topical agent and the like.

Oral agent can be manufactured according to the usual methods using a carrier or a filler such as gelatin, sodium alginate, starch, cornstarch, saccharose, lactose, dextrose, mannitol, carboxymethylcellulose, dextrin, polyvinylpyrrolidine, crystalline cellulose, soy lecithin, sucrose, fatty acid esters, talc, magnesium stearate, poly(ethylene glycol), magnesium silicate, silicic anhydride, and the like; a pharmaceutical excipient such as a binder, disintegrant, surfactant, lubricant, flow agent, diluent, preservative, colorant, fragrance, stabilizer, humectant, antiseptic agent, antioxidant, and the like.

The administered dose will vary according to the mammal's age, sex, body weight, severity of the disease, type of the compound of the present invention, dosage form, and the like, but normally for an adult human when taken orally, approximately 1 mg to 2 g of the active ingredient per day, preferably approximately 5 mg to 1 g of the active ingredient can be administered. Moreover, the abovementioned daily administered dose can be administered once or can be divided and administered several times.

Among the non-oral agents, an injectable agent can be manufactured by the usual methods using a water-soluble solvent such as physiological saline, sterilized water, Ringer's solution, and the like; non-water-soluble solvent such as vegetable oil, fatty acid esters or the like; tonicity agent such as glucose, sodium chloride, or the like; and pharmaceutical excipient such as solubilizing agent, antiseptic agent, suspending agent, emulsifier, and the like. The agent for transdermal absorption such as liquid form for external use, gel ointment, and the like, as well as suppository for intrarectal use and the like can be manufactured by the usual methods. Such non-oral agent can be administered by injection (subcutaneous, intravenous, and the like), percutaneous administration or rectal administration. The topical agent can be manufactured, for example, by introduction of the compound of the present invention into sustained-release polymer pellet such as ethylene/vinyl acetate polymer and the like. Such pellet can be surgically transplanted into the tissues to be treated.

The administered dose will vary according to the mammal's age, sex, body weight, severity of the disease, type of composition of the present invention or the compound of the present invention, dosage form, and the like, but normally for an adult human when given by injection, approximately 0.1 mg to 500 mg of the active ingredient can be administered. Moreover, the abovementioned daily administered dose can be administered once or can be divided and administered several times.

Working Examples

Synthesis examples, working examples, manufacturing examples, and testing examples of the present invention are explained in greater detail below, but the present invention is not limited to these examples in any way.

Synthesis Example 1

Synthesis of 5-(benzothiazol-2-yl)-2-methyl-1-phenylbenzimidazole

Synthesis Example 1-1

Synthesis of 3-nitro-4-phenylaminobenzoic acid

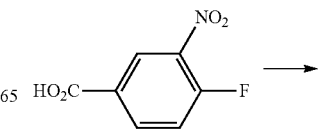

-continued

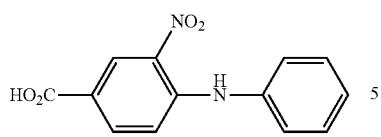

An eggplant flask was charged with 4-fluoro-3-nitrobenzoic acid (2.51 g, 13.56 mmol), aniline (2.52 g, 27.12 mmol), and ethanol (9.5 mL), and this was heated to reflux with stirring for 16 hours. After cooling to room temperature, the mixture was poured into dilute hydrochloric acid (1 M, 50 mL), diluted with distilled water (100 mL), was left to stir as is at room temperature for 30 minutes. The precipitated crystals were filtered off, and washed successively with dilute hydrochloric acid (1 M, with approx. 3 mL 3 times), distilled water (approx. 5 mL 2 times), and with diethyl ether (approx. 3 mL). The crystals obtained were dried at reduced pressure with heating to yield the title compound (3.39 g, quant.) as a reddish-orange solid.

$^1$H-NMR (DMSO-$d_6$) δ (ppm): 7.13 (d, 1H, J=9.0 Hz), 7.30 (t, 1H, J=7.3 Hz), 7.37 (d, 1H, J=7.5 Hz), 7.48 (t, 2H, J=7.4 Hz), 7.93 (dd, 1H, J=2.0, 9.0 Hz), 8.64 (d, 1H, J=2.1 Hz), 9.80 (s, 1H), 13.00 (brs, 1H).

Synthesis Example 1-2

Synthesis of 3-amino-4-phenylaminobenzoic acid

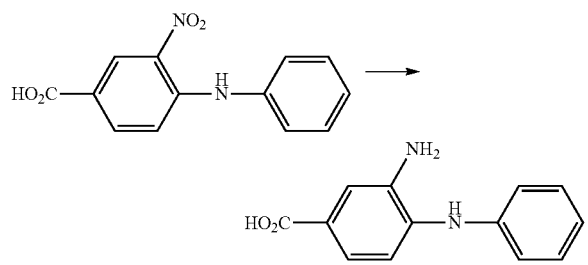

A 3-neck flask was charged with 3-nitro-4-phenylaminobenzoic acid (see Synthesis Example 1-1) (1.67 g, 6.70 mmol), palladium/carbon (Pd:10%, 0.170 g), and tetrahydrofuran (34 mL), the atmosphere was replaced with hydrogen using three cycles of vacuum/hydrogen purge, and this was stirred at room temperature for 2.5 hours. After substituting in nitrogen, distilled water (20 mL) was added and this was stirred for 10 minutes, insoluble material was filtered off through a Celite layer (20 mm thickness), and this same layer was further washed with tetrahydrofuran (20 mL, 3 times). The filtrate and the wash solutions were combined, and the solvent was distilled off under reduced pressure. This was successively extracted with ethyl acetate (approx. 50 mL, 4 times), washed with distilled water (30 mL), and dried over anhydrous sodium sulfate, the solvent was distilled off under reduced pressure, and further drying under reduced pressure yielded the title compound (1.45 g, 95.3% yield) as a pale yellow solid.

$^1$H-NMR (DMSO-$d_6$) δ (ppm): 4.98 (brs, 2H), 6.83 (dt, 1H, J=7.4, 1.0 Hz), 6.97 (dd, 2H, J=7.6, 1.0 Hz), 7.06 (d, 1H, J=8.3 Hz), 7.15 (dd, 1H, J=8.2, 1.9 Hz), 7.23 (t, 2H, J=7.4 Hz), 7.33 (d, 1H, J=1.9 Hz), 7.35 (s, 1H), 12.25 (brs, 1H).

Synthesis Example 1-3

Synthesis of 2-methyl-1-phenylbenzimidazole-5-carboxylic acid

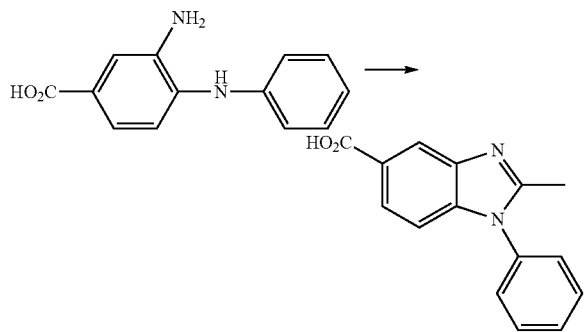

A 2-neck flask was charged with 3-amino-4-phenylaminobenzoic acid (see Synthesis Example 1-2) (1.40 g, 6.35 mmol) and anhydrous toluene (15 mL) and this was refluxed. To this was added dropwise over approx. 15 minutes acetyl chloride (1.00 g, 12.70 mmol) in toluene solution (approx. 2.5 mL), and this was stirred under these conditions for 2.5 hours. This was allowed to cool to room temperature, and was extracted with dilute aqueous sodium hydroxide solution (10%, 200 mL). After separating the dark orange aqueous layer, it was cooled in ice (5 to 10° C.), and concentrated hydrochloric acid (12 M) was added to the liquid to give approx. pH 4. The precipitated crystals were filtered off, washed with distilled water, and dried under reduced pressure with heating to yield the title compound (1.34 g, 83.5% yield) as a light purple solid.

$^1$H-NMR (DMSO-$d_6$) δ (ppm): 2.47 (s, 3H), 7.18 (d, 1H, J=8.4 Hz), 7.58 (d, 2H, J=7.0 Hz), 7.59 (dt, 1H, J=9.1, 1.5 Hz), 7.67 (t, 2H, J=7.7 Hz), 7.83 (dd, 1H, J=8.5, 1.4 Hz), 8.21 (d, 1H, J=1.0 Hz), 12.75 (brs, 1H).

Synthesis Example 1-4

Synthesis of 5-(benzothiazol-2-yl)-2-methyl-1-phenylbenzimidazole

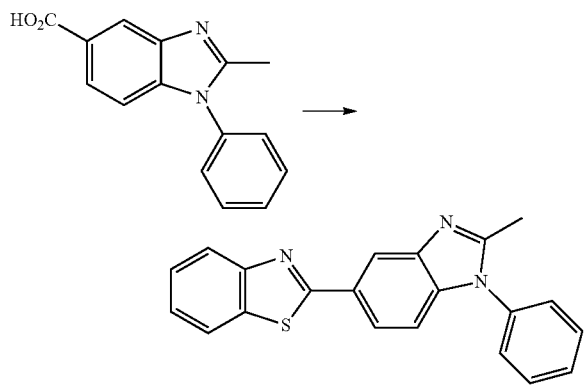

A 2-neck flask was charged with 2-methyl-1-phenylbenzimidazole-5-carboxylic acid (see Synthesis Example 1-3) (1.33 g, 5.28 mmol) and anhydrous tetrahydrofuran (30 mL), and this was treated dropwise at room temperature with oxalyl chloride (0.70 g, 5.30 mmol). The reaction mixture was then stirred at 50° C. for 3 hours. After being allowed to cool to room temperature, the solvent was distilled off under reduced pressure to give a pale yellow residue, which was taken up in anhydrous tetrahydrofuran (10 mL) to which 2-aminobenzenethiol (0.66 g, 5.27 mmol) was added, and this was stirred for 16 hours at 50° C. After being allowed to cool to room temperature, this was extracted with chloroform (50 mL, 3 times) and then successively washed with saturated aqueous sodium hydrogen carbonate, then with brine (approx. 50 mL), and dried over anhydrous magnesium sulfate. The solvent being distilled off under reduced pressure gave a dark yellow residue (1.84 g), which was purified by silica gel column chromatography (silica gel: 90 g; EtOAc/CHCl$_3$=1/5 to 1/4) to yield the title compound (0.46 g, 25.5% yield) as an orange powder.

$^1$H-NMR (CDCl$_3$) δ (ppm): 2.55 (s, 3H), 7.21 (d, 1H, J=8.4 Hz), 7.37 (dt, 1H, J=7.1, 1.1 Hz), 7.40-7.43 (m, 2H), 7.48 (dt, 1H, J=8.3, 1.2 Hz), 7.53-7.58 (m, 1H), 7.58-7.67 (m, 2H), 7.90 (d, 1H, J=7.9 Hz), 8.06 (dd, 1H, J=8.5, 1.6 Hz), 8.07 (d, 1H, J=8.0 Hz), 8.41 (d, 1H, J=1.3 Hz).

Synthesis Example 2

Synthesis of 5-(benzimidazol-2-yl)-2-methyl-1-phenylbenzimidazole

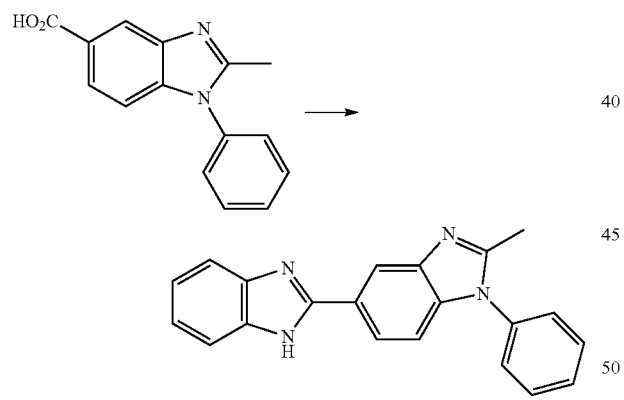

A 2-neck flask (20 mL) equipped with reflux condenser was charged with 2-methyl-1-phenylbenzimidazole-5-carboxylic acid (see Synthesis Example 1-3) (0.15 g, 0.59 mmol) and polyphosphoric acid (approx. 2 g), and this was heated to 120° C. To this was added 1,2-diaminobenzene (0.09 g, 0.83 mmol), and this was heated to 160° C. and stirred under those conditions for 20 hours. After being allowed to cool to room temperature, ice was added and concentrated aqueous ammonia (28%) was added to the liquid to give approx. pH 9. The precipitated crystals were filtered off, these were washed with distilled water (approx. 3 mL, 2 times), and then dried to yield the title compound (0.25 g, quant.) as greenish pale yellow crystals.

$^1$H-NMR (DMSO-d$_6$) δ (ppm): 2.50 (s, 3H), 7.15-7.23 (m, 2H), 7.27 (d, 1H, J=8.5 Hz), 7.58-7.65 (m, 4H), 7.65-7.73 (m, 3H), 8.09 (dd, 1H, J=8.5, 1.5 Hz), 8.44 (d, 1H, J=0.9 Hz), 12.87 (brs, 1H).

Synthesis Example 3

Synthesis of 5-(benzoxazol-2-yl)-2-methyl-1-phenylbenzimidazole

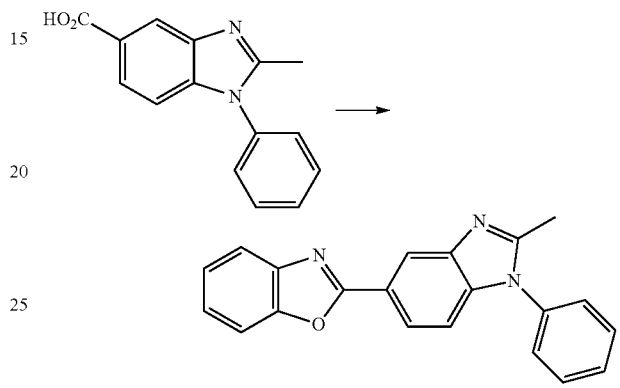

A 2-neck flask (20 mL) equipped with reflux condenser was charged with 2-methyl-1-phenylbenzimidazole-5-carboxylic acid (see Synthesis Example 1-3) (0.15 g, 0.59 mmol), 2-aminophenol (0.09 g, 0.82 mmol) and polyphosphoric acid (approx. 2 g), and this was heated to 160° C. and stirred under those conditions for 20 hours. After being allowed to cool to room temperature, ice was added and concentrated aqueous ammonia (28%) was added to the liquid to give approx. pH 9. The precipitated crystals were filtered off, these were washed with distilled water (approx. 3 mL, 2 times), and then dried to yield the title compound (0.13 g, 68% yield) as greenish pale yellow crystals.

$^1$H-NMR (CDCl$_3$) δ (ppm): 2.56 (s, 3H), 7.24 (d, 1H, J=8.4 Hz), 7.32-7.38 (m, 2H), 7.39-7.44 (m, 2H), 7.57-7.65 (m, 4H), 7.75-7.79 (m, 1H), 8.17 (dd, 1H, J=8.5, 1.6 Hz), 8.63 (d, 1H, J=1.1 Hz).

Synthesis Example 4

Synthesis of 2-amino-1-(tetrahydropyran-4-yl)amino-4-trifluoromethylbenzene

Synthesis Example 4-1

Synthesis of 1-(tetrahydropyran-4-yl)amino-2-nitro-4-trifluoromethylbenzene

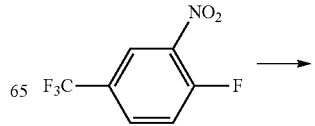

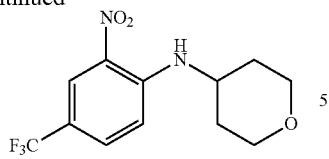

A 3-neck flask (200 mL) was charged with 1-fluoro-2-nitro-4-trifluoromethylbenzene (1.59 g, 7.61 mmol), 4-aminotetrahydropyran (1.00 g, 9.89 mmol), and pyridine (16 mL), and this was stirred at 98° C. for 23 hours. The yellow oil produced was allowed to cool, distilled water (approx. 20 mL) was added with stirring, and the precipitated crystals were filtered off. These were washed with distilled water and dried with heating at reduced pressure to yield the title compound (2.00 g, 90.5% yield) as yellow crystals.

$^1$H-NMR (CDCl$_3$) δ (ppm): 1.66-1.76 (m, 2H), 2.06-2.10 (m, 2H), 3.56-3.62 (m, 2H), 3.77-3.80 (m, 1H), 4.02-4.07 (m, 2H), 6.97 (d, 1H, J=9.1 Hz), 7.61 (dd, 1H, J=9.1, 2.3 Hz), 8.33 (brd, 1H, J=6.3 Hz), 8.49 (d, 1H, J=1.2 Hz).

Synthesis Example 4-2

Synthesis of 2-amino-1-(tetrahydropyran-4-yl)amino-4-trifluoromethylbenzene

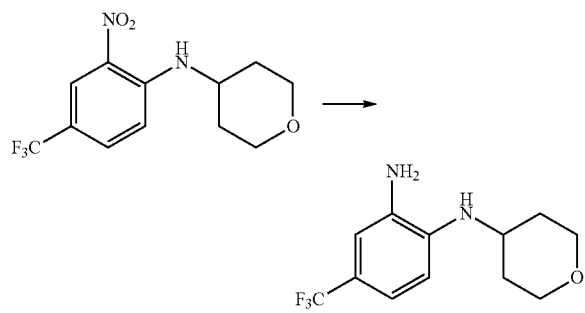

A 3-neck flask (200 mL) was charged with 1-(tetrahydropyran-4-yl)amino-2-nitro-4-trifluoromethylbenzene (see Synthesis Example 4-1) (1.00 g, 3.45 mmol) and tetrahydrofuran (17 mL), and this was shaken to give a homogeneous solution. To this was added palladium-carbon (Pd: 10%, 0.09 g), and this was again shaken. Hydrogen was substituted in by successively reducing the pressure and purging with hydrogen gas 3 times, and after vigorous shaking at room temperature under these conditions for 4 h, this was purged with nitrogen, distilled water (40 mL) was added and this was shaken for 10 minutes, then insoluble material was filtered off through a Celite layer (20 mm thickness), and this same layer was further washed with ethyl acetate. The filtrate and wash solutions were combined and the solvent was distilled off under reduced pressure to yield the title compound (0.66 g, 73.6% yield) as a white powder.

$^1$H-NMR (CDCl$_3$) δ (ppm): 1.53-1.57 (m, 2H), 2.04-2.07 (m, 2H), 3.35 (brs, 2H), 3.51-3.58 (m, 3H), 3.65 (brs, 1H), 4.00-4.05 (m, 2H), 6.65 (d, 1H, J=8.3 Hz), 6.95 (d, 1H, J=1.9 Hz), 7.07 (dd, 1H, J=8.3, 1.1 Hz).

Synthesis Example 5

Synthesis of 5-(benzoxazol-2-yl)-1,2-dimethylbenzimidazole

Synthesis Example 5-1

Synthesis of (2-methylaminoaniln-5-yl)benzoxazole

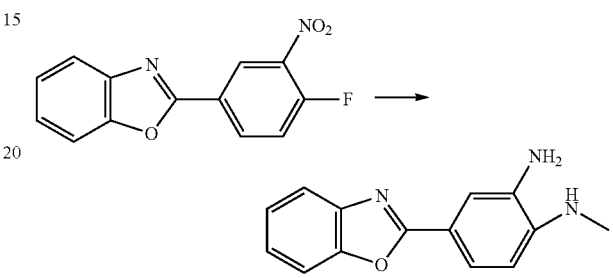

2-(4-fluoro-3-nitrophenyl)benzoxazole (see Working Example 15-2) (300 mg, 1.2 mmol) was added to an ethanol solution (5 mL) containing potassium carbonate (50 mg, 3.5 mmol) and 40% aqueous monomethylamine solution (270 mg, 3.5 mmol), and this was heated to reflux for 2 hours with stirring. After the reaction was complete, this was cooled to room temperature, and the crystals precipitated by the addition of water were filtered. After the crystals were washed with water, they were dried under reduced pressure with heating to give crystals that were added to a solution of a 1:1 solvent mixture of methanol:tetrahydrofuran (20 mL) including 10% palladium-carbon (50 mg). A hydrogen atmosphere was substituted in the flask and was stirred at room temperature for 8 hours. After the reaction was complete, this was filtered through Celite and the filtrate was concentrated. The residue obtained was purified by silica gel column chromatography to yield the title compound (80 mg, 53% yield) as light red crystals.

$^1$H-NMR (CDCl$_3$) δ (ppm): 2.95 (3H, s), 6.71 (1H, d, J=8.2 Hz), 7.24-7.34 (3H, m), 7.50-7.53 (1H, m), 7.63 (1H, d, J=1.8 Hz), 7.69-7.72 (1H, m), 7.80 (1H, dd, J=8.2, 1.8 Hz).

Synthesis Example 5-2

Synthesis of 5-(benzoxazol-2-yl)-1,2-dimethylbenzimidazole

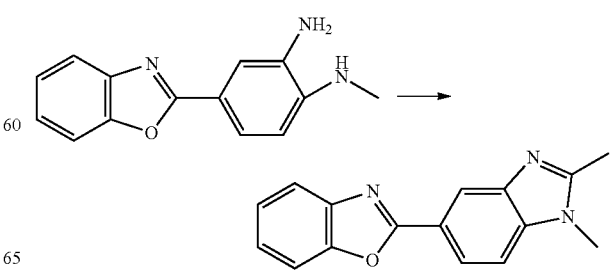

(2-Methylaminoaniln-5-yl)benzoxazole (see Synthesis Example 5-2) (75 mg, 0.31 mmol) was dissolved in DMF (2 mL), and to this was added 90% aqueous acetaldehyde solution (46 mg, 0.94 mmol) and then oxone (192 mg, 0.31 mmol), and this was stirred at room temperature for 2 hours. Aqueous potassium carbonate solution (0.10 g/15 mL) was added to the reaction solution. This was extracted with chloroform, washed with water, and after drying over magnesium sulfate, this was concentrated and purified by silica gel column chromatography. The crystals obtained were washed with hexane and a small amount of ethyl acetate, and dried to yield the title compound (50.3 mg, 61% yield) as light brown crystals.

$^1$H-NMR (CDCl$_3$) δ (ppm): 2.66 (3H, s), 3.78 (3H, s), 7.33-7.35 (2H, m), 7.41 (1H, d, J=8.6 Hz), 7.59-7.62 (1H, m), 7.74-7.80 (1H, m), 8.22 (1H, dd, J=8.6, 1.4 Hz), 8.56 (1H, d, J=1.4 Hz).

Synthesis Example 6

Synthesis of 5-(benzoxazol-2-yl)-2-methylbenzimidazole methanesulfonate

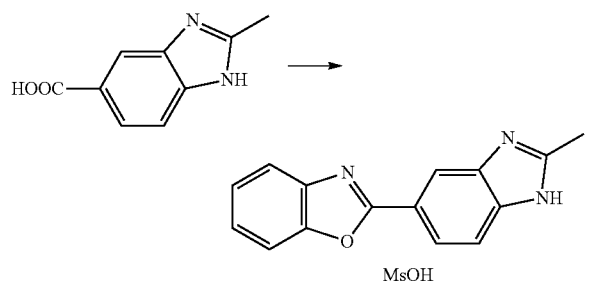

2-Methylbenzimidazole-5-carboxylic acid (1.00 g, 5.7 mmol), 2-aminophenol (0.68 g, 6.2 mmol), chloroform (20 mL), triethylamine (0.69 g, 6.8 mmol), and WSC (1.20 g, 6.2 mmol) were stirred overnight at room temperature. After the reaction was complete, water (50 mL) was added to the residue from concentration, and this was extracted with ethyl acetate. After the organic layer was dried over anhydrous sodium sulfate, filtration and concentration gave crystals that were dissolved in dioxane (30 mL), to which methanesulfonic acid (0.48 mL) was added and this was stirred at reflux for 10 hours. After cooling a precipitated solid was filtered off, and washing with THF and drying under reduced pressure at 50° C. yielded the title compound (0.82 g, 42% yield) as a white solid.

$^1$H-NMR (DMSO-d$_6$) δ: 2.36 (3H, s), 2.83 (3H, s), 7.42-7.51 (2H, m), 7.83-7.86 (2H, m), 7.98 (1H, d, J=8.6 Hz), 8.33 (1H, d, J=8.6 Hz), 8.52 (1H, s).

Synthesis Example 7

Synthesis of 5-(benzoxazol-2-yl)-1-ethyl-2-methylbenzimidazole

Synthesis Example 7-1

Synthesis of 2-(4-ethylamino-3-nitrophenyl)benzoxazole

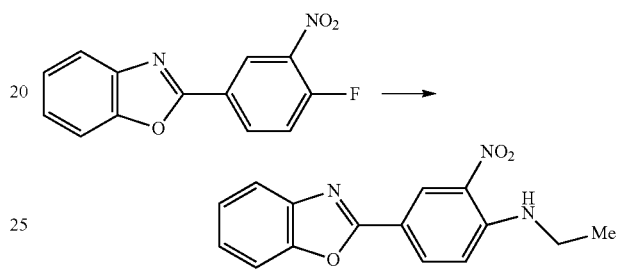

To a suspension of 2-(4-fluoro-3-nitrophenyl)benzoxazole (see Working Example 15-2) (300 mg, 1.16 mmol) in ethanol (5 mL) was added potassium carbonate (321 mg, 2.32 mmol) and aqueous ethylamine solution (ca. 70%, 149 mg, 2.32 mmol), and this was heated to reflux for 4 hours. After the reaction was complete, this was cooled to room temperature, water was added, and after the precipitated crystals were filtered and washed with water, they were dried to yield the title compound (310 mg, 94.3% yield).

$^1$H-NMR (CDCl$_3$) δ: 1.43 (3H, t, J=7.3 Hz), 3.45 (2H, ddd, J=14.3, 7.2, 5.2 Hz), 6.99 (1H, d, J=9.1 Hz), 7.32-7.36 (2H, m), 7.55-7.58 (1H, m), 7.71-7.74 (1H, m), 8.27-8.31 (2H, m), 9.05 (1H, d, J=2.1 Hz).

Synthesis Example 7-2

2-(2-Ethylaminoanilin-5-yl)benzoxazole

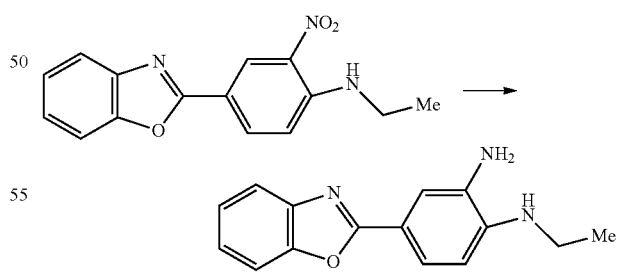

To a tetrahydrofuran solution (5 mL) of the nitro compound (300 mg, 1.06 mmol) was added 10% palladium-carbon (50 mg), and the flask was put under a hydrogen atmosphere and stirred at room temperature for 15 hours. After the reaction was complete, this was filtered through Celite and the filtrate was concentrated. The residue obtained was purified by silica gel column chromatography to yield the title compound (246 mg, 92% yield).

¹H-NMR (CDCl₃) δ: 1.35 (3H, t, J=7.2 Hz), 3.26 (2H, q, J=7.1 Hz), 6.71 (1H, d, J=8.4 Hz), 7.24-7.33 (2H, m), 7.50-7.79 (4H, m).

5-(Benzoxazol-2-yl)-1-ethyl-2-methylbenzimidazole

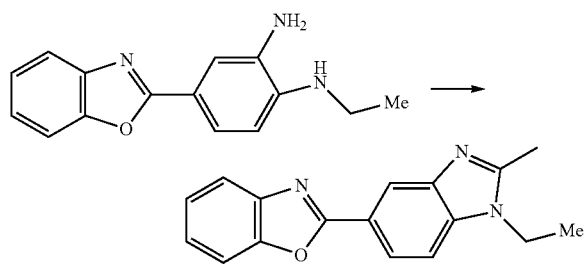

To a methanol solution (5 mL) of the amine compound (248 mg, 0.979 mmol) was added methyl acetimidate hydrochloride (161 mg, 1.47 mmol), and this was heated to reflux for 3 hours. After the reaction was complete, saturated aqueous sodium hydrogen carbonate solution was added, and this was extracted with chloroform. After the organic layer obtained was dried over anhydrous sodium sulfate, it was filtered and concentrated. The crystals obtained were purified by silica gel column chromatography to yield the title compound (230 mg, 83% yield) as pink crystals.

¹H-NMR (CDCl₃) δ: 1.45 (3H, t, J=7.3 Hz), 2.65 (3H, s), 4.20 (2H, q, J=7.3 Hz), 7.26-7.43 (3H, m), 7.59-7.62 (1H, m), 7.75-7.79 (1H, m), 8.21 (1H, dd, J=8.6, 1.5 Hz), 8.56 (1H, s).

Working Example 1

Synthesis of 5-(benzothiazol-2-yl)-1-phenyl-2-(phenylmethoxy)methylbenzimidazole Working Example 1-1

Synthesis of 1-phenyl-2-(phenylmethoxy)methylbenzimidazole-5-carboxylic acid

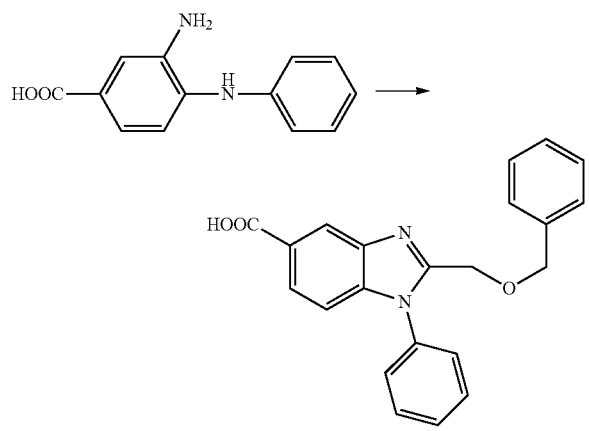

A 4-neck flask equipped with a reflux condenser was charged with 3-amino-4-phenylaminobenzoic acid (see Synthesis Example 1-2) (3.09 g, 13.54 mmol) and anhydrous toluene (45 mL) and this was refluxed. To this was added dropwise benzyloxyacetyl chloride (5 g, 27.08 mmol) in toluene solution (approx. 3 mL) over approx. 10 minutes. This was stirred under these conditions for 15 hours. This was allowed to cool to room temperature, and was extracted with dilute aqueous sodium hydroxide solution (10%, 100 mL). This was washed with toluene, and after separating the dark orange aqueous layer, this was cooled (5 to 10° C.), and concentrated hydrochloric acid (12 M) was added to the liquid to give pH 4. The precipitated crystals were filtered off, washed with distilled water, and dried under reduced pressure with heating to yield the title compound (4.21 g, 86.8% yield) as a light purple powder.

¹H-NMR (DMSO-d₆) δ (ppm): 4.46 (s, 2H), 4.71 (s, 2H), 7.14 (dd, 2H, J=7.9, 1.5 Hz), 7.25-7.32 (m, 4H), 7.58-7.68 (m, 5H), 7.91 (dd, 1H, J=8.6, 1.5 Hz), 8.33 (d, 1H, J=1.5 Hz), 12.90 (brs, 1H).

Working Example 1-2

Synthesis of 5-(benzothiazol-2-yl)-1-phenyl-2-(phenylmethoxy)methylbenzimidazole

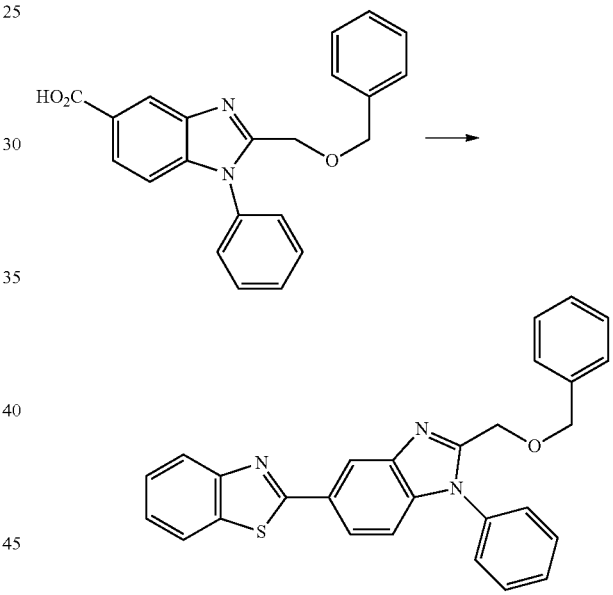

A 4-neck flask (500 mL) equipped with a reflux condenser was charged with 1-pheny-2-(phenylmethoxy)methylbenzimidazole-5-carboxylic acid (see Working Example 1-1) (4.00 g, 11.16 mmol) and anhydrous tetrahydrofuran (63 mL), and after the addition of oxalyl chloride (1.65 g, 13.0 mmol), this was warmed to 50° C. and stirred for 3 hours. After cooling to room temperature, the solvent was distilled off under reduced pressure. Anhydrous THF (30 mL) was again added to the greenish-milky white semisolid residue, and after gradual addition of 2-aminobenzenethiol (1.40 g, 11.22 mmol), this was warmed to 50° C. and stirred for 16 hours. After cooling to room temperature, the precipitated crystals were filtered off and washed with saturated aqueous sodium hydrogen carbonate solution (approx. 20 mL), and the precipitated solid was filtered off to yield a mixture of starting material and the title compound (2.43 g, an approx. 1:1 mixture of starting material/title compound, based on ¹H-NMR). The filtrate was allowed to stand for a further 16 hours at room temperature and the precipitated crystals were filtered off, washed with saturated aqueous potassium carbonate solution, washed with distilled water, and then dried under reduced pressure with heating to yield the title compound (0.82 g, 16% yield) as a white powder.

$^1$H-NMR (DMSO-d$_6$) δ (ppm): 4.48 (s, 2H), 4.72 (s, 2H), 7.16 (dd, 2H, J=7.9, 1.9 Hz), 7.27-7.33 (m, 3H), 7.38 (d, 1H, J=8.5 Hz), 7.46 (dt, 1H, J=8.1, 1.1 Hz), 7.55 (dt, 1H, 8.3, 1.1 Hz), 7.60-7.70 (m, 5H), 8.06 (d, 1H, J=7.8 Hz), 8.08 (dd, 1H, J=8.5, 1.7 Hz), 8.14 (d, 1H, J=7.5 Hz), 8.44 (d, 1H, J=1.3 Hz).

Working Example 2

Synthesis of 5-(benzothiazol-2-yl)-2-hydroxymethyl-1-phenylbenzimidazole

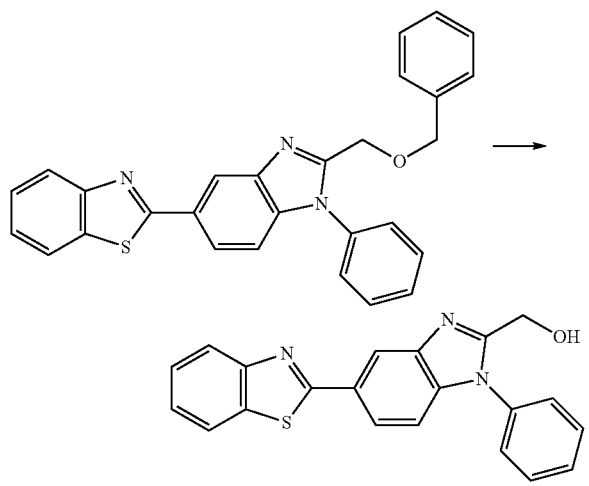

An eggplant flask (50 mL) equipped with a reflux condenser was charged with 5-(benzothiazol-2-yl)-1-phenyl-2-(phenylmethoxy)methylbenzimidazole (see Working Example 1-2) (0.40 g, 0.89 mmol) and dilute hydrochloric acid (6 M, 5 mL), and this was refluxed for 2 hours. When the pale yellow clear solution obtained was cooled in ice, it became a milky white suspension. The precipitated crystals were filtered off, washed successively with distilled water, and then t-butyl methyl ether, and dried under reduced pressure to yield the title compound (0.30 g, 94% yield) as a white powder.

$^1$H-NMR (DMSO-d$_6$) δ (ppm): 4.73-4.77 (m, 2H), 7.49 (d, 1H, J=8.6 Hz), 7.49 (t, 1H, J=7.3 Hz), 7.58 (t, 1H, J=7.2 Hz), 7.64-7.77 (m, 5H), 8.10 (d, 1H, J=8.2 Hz), 8.15 (dd, 1H, J=8.6, 1.6 Hz), 8.17 (d, 1H, J=8.1 Hz), 8.45-8.50 (m, 1H).

Working Example 3

Synthesis of 5-(benzothiazol-2-yl)-2-(N,N-dimethylamino)methyl-1-phenylbenzimidazole

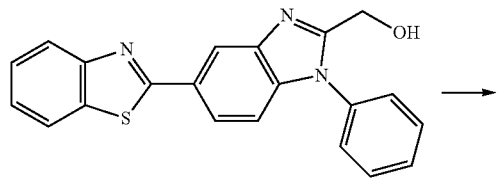

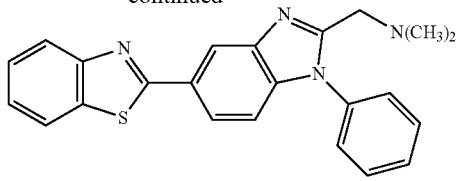

A 2-neck flask (20 mL) was charged with 5-(benzothiazol-2-yl)-2-hydroxymethyl-1-phenylbenzimidazole (Working Example 2) (0.24 g, 0.67 mmol) and anhydrous dichloromethane (3 mL), and this was cooled (5 to 10° C.). To this was added dropwise thionyl chloride (0.114 g, 0.96 mmol). This was stirred at room temperature for 10 minutes, then anhydrous N,N-dimethylformamide (3 drops) was added, and this was then refluxed for 1 hour. This was allowed to cool to room temperature, and the corresponding chloride was prepared as a greenish milky-white solid by distilling off the solvent under reduced pressure. To this was added anhydrous tetrahydrofuran (3 mL), and a solution of dimethylamine in tetrahydrofuran (2.0 M, 1.1 mL) was then added dropwise. This was warmed to 40° C. and stirred for 2 hours. This was allowed to cool to room temperature, the solvent was distilled off under reduced pressure, and the residue was extracted with ethyl acetate (50 mL, 2 times). This was washed with saturated aqueous sodium hydrogen carbonate solution (approx. 30 mL, 2 times), then with distilled water (approx. 30 mL), dried over anhydrous sodium sulfate. The solvent was distilled off under reduced pressure to give a pale yellow residue (0.25 g) from which an adsorbed powder was prepared using silica gel/chloroform (0.5 g). This was purified by silica gel column chromatography (silica gel: 10 g; CHCl$_3$/MeOH=20/1) and further isolated by PTLC to yield the title compound (0.008 g, 2.9%) as pale yellow crystals.

$^1$H-NMR (CDCl$_3$) δ (ppm): 2.31 (s, 6H), 3.59 (s, 2H), 7.28 (d, 1H, J=8.6 Hz), 7.37 (dt, 1H, J=7.6, 1.1 Hz), 7.49 (dt, 1H, J=7.7, 1.1 Hz), 7.50-7.66 (m, 5H), 7.90 (d, 1H, J=7.9 Hz), 8.06 (d, 1H, J=8.1 Hz), 8.11 (d, 1H, J=8.5 Hz), 8.48 (s, 1H).

Working Example 4

Synthesis of 5-(benzothiazol-2-yl)-2-methyl-1-(tetrahydropyran-4-yl)benzimidazole Working Example 4-1

Synthesis of 4-((tetrahydropyran-4-yl)amino)-3-nitrobenzoic acid

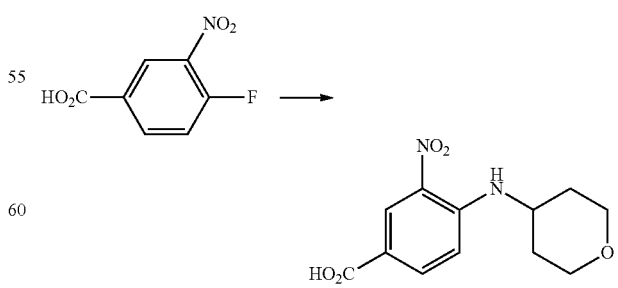

4-Fluoro-3-nitrobenzoic acid (126.4 g, 0.68 mol) was dissolved in ethanol (880 mL). Triethylamine (82.6 g, 0.82 mol), 4-aminotetrahydropyran (82.7 g, 0.81 mol) were added in turn dropwise, and after the additions the reaction solution was heated to reflux. After refluxing for 5 h, triethylamine (8.3 g, 82 mmol), aminotetrahydropyran (8.3 g, 81 mmol) were added, and this was refluxed for a further 9 hours. After the reaction mixture was allowed to cool to room temperature, 2N HCl (880 mL) and water (880 mL) were added and after stirring for awhile, the solid obtained was filtered off. This was forced air-dried at 60° C. to yield the title compound (183.3 g, quant.) as a yellow solid.

$^1$H-NMR (DMSO-d$_6$) δ (ppm): 1.55-1.70 (2H, m), 1.95 (2H, d, J=10.9 Hz), 3.44-3.53 (2H, m), 3.84-4.01 (3H, m), 7.27 (1H, d, J=9.2 Hz), 7.96 (1H, dd, J=9.2, 2.0 Hz), 8.21 (1H, d, J=7.7 Hz), 8.62 (1H, d, J=2.0 Hz).

Working Example 4-2

Synthesis of 3-amino-4-((tetrahydropyran-4-yl)amino)benzoic acid

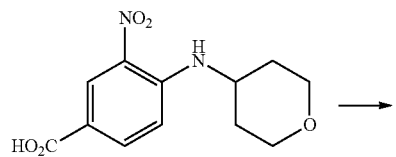

4-((Tetrahydropyran-4-yl)amino)-3-nitrobenzoic acid (see Working Example 4-1) (202 g, 0.76 mol) was dissolved in a solvent mixture of THF (2.2 L) and methanol (1.5 L), Pd/C (5%, wet, 20 g) was added, and hydrogenation was carried out under 5 atm. Hydrogen absorption stopped at 3 h, and after the system was purged with argon the catalyst was removed by filtration, and the filtrate was concentrated at reduced pressure to yield the title compound (180 g, quant.) as a dark gray solid.

$^1$H-NMR (DMSO-d$_6$) δ (ppm): 1.36-1.51 (2H, m), 1.87-1.95 (2H, m), 3.38-3.48 (2H, m), 3.85-3.92 (2H, m), 4.92 (1H, d, J=6.1 Hz), 6.52 (1H, d, J=8.9 Hz), 7.16-7.20 (2H, m).

Working Example 4-3

Synthesis of 2-methyl-1-(tetrahydropyran-4-yl)benzimidazole-5-carboxylic acid HCl salt

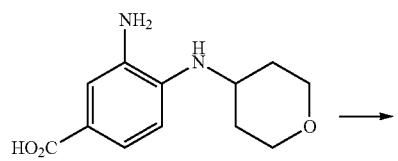

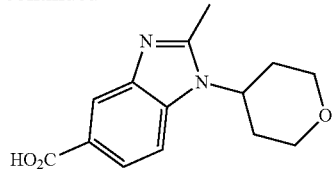

3-Amino-4-((tetrahydropyran-4-yl)amino)benzoic acid (see Working Example 4-2) (90 g, 0.38 mol) was dissolved in dioxane (900 mL), and after cooling to 10° C., a solution of acetyl chloride (35.0 g, 0.45 mol) in dioxane (900 mL) was added dropwise over the course of 35 minutes. After heating to reflux with stirring for 2.5 h, another solution of acetyl chloride (15.8 g, 0.20 mol) in dioxane (200 mL) was added to the reaction solution, and this was further heated to reflux with stirring for 3 hours. Next, a 4N HCl dioxane solution (100 mL) was added, and after heating to reflux with stirring for 8 h, this was allowed to cool to room temperature, the solid obtained was filtered off and washed with hexane to yield the title compound (105 g, quant.) as a light purple solid.

$^1$H-NMR (DMSO-d$_6$) δ (ppm): 1.95-2.02 (2H, m), 2.49-2.52 (2H, m), 2.96 (3H, s), 3.53-3.64 (2H, m), 4.06 (2H, dd, J=11.6, 3.9 Hz), 4.82-4.91 (1H, m), 8.04 (1H, dd, J=8.8, 1.3 Hz), 8.15 (1H, d, J=8.8 Hz), 8.27 (1H, d, J=1.3 Hz).

Working Example 4-4

Synthesis of 5-(benzothiazol-2-yl)-2-methyl-1-(tetrahydropyran-4-yl)benzimidazole

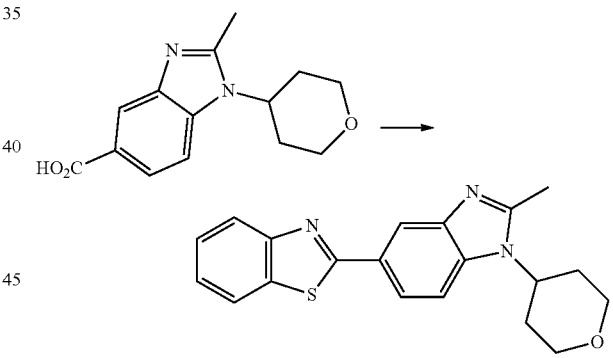

A 4-neck flask (50 mL) equipped with reflux condenser was charged with 2-methyl-1-(tetrahydropyran-4-yl)benzimidazole-5-carboxylic acid HCl salt (see Working Example 4-3) (0.28 g, 1.08 mmol), 2-aminobenzenethiol (0.14 g, 1.08 mmol) and polyphosphoric acid (approx. 11 g), and this was heated to 150° C. and stirred for 17 hours. After being allowed to cool to room temperature, this was cooled in ice (0 to 5° C.), and concentrated aqueous ammonia (28%) was added to the liquid to give approx. pH 9. After distilling off the solvent under reduced pressure, the brown viscous residue was extracted with ethyl acetate, this was dried over anhydrous magnesium sulfate. The residue obtained after again distilling off the solvent under reduced pressure was purified by PTLC to yield the title compound (0.007 g, 1.8% yield) as greenish-pale yellow crystals.

$^1$H-NMR (CDCl$_3$) δ (ppm): 1.87-1.91 (m, 2H), 2.55-2.65 (m, 2H), 2.70 (s, 3H), 3.57-3.64 (m, 2H), 4.21-4.25 (m, 2H), 4.40-4.50 (m, 1H), 7.37 (dt, 1H, J=7.2, 1.1 Hz), 7.48 (dt, 1H, J=8.3, 1.1 Hz), 7.63 (d, 1H, J=8.6 Hz), 7.91 (d, 1H, J=8.0 Hz), 8.07 (d, 1H, J=8.6 Hz), 8.08 (d, 1H, J=8.6 Hz), 8.35 (d, 1H, J=1.8 Hz).

Working Example 5

Synthesis of 5-(benzothiazol-2-yl)-2-methyl-1-(tetrahydropyran-4-yl)benzimidazole methanesulfonate

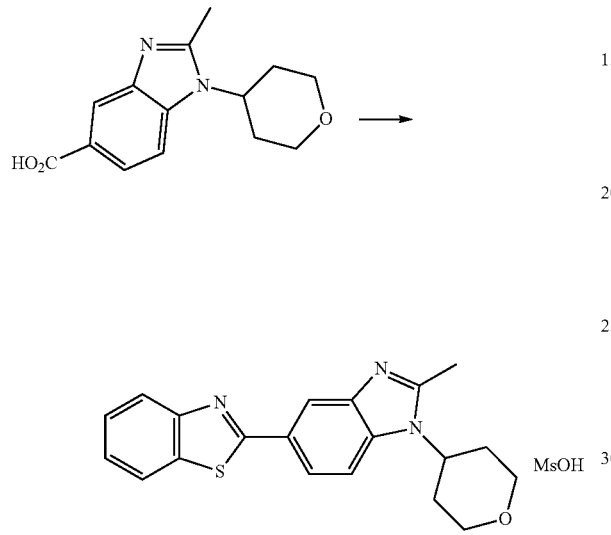

2-methyl-1-(tetrahydropyran-4-yl)benzimidazole-5-carboxylic acid HCl salt (43.0 g, 0.17 mol), toluene (400 mL), thionyl chloride (39.3 g, 0.33 mol) and DMF (1.3 g) were heated to 90° C. under a stream of argon. After stirring for 4 h, the solvent was concentrated under reduced pressure. This was suspended in a solvent mixture of toluene (250 mL) and THF (150 mL), and a solution of 2-aminothiophenol (20.7 g, 0.17 mol) in toluene (100 mL) was added dropwise over 25 m at 0° C. More toluene (100 mL) and THF (900 mL) were added, and this was stirred at room temperature for 24 hours. Then, more 2-aminothiophenol (30.7 g, 0.25 mol) was added, and this was stirred for 16 hours. The reaction mixture was filtered and washed with ethyl acetate, and the solid obtained was dissolved in water (1 L) to which was chloroform (1 L) was added, and the aqueous layer was made alkaline (pH=10) with a 24% aqueous NaOH solution. More chloroform (1 L) was added and the layers were separated, and after the chloroform layer was washed with water (500 mL), it was dried with $Na_2SO_4$. After filtration, the solvent was concentrated under reduced pressure and the residue was purified by silica gel column chromatography ($SiO_2$: 800 g; chloroform/methanol=50/1 to 30/1) to give a solid (29.7 g). This was dissolved in a solvent mixture of methanol (100 mL) and chloroform (150 mL), and methanesulfonic acid (24.6 g) was added. After stirring for awhile, ethyl acetate (100 mL) was added and this was cooled, the crystals obtained were filtered off and washed with ethyl acetate/methanol, and dried at reduced pressure at 40° C. to yield the title compound (22.0 g, 29.9% yield) as a slightly greenish-gray solid.

$^1$H-NMR (DMSO-$d_6$) δ (ppm): 1.99-2.07 (2H, m), 2.36 (3H, s), 2.39-2.52 (2H, m), 2.95 (3H, s), 3.61 (2H, t, J=11.4 Hz), 4.09 (2H, dd, J=11.4 3.8 Hz), 4.85-4.96 (1H, m), 7.48-7.63 (2H, m), 8.12 (1H, d, J=7.4 Hz), 8.18-8.24 (3H, m), 8.46 (1H, d, J=1.2 Hz).

Working Example 6

Synthesis of 5-(benzothiazol-2-yl)-2-methoxymethyl-1-(tetrahydropyran-4-yl)benzimidazole

Working Example 6-1

Synthesis of 2-methoxymethyl-1-(tetrahydropyran-4-yl)-5-trifluoromethylbenzimidazole

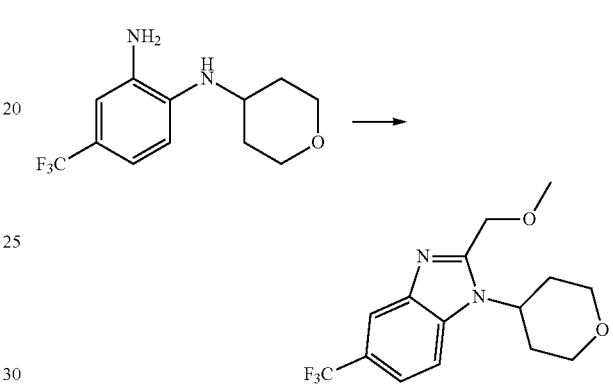

A 4-neck flask equipped with a reflux condenser was charged with 2-amino-1-(tetrahydropyran-4-yl)amino-4-trifluoromethylbenzene (see Synthesis Example 4) (0.62 g, 2.38 mmol) and anhydrous 1,4-dioxane (8.5 mL) and this was refluxed. Methoxyacetyl chloride (0.57 g, 5.25 mmol) in 1,4-dioxane solution (approx. 1.5 mL) was added dropwise to this over approximately 10 m. This was stirred under these conditions for 2 hours. This was allowed to cool, distilled water was added, and the solvent was distilled off under reduced pressure. This was successively extracted with t-butyl methyl ether, washed with brine, and dried over anhydrous sodium sulfate, the solvent was distilled off under reduced pressure to yield the title compound (0.58 g, 77.4% yield) as a white powder.

$^1$H-NMR (DMSO-$d_6$) δ (ppm): 1.89-1.92 (m, 2H), 2.37-2.50 (m, 2H), 3.40 (s, 3H), 3.50-3.58 (m, 2H), 4.04-4.08 (m, 2H), 4.75-4.85 (m, 1H), 4.95 (s, 2H), 7.68 (dd, 1H, J=8.7, 1.5 Hz), 8.07 (s, 1H), 8.12 (d, 1H, J=8.7 Hz).

Working Example 6-2

Synthesis of 5-(benzothiazol-2-yl)-2-methoxymethyl-1-(tetrahydropyran-4-yl)benzimidazole

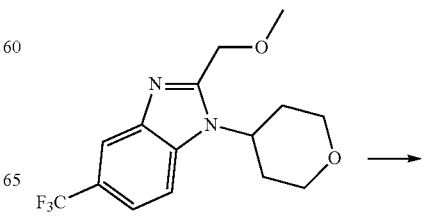

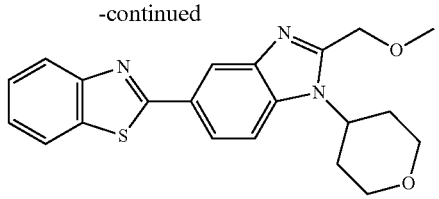

An eggplant flask was charged with 2-methoxymethyl-1-(tetrahydropyran-4-yl)-5-trifluoromethylbenzimidazole (see Working Example 6-1) (0.102 g, 0.32 mmol), 2-aminobenzenethiol (0.041 g, 0.33 mmol) and polyphosphoric acid (approx. 2 g), and this was heated to 120° C. and stirred for 48 hours. After being allowed to cool, ice was added and concentrated aqueous ammonia (28%) was added to the liquid to give approx. pH 9. Chloroform extraction, drying over anhydrous magnesium sulfate, and the solvent being distilled off gave a crude product (0.21 g), which was purified by silica gel column chromatography (MeOH/CHCl$_3$=1/20) to yield the title compound (0.010 g, 8.1% yield) as a pale yellow powder.

$^1$H-NMR (CDCl$_3$) δ (ppm): 1.90-1.94 (m, 2H), 2.58-2.70 (m, 2H), 3.41 (s, 3H), 3.58-3.65 (m, 2H), 4.20-4.24 (m, 2H), 4.69-4.78 (m, 1H), 4.81 (s, 2H), 7.38 (dt, 1H, J=8.1, 1.1 Hz), 7.49 (dt, 1H, J=7.5, 1.2 Hz), 7.72 (d, 1H, J=8.8 Hz), 7.90 (d, 1H, J=8.0 Hz), 8.08 (d, 1H, J=7.7 Hz), 8.14 (dd, 1H, J=8.7, 1.7 Hz), 8.42 (d, 1H, J=1.4 Hz).

Working Example 7

Synthesis of 2-acetoxymethyl-5-(benzothiazol-2-yl)-1-(tetrahydropyran-4-yl)benzimidazole Working Example 7-1

Synthesis of 2-acetoxymethyl-1-(tetrahydropyran-4-yl)benzimidazole-5-carboxylic acid

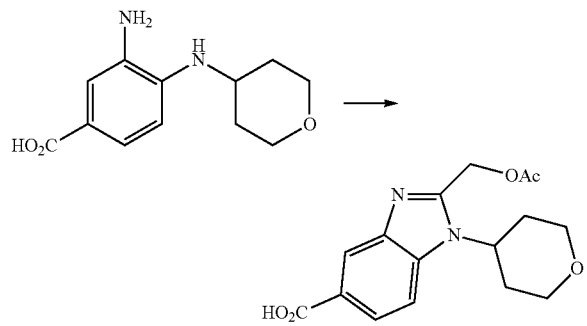

A 4-neck flask (1 L) equipped with a reflux condenser was charged with 3-amino-4-((tetrahydropyran-4-yl)amino)benzoic acid (14.53 g, 45.65 mmol) and anhydrous 1,4-dioxane (226 mL) and this was refluxed. Acetoxyacetyl chloride (12.57 g, 92.07 mmol) in 1,4-dioxane solution (100 mL) was added dropwise to this over approx. 15 minutes. This was stirred under these conditions for 13 hours. This was allowed to cool to room temperature, and after the precipitated crystals were filtered off, they were washed with distilled water, and dried under reduced pressure with heating to yield the title compound (13.46 g, 92.6% yield) as a white solid.

$^1$H-NMR (DMSO-d$_6$) δ (ppm): 1.89-1.92 (m, 2H), 2.13 (s, 3H), 2.38-2.46 (m, 2H), 3.53-3.59 (m, 2H), 4.03-4.07 (m, 2H), 4.70-4.82 (m, 1H), 5.52 (s, 2H), 7.94-7.96 (m, 2H), 8.26 (s, 1H).

Working Example 7-2

Synthesis of 2-acetoxymethyl-5-(benzothiazol-2-yl)-1-(tetrahydropyran-4-yl)benzimidazole

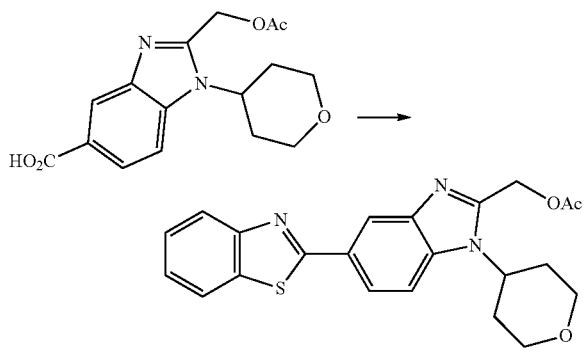

A 4-neck flask (500 mL) equipped with a reflux condenser was charged with 2-acetoxymethyl-1-(tetrahydropyran-4-yl)benzimidazole-5-carboxylic acid (5.98 g, 18.79 mmol), anhydrous tetrahydrofuran (158 mL), and oxalyl chloride (2.86 g, 22.50 mmol), and anhydrous N,N-dimethylformamide (1 mL) was then added dropwise at room temperature, after which the reaction mixture was stirred at 50° C. for 5 hours. After being allowed to cool to room temperature, the solvent was distilled off under reduced pressure to give a pale yellow residue, which was taken up in anhydrous tetrahydrofuran (100 mL), and then 2-aminobenzenethiol (2.35 g, 18.79 mmol) was added, and this was stirred for 19 hours at 50° C. This was allowed to cool to room temperature, and after the precipitated crystals were filtered off, they were successively washed with distilled water and dried under reduced pressure with heating to yield the title compound (9.00 g, quant.) as a white solid.

$^1$H-NMR (CDCl$_3$) δ (ppm): 1.90-1.94 (m, 2H), 2.15 (s, 3H), 2.59-2.70 (m, 2H), 3.56-3.62 (m, 2H), 4.21-4.30 (m, 2H), 4.52-4.62 (m, 1H), 5.45 (s, 2H), 7.38 (dt, 1H, J=7.6, 1.1 Hz), 7.49 (dt, 1H, J=7.7, 1.2 Hz), 7.72 (d, 1H, J=8.7 Hz), 7.90 (d, 1H, J=8.0 Hz), 8.07 (d, 1H, J=8.1 Hz), 8.16 (dd, 1H, J=8.6, 1.7 Hz), 8.45 (d, 1H, J=1.4 Hz).

Working Example 8

Synthesis of 5-(benzothiazol-2-yl)-2-hydroxymethyl-1-(tetrahydropyran-4-yl)benzimidazole

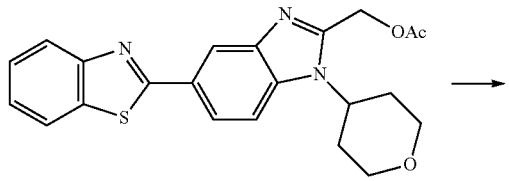

-continued

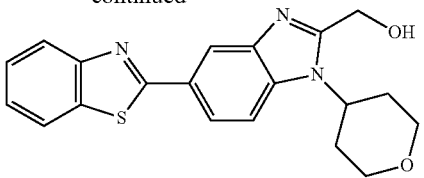

A 4-neck flask (1 L) was charged with 2-acetoxymethyl-5-(benzothiazol-2-yl)-1-(tetrahydropyran-4-yl)benzimidazole (see Working Example 7-2) (5.00 g, 12.27 mmol), and methanol (253 mL), and an aqueous lithium hydroxide solution (1.0 M, 61 mL) was added at room temperature. After stirring under these conditions for 2 h, this was cooled in ice (0 to 10° C.) and dilute hydrochloric acid was added to the liquid to give an approximate pH of 5. The precipitated crystals were filtered off, washed with distilled water, and then dried under reduced pressure with heating to yield the title compound (4.28 g, 95.4% yield) as a greenish-white powder.

$^1$H-NMR (DMSO-$d_6$) δ (ppm): 2.00-2.03 (m, 2H), 2.38-2.45 (m, 2H), 3.55-3.61 (m, 2H), 4.06-4.10 (m, 2H), 4.82-4.86 (m, 1H), 5.12 (s, 2H), 7.50 (dt, 1H, J=8.1, 1.2 Hz), 7.59 (dt, 1H, J=8.3, 1.3 Hz), 8.12 (d, 1H, J=7.8 Hz), 8.15-8.23 (m, 3H), 8.42 (s, 1H).

Working Example 9

Synthesis of 5-(benzothiazol-2-yl)-2-(N,N-dimethylaminomethyl)-1-(tetrahydropyran-4-yl)benzimidazole

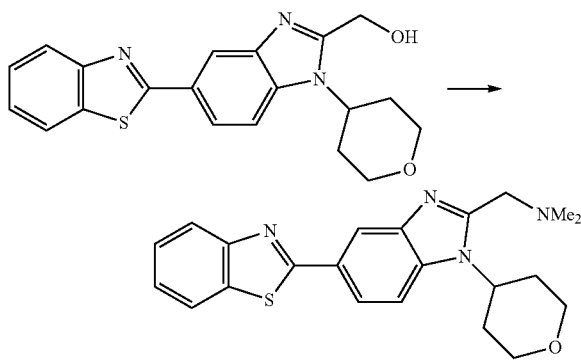

An eggplant flask was charged with 5-(benzothiazol-2-yl)-2-hydroxymethyl-1-(tetrahydropyran-4-yl)benzimidazole (see Working Example 8) (0.431 g, 1.179 mmol), oxalyl chloride (0.178 g, 1.40 mmol), and anhydrous dichloromethane (22 mL), and after the addition of anhydrous N,N-dimethylformamide (5 drops) at room temperature, this was refluxed for 3.5 hours. After cooling to room temperature, the solvent was distilled off under reduced pressure. To the yellow residue was added anhydrous tetrahydrofuran (1 mL) and anhydrous sodium iodide (0.267 g, 1.78 mmol), followed by a tetrahydrofuran solution of dimethylamine (2.0 M, 5 mL), and this was refluxed for 16 hours. After being allowed to cool to room temperature, the solvent was distilled off under reduced pressure. An adsorbed silica gel powder was prepared from the yellow residue (0.8 g) using chloroform (approx. 30 mL) and silica gel (3.2 g), and this was purified by silica gel column chromatography (silica gel: 32 g, MeOH/CHCl$_3$=1/20) to yield the title compound (0.176 g, 38.0% yield) as a pale yellow powder.

$^1$H-NMR (CDCl$_3$) δ (ppm): 1.86-1.90 (m, 2H), 2.29 (s, 6H), 2.55-2.66 (m, 2H), 3.53-3.61 (m, 2H), 3.76 (s, 2H), 4.18-4.23 (m, 2H), 4.84-4.93 (m, 1H), 7.35 (t, 1H, J=7.3 Hz), 7.48 (t, 1H, J=7.4 Hz), 7.69 (d, 1H, J=8.6 Hz), 7.89 (d, 1H, J=7.8 Hz), 8.06 (d, 1H, J=7.9 Hz), 8.11 (dd, 1H, J=8.6, 1.4 Hz), 8.38 (d, 1H, J=1.5 Hz).

Working Example 10

Synthesis of 5-(benzothiazol-2-yl)-2-(N,N-dimethylaminomethyl)-1-(tetrahydropyran-4-yl)benzimidazole hydrochloride

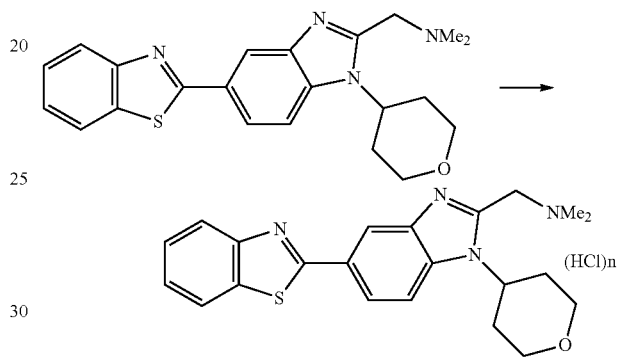

An eggplant flask was charged with 5-(benzothiazol-2-yl)-2-(N,N-dimethylaminomethyl)-1-(tetrahydropyran-4-yl)benzimidazole (see Working Example 9) (0.176 g, 0.448 mmol), anhydrous diethyl ether (1 mL), and anhydrous 1,4-dioxane (7 mL), and this was stirred at 0 to 5° C. To this was added slowly a solution of hydrogen chloride in diethyl ether (2.0 M, 2 mL), after which this was stirred under these conditions for 30 minutes. The generated crystals were filtered off, these were then washed with diethyl ether (approx. 2 mL, 3 times) and dried under reduced pressure to yield the title compound (0.186 g, 96.9% yield) as a pale yellow powder.

$^1$H-NMR (DMSO-$d_6$) δ (ppm): 1.95-2.02 (m, 2H), 2.35-2.55 (m, 2H), 3.01 (s, 6H), 3.56-3.65 (m, 2H), 4.02-4.11 (m, 2H), 4.71-4.85 (m, 1H), 4.93 (s, 2H), 7.46 (dt, 1H, J=7.6, 1.2 Hz), 7.56 (dt, 1H, J=7.7, 1.3 Hz), 8.01 (d, 1H, J=8.7 Hz), 8.06 (d, 1H, J=8.5 Hz), 8.08 (dd, 1H, J=8.5, 1.7 Hz), 8.15 (d, 1H, J=8.0 Hz), 8.37 (d, 1H, J=1.6 Hz), 10.95 (brs, 1H).

Working Example 11

Synthesis of 5-(benzoxazol-2-yl)-2-methyl-1-(tetrahydropyran-4-yl)benzimidazole

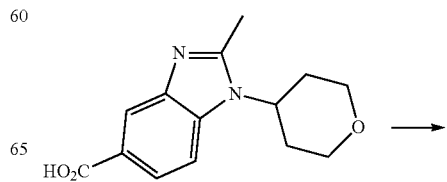

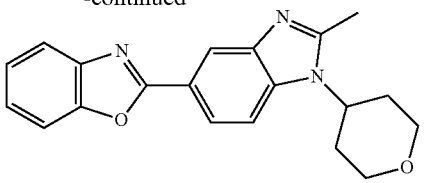

An eggplant flask (100 mL) was charged with 2-methyl-1-(tetrahydropyran-4-yl)benzimidazole-5-carboxylic acid HCl salt (see Working Example 4-3) (0.64 g, 2.46 mmol), 2-aminophenol (0.32 g, 2.95 mmol) and polyphosphoric acid (approx. 18 g), and this was heated to 160° C. and stirred for 17 hours. After being allowed to cool, ice was added and concentrated aqueous ammonia (28%) was added to the liquid to give approx. pH 9. This was extracted with chloroform (approx. 50 mL, 3 times) and dried over anhydrous magnesium sulfate. The crude product (0.08 g) obtained after the solvent was distilled off was purified by PTLC (CHCl$_3$) with double development to yield the title compound (0.002 g, 0.2% yield) as a yellowish-brown semisolid.

$^1$H-NMR (CDCl$_3$) δ (ppm): 1.88-1.92 (m, 2H), 2.58-2.68 (m, 2H), 2.70 (s, 3H), 3.57-3.64 (m, 2H), 4.21-4.25 (m, 2H), 4.43-4.49 (m, 1H), 7.29 (d, 1H, J=9.2 Hz), 7.33-7.35 (m, 2H), 7.59-7.62 (m, 1H), 7.76-7.78 (m, 1H), 8.18 (dd, 1H, J=8.6, 1.6 Hz), 8.57 (d, 1H, J=1.4 Hz).

Working Example 12

Synthesis of 5-(benzoxazol-2-yl)-2-methyl-1-(tetrahydropyran-4-yl)benzimidazole methanesulfonate

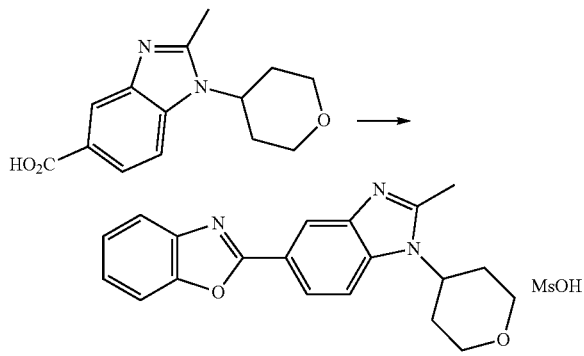

2-methyl-1-(tetrahydropyran-4-yl)benzimidazole-5-carboxylic acid HCl salt (see Working Example 4-3) (51.2 g, 0.19 mol), 2-aminophenol (24.0 g, 0.21 mol), anhydrous DMF (500 mL) and WSC (45.0 g, 0.23 mol) was stirred for 3 hours under an argon atmosphere. Water (2 L) was added, the solid obtained was filtered off, washed with water, After drying at reduced pressure at 50° C., an obtained solid (45.2 gm 0.13 mol) was dissolved in dioxane (500 mL). Methanesulfonic acid (62.5 g, 0.65 mol) was added thereto and this was stirred at 90° C. for 8 hours. The solvent was concentrated at reduced pressure, water (1 L) was added, and the pH was adjusted to 4 with 1N NaOH. Chloroform (2 L) was added for extraction, and then the aqueous layer was extracted with chloroform (1 L), these were combined and the organic layer was washed with brine (1 L). After MgSO$_4$ drying and filtration, the solvent was concentrated under reduced pressure.

The residue obtained was dissolved in chloroform (100 mL) and ethyl acetate (150 mL) and methanesulfonic acid (25.0 g) was added. After stirring awhile in the cold, the precipitated solid was filtered off and this was dried under reduced pressure at 50° C. to yield the title compound (23.7 g, 28.1% yield) as a light purple solid.

$^1$H-NMR (DMSO-d$_6$) δ (ppm): 1.99-2.07 (2H, m), 2.36 (3H, s), 2.39-2.51 (2H, m), 2.95 (3H, s), 3.61 (2H, t, J=11.4 Hz), 4.09 (2H, dd, J=11.4, 3.8 Hz), 4.87-4.96 (1H, m), 7.42-7.52 (2H, m), 7.82-7.89 (2H, m), 8.31-8.32 (2H, m), 8.54 (1H, s).

Working Example 13

Synthesis of 5-(benzoxazol-2-yl)-2-hydroxymethyl-1-(tetrahydropyran-4-yl)benzimidazole Working Example 13-1

Synthesis of 2-acetoxymethyl-5-(2-hydroxyanilinocarbonyl)-1-(tetrahydropyran-4-yl)benzimidazole

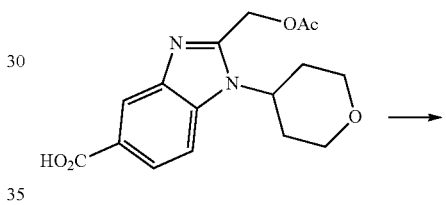

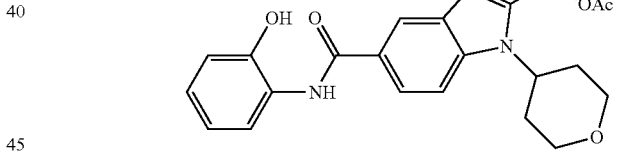

A 4-neck flask (200 mL) equipped with a reflux condenser was charged with 2-acetoxymethyl-1-(tetrahydropyran-4-yl)benzimidazole-5-carboxylic acid (see Working Example 7-1) (1.50 g, 4.71 mmol), anhydrous tetrahydrofuran (40 mL), and oxalyl chloride (0.657 g, 5.18 mmol), and anhydrous N,N-dimethylformamide (0.4 mL) was then added dropwise at room temperature, after which the reaction mixture was stirred at 50° C. for 14 hours. After being allowed to cool to room temperature, the solvent was distilled off under reduced pressure to give a pale yellow residue which was cooled to 0 to 5° C., which was taken up in anhydrous tetrahydrofuran (40 mL) and diisopropylamine (0.79 mL, 5.65 mmol), followed by 2-aminophenol (0.57 g, 5.81 mmol), and this was stirred for 24 hours at room temperature. The precipitated crystals were filtered off, these were washed with tetrahydrofuran and dried under reduced pressure with heating to yield the title compound (2.40 g, quant.) as a white powder.

$^1$H-NMR (DMSO-d$_6$) δ (ppm): 1.90-1.93 (m, 2H), 2.14 (s, 3H), 2.41-2.53 (m, 2H), 3.54-3.60 (m, 2H), 4.05-4.09 (m, 2H), 4.76-4.82 (m, 1H), 5.54 (s, 2H), 6.85 (dt, 1H, J=7.7, 1.5

Hz), 6.94 (dd, 1H, J=8.1, 1.4 Hz), 7.05 (dt, 1H, J=8.1, 1.4 Hz), 7.69 (dd, 1H, J=7.9, 1.5 Hz), 7.98-8.00 (m, 2H), 8.36 (s, 1H), 9.68 (s, 1H), 10.00 (brs, 1H).

Working Example 13-2

Synthesis of 5-(benzoxazol-2-yl)-2-hydroxymethyl-1-(tetrahydropyran-4-yl)benzimidazole

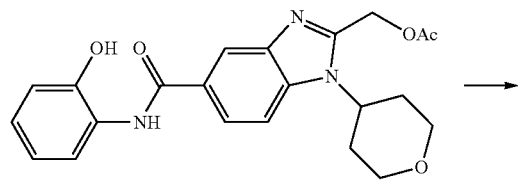

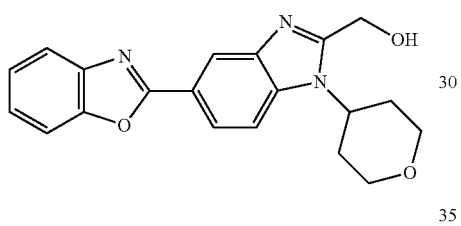

An eggplant flask (50 mL) was charged with 2-acetoxymethyl-5-(2-hydroxyanilinocarbonyl)-1-(tetrahydropyran-4-yl)benzimidazole (see Working Example 13-1) (0.50 g, 1.22 mmol) toluene (6.3 mL), and p-toluenesulfonic acid hydrate (1.60 g, 8.41 mmol), and this was refluxed for 1.5 hours. After being allowed to cool, the liquid was made neutral with saturated aqueous sodium hydrogen carbonate. The precipitated crystals were filtered off and washed successively with toluene and hexane, then dried under reduced pressure with heating to yield a mixture of the title compound and 5-(benzoxazol-5-yl)-2-acetoxymethyl-1-(tetrahydropyran-4-yl)benzimidazole (0.25 g: estimated to contain 0.57 mmol and 0.13 mmol, respectively, according to ¹H-NMR) as a white powder. This mixture and methanol (7 mL) were charged to an eggplant flask (50 mL) to which was then added an aqueous solution of lithium hydroxide (1 M, 0.3 mL), and after stirring for 30 m the liquid was made pH 6 with dilute hydrochloric acid (1 M). The precipitated crystals were filtered off, washed with distilled water, and dried under reduced pressure with heating to yield the title compound (0.07 g, 16.4% yield) as a light pinkish-white powder.

¹H-NMR (DMSO-d₆) δ (ppm): 1.99-2.02 (m, 2H), 2.40-2.50 (m, 2H), 3.54-3.60 (m, 2H), 4.06-4.10 (m, 2H), 4.82-4.89 (m, 1H), 5.09 (s, 2H), 7.41-7.49 (m, 2H), 7.82-7.88 (m, 2H), 8.23 (d, 1H, J=8.8 Hz), 8.29 (dd, 1H, J=8.8, 1.5 Hz), 8.48 (d, 1H, J=1.3 Hz).

Working Example 14

Synthesis of 5-(benzoxazol-2-yl)-2-(N,N-dimethylaminomethyl)-1-(tetrahydropyran-4-yl)benzimidazole

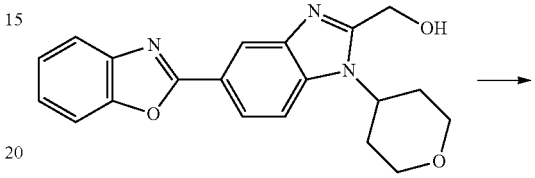

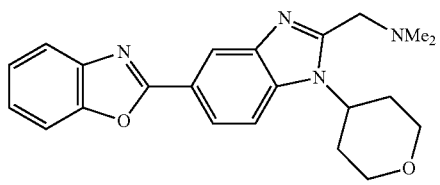

An eggplant flask (50 mL) equipped with a reflux condenser was charged with 5-(benzoxazol-2-yl)-2-hydroxymethyl-1-(tetrahydropyran-4-yl)benzimidazole (see Working Example 13) (0.055 g, 0.16 mmol), oxalyl chloride (0.024 g, 0.19 mmol), and anhydrous dichloromethane (3 mL), and after the addition of anhydrous N,N-dimethylformamide (5 drops) at room temperature, this was refluxed for 3.5 hours. After cooling to room temperature, the solvent was distilled off under reduced pressure. To the yellow residue was added anhydrous tetrahydrofuran (5 mL) and anhydrous sodium iodide (0.036 g, 0.24 mmol), followed by a tetrahydrofuran solution of dimethylamine (2.0 M, 3 mL), and this was refluxed for 14 hours. After being allowed to cool to room temperature, the solvent was distilled off under reduced pressure. The yellow residue (0.70 g) was purified by silica gel column chromatography (silica gel: 2.6 g; MeOH/CHCl₃=1/5) to yield the title compound (0.026 g, 43% yield) as a pale yellow powder.

¹H-NMR (acetone-d₆) δ (ppm): 2.07 (s, 6H), 2.10-2.16 (m, 2H), 2.54-2.63 (m, 2H), 3.76-3.80 (m, 2H), 3.79 (s, 2H), 4.06-4.10 (m, 2H), 5.02-5.08 (m, 1H), 7.38-7.46 (m, 2H), 7.70-7.75 (m, 1H), 7.75-7.80 (m, 1H), 8.06 (d, 1H, J=8.7 Hz), 8.27 (dd, 1H, J=8.7, 1.6 Hz), 8.56 (d, 1H, 1.3 Hz).

Working Example 15

Synthesis of 5-(benzoxazol-2-yl)-1-(4-methoxyphenyl)-2-methylbenzimidazole

Working Example 15-1

Synthesis of 4-fluoro-N-(2-hydroxyphenyl)-3-nitrobenzanilide

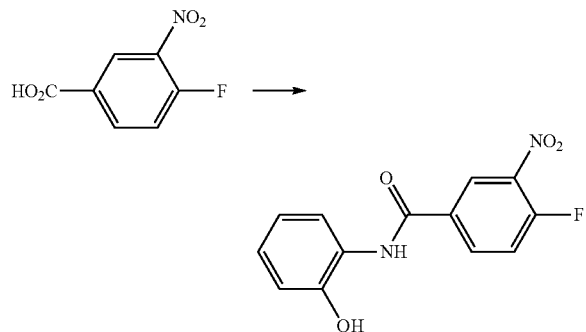

To a solution of 4-fluoro-3-nitrobenzoic acid (2.00 g, 10.8 mmol) in chloroform (40 mL) was added 2-aminophenol (1.18 g, 10.8 mmol), 1-ethyl-3-(3-dimethylaminopropyl)carbodiimide hydrochloride (2.17 g, 11.3 mmol), and triethylamine (1.15 g, 11.3 mmol), and this was stirred at room temperature for 2.5 hours. After the reaction was complete, this was diluted by adding ethyl acetate, and this was washed with water, 1N hydrochloric acid, and saturated aqueous sodium hydrogen carbonate. The organic layer obtained was dried over anhydrous sodium sulfate, after which it was filtered and concentrated to yield the title compound (2.02 g, 68% yield) as orange crystals.

$^1$H-NMR (DMSO-d$_6$) δ (ppm): 6.84 (1H, td, J=7.6, 1.4 Hz), 6.93 (1H, dd, J=8.1, 1.5 Hz), 7.08 (1H, ddd, J=8.5, 6.9, 1.2 Hz), 7.54 (1H, dd, J=7.8, 1.6 Hz), 7.76 (1H, dd, J=11.2, 8.7 Hz), 8.39 (1H, ddd, J=8.7, 4.2, 2.3 Hz), 8.75 (1H, dd, J=7.3, 2.3 Hz), 9.69 (1H, br s), 9.94 (1H, br s).

Working Example 15-2

Synthesis of 2-(4-fluoro-3-nitrophenyl)benzoxazole

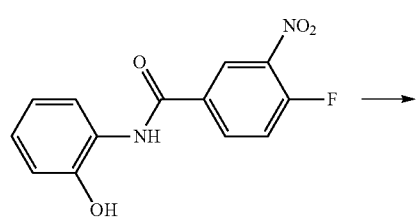

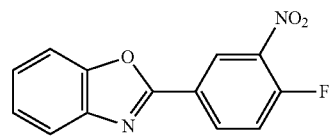

To a suspension of 4-fluoro-N-(2-hydroxyphenyl)-3-nitrobenzanilide (see Working Example 15-1) (2.00 g, 7.24 mmol) in toluene (50 mL) was added p-toluenesulfonic acid monohydrate (2.07 g, 10.9 mmol), and this was stirred and heated to reflux for 4 hours. After the reaction was complete, this was cooled to room temperature, and after the solvent was distilled off, saturated aqueous sodium hydrogen carbonate solution was added and this was stirred for 10 minutes at room temperature. The precipitated crystals were filtered off, and after washing with toluene the crystals were dried to yield the title compound (1.30 g, 70% yield) as yellow crystals.

$^1$H-NMR (DMSO-d$_6$) δ (ppm): 7.44-7.53 (2H, m), 7.82-7.89 (3H, m), 8.55-8.61 (1H, m), 8.80-8.84 (1H, m).

Working Example 15-3

Synthesis of 2-(4-(4-methoxyphenylamino)-3-nitrophenyl)benzoxazole

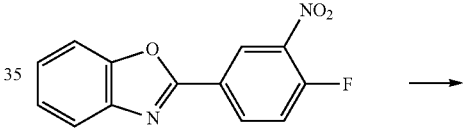

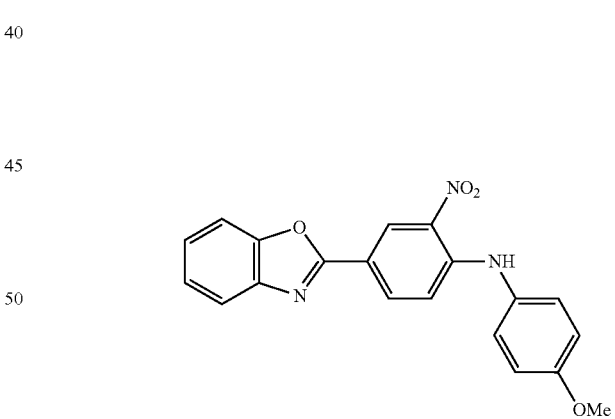

To a suspension of 2-(4-fluoro-3-nitrophenyl)benzoxazole (see Working Example 15-2) (300 mg, 1.19 mmol) in ethanol (5 mL) was added sodium hydrogen carbonate (295 mg, 2.32 mmol) and p-anisidine (357 mg, 2.90 mmol), and this was heated to reflux with stirring for 4 hours. After the reaction was complete, this was cooled to room temperature, the precipitated crystals were filtered off, and after washing with water and ethanol the crystals were dried to yield the title compound (359 mg, 86% yield) as orange crystals.

¹H-NMR (DMSO-d₆) δ (ppm): 3.81 (3H, s), 7.05-7.11 (3H, m), 7.30-7.44 (4H, m), 7.73-7.81 (2H, m), 8.17 (1H, dd, J=9.1, 2.1 Hz), 8.85 (1H, d, J=2.1 Hz), 9.83 (1H, br s).

Working Example 15-4

Synthesis of 5-(benzoxazol-2-yl)-1-(4-methoxyphenyl)-2-methylbenzimidazole

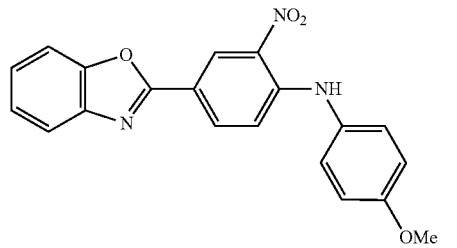

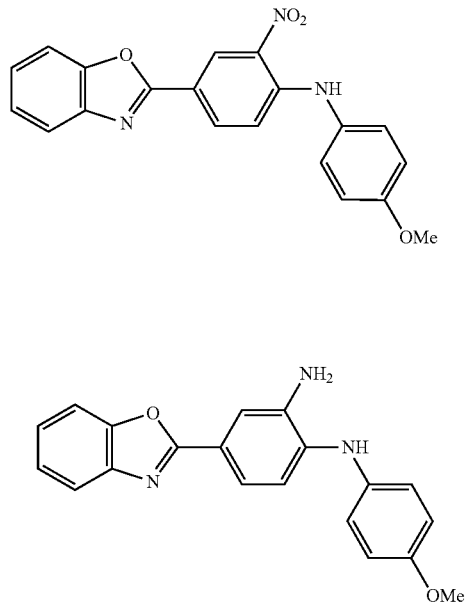

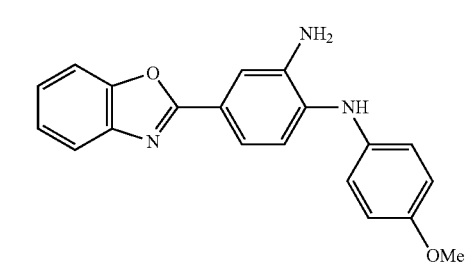

2-(4-(4-methoxyphenylamino)-3-nitrophenyl)benzoxazole (Working Example 15-3) (150 mg, 0.415 mmol) was added to a tetrahydrofuran (5 mL) solution containing 10% palladium-carbon (50 mg), and a hydrogen atmosphere was substituted in the flask and this was stirred at room temperature for 3 hours. After the reaction was complete, this was filtered through Celite and the filtrate was concentrated. To a solution of the oil obtained in toluene (5 mL) was added acetyl chloride (70.8 mg, 0.902 mmol), and this was heated to reflux with stirring for 2.5 hours. After the reaction was complete, this was cooled to room temperature, saturated aqueous sodium hydrogen carbonate solution was added, and this was extracted with ethyl acetate. The organic layer obtained was dried over anhydrous sodium sulfate, filtered, and concentrated to give crystals that were purified by silica gel column chromatography to yield the title compound (47 mg, 32% yield) as dark brown crystals.

¹H-NMR (CDCl₃) δ (ppm): 2.53 (3H, s), 3.90 (3H, s), 7.05-7.37 (7H, m), 7.59-7.64 (1H, m), 7.74-7.80 (1H, m), 8.16 (1H, dd, J=8.4, 1.5 Hz), 8.62 (1H, d, J=1.5 Hz).

Working Example 16

Synthesis of 5-(benzoxazol-2-yl)-1-cyclohexyl-2-methylbenzimidazole

Working Example 16-1

Synthesis of 2-(4-cyclohexylamino-3-nitrophenyl)benzoxazole

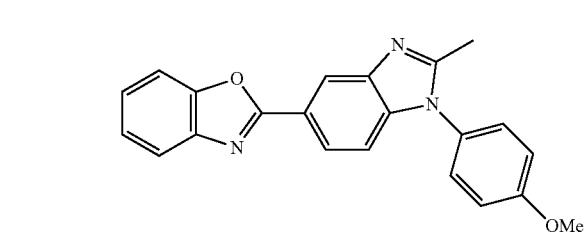

To a suspension of 2-(4-fluoro-3-nitrophenyl)benzoxazole (see Working Example 15-2) (300 mg, 1.19 mmol) in ethanol (5 mL) was added sodium hydrogen carbonate (295 mg, 2.32 mmol) and cyclohexylamine (288 mg, 2.32 mmol), and this was heated to reflux with stirring for 4 hours. After the reaction was complete, this was cooled to room temperature, water was added, and this was extracted with ethyl acetate. The organic layer obtained was dried over anhydrous sodium sulfate, filtered, and concentrated to give crystals that were purified by silica gel column chromatography to yield the title compound (191 mg, 48% yield) as orange crystals.

¹H-NMR (CDCl₃) δ (ppm): 1.36-2.11 (10H, m), 3.56-3.66 (1H, m), 7.01 (1H, d, J=9.2 Hz), 7.32-7.36 (2H, m), 7.55-7.59 (1H, m), 7.71-7.75 (1H, m), 8.26 (1H, ddd, J=9.2, 3.1, 0.5 Hz), 8.46 (1H, d, J=7.3 Hz), 9.06 (1H, d, J=2.0 Hz).

Working Example 16-2

Synthesis of 5-(benzoxazol-2-yl)-1-cyclohexyl-2-methylbenzimidazole

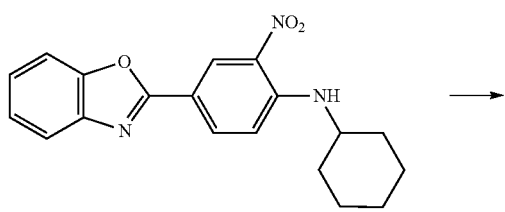

-continued

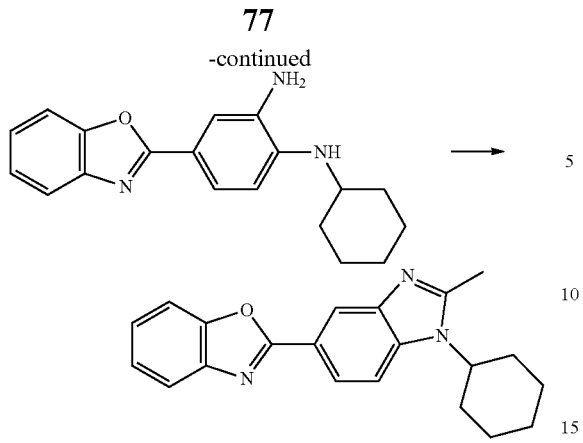

2-(4-cyclohexylamino-3-nitrophenyl)benzoxazole (Working Example 16-1) (185 mg, 0.548 mmol) was added to a tetrahydrofuran (5 mL) solution including 10% palladium-carbon (50 mg), and a hydrogen atmosphere was substituted in the flask and this was stirred at room temperature for 5 hours. After the reaction was complete, this was filtered through Celite and the filtrate was concentrated. To a solution of the oil obtained in dimethylformamide (1.5 mL) was added a solution of acetaldehyde in dimethylformamide (approx. 2%, 1.35 mL, 0.586 mmol), water (0.1 mL), and oxone (117 mg, 0.190 mmol), and this was stirred at room temperature for 2.5 hours. After the reaction was complete, aqueous potassium carbonate solution was added, and this was extracted with ethyl acetate. The organic layer obtained was dried over anhydrous sodium sulfate, filtered, and concentrated to give an oil that was purified by silica gel column chromatography to yield the title compound (24.5 mg, 14% yield) as a light brown oil.

$^1$H-NMR (CDCl$_3$) δ (ppm): 1.26-2.30 (10H, m), 2.68 (3H, s), 4.17-4.26 (1H, m), 7.30-7.37 (2H, m), 7.58-7.64 (2H, m), 7.75-7.79 (1H, m), 8.15 (1H, dd, J=8.6, 1.6 Hz), 8.54 (1H, d, J=1.6 Hz).

Working Example 17

Synthesis of 5-(benzoxazol-2-yl)-1-benzyl-2-methylbenzimidazole

Working Example 17-1

Synthesis of 2-(4-benzylamino-3-nitrophenyl)benzoxazole

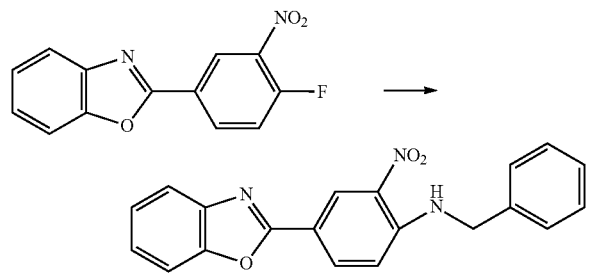

To a suspension of 2-(4-fluoro-3-nitrophenyl)benzoxazole (see Working Example 15-2) (300 mg, 1.19 mmol) in ethanol (5 mL) was added sodium hydrogen carbonate (195 mg, 2.32 mmol) and benzylamine (311 mg, 2.90 mmol), and this was heated to reflux with stirring for 4 hours. After the reaction was complete, it was cooled to room temperature and water was added. The precipitated crystals were filtered off, and after washing with water and ethanol the crystals were dried to yield the title compound (347 mg, 84% yield) as orange crystals.

$^1$H-NMR (CDCl$_3$) δ (ppm): 4.64 (2H, d, J=5.6 Hz), 6.99 (1H, d, J=8.9 Hz), 7.31-7.44 (7H, m), 7.55-7.58 (1H, m), 7.71-7.75 (1H, m), 8.24-8.28 (1H, m), 8.72 (1H, br s), 9.09 (1H, d, J=2.1 Hz).

Working Example 17-2

Synthesis of 2-(2-benzylaminoanilin-5-yl)benzoxazole

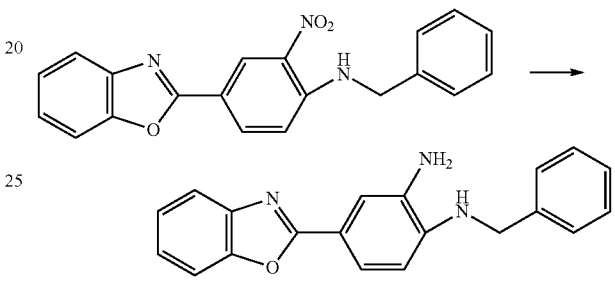

To a suspension of 2-(4-benzylamino-3-nitrophenyl)benzoxazole (see Working Example 17-1) (340 mg, 0.985 mmol) was added 10% aqueous acetic acid solution (5 mL), ethanol (8 mL), and iron powder (165 mg, 2.95 mmol), and this was heated to reflux with stirring for 4 hours. After the reaction was complete, saturated aqueous sodium hydrogen carbonate solution and chloroform were added, this was filtered through Celite and then extracted with chloroform. The organic layer obtained was dried over anhydrous sodium sulfate, filtered, and concentrated to give an oil that was purified by silica gel column chromatography to yield the title compound (87 mg, 28% yield) as brown crystals.

$^1$H-NMR (CDCl$_3$) δ (ppm): 4.42 (2H, s), 6.74 (2H, d, J=8.1 Hz), 7.24-7.76 (10H, m).

Working Example 17-3

Synthesis of 5-(benzoxazol-2-yl)-1-benzyl-2-methylbenzimidazole

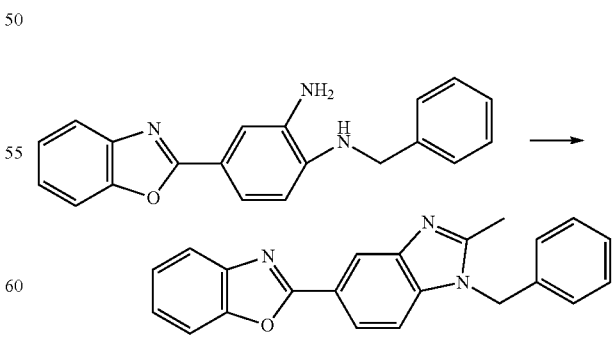

To a solution of 2-(2-benzylaminoanilin-5-yl)benzoxazole (see Working Example 17-2) (80.0 mg, 0.254 mmol) in dimethylformamide (2 mL) was added an aqueous solution of acetaldehyde (approx. 90%, 47.7 μL, 0.761 mmol) and oxone (102 mg, 0.165 mmol), and this was stirred at room temperature for 3 hours. After the reaction was complete, aqueous potassium carbonate solution was added, and this was extracted with ethyl acetate. The organic layer obtained was dried over anhydrous sodium sulfate, filtered, and concentrated to give an oil that was purified by silica gel column chromatography to yield the title compound (35.2 mg, 41% yield) as light brown crystals.

$^1$H-NMR (CDCl$_3$) δ (ppm): 2.62 (3H, s), 5.38 (2H, s), 7.06-7.10 (2H, m), 7.30-7.37 (6H, m), 7.59-7.62 (1H, m), 7.75-7.79 (1H, m), 8.18 (1H, dd, J=8.5, 1.6 Hz), 8.60 (1H, d, J=1.6 Hz).

Working Example 18

Synthesis of 5-(benzothiophen-2-yl)-2-methyl-1-(tetrahydropyran-4-yl)benzimidazole Working Example 18-1

Synthesis of 5-bromo-2-(tetrahydropyran-4-yl)nitrobenzene

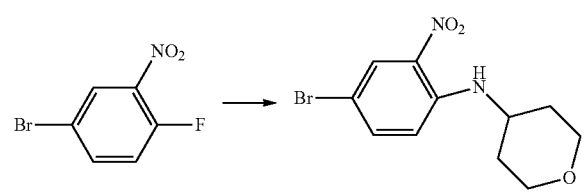 [SMILES: O=[N+]([O-])c1cc(Br)ccc1F ; O=[N+]([O-])c1cc(Br)ccc1NC1CCOCC1]

An eggplant flask was charged with 5-bromo-2-fluoronitrobenzene (3.0 g, 13.6 mmol), triethylamine (1.66 g, 16.3 mmol), 4-aminotetrahydropyran (1.52 g, 15.0 mmol), and ethanol (60 mL), and this was heated to reflux with stirring for 2 hours. After concentration of the reaction mixture under reduced pressure, water (60 mL) was added and this was stirred as is at room temperature for 30 minutes. The precipitated crystals were filtered off and washed with water. The crystals obtained were dried at reduced pressure with heating to yield the title compound (3.55 g, 86% yield) as a reddish-orange solid.

$^1$H-NMR (CDCl$_3$) δ (ppm): 1.60-1.74 (2H, m), 2.04-2.08 (2H, m), 3.52-3.78 (3H, m), 4.03 (2H, td, J=8.0, 4.1 Hz), 6.79 (1H, d, J=9.2 Hz), 7.49 (1H, ddd, J=9.2, 2.4, 0.6 Hz), 8.06-8.08 (1H, m), 8.33 (1H, d, J=2.4 Hz).

Working Example 18-2

Synthesis of 5-bromo-2-(tetrahydropyran-4-yl)aminoaniline

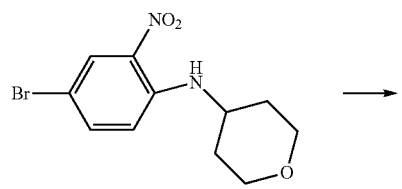

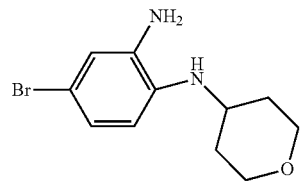

A 3-neck flask was charged with 5-bromo-2-(tetrahydropyran-4-yl)nitrobenzene (see Working Example 18-1) (3.54 g, 11.8 mmol) and 10% aqueous acetic acid solution (65 mL), after which electrolytic iron (6.56 g, 118 mmol) was added and this was refluxed with stirring for 15 minutes. After this was allowed to cool to room temperature, the insoluble material was filtered off through Celite, and this same layer was further washed with 10% aqueous acetic acid solution (65 mL). The filtrate and the wash solutions were combined and then successively extracted with ethyl acetate (approx. 50 mL, 4 times), washed with distilled water (30 mL), and dried over anhydrous sodium sulfate. The solvent was distilled off under reduced pressure, and further drying under reduced pressure yielded the title compound (2.72 g, 85.4% yield) as a pale yellow solid.

$^1$H-NMR (CDCl$_3$) δ (ppm): 1.43-1.58 (2H, m), 1.98-2.05 (2H, m), 3.36-3.56 (3H, m), 4.00 (2H, dt, J=11.8, 3.6 Hz), 6.53 (1H, d, J=8.1 Hz), 6.85-6.90 (2H, m).

Working Example 18-3

Synthesis of 5-bromo-2-methyl-1-(tetrahydropyran-4-yl)benzimidazole hydrochloride

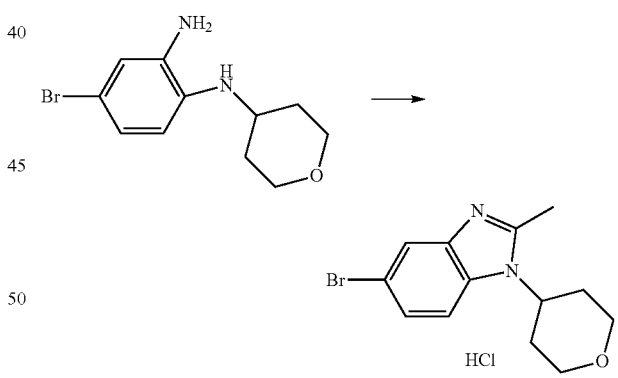

A 2-neck flask was charged with 5-bromo-2-(tetrahydropyran-4-yl)aminoaniline (see Synthesis Example 18-2) (2.72 g, 10.0 mmol) and anhydrous toluene (20 mL) and this was refluxed. To this was added dropwise over approx. 15 m acetyl chloride (1.57 g, 20.0 mmol) in toluene solution (approx. 2.5 mL), and this was stirred under these conditions for 2 hours. After being allowed to cool to room temperature, this was concentrated under reduced pressure and the residue was reslurried in hexane (20 mL). The precipitated crystals were filtered off and washed with hexane. The crystals obtained were dried at reduced pressure with heating to yield the title compound (3.14 g, 94.7% yield) as a light purple solid.

¹H-NMR (DMSO-d₆) δ (ppm): 1.94-1.97 (2H, m), 2.30-2.49 (2H, m), 2.87 (3H, s), 3.57 (2H, t, J=11.5 Hz), 4.05 (2H, dd, J=11.5, 4.0 Hz), 4.79-4.88 (1H, m), 7.64 (1H, dd, J=8.9, 1.8 Hz), 8.00-8.03 (2H, m).

Working Example 18-4

Synthesis of 5-(benzothiophen-2-yl)-2-methyl-1-(tetrahydropyran-4-yl)benzimidazole

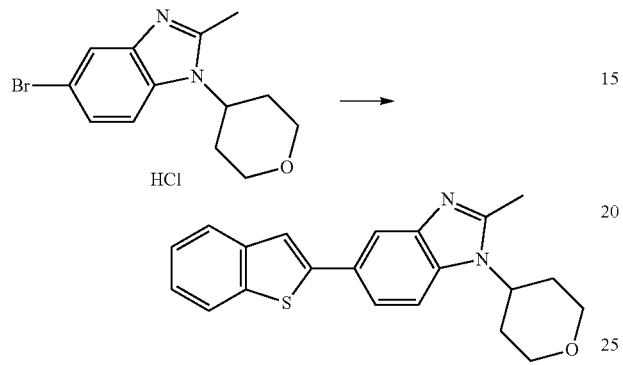

5-Bromo-2-methyl-1-(tetrahydropyran-4-yl)benzimidazole hydrochloride (see Synthesis Example 18-3) (0.38 g, 1.15 mmol), 2-benzothiopheneboronic acid (0.25 g, 1.40 mmol), ethanol (5 mL), toluene (5 mL), and 2M aqueous sodium carbonate solution (2.1 mL) were prepared, and this was degassed. Tetrakis(triphenylphosphine)palladium (0.08 g, 0.07 mmol) was added, and this was refluxed for 3 hours. After cooling, ethanol and water were added and this was filtered through Celite and the material on the filter was washed with ethanol and water. The filtrate was concentrated, the precipitated crystals were filtered off and washed with water and hexane, and dried to yield the title compound (315 mg, 78.9% yield) as light brown crystals.

¹H-NMR (CDCl₃) δ (ppm): 1.88 (2H, dd, J=12.7, 2.1 Hz), 2.56-2.62 (2H, m), 2.68 (3H, s), 3.60 (2H, dd, J=12.1, 10.3 Hz), 4.20-4.25 (2H, m), 4.39-4.45 (1H, m), 7.29-7.39 (3H, m), 7.52-7.59 (2H, m), 7.78-7.82 (2H, m), 8.04 (1H, s).

Working Example 19

Synthesis of 5-(benzofuran-2-yl)-2-methyl-1-(tetrahydropyran-4-yl)benzimidazole

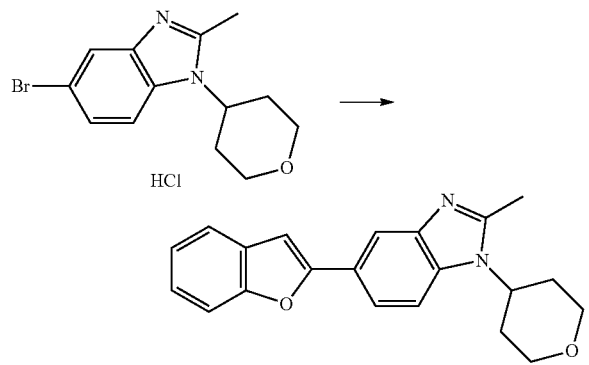

5-Bromo-2-methyl-1-(tetrahydropyran-4-yl)benzimidazole hydrochloride (see Synthesis Example 18-3) (0.41 g, 1.24 mmol), 2-benzofuranboronic acid (0.25 g, 1.40 mmol), ethanol (5 mL), toluene (5 mL), and 2M aqueous sodium carbonate solution (2.1 mL) were prepared, and this was degassed. Tetrakis(triphenylphosphine)palladium (0.08 g, 0.07 mmol) was added, and this was refluxed for 3 hours. After cooling, ethanol and water were added and this was filtered through Celite and the material on the filter was washed with ethanol and water. The filtrate and wash solutions were combined and successively extracted with ethyl acetate (approx. 50 mL, 4 times) and distilled water (30 mL), dried over anhydrous sodium sulfate, and the solvent was distilled off under reduced pressure. The residue obtained was purified by silica gel column chromatography to yield the title compound (145 mg, 35.3% yield) as light brown crystals.

¹H-NMR (CDCl₃) δ (ppm): 1.86-1.90 (2H, m), 2.57-2.63 (2H, m), 2.67 (3H, s), 3.60 (2H, td, J=11.8, 1.8 Hz), 4.22 (2H, dd, J=11.8, 4.6 Hz), 4.41-4.45 (1H, m), 7.01 (1H, d, J=0.8 Hz), 7.22-7.27 (2H, m), 7.57-7.59 (3H, m), 7.75 (1H, dd, J=8.6, 1.4 Hz), 8.18 (1H, d, J=1.4 Hz).

Working Example 20

Synthesis of 5-(benzoxazol-2-yl)-1-(tetrahydropyran-4-yl)benzimidazole

Working Example 20-1

Synthesis of 5-(benzoxazol-2-yl)-2-(tetrahydropyran-4-yl)nitrobenzene

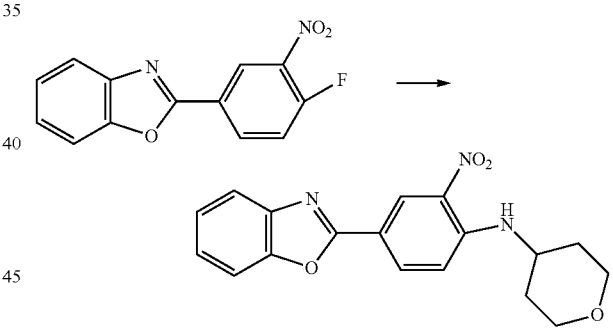

5-(Benzoxazol-2-yl)-2-fluoronitrobenzene (see Working Example 15-2) (0.55 g, 2.13 mmol), triethylamine (0.26 g, 2.57 mmol), and aminotetrahydropyran (0.24 g, 2.34 mmol) were added to ethanol (10 mL), and this reaction mixture liquid was heated to reflux with stirring for 2 hours. The reaction mixture was cooled to room temperature and was concentrated under reduced pressure, and 0.1N aqueous hydrochloric acid solution (50 mL) was added to the residue obtained, this was successively extracted with ethyl acetate (approx. 50 mL, 4 times), washed with water (30 mL), and dried over anhydrous sodium sulfate, and the solvent was distilled off at reduced pressure. The residue obtained was purified by silica gel column chromatography to yield the title compound (440 mg, 60.9% yield) as light brown crystals.

¹H-NMR (CDCl₃) δ (ppm): 1.67-1.81 (2H, m), 2.07-2.17 (2H, m), 3.7-3.67 (2H, m), 3.76-3.77 (1H, m), 4.03-4.10 (2H, m), 7.01 (1H, t, J=8.6 Hz), 7.35 (2H, tt, J=6.5, 2.5 Hz), 7.54-7.59 (1H, m), 7.71-7.77 (1H, m), 8.30 (1H, dd, J=9.1, 2.1 Hz), 8.43 (1H, d, J=7.4 Hz), 9.08 (1H, d, J=2.1 Hz)

In addition, this intermediate can also be obtained from 4-((tetrahydropyran-4-yl)amino)-3-nitrobenzoic acid (see Working Example 4-1) as shown below.

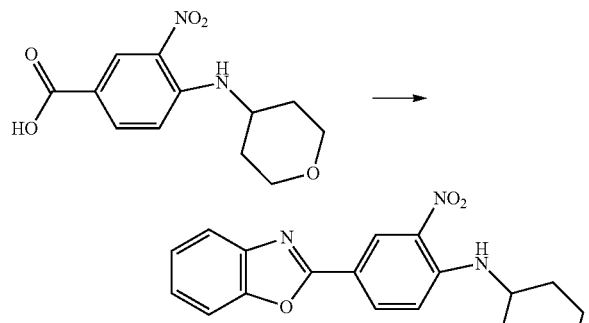

4-((Tetrahydropyran-4-yl)amino)-3-nitrobenzoic acid (see Working Example 4-1) (8.0 g, 30.0 mmol), 2-aminophenol (3.61 g, 33.0 mmol), chloroform (350 mL), and WSC (19.7 g, 100 mmol) were stirred at room temperature for 3 hours. After concentration of the reaction mass at reduced pressure, water (500 mL) was added to reslurry it and the slurried mass was filtered. The solid material obtained was washed with water and ethanol, and then dried at 50° C. under reduced pressure. The solid obtained was dissolved in dioxane (160 mL), methanesulfonic acid (17.0 g) was added, and this was heated to reflux for 10 hours. After being allowed to cool to room temperature, the solvent was concentrated at reduced pressure and the residue obtained was reslurried by adding hexane (160 mL). The solid portion was filtered off, and dried at 50° C. under reduced pressure to yield the title compound (7.70 g, 75.5% yield) as a pale yellow solid.

Working Example 20-2

Synthesis of 5-(benzoxazol-2-yl)-2-(tetrahydropyran-4-yl)aminoaniline

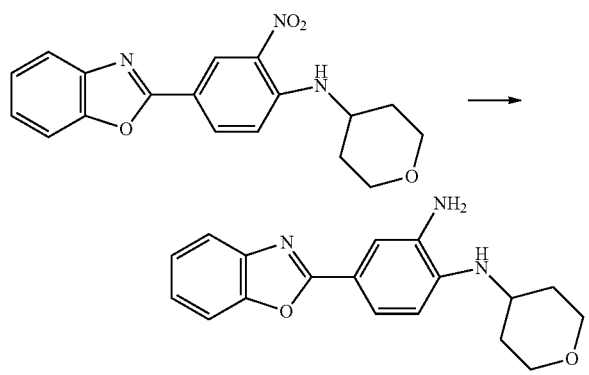

5-(Benzoxazol-2-yl)-2-(tetrahydropyran-4-yl)nitrobenzene (see Working Example 20-1) (1.00 g, 0.76 mol) was dissolved in a solvent mixture of THF (50 mL) and methanol (50 mL), and Pd/C (5%, wet, 0.5 g) was added to carry out a hydrogenation reaction. After being stirred overnight at room temperature, the catalyst was removed by filtration and the filtrate was concentrated under reduced pressure to yield the title compound (812 mg, 89.1%) as a gray solid.

$^1$H-NMR (CDCl$_3$) δ (ppm): 1.56-1.61 (2H, m), 1.90-2.27 (2H, m), 3.25-3.83 (5H, m), 4.06-4.11 (2H, m), 6.73 (1H, d, J=8.4 Hz), 7.24-7.31 (2H, m), 7.47-7.55 (1H, m), 7.59-7.77 (3H, m).

Working Example 20-3

Synthesis of 5-(benzoxazol-2-yl)-1-(tetrahydropyran-4-yl)benzimidazole

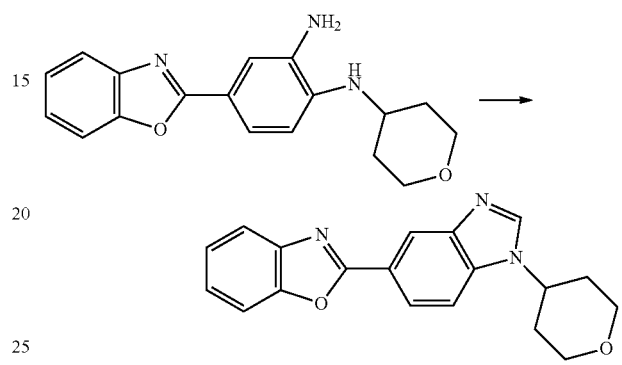

To 5-(benzoxazol-2-yl)-2-(tetrahydropyran-4-yl)aminoaniline (see Working Example 20-2) (0.20 g, 0.646 mmol), triethyl orthoformate (5 mL) was added a catalytic amount of p-toluenesulfonic acid monohydrate, and this was heated to 100° C. for 1.5 hours. The reaction mixture was cooled, ethyl acetate and water added, and this was extracted. This was washed with water, dried over magnesium sulfate, and after concentration the precipitated crystals were filtered off. These were washed with a hexane/ethyl acetate mixture solution, and dried to yield the title compound (65 mg, 31.5% yield) as light reddish-brown crystals.

$^1$H-NMR (CDCl$_3$) δ (ppm): 2.21-2.30 (4H, m), 3.65 (2H, dt, J=16.0, 8.0 Hz), 4.16-4.24 (2H, m), 4.45-4.57 (1H, m), 7.32-7.39 (2H, m), 7.59-7.62 (2H, m), 7.77-7.80 (1H, m), 8.11 (1H, s), 8.28 (1H, dd, J=8.6, 1.5 Hz), 8.71 (1H, s).

Working Example 21

Synthesis of 5-(benzoxazol-2-yl)-2-(2-pyridyl)-1-(tetrahydropyran-4-yl)benzimidazole

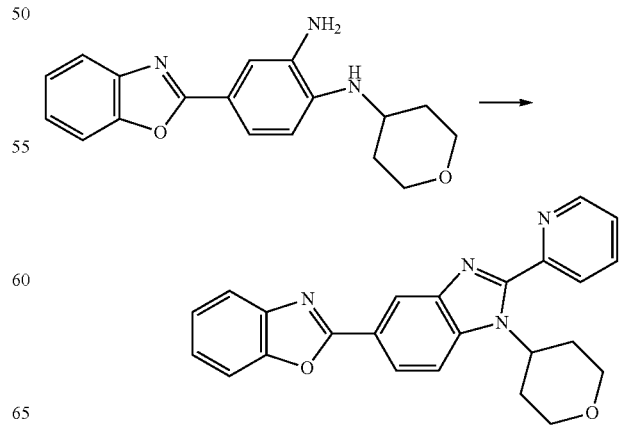

5-(Benzoxazol-2-yl)-2-(tetrahydropyran-4-yl)aminoaniline (see Working Example 20-2) (0.15 g, 0.484 mmol) was dissolved in DMF (3 mL) and water (0.1 mL), 2-pyridinecarboxaldehyde (0.06 g, 0.561 mmol) was added followed by oxone (0.19 g, 0.310 mmol), and this was stirred at room temperature for 2.5 hours. Aqueous potassium carbonate solution (0.09 g/15 mL) was added to the reaction solution. This was extracted with chloroform, washed with water, and after drying over magnesium sulfate, this was concentrated and purified by silica gel column chromatography. The crystals obtained were washed with hexane and a small amount of ethyl acetate, and dried to yield the title compound (135 mg, 70.2% yield) as white crystals.

$^1$H-NMR (CDCl$_3$) δ (ppm): 2.03-2.08 (2H, m), 2.65-2.77 (2H, m), 3.53-3.62 (2H, m), 4.18-4.24 (2H, m), 5.85-5.92 (1H, m), 7.31-7.44 (3H, m), 7.59-7.65 (1H, m), 7.76-7.82 (1H, m), 7.88-7.93 (2H, m), 8.24-8.35 (2H, m), 8.71-8.75 (2H, m).

Working Example 22

Synthesis of 5-(benzoxazol-2-yl)-2-isopropyl-1-(tetrahydropyran-4-yl)benzimidazole

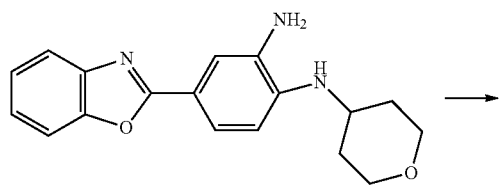

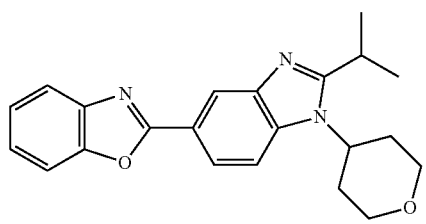

5-(Benzoxazol-2-yl)-2-(tetrahydropyran-4-yl)aminoaniline (see Working Example 20-2) (0.15 g, 0.484 mmol) was dissolved in DMF (3 mL) and water (0.1 mL), isopropyl aldehyde (0.04 g, 0.561 mmol) was added followed by oxone (0.19 g, 0.310 mmol), and this was stirred at room temperature for 2.5 hours. Aqueous potassium carbonate solution (0.09 g/15 mL) was added to the reaction solution. This was extracted with chloroform, washed with water, and after drying over magnesium sulfate, this was concentrated and purified by silica gel column chromatography. The crystals obtained were washed with hexane and a small amount of ethyl acetate, and dried to yield the title compound (70 mg, 43.9% yield) as white crystals.

$^1$H-NMR (CDCl$_3$) δ (ppm): 1.50 (6H, d, J=6.8 Hz), 1.88 (2H, d, J=11.0 Hz), 2.65-2.75 (2H, m), 3.23-3.33 (1H, m), 3.61 (2H, t, J=11.7 Hz), 4.24 (2H, dd, J=11.7, 4.1 Hz), 4.50-4.54 (1H, m), 7.33-7.34 (2H, m), 7.61-7.75 (3H, m), 8.18 (1H, d, J=8.6 Hz), 8.63 (1H, s).

Working Example 23

Synthesis of 5-(benzoxazol-2-yl)-2-cyclohexyl-1-(tetrahydropyran-4-yl)benzimidazole

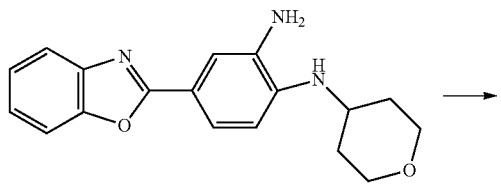

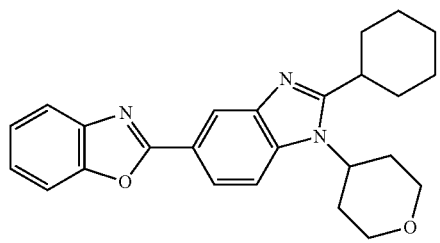

5-(Benzoxazol-2-yl)-2-(tetrahydropyran-4-yl)aminoaniline (see Working Example 20-2) (0.15 g, 0.484 mmol) was dissolved in DMF (3 mL) and water (0.1 mL), cyclohexyl aldehyde (0.06 g, 0.561 mmol) was added followed by oxone (0.19 g, 0.310 mmol), and this was stirred at room temperature for 2.5 hours. Aqueous potassium carbonate solution (0.09 g/15 mL) was added to the reaction solution. This was extracted with chloroform, washed with water, and after drying over magnesium sulfate, this was concentrated and purified by silica gel column chromatography. The crystals obtained were washed with hexane and a small amount of ethyl acetate, and dried to yield the title compound (116 mg, 59.6% yield) as white crystals.

$^1$H-NMR (CDCl$_3$) δ (ppm): 1.35-1.55 (3H, m), 1.86-2.05 (9H, m), 2.61-2.77 (2H, m), 2.84-2.93 (1H, m), 3.63 (2H, t, J=11.2 Hz), 4.24 (2H, dd, J=11.8, 4.2 Hz), 4.45-4.54 (1H, m), 7.30-7.33 (2H, m), 7.56-7.78 (3H, m), 8.18 (1H, dd, J=8.6, 1.6 Hz), 8.62 (1H, d, J=1.6 Hz).

Working Example 24

Synthesis of 5-(benzoxazol-2-yl)-2-(3-pyridyl)-1-(tetrahydropyran-4-yl)benzimidazole

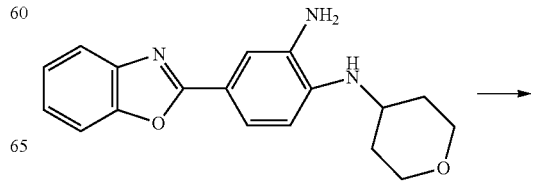

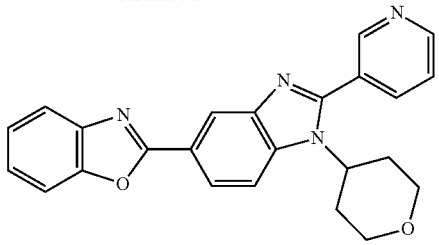

5-(Benzoxazol-2-yl)-2-(tetrahydropyran-4-yl)aminoaniline (see Working Example 20-2) (0.15 g, 0.484 mmol) was dissolved in DMF (3 mL) and water (0.1 mL), 3-pyridinecarboxaldehyde (0.06 g, 0.561 mmol) was added followed by oxone (0.19 g, 0.310 mmol), and this was stirred at room temperature for 2.5 hours. Aqueous potassium carbonate solution (0.09 g/15 mL) was added to the reaction solution. This was extracted with chloroform, washed with water, and after drying over magnesium sulfate, this was concentrated and purified by silica gel column chromatography. The crystals obtained were washed with hexane and a small amount of ethyl acetate, and dried to yield the title compound (95.0 mg, 49.5% yield) as white crystals.

$^1$H-NMR (CDCl$_3$) δ (ppm): 1.93 (2H, dd, J=12.5, 2.6 Hz), 2.68-2.83 (2H, m), 3.43-3.52 (2H, m), 4.19 (2H, dd, J=11.5, 4.3 Hz), 4.51-4.63 (1H, m), 7.33-7.40 (2H, m), 7.52-7.57 (1H, m), 7.60-7.64 (1H, m), 7.77-7.86 (2H, m), 8.07 (1H, dt, J=7.9, 1.8 Hz), 8.29 (1H, dd, J=8.7, 1.8 Hz), 8.71 (1H, d, J=1.2 Hz), 8.83 (1H, dd, J=4.9, 1.8 Hz), 8.91 (1H, d, J=1.2 Hz).

Working Example 25

Synthesis of 5-(benzoxazol-2-yl)-2-phenyl-1-(tetrahydropyran-4-yl)benzimidazole

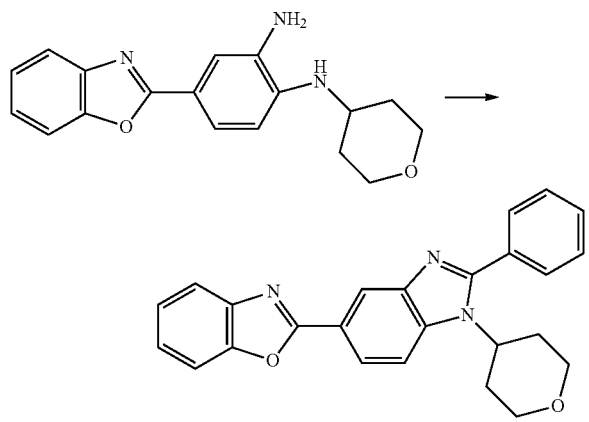

5-(Benzoxazol-2-yl)-2-(tetrahydropyran-4-yl)aminoaniline (see Working Example 20-2) (0.15 g, 0.484 mmol) was dissolved in DMF (3 mL) and water (0.1 mL), phenyl aldehyde (0.06 g, 0.561 mmol) was added followed by oxone (0.19 g, 0.310 mmol), and this was stirred at room temperature for 2.5 hours. Aqueous potassium carbonate solution (0.09 g/15 mL) was added to the reaction solution. This was extracted with chloroform, washed with water, and after drying over magnesium sulfate, this was concentrated and purified by silica gel column chromatography. The crystals obtained were washed with hexane and a small amount of ethyl acetate, and dried to yield the title compound (115 mg, 59.9% yield) as white crystals.

$^1$H-NMR (CDCl$_3$) δ (ppm): 1.91 (2H, dd, J=13.2, 3.1 Hz), 2.66-2.81 (2H, m), 3.43-3.48 (2H, m), 4.15-4.19 (2H, m), 4.61-4.66 (1H, m), 7.32-7.39 (2H, m), 7.56-7.68 (6H, m), 7.78-7.82 (2H, m), 8.26 (1H, dd, J=8.7, 1.6 Hz), 8.69-8.69 (1H, m).

Working Example 26

Synthesis of 5-(benzoxazol-2-yl)-2-(4-pyridyl)-1-(tetrahydropyran-4-yl)benzimidazole

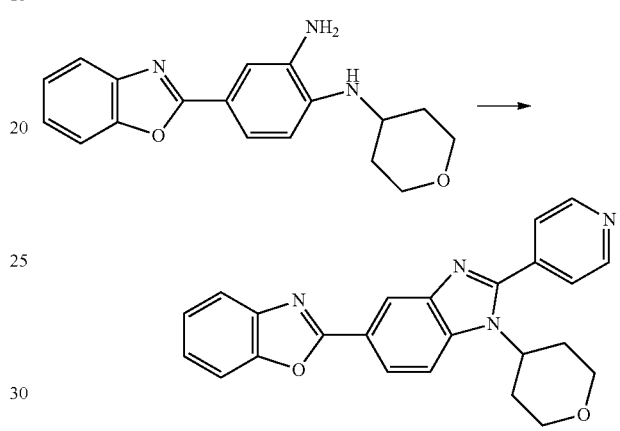

5-(Benzoxazol-2-yl)-2-(tetrahydropyran-4-yl)aminoaniline (see Working Example 20-2) (0.15 g, 0.484 mmol) was dissolved in DMF (3 mL) and water (0.1 mL), 4-pyridinecarboxaldehyde (0.06 g, 0.561 mmol) was added followed by oxone (0.19 g, 0.310 mmol), and this was stirred at room temperature for 2.5 hours. Aqueous potassium carbonate solution (0.09 g/15 mL) was added to the reaction solution. This was extracted with chloroform, washed with water, and after drying over magnesium sulfate, this was concentrated and purified by silica gel column chromatography. The crystals obtained were washed with hexane and a small amount of ethyl acetate, and dried to yield the title compound (117 mg, 60.9% yield) as white crystals.

$^1$H-NMR (CDCl$_3$) δ (ppm): 1.93 (2H, dd, J=12.8, 2.7 Hz), 2.67-2.83 (2H, m), 3.45-3.53 (2H, m), 4.20 (2H, dd, J=11.8, 4.5 Hz), 4.54-4.66 (1H, m), 7.33-7.40 (2H, m), 7.59-7.65 (3H, m), 7.78-7.86 (2H, m), 8.30 (1H, dd, J=8.6, 1.6 Hz), 8.71-8.72 (1H, m), 8.87 (2H, dd, J=4.3, 1.6 Hz).

Working Example 27

Synthesis of 5-(benzoxazol-2-yl)-1-(tetrahydropyran-4-yl)-2-trifluoromethylbenzimidazole

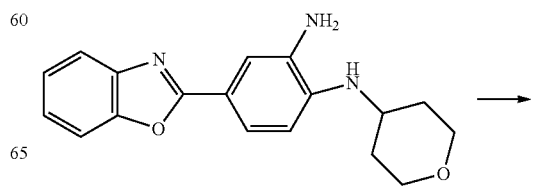

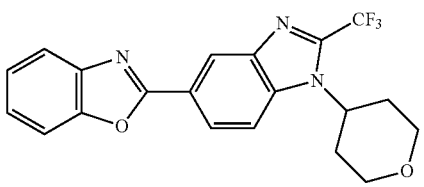

5-(Benzoxazol-2-yl)-2-(tetrahydropyran-4-yl)aminoaniline (see Working Example 20-2) (0.20 g, 0.646 mmol) in trifluoroacetic acid (7 mL) was heated to reflux for 4.5 hours. The reaction mixture was cooled, water was added, and this was extracted with ethyl acetate. The organic layer was washed with aqueous sodium carbonate solution and water, then dried over magnesium sulfate, and concentrate. The residue was purified by silica gel column chromatography to yield the title compound (139 mg, 55.5% yield) as white crystals.

$^1$H-NMR (CDCl$_3$) δ (ppm): 1.99 (2H, dd, J=12.4, 2.9 Hz), 2.60-2.76 (2H, m), 3.61 (2H, td, J=12.0, 1.8 Hz), 4.24 (2H, dd, J=11.9, 4.6 Hz), 4.67-4.79 (1H, m), 7.34-7.41 (2H, m), 7.59-7.66 (1H, m), 7.76-7.87 (2H, m), 8.37 (1H, dd, J=8.7, 1.6 Hz), 8.76-8.77 (1H, m).

Working Example 28

Synthesis of 5-(benzoxazol-2-yl)-1-(tetrahydropyran-4-yl)benzotriazole

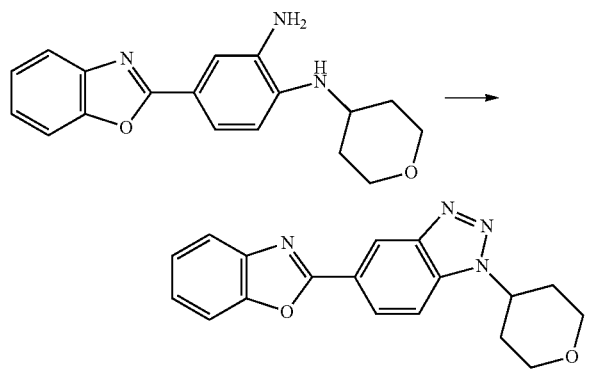

To a solution of 5-(benzoxazol-2-yl)-2-(tetrahydropyran-4-yl)aminoaniline (see Working Example 20-2) (0.35 g, 1.13 mmol) in concentrated hydrochloric acid (2 mL) was added dropwise an aqueous solution containing sodium nitrite (0.09 g, 1.24 mmol) with cooling to 0° C. After stirring for 2 hours at room temperature, this was cooled to 0° C. and was made alkaline with 1N aqueous sodium hydroxide solution, then extracted with ethyl acetate, washed with water, dried over magnesium sulfate and concentrated. The residue was purified by silica gel column chromatography to yield the title compound (0.17 g, 46.9% yield) as dark brown crystals.

$^1$H-NMR (CDCl$_3$) δ (ppm): 2.17-2.22 (2H, m), 2.53-2.59 (2H, m), 3.69 (2H, td, J=11.9, 2.1 Hz), 4.22-4.27 (2H, m), 4.96-5.01 (1H, m), 7.36-7.43 (2H, m), 7.60-7.67 (1H, m), 7.74 (1H, dd, J=8.8, 0.7 Hz), 7.79-7.82 (1H, m), 8.45 (1H, dd, J=8.9, 1.5 Hz), 8.96 (1H, dd, J=1.4, 0.7 Hz).

Working Example 29

Synthesis of 5-(benzoxazol-2-yl)-2-methyl-1-tert-butylbenzimidazole

Working Example 29-1

Synthesis of 2-(2-tert-butylaminoanilin-5-yl)benzoxazole

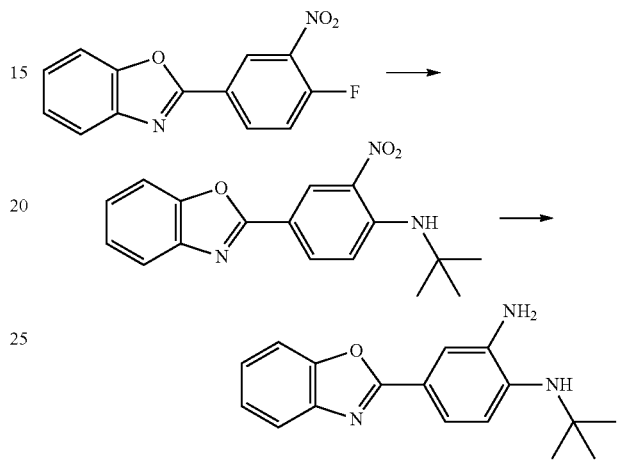

To a suspension of 2-(4-fluoro-3-nitrophenyl)benzoxazole (see Working Example 15-2) (300 mg, 1.16 mmol) in ethanol (5 mL) was added sodium hydrogen carbonate (195 mg, 2.32 mmol) and tert-butylamine (212 mg, 2.90 mmol), and this was heated to reflux with stirring for 4 hours. After the reaction was complete, this was cooled to room temperature, water was added, and this was extracted with chloroform. After the organic layer obtained was dried over anhydrous sodium sulfate, it was filtered and concentrated. The crystals obtained were added to a tetrahydrofuran (5 mL) solution containing 10% palladium-carbon (50 mg), a hydrogen atmosphere was substituted in the flask and this was stirred at room temperature for 8 hours. After the reaction was complete, this was filtered through Celite and the filtrate was concentrated. The residue obtained was purified by silica gel column chromatography to yield the title compound (50.1 mg, 19% yield) as red crystals.

$^1$H-NMR (CDCl$_3$) δ (ppm): 1.45 (9H, m), 6.96 (1H, d, J=8.4 Hz), 7.19-7.33 (2H, m), 7.47-7.54 (1H, m), 7.64 (1H, d, J=2.0 Hz), 7.67-7.73 (2H, m).

Working Example 29-2

Synthesis of 5-(benzoxazol-2-yl)-2-methyl-1-tert-butylbenzimidazole

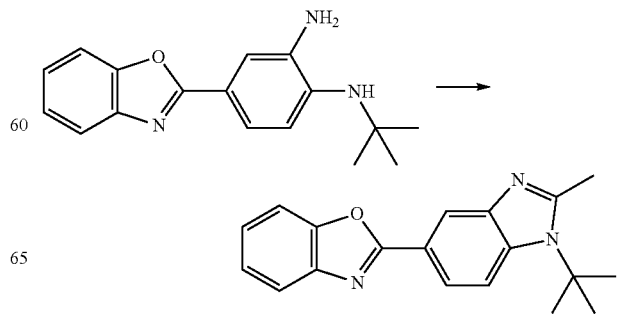

To a solution of 2-(2-tert-butylaminoanilin-5-yl)benzoxazole (see Working Example 29-1) (45.0 mg, 0.160 mmol) in dimethylformamide (2 mL) was added an aqueous solution of acetaldehyde (approx. 90%, 235 µL, 0.480 mmol) and oxone (63.9 mg, 0.104 mmol), and this was stirred at room temperature for 3 hours. After the reaction was complete, aqueous potassium carbonate solution was added, this was filtered and washed with water. The crystals obtained were purified by silica gel column chromatography to yield the title compound (18.2 mg, 38% yield) as white crystals.

$^1$H-NMR (CDCl$_3$) δ (ppm): 1.86 (9H, s), 2.85 (3H, s), 7.32-7.37 (2H, m), 7.57-7.62 (1H, m), 7.75-7.79 (2H, m), 8.12 (1H, dd, J=8.8, 1.7 Hz), 8.51 (1H, d, J=1.7 Hz).

Working Example 30

Synthesis of 5-(benzoxazol-2-yl)-1-(2-methoxyphenyl)-2-methylbenzimidazole

Working Example 30-1

Synthesis of 2-(2-(2-methoxyphenyl)aminoanilin-5-yl)benzoxazole

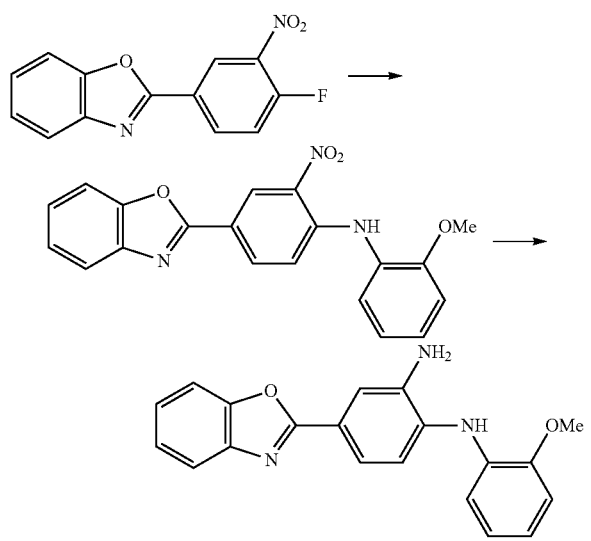

To a suspension of 2-(4-fluoro-3-nitrophenyl)benzoxazole (see Working Example 15-2) (300 mg, 1.16 mmol) in ethanol (5 mL) was added sodium hydrogen carbonate (195 mg, 2.32 mmol) and o-anisidine (357 mg, 2.90 mmol), and this was heated to reflux with stirring for 4 hours. After the reaction was complete, this was cooled to room temperature, water was added, and this was extracted with chloroform. After the organic layer obtained was dried over anhydrous sodium sulfate, it was filtered and concentrated. The crystals obtained were added to a tetrahydrofuran (5 mL) solution containing 10% palladium-carbon (50 mg), a hydrogen atmosphere was substituted in the flask, and this was stirred at room temperature for 8 hours. After the reaction was complete, this was filtered through Celite and the filtrate was concentrated. The residue obtained was purified by silica gel column chromatography to yield the title compound (51.9 mg, 14% yield) as red crystals.

$^1$H-NMR (CDCl$_3$) δ (ppm): 3.92 (3H, s), 6.87-7.00 (4H, m), 7.30-7.35 (3H, m), 7.54-7.57 (1H, m), 7.65-7.75 (3H, m).

Working Example 30-2

Synthesis of 5-(benzoxazol-2-yl)-1-(2-methoxyphenyl)-2-methylbenzimidazole

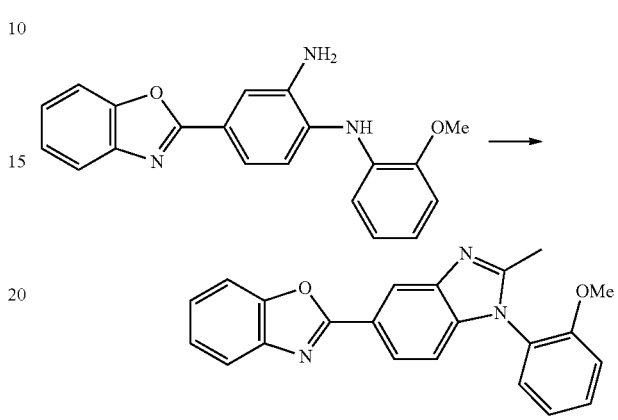

To a solution of 2-(2-(2-methoxyphenyl)aminoanilin-5-yl)benzoxazole (see Working Example 30-1) (48.0 mg, 0.135 mmol) in dimethylformamide (2 mL) was added an aqueous solution of acetaldehyde (approx. 90%, 20.5 µL, 0.405 mmol) and oxone (53.9 mg, 0.0878 mmol), and this was stirred at room temperature for 3 hours. After the reaction was complete, aqueous potassium carbonate solution was added, this was filtered and washed with water. The crystals obtained were purified by silica gel column chromatography to yield the title compound (18.2 mg, 38% yield) as white crystals.

$^1$H-NMR (CDCl$_3$) δ (ppm): 2.46 (3H, s), 3.78 (3H, s), 7.12-7.16 (3H, m), 7.32-7.37 (3H, m), 7.51-7.62 (2H, m), 7.74-7.79 (1H, m), 8.15 (1H, dd, J=8.5, 1.6 Hz), 8.61-8.62 (1H, m).

Working Example 31

Synthesis of 5-(benzoxazol-2-yl)-1-(3-methoxyphenyl)-2-methylbenzimidazole

Working Example 31-1

Synthesis of 2-(2-(3-methoxyphenyl)aminoanilin-5-yl)benzoxazole

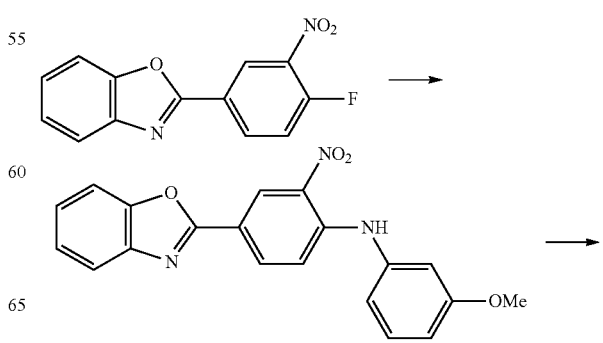

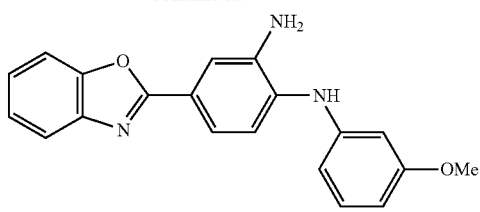

To a suspension of 2-(4-fluoro-3-nitrophenyl)benzoxazole (see Working Example 15-2) (300 mg, 1.16 mmol) in ethanol (5 mL) was added sodium hydrogen carbonate (195 mg, 2.32 mmol) and m-anisidine (357 mg, 2.90 mmol), and this was heated to reflux with stirring for 4 hours. After the reaction was complete, this was cooled to room temperature, water was added, and this was extracted with chloroform. After the organic layer obtained was dried over anhydrous sodium sulfate, it was filtered and concentrated. The crystals obtained were added to a tetrahydrofuran (5 mL) solution containing 10% palladium-carbon (50 mg), a hydrogen atmosphere was substituted in the flask and this was stirred at room temperature for 8 hours. After the reaction was complete, this was filtered through Celite and the filtrate was concentrated. The residue obtained was purified by silica gel column chromatography to yield the title compound (58.5 mg, 15% yield) as a pale yellow oil.

$^1$H-NMR (CDCl$_3$) δ (ppm): 3.79 (3H, s), 6.50-6.58 (3H, m), 7.16-7.35 (4H, m), 7.54-7.57 (1H, m), 7.65-7.76 (3H, m).

Working Example 31-2

Synthesis of 5-(benzoxazol-2-yl)-1-(3-methoxyphenyl)-2-methylbenzimidazole

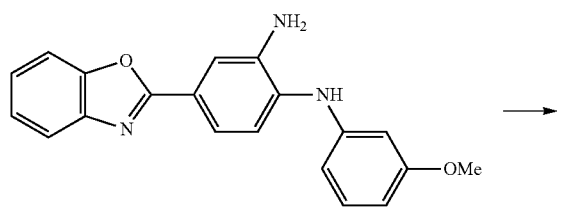

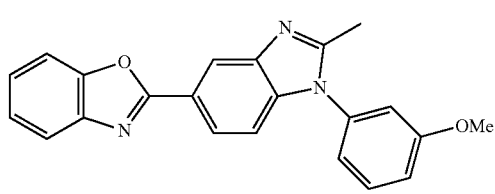

To a solution of 2-(2-(3-methoxyphenyl)aminoanilin-5-yl)benzoxazole (see Working Example 31-1) (55.0 mg, 0.166 mmol) in dimethylformamide (2 mL) was added an aqueous solution of acetaldehyde (approx. 90%, 31.2 μL, 0.405 mmol) and oxone (66.3 mg, 0.108 mmol), and this was stirred at room temperature for 3 hours. After the reaction was complete, aqueous potassium carbonate solution was added, this was filtered and washed with water. The crystals obtained were purified by silica gel column chromatography to yield the title compound (17.3 mg, 29% yield) as light brown crystals.

$^1$H-NMR (CDCl$_3$) δ (ppm): 2.57 (3H, s), 3.88 (3H, s), 6.92 (1H, t, J=2.1 Hz), 6.96-7.00 (1H, m), 7.09 (1H, dd, J=8.4, 2.5 Hz), 7.25-7.38 (3H, m), 7.52 (1H, t, J=8.1 Hz), 7.59-7.63 (1H, m), 7.75-7.79 (1H, m), 8.17 (1H, dd, J=8.6, 1.5 Hz), 8.62 (1H, d, J=1.5 Hz).

Working Example 32

Synthesis of 5-(benzoxazol-2-yl)-2-benzylaminomethyl-1-(tetrahydropyran-4-yl)benzimidazole

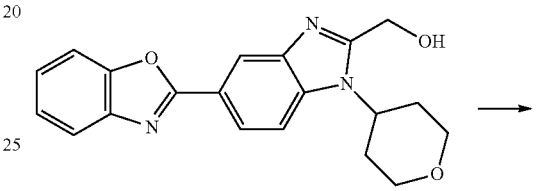

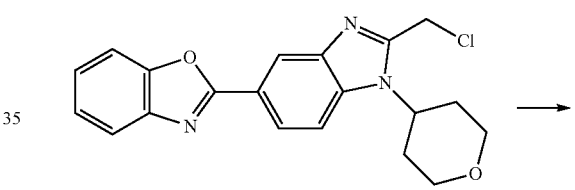

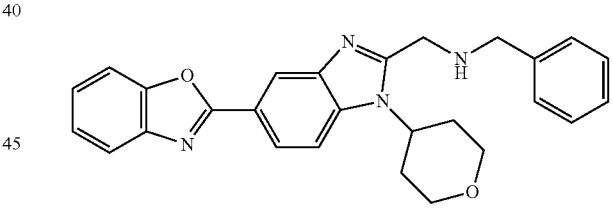

To 5-(benzoxazol-2-yl)-2-hydroxymethyl-1-(tetrahydropyran-4-yl)benzimidazole (see Working Example 13-2) (168 mg, 0.481 mmol) was added thionyl chloride (1.5 mL), and this was heated to reflux with stirring for 2 hours. After the reaction was complete, this was cooled to room temperature and concentrated. The crystals obtained were suspended in tetrahydrofuran, and to this was added sodium iodide (108 mg, 0.722 mmol) and benzylamine (258 mg, 2.41 mmol), and this was heated to reflux with stirring for 1.5 hours. After the reaction was complete, this was cooled to room temperature, water was added, and this was extracted with ethyl acetate. The organic layer obtained was dried over anhydrous sodium sulfate, filtered, and concentrated to give an residue that was purified by silica gel column chromatography to yield the title compound (182 mg, 86% yield) as a colorless amorphous mass.

$^1$H-NMR (CDCl$_3$) δ (ppm): 1.83-1.91 (2H, m), 2.54-2.66 (2H, m), 3.48-3.58 (2H, m), 3.98 (2H, s), 4.11-4.21 (4H, m), 4.60-4.74 (1H, m), 7.31-7.43 (7H, m), 7.56-7.61 (1H, m), 7.69-7.78 (2H, m), 8.20 (1H, dd, J=8.7, 1.6 Hz), 8.59 (1H, d, J=1.2 Hz).

Working Example 33

Synthesis of 5-(benzoxazol-2-yl)-1-((1-ethoxycarbonyl)piperidine-4-yl)-2-methylbenzimidazole Working Example 33-1

Synthesis of 2-(2-(4-(1-ethoxycarbonyl)piperidinoamino)anilin-5-yl)benzoxazole

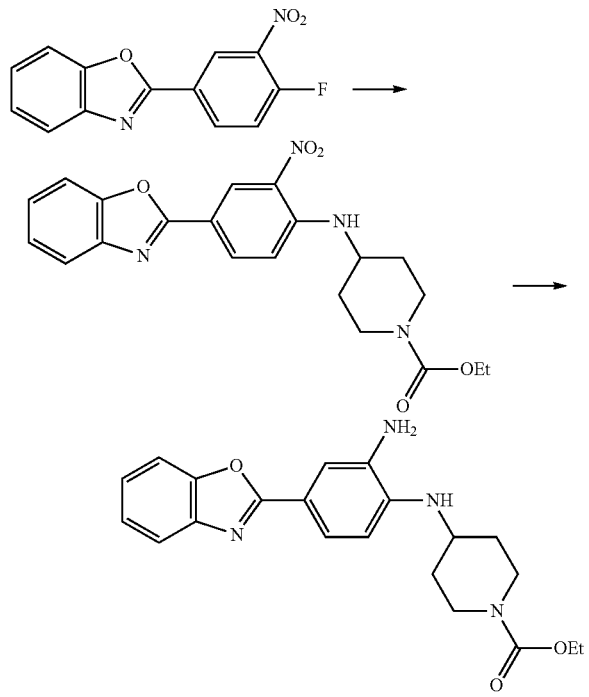

To a suspension of 2-(4-fluoro-3-nitrophenyl)benzoxazole (see Working Example 15-2) (300 mg, 1.16 mmol) in ethanol (5 mL) was added sodium hydrogen carbonate (195 mg, 2.32 mmol) and ethyl 4-amino-1-piperidinecarboxylate (499 mg, 2.90 mmol), and this was heated to reflux with stirring for 3 hours. After the reaction was complete, this was cooled to room temperature, water was added, and this was extracted with ethyl acetate. After the organic layer obtained was dried over anhydrous sodium sulfate, it was filtered and concentrated. The crystals obtained were added to a tetrahydrofuran (5 mL) solution containing 10% palladium-carbon (50 mg), a hydrogen atmosphere was substituted in the flask, and this was stirred at room temperature for 5 hours. After the reaction was complete, this was filtered through Celite and the filtrate was concentrated. The residue obtained was purified by silica gel column chromatography to yield the title compound (162 mg, 37% yield) as a brown oil.

$^1$H-NMR (CDCl$_3$) δ (ppm): 1.28 (3H, t, J=7.1 Hz), 1.38-1.53 (2H, m), 2.08-2.14 (2H, m), 3.00-3.10 (2H, m), 3.52-3.60 (1H, m), 4.08-4.20 (4H, m), 6.72 (1H, d, J=8.4 Hz), 7.27-7.32 (2H, m), 7.51-7.54 (1H, m), 7.65 (1H, d, J=1.8 Hz), 7.67-7.71 (1H, m), 7.76 (1H, dd, J=8.4, 2.0 Hz).

Working Example 33-2

Synthesis of 5-(benzoxazol-2-yl)-1-((1-ethoxycarbonyl)piperidine-4-yl)-2-methylbenzimidazole

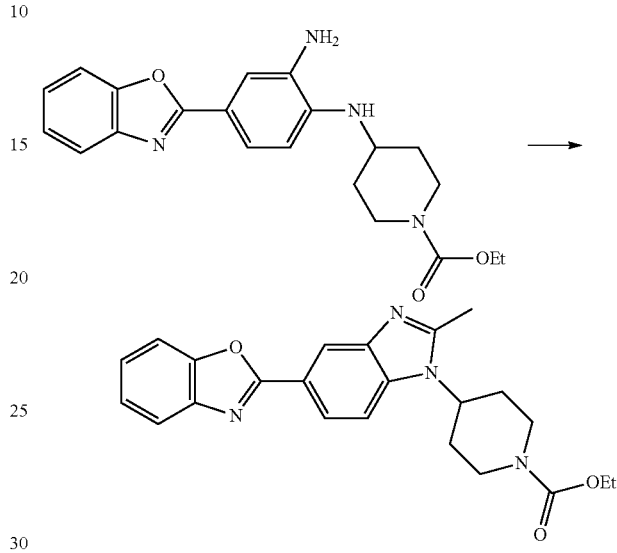

To a solution of 2-(2-(4-(1-ethoxycarbonyl)piperidinoamino)anilin-5-yl)benzoxazole (see Working Example 33-1) (157 mg, 0.413 mmol) in dimethylformamide (3 mL) was added an aqueous solution of acetaldehyde (approx. 90%, 77.7 µL, 1.24 mmol) and oxone (254 mg, 0.413 mmol), at room temperature. This was stirred for 1.5 hours. After the reaction was complete, aqueous potassium carbonate solution was added, and this was extracted with chloroform. After the organic layer obtained was dried over anhydrous sodium sulfate, it was filtered and concentrated. The crystals obtained were purified by silica gel column chromatography to yield the title compound (76.7 mg, 46% yield) as gray crystals.

$^1$H-NMR (CDCl$_3$) δ (ppm): 1.34 (3H, t, J=7.1 Hz), 1.96 (2H, d, J=10.9 Hz), 2.36-2.52 (2H, m), 2.70 (3H, s), 2.88-3.00 (2H, m), 4.23 (2H, q, J=7.1 Hz), 4.33-4.54 (3H, m), 7.33-7.36 (2H, m), 7.54-7.62 (2H, m), 7.75-7.79 (1H, m), 8.16 (1H, d, J=8.6 Hz), 8.55 (1H, s).

Working Example 34

Synthesis of 5-(benzoxazol-2-yl)-1-(4-fluorophenyl)-2-methylbenzimidazole

Working Example 34-1

Synthesis of 2-(2-(4-fluorophenyl)aminoanilin-5-yl)benzoxazole

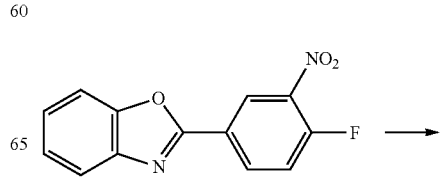

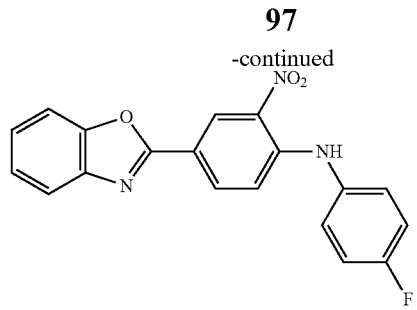

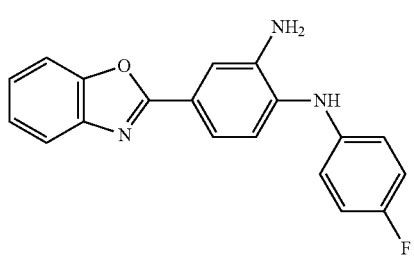

To a suspension of 2-(4-fluoro-3-nitrophenyl)benzoxazole (see Working Example 15-2) (300 mg, 1.16 mmol) in ethanol (5 mL) was added sodium hydrogen carbonate (195 mg, 2.32 mmol) and 4-fluoroaniline (322 mg, 2.90 mmol), and this was heated to reflux with stirring for 4 hours. After the reaction was complete, this was cooled to room temperature, water was added, and this was extracted with chloroform. After the organic layer obtained was dried over anhydrous sodium sulfate, it was filtered and concentrated. The crystals obtained were added to a tetrahydrofuran (5 mL) solution containing 10% palladium-carbon (50 mg), a hydrogen atmosphere was substituted in the flask, and this was stirred at room temperature for 4 hours. After the reaction was complete, this was filtered through Celite and the filtrate was concentrated. The residue obtained was purified by silica gel column chromatography to yield the title compound (40.0 mg, 11% yield) as brown crystals.

$^1$H-NMR (CDCl$_3$) δ (ppm): 6.92-7.05 (4H, m), 7.15 (1H, d, J=8.4 Hz), 7.29-7.36 (2H, m), 7.53-7.57 (1H, m), 7.65-7.75 (3H, m).

Working Example 34-2

Synthesis of 5-(benzoxazol-2-yl)-1-(4-fluorophenyl)-2-methylbenzimidazole

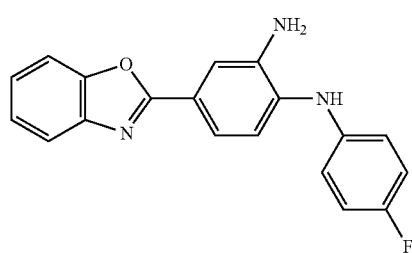

To a solution of 2-(2-(4-fluorophenyl)aminoanilin-5-yl)benzoxazole (see Working Example 34-1) (38.0 mg, 0.119 mmol) in dimethylformamide (2 mL) was added an aqueous solution of acetaldehyde (approx. 90%, 22.6 μL, 0.360 mmol) and oxone (73.2 mg, 0.119 mmol), and this was stirred at room temperature for 3 hours. After the reaction was complete, aqueous potassium carbonate solution was added, this was filtered and washed with water. The crystals obtained were purified by silica gel column chromatography to yield the title compound (20.0 mg, 49% yield) as light brown crystals.

$^1$H-NMR (CDCl$_3$) δ (ppm): 2.54 (3H, s), 7.20 (1H, d, J=8.6 Hz), 7.28-7.43 (6H, m), 7.59-7.63 (1H, m), 7.75-7.79 (1H, m), 8.18 (1H, dd, J=8.5, 1.6 Hz), 8.62 (1H, d, J=1.0 Hz).

Working Example 35

Synthesis of 5-(benzoxazol-2-yl)-1-(piperidine-4-yl)-2-methylbenzimidazole

Working Example 35-1

Synthesis of 2-(2-(4-(1-tert-butoxycarbonyl)piperidinoamino)anilin-5-yl)benzoxazole

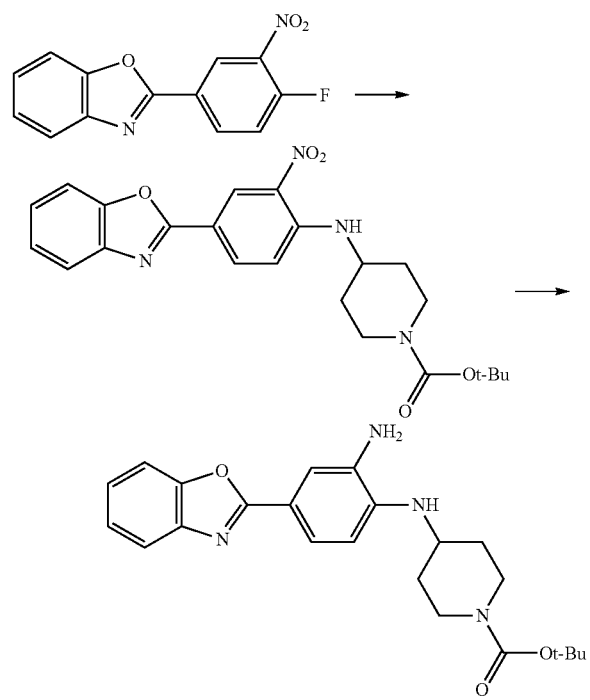

To a suspension of 2-(4-fluoro-3-nitrophenyl)benzoxazole (see Working Example 15-2) (500 mg, 1.94 mmol) in ethanol (5 mL) was added sodium hydrogen carbonate (329 mg, 3.88 mmol) and 4-amino-1-tert-butoxycarbonylpiperidine (970 mg, 4.84 mmol), and this was heated to reflux with stirring for 2 hours. After the reaction was complete, this was cooled to room temperature, water was added, and this was extracted with chloroform. After the organic layer obtained was dried over anhydrous sodium sulfate, it was filtered and concentrated. The crystals obtained were added to a tetrahydrofuran (5 mL) solution containing 10% palladium-carbon (100 mg), a hydrogen atmosphere was substituted in the flask, and this was stirred at room temperature for 22 hours. After the reaction was complete, this was filtered through Celite and the filtrate was concentrated. The residue obtained was purified by silica gel column chromatography to yield the title compound (353 mg, 45% yield) as a brown oil.

$^{1}$H-NMR (CDCl$_{3}$) δ (ppm): 1.37-1.45 (2H, m), 1.48 (9H, s), 2.05-2.12 (2H, m), 2.99 (2H, t, J=11.5 Hz), 3.50-3.58 (1H, m), 4.05-4.16 (2H, m), 7.27-7.31 (3H, m), 7.50-7.54 (1H, m), 7.65 (1H, d, J=2.0 Hz), 7.68-7.71 (1H, m), 7.75 (1H, dd, J=8.3, 1.9 Hz).

Working Example 35-2

Synthesis of 5-(benzoxazol-2-yl)-1-(piperidine-4-yl)-2-methylbenzimidazole

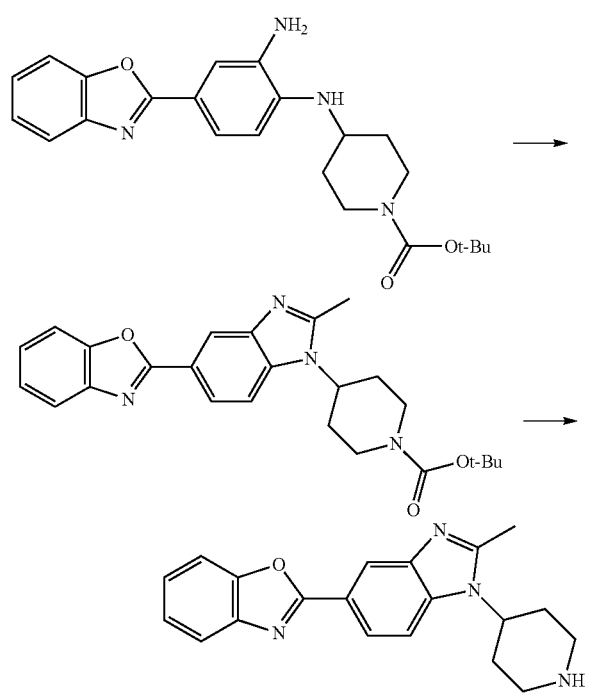

To a solution of 2-(2-(4-(1-tert-butoxycarbonyl)piperidinoamino)anilin-5-yl)benzoxazole (see Working Example 35-1) (350 mg, 0.857 mmol) in dimethylformamide (3 mL) was added an aqueous solution of acetaldehyde (approx. 90%, 161 μL, 2.57 mmol) and oxone (527 mg, 0.887 mmol), and this was stirred at room temperature for 1 hour. After the reaction was complete, aqueous potassium carbonate solution was added, and this was extracted with chloroform. After the organic layer obtained was dried over anhydrous sodium sulfate, it was filtered and concentrated. The residue obtained was dissolved in chloroform (5 mL), trifluoroacetic acid was added, and this was stirred at room temperature for 1 hour. After the reaction was complete, water was added, and the water layer was washed 2 times with chloroform and once with ethyl acetate. Saturated aqueous sodium hydrogen carbonate solution was added to the aqueous layer obtained, and this was extracted with ethyl acetate. After the organic layer obtained was dried over anhydrous sodium sulfate, it was filtered and concentrated. The residue obtained was purified by silica gel column chromatography to yield the title compound (20.0 mg, 7% yield) as a colorless taffy-like material.

$^{1}$H-NMR (CDCl$_{3}$) δ (ppm): 1.93-2.03 (2H, m), 2.48-2.64 (2H, m), 2.70 (3H, s), 2.85-2.96 (2H, m), 3.41 (2H, d, J=12.0 Hz), 4.29-4.38 (1H, m), 7.33-7.36 (2H, m), 7.59-7.63 (1H, m), 7.70-7.79 (2H, m), 8.15-8.20 (1H, m), 8.56 (1H, d, J=1.5 Hz).

Working Example 36

Synthesis of 1-adamantyl-5-(benzoxazol-2-yl)-2-methylbenzimidazole

Working Example 36-1

Synthesis of 2-(2-(1-adamantylamino)anilin-5-yl)benzoxazole

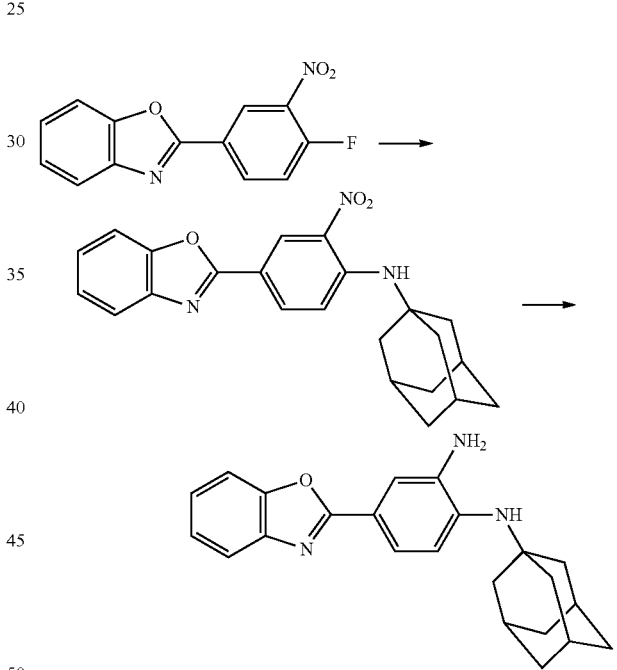

To a suspension of 2-(4-fluoro-3-nitrophenyl)benzoxazole (see Working Example 15-2) (300 mg, 1.16 mmol) in ethanol (5 mL) was added sodium hydrogen carbonate (195 mg, 2.32 mmol) and 1-adamantylamine (185 mg, 1.22 mmol), and this was heated to reflux with stirring for 4 hours. After the reaction was complete, this was cooled to room temperature, water was added, and the precipitated crystals were filtered off, washed with water and then dried. The crystals obtained were added to a tetrahydrofuran (5 mL) solution containing 10% palladium-carbon (100 mg), a hydrogen atmosphere was substituted in the flask, and this was stirred at room temperature for 6 hours. After the reaction was complete, this was filtered through Celite and the filtrate was concentrated. The residue obtained was purified by silica gel column chromatography to yield the title compound (67.0 mg, 16% yield) as brown crystals.

$^1$H-NMR (CDCl$_3$) δ (ppm): 1.72 (6H, br s), 2.01 (6H, br s), 2.16 (3H, br s), 7.03 (1H, d, J=8.2 Hz), 7.26-7.31 (2H, m), 7.49-7.53 (1H, m), 7.62-7.71 (3H, m).

Working Example 36-2

Synthesis of 1-adamantyl-5-(benzoxazol-2-yl)-2-methylbenzimidazole

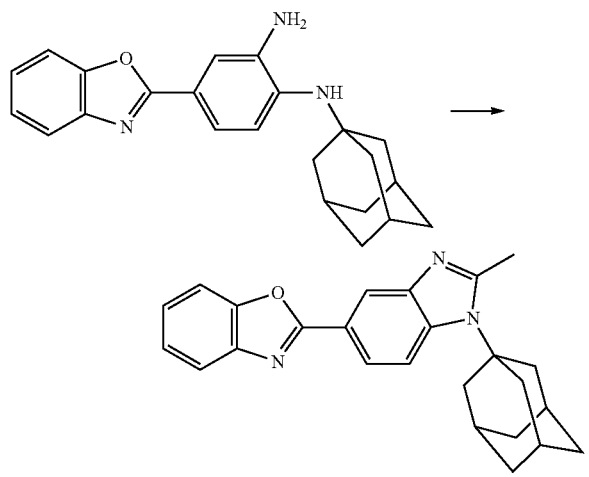

To a solution of 2-(2-(1-adamantylamino)anilin-5-yl)benzoxazole (see Working Example 36-1) (65.0 mg, 0.181 mmol) in dimethylformamide (2 mL) was added an aqueous solution of acetaldehyde (approx. 90%, 34.0 μL, 0.542 mmol) and oxone (111 mg, 0.181 mmol), and this was stirred at room temperature for 2 hours. After the reaction was complete, aqueous potassium carbonate solution was added, and this was extracted with ethyl acetate. After the organic layer obtained was dried over anhydrous sodium sulfate, it was filtered and concentrated. The crystals obtained were purified by silica gel column chromatography to yield the title compound (33.4 mg, 48% yield) as light brown crystals.

$^1$H-NMR (CDCl$_3$) δ (ppm): 1.86 (6H, br s), 2.34 (3H, br s), 2.55 (6H, br s), 2.89 (3H, s), 7.32-7.35 (2H, m), 7.58-7.62 (1H, m), 7.75-7.79 (1H, m), 7.83 (1H, d, J=8.9 Hz), 8.09 (1H, dd, J=8.9, 1.7 Hz), 8.51 (1H, d, J=1.7 Hz).

Working Example 37

Synthesis of 5-(N-t-butoxycarbonylindol-2-yl)-2-methyl-1-(tetrahydropyran-4-yl)benzimidazole

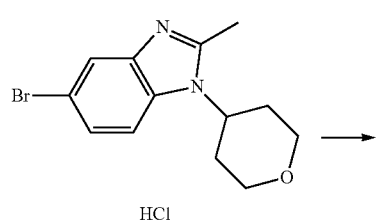

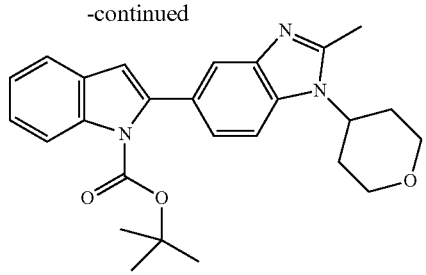

5-Bromo-2-methyl-1-(tetrahydropyran-4-yl)benzimidazole hydrochloride (see Synthesis Example 18-3) (0.40 g, 1.21 mmol), 2-(N-t-butoxycarbonylindole-2-yl)boronic acid (0.35 g, 0.242 mmol), ethanol (5 mL), toluene (5 mL), and 2M aqueous sodium carbonate solution (1.8 mL) were prepared, and this was degassed. Tetrakis(triphenylphosphine)palladium (0.07 g, 0.07 mmol) was added, and this was refluxed for 3 hours. After cooling, ethanol and water were added and this was filtered through Celite and the material on the filter was washed with ethanol and water. The filtrate was concentrated, the precipitated crystals were filtered off and washed with water and hexane, and dried to yield the title compound (215 mg, 41.3% yield) as white crystals.

$^1$H-NMR (CDCl$_3$) δ (ppm): 1.31 (9H, s), 1.87 (2H, dd, J=12.5, 2.6 Hz), 2.59-2.68 (2H, m), 2.59 (3H, s), 3.60 (2H, td, J=12.1, 1.9 Hz), 4.22 (2H, dd, J=11.7, 4.5 Hz), 4.41-4.46 (1H, m), 6.57 (1H, d, J=0.7 Hz), 7.22-7.35 (3H, m), 7.55 (2H, d, J=8.4 Hz), 7.76 (1H, d, J=1.5 Hz), 8.19 (1H, d, J=8.4 Hz).

Working Example 38

Synthesis of 5-(indol-2-yl)-1-(tetrahydropyran-4-yl)-2-methylbenzimidazole

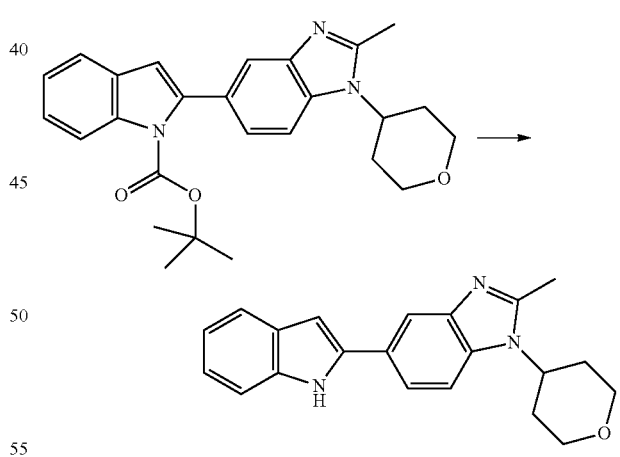

5-(N-t-butoxycarbonylindol-2-yl)-2-methyl-1-(tetrahydropyran-4-yl)benzimidazole (see Synthesis Example 37 (200 mg, 0.463 mmol) was added to a 1N aqueous hydrochloric acid solution (10 mL), and this was stirred at room temperature for 3 hours. After the reaction was complete, this was allowed to stand for 3 days and the precipitated crystals were filtered off, and to this was added saturated aqueous sodium hydrogen carbonate (5 mL) and this was stirred for 30 minutes. The precipitated crystals were filtered off, washed with water and dried to yield the title compound (155 mg, quant.) as light brown crystals.

¹H-NMR (DMSO-d₆) δ (ppm): 2.00 (2H, d, J=9.6 Hz), 2.40-2.45 (2H, m), 2.93 (3H, s), 3.60 (2H, t, J=11.3 Hz), 4.08 (2H, dd, J=11.3, 3.6 Hz), 4.84-4.88 (1H, m), 7.04-7.12 (3H, m), 7.44 (1H, d, J=7.9 Hz), 7.56 (1H, d, J=7.9 Hz), 8.01-8.13 (2H, m), 8.24 (1H, s), 11.88 (1H, s).

Working Example 39

Synthesis of 5-(5-methylbenzoxazol-2-yl)-2-methyl-1-(tetrahydropyran-4-yl)benzimidazole

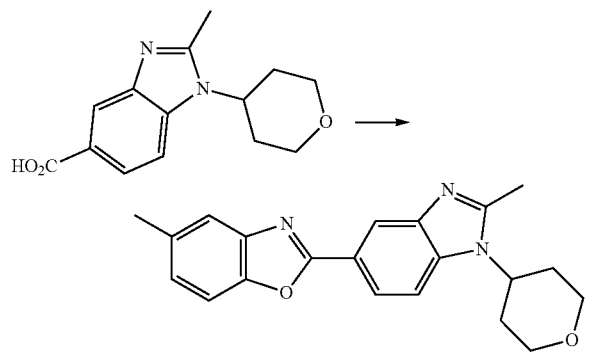

2-methyl-1-(tetrahydropyran-4-yl)benzimidazole-5-carboxylic acid HCl salt (see Working Example 4-3) (0.25 g, 0.96 mmol), 2-amino-4-methylphenol (0.13 g, 1.05 mmol), anhydrous DMF (500 mL) and WSC (0.22 g, 1.14 mmol) were stirred for 3 hours at room temperature. After the reaction was complete, water (50 mL) was added, the precipitated crystals were filtered off, and the filter residue was extracted with water/chloroform. After the organic layer was dried over anhydrous sodium sulfate, filtration and concentration gave crystals that were dissolved in toluene (5 mL), to which p-toluenesulfonic acid hydrate (0.43 g, 2.26 mmol) was added and this was stirred at reflux for 2 hours. After the solvent was concentrated at reduced pressure, water (5 mL) was added and the solid obtained was filtered off, and after washing with water, drying at reduced pressure at 50° C. yielded the title compound (95 mg, 28.5% yield) as a light yellow solid.

¹H-NMR (DMSO-d₆) δ (ppm): 1.88 (2H, d, J=9.4 Hz), 2.30-2.45 (5H, m), 2.67 (3H, s), 3.58 (2H, t, J=11.2 Hz), 4.06 (2H, dd, J=11.2, 4.1 Hz), 4.61-4.70 (1H, m), 7.21 (1H, dd, J=8.6 1.3 Hz), 7.58 (1H, s), 7.65 (1H, d, J=8.6 Hz), 7.88 (1H, d, J=8.6 Hz), 8.03 (1H, d, J=1.3 Hz), 8.30 (1H, d, J=1.3 Hz).

Working Example 40

Synthesis of 5-(5-chlorobenzoxazol-2-yl)-2-methyl-1-(tetrahydropyran-4-yl)benzimidazole

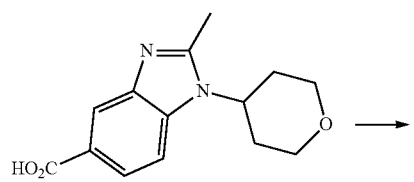

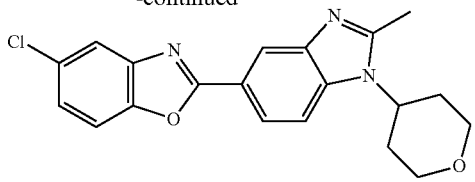

2-methyl-1-(tetrahydropyran-4-yl)benzimidazole-5-carboxylic acid HCl salt (see Working Example 4-3) (0.25 g, 0.96 mmol), 2-amino-4-chlorophenol (0.15 g, 1.05 mmol), anhydrous DMF (10 mL) and WSC (0.22 g, 1.14 mmol) were stirred overnight at room temperature. After the reaction was complete, water (50 mL) was added, the precipitated crystals were filtered off, and the filter residue was extracted with water/chloroform. After the organic layer was dried over anhydrous sodium sulfate, filtration and concentration gave crystals that were dissolved in toluene (5 mL), to which p-toluenesulfonic acid hydrate (0.32 g, 1.68 mmol) was added and this was stirred at reflux for 2 hours. After the solvent was concentrated at reduced pressure, water (5 mL) was added and the solid obtained was filtered off, and after washing with water, drying at reduced pressure at 50° C. yielded the title compound (54 mg, 15.3% yield) as a light brown solid.

¹H-NMR (DMSO-d₆) δ (ppm): 1.88 (2H, d, J=10.6 Hz), 2.36-2.41 (2H, m), 2.67 (3H, s), 3.58 (2H, t, J=11.0 Hz), 4.02-4.09 (2H, m), 4.64-4.69 (1H, m), 7.43-7.46 (1H, m), 7.83 (1H, d, J=8.7 Hz), 7.89-7.91 (2H, m), 8.05 (1H, dd, J=8.7, 1.6 Hz), 8.32 (1H, d, J=1.2 Hz).

Working Example 41

Synthesis of 5-(6-chlorobenzoxazol-2-yl)-2-methyl-1-(tetrahydropyran-4-yl)benzimidazole 2-methyl-1-(tetrahydropyran-4-yl)benzimidazole-5-carboxylic acid HCl salt (see Working Example 4-3) (0.25 g, 0.96 mmol), 2-amino-5-chlorophenol (0.15 g, 1.05 mmol), anhydrous DMF (10 mL) and WSC (0.22 g, 1.14 mmol) were stirred overnight at room temperature. After the reaction was complete, water (50 mL) was added, the precipitated crystals were filtered off, and the filter residue was extracted with water/chloroform. After the organic layer was dried over anhydrous sodium sulfate, filtration and concentration gave crystals that were dissolved in toluene (5 mL), to which p-toluenesulfonic acid hydrate (0.38 g, 2.00 mmol) was added and this was stirred at reflux for 2 hours. After the solvent was concentrated at reduced pressure, water (5 mL)

was added and the solid obtained was filtered off, and after washing with water, drying at reduced pressure at 50° C. yielded the title compound (5 mg, 1.4% yield) as an orange solid.

$^1$H-NMR (DMSO-d$_6$) δ (ppm): 1.88 (2H, d, J=9.4 Hz), 2.38-2.43 (2H, m), 2.67 (3H, s), 3.58 (2H, t, J=11.0 Hz), 4.02-4.08 (2H, m), 4.65-4.68 (1H, m), 7.45 (1H, dd, J=8.6, 2.0 Hz), 7.80 (1H, d, J=8.6 Hz), 7.90 (1H, d, J=8.6 Hz), 7.99 (1H, d, J=2.0 Hz), 8.03 (1H, dd, J=8.6, 1.6 Hz), 8.31 (1H, d, J=1.6 Hz).

Working Example 42

Synthesis of 5-(6-methylbenzoxazol-2-yl)-2-methyl-1-(tetrahydropyran-4-yl)benzimidazole

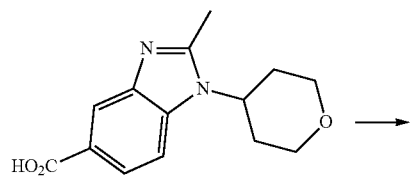

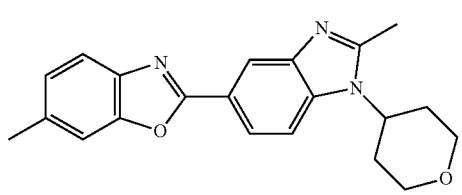

2-methyl-1-(tetrahydropyran-4-yl)benzimidazole-5-carboxylic acid HCl salt (see Working Example 4-3) (0.25 g, 0.96 mmol), 2-amino-5-methylphenol (0.13 g, 1.05 mmol), anhydrous DMF (10 mL) and WSC (0.22 g, 1.14 mmol) were stirred overnight at room temperature. After the reaction was complete, water (50 mL) was added, the precipitated crystals were filtered off, and the filter residue was extracted with water/chloroform. After the organic layer was dried over anhydrous sodium sulfate, filtration and concentration gave crystals that were dissolved in toluene (5 mL), to which p-toluenesulfonic acid hydrate (0.45 g, 2.37 mmol) was added and this was stirred at reflux for 2 hours. After the solvent was concentrated at reduced pressure, water (5 mL) was added and the solid obtained was filtered off, and after washing with water, drying at reduced pressure at 50° C. yielded the title compound (16 mg, 4.8% yield) as an orange solid.

$^1$H-NMR (DMSO-d$_6$) δ (ppm): 1.85-1.90 (2H, m), 2.34-2.52 (8H, m), 3.58 (2H, t, J=11.0 Hz), 4.00-4.08 (2H, m), 4.62-4.72 (1H, m), 7.22 (1H, d, J=8.1 Hz), 7.60 (1H, s), 7.65 (1H, d, J=8.1 Hz), 7.87 (1H, d, J=8.8 Hz), 8.03 (1H, dd, J=8.8, 1.6 Hz), 8.29 (1H, d, J=1.6 Hz).

Working Example 43

Synthesis of 5-(benzoxazol-2-yl)-2-ethyl-1-(tetrahydropyran-4-yl)benzimidazole

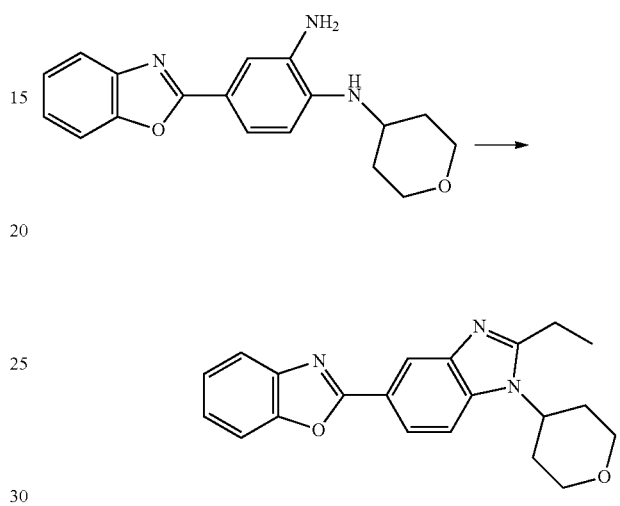

5-(Benzoxazol-2-yl)-2-(tetrahydropyran-4-yl)aminoaniline (see Working Example 20-2) (0.15 g, 0.484 mmol) was dissolved in DMF (3 mL) and water (0.1 mL), propyl aldehyde (0.03 g, 0.561 mmol) was added followed by oxone (0.19 g, 0.310 mmol), and this was stirred at room temperature for 2.5 hours. Aqueous potassium carbonate solution (0.10 g/15 mL) was added to the reaction solution. This was extracted with chloroform, washed with water, and after drying over magnesium sulfate, this was concentrated and purified by silica gel column chromatography. The crystals obtained were washed with hexane and a small amount of ethyl acetate, and dried to yield the title compound (44.7 mg, 26.6% yield) as light brown crystals.

$^1$H-NMR (DMSO-d$_6$) δ (ppm): 1.37 (3H, t, J=7.4 Hz), 1.86 (2H, d, J=9.1 Hz), 2.39-2.49 (2H, m), 3.03 (2H, q, J=7.4 Hz), 3.59 (2H, t, J=11.1 Hz), 4.02-4.08 (2H, m), 4.63-4.72 (1H, m), 7.39-7.44 (2H, m), 7.76-7.81 (2H, m), 7.90 (1H, d, J=8.6 Hz), 8.06 (1H, dd, J=8.6, 1.5 Hz), 8.36 (1H, d, J=1.5 Hz).

Working Example 44

Synthesis of 5-(benzoxazol-2-yl)-2-(imidazol-2-yl)-1-(tetrahydropyran-4-yl)benzimidazole

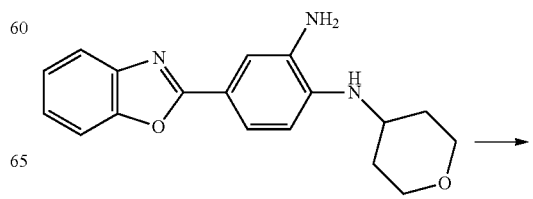

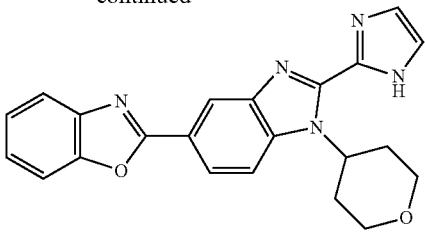

5-(Benzoxazol-2-yl)-2-(tetrahydropyran-4-yl)aminoaniline (see Working Example 20-2) (0.10 g, 0.32 mmol) was dissolved in DMF (3 mL) and water (0.1 mL), 2-imidazolecarbaldehyde (0.03 g, 0.31 mmol) was added followed by oxone (0.13 g, 0.21 mmol), and this was stirred at room temperature for 2.5 hours. Aqueous potassium carbonate solution (0.10 g/15 mL) was added to the reaction solution. This was extracted with chloroform, washed with water, and after drying over magnesium sulfate, this was concentrated and purified by silica gel column chromatography. The crystals obtained were washed with hexane and a small amount of ethyl acetate, and dried to yield the title compound (15 mg, 12.1% yield) as light brown crystals.

$^1$H-NMR (CDCl$_3$) δ (ppm): 2.13 (2H, dd, J=12.4, 3.4 Hz), 2.66-2.82 (2H, m), 3.78 (2H, t, J=11.5 Hz), 4.26 (2H, dd, J=11.5, 4.0 Hz), 6.66-6.79 (1H, m), 7.22-7.40 (4H, m), 7.55-7.59 (1H, m), 7.72-7.76 (1H, m), 7.91 (1H, d, J=8.7 Hz), 8.23 (1H, dd, J=8.7, 1.4 Hz), 8.53 (1H, d, J=1.4 Hz).

Working Example 45

Synthesis of 5-(benzoxazol-2-yl)-2-(thiophen-2-yl)-1-(tetrahydropyran-4-yl)benzimidazole

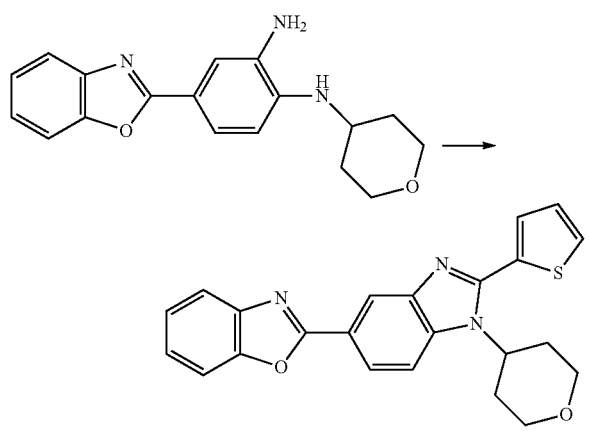

5-(Benzoxazol-2-yl)-2-(tetrahydropyran-4-yl)aminoaniline (see Working Example 20-2) (0.13 g, 0.42 mmol) was dissolved in DMF (3 mL) and water (0.1 mL), 2-thiophenecarbaldehyde (0.05 g, 0.45 mmol) was added followed by oxone (0.17 g, 0.28 mmol), and this was stirred at room temperature for 2.5 hours. Aqueous potassium carbonate solution (0.10 g/15 mL) was added to the reaction solution. This was extracted with ethyl acetate, washed with water, and after drying over magnesium sulfate, this was concentrated and purified by silica gel column chromatography. The crystals obtained were washed with hexane and a small amount of ethyl acetate, and dried to yield the title compound (60 mg, 36% yield) as light brown crystals.

$^1$H-NMR (CDCl$_3$) δ (ppm): 1.96 (2H, dd, J=12.9, 2.8 Hz), 2.71-2.80 (2H, m), 3.55 (2H, td, J=12.0, 1.8 Hz), 4.22 (2H, dd, J=11.6, 4.7 Hz), 4.93-4.98 (1H, m), 7.23-7.26 (1H, m), 7.34-7.37 (2H, m), 7.46 (1H, dd, J=3.6, 1.2 Hz), 7.59-7.65 (2H, m), 7.77-7.81 (2H, m), 8.25 (1H, dd, J=8.7, 1.6 Hz), 8.68 (1H, d, J=1.6 Hz).

Working Example 46

Synthesis of 2-methyl-5-(4-methylbenzoxazol-2-yl)-1-(tetrahydropyran-4-yl)benzimidazole Working Example 46-1

Synthesis of 2-fluoro-5-(4-methylbenzoxazol-2-yl)nitrobenzene

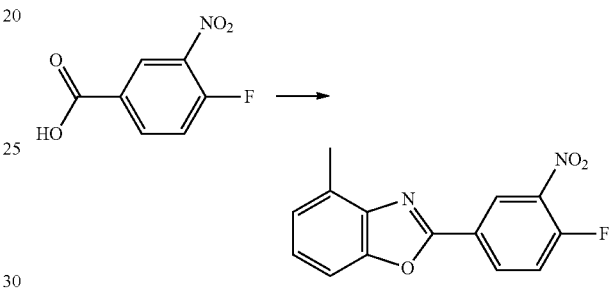

To a suspension of 3-fluoro-2-nitrobenzoic acid (1.00 g, 5.40 mmol) and DMF (1 drop) in toluene (10 mL) was added thionyl chloride (0.78 g, 6.56 mmol) and this was stirred at reflux for 3 hours. After the reaction was complete, concentration at reduced pressure gave a residue that was added to 2-hydroxy-6-methylaniline (0.66 g, 5.4 mmol), triethylamine (0.66 g, 6.5 mmol) and tetrahydrofuran (5 mL), and this was stirred at room temperature for 3 hours. After the reaction was complete, water (50 mL) was added, and this was extracted with ethyl acetate. After the organic layer was dried over anhydrous sodium sulfate, filtration and concentration gave crystals that were added to toluene (20 mL), to which p-toluenesulfonic acid hydrate (1.14 g, 5.99 mmol) was next added and this was stirred at reflux for 2 hours. After concentration of the solvent at reduced pressure, water (5 mL) was added, after which this was extracted with ethyl acetate. The organic layer obtained was dried over anhydrous sodium sulfate, after which it was filtered and concentrated to yield the title compound (0.50 g, 37% yield) as a light brown solid.

$^1$H-NMR (CDCl$_3$) δ (ppm): 2.67 (3H, s), 7.26-7.33 (1H, m), 7.27-7.32 (1H, m), 7.41-7.49 (2H, m), 8.52-8.55 (1H, m), 8.95 (1H, dd, J=7.1, 2.1 Hz).

Working Example 46-2

Synthesis of 2-(2-(tetrahydropyran-4-yl)aminoanilin-5-yl)benzoxazole

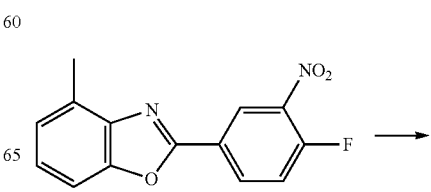

-continued

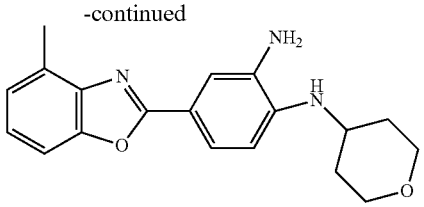

To a suspension of 2-fluoro-5-(4-methylbenzoxazol-2-yl)nitrobenzene (see Working Example 46-1) (0.50 g, 1.8 mmol) in ethanol (10 mL) was added triethylamine (0.22 g, 2.17 mmol) and aminotetrahydropyran (0.20 g, 1.9 mmol), and this was heated to reflux for 3 hours. After the reaction was complete, this was cooled to room temperature and then the mixture was poured into dilute hydrochloric acid (1 M, 10 mL), this was extracted with chloroform (50 mL), and washed with saturated sodium hydrogen carbonate (approx. 50 mL) and then with brine (approx. 50 mL). The organic layer was dried over anhydrous magnesium sulfate, and then the solvent was distilled away at reduced pressure to give crystals, which were added to palladium-carbon (Pd: 10%, 0.06 g) and a solvent mixture of ethyl acetate/methanol (1:1, 20 mL), hydrogen was substituted in by successively reducing the pressure and purging with hydrogen gas 3 times, and this was stirred at room temperature for 2.5 hours. After substituting in nitrogen, the insoluble material was filtered off through a Celite layer (20 mm thickness), and this same layer was washed with methanol (20 mL, 3 times). The filtrate and wash solutions were combined and the solvent was distilled away under reduced pressure to yield the title compound (0.56 g, 94.3% yield) as a blackish brown solid.

$^1$H-NMR (CDCl$_3$) δ (ppm): 1.71-1.77 (2H, m), 2.12 (2H, d, J=12.9 Hz), 2.66 (3H, s), 3.57-3.66 (2H, m), 3.80-3.90 (1H, m), 4.05-4.08 (2H, m), 7.01 (1H, d, J=9.2 Hz), 7.14 (1H, d, J=7.9 Hz), 7.20-7.23 (1H, m), 7.39 (1H, d, J=7.9 Hz), 8.31 (1H, dd, J=9.2, 2.0 Hz), 8.42 (1H, d, J=7.9 Hz), 9.08 (1H, d, J=2.0 Hz).

Working Example 46-3

Synthesis of 2-methyl-5-(4-methylbenzoxazol-2-yl)-1-(tetrahydropyran-4-yl)benzimidazole

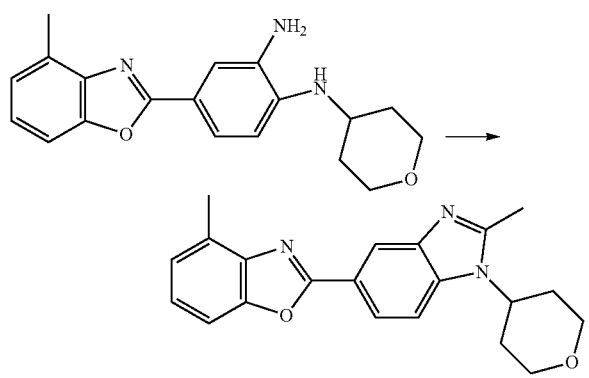

To a solution of 2-(2-(tetrahydropyran-4-yl)aminoanilin-5-yl)benzoxazole (see Working Example 46-2) (0.56 g, 1.7 mmol) in dimethylformamide (5 mL) containing water (0.18 mL) was added an aqueous solution of acetaldehyde (approx. 90%, 90 mg, 1.8 mmol) and oxone (0.69 mg, 1.1 mmol), and this was stirred at room temperature for 3 hours. After the reaction was complete, aqueous potassium carbonate solution was added, this was filtered and washed with water. The crystals obtained were purified by silica gel column chromatography to yield the title compound (123 mg, 20.4% yield) as light brown crystals.

$^1$H-NMR (DMSO-d$_6$) δ (ppm): 1.85-1.91 (2H, m), 2.39 (2H, td, J=12.4, 4.4 Hz), 2.60 (3H, s), 2.67 (3H, s), 3.58 (2.2H, t, J=11.3 Hz), 4.06 (2H, dd, J=11.3, 4.0 Hz), 4.62-4.71 (1H, m), 7.20 (1H, d, J=7.7 Hz), 7.29 (1H, t, J=7.7 Hz), 7.58 (1H, d, J=7.7 Hz), 7.88 (1H, d, J=8.6 Hz), 8.06 (1H, dd, J=8.6, 1.5 Hz), 8.31 (1H, d, J=1.5 Hz).

Working Example 47

Synthesis of 2-methyl-5-(6-nitrobenzoxazol-2-yl)-1-(tetrahydropyran-4-yl)benzimidazole Working Example 47-1

Synthesis of 5-(2-hydroxy-4-nitroanilinocarbonyl)-2-methyl-1-(tetrahydropyran-4-yl)benzimidazole

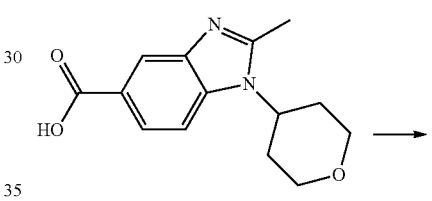

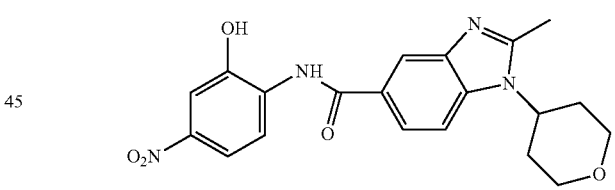

To a suspension of 2-methyl-1-(tetrahydropyran-4-yl)benzimidazole-5-carboxylic acid HCl salt (see Working Example 4-3) (0.75 g, 2.9 mmol) in toluene (10 mL) containing DMF (1 drop) was added thionyl chloride (0.41 g, 3.4 mmol), and this was refluxed for 7 hours with stirring. After the reaction was complete, concentration at reduced pressure gave a residue that was added to 2-hydroxy-5-nitroaniline (0.44 g, 2.9 mmol), triethylamine (0.32 g, 3.2 mmol) and tetrahydrofuran (5 mL), and this was stirred at room temperature for 3 hours. After the reaction was complete, water (30 mL) was added and the precipitated crystals were filtered off. After the crystals were washed with water, they were dried with heating at reduced pressure to yield the title compound (195 mg, 17.1%) as a light brown solid.

$^1$H-NMR (DMSO-d$_6$) δ (ppm): 1.99 (2H, d, J=9.5 Hz), 2.49-2.52 (2H, m), 2.92 (3H, s), 3.60 (2H, t, J=11.2 Hz), 4.08 (2H, dd, J=11.2, 3.8 Hz), 4.85-4.89 (1H, m), 7.78-7.83 (2H, m), 8.08 (1H, dd, J=8.8, 1.5 Hz), 8.16-8.20 (2H, m), 8.38 (1H, d, J=1.5 Hz), 9.95 (1H, s), 11.22 (1H, s).

Working Example 47-2

Synthesis of 2-methyl-5-(6-nitrobenzoxazol-2-yl)-1-(tetrahydropyran-4-yl)benzimidazole

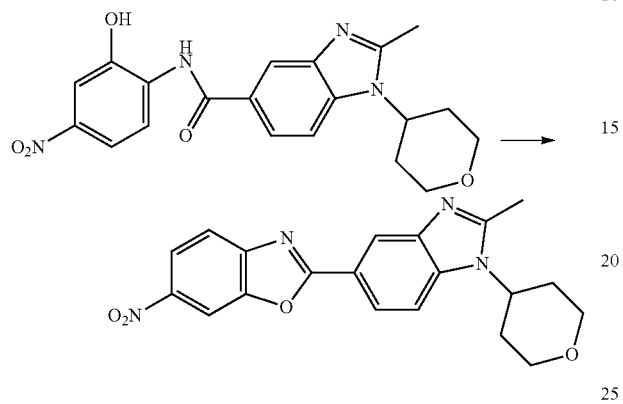

5-(2-Hydroxy-4-nitroanilinocarbonyl)-2-methyl-1-(tetrahydropyran-4-yl)benzimidazole (see Working Example 47-1) (195 mg, 0.492 mmol) was added to toluene (20 mL), after which p-toluenesulfonic acid hydrate (280 mg, 1.47 mmol) was added and this was refluxed with stirring for 4 hours. After the solvent was concentrated under reduced pressure, a sodium bicarbonate water (10 mL) was added and this was stirred at room temperature for 1 hour. The precipitated crystals were filtered off, and after being washed with water were dried with heating at reduced pressure to yield the title compound (144 mg, 77.4% yield) as a pale yellow solid.

$^1$H-NMR (DMSO-$d_6$) δ (ppm): 1.87 (2H, d, J=12.7 Hz), 2.34-2.51 (2H, m), 2.67 (3H, s), 3.57 (2H, t, J=11.0 Hz), 4.05 (2H, d, J=7.6 Hz), 4.60-4.75 (1H, m), 7.92-8.00 (2H, m), 8.09 (1H, d, J=8.6 Hz), 8.31 (1H, dd, J=9.0, 2.1 Hz), 8.37 (1H, s), 8.73 (1H, d, J=2.1 Hz).

Working Example 48

Synthesis of 2-methyl-5-(6-aminobenzoxazol-2-yl)-1-(tetrahydropyran-4-yl)benzimidazole

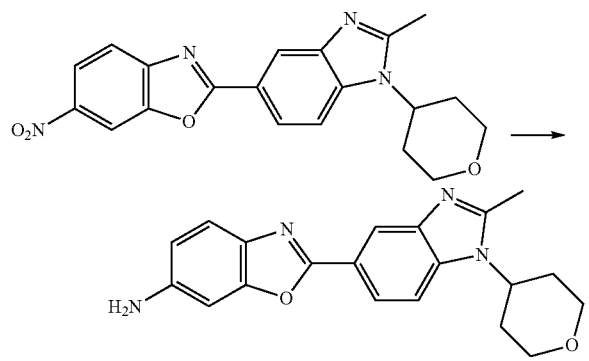

2-Methyl-5-(6-nitrobenzoxazol-2-yl)-1-(tetrahydropyran-4-yl)benzimidazole (see Working Example 47-2) (135 mg, 0.357 mmol) was added to methanol (20 mL) containing palladium/carbon (Pd: 10%, 0.06 g), hydrogen was substituted in by successively reducing the pressure and purging with hydrogen gas 3 times, and this was stirred at room temperature for 2.5 hours. After substituting in nitrogen, the insoluble material was filtered off through a Celite layer (20 mm thickness), and this same layer was washed with methanol (20 mL, 3 times). The filtrate was combined with the wash solutions and the solvent was distilled out at reduced pressure, the residue obtained was purified by silica gel column chromatography to yield the title compound (50 mg, 40.2% yield) as brown crystals.

$^1$H-NMR (CDCl$_3$) δ (ppm): 1.87 (2H, dd, J=12.6, 2.6 Hz), 2.58-2.69 (2H, m), 2.63 (3H, s), 3.59 (2H, t, J=11.5 Hz), 4.21 (2H, dd, J=11.5, 4.5 Hz), 4.41-4.46 (1H, m), 6.68 (1H, dd, J=8.4, 2.0 Hz), 6.89 (1H, d, J=2.0 Hz), 7.50 (1H, d, J=8.5 Hz), 7.62 (1H, d, J=8.5 Hz), 8.09 (1H, d, J=8.5 Hz), 8.47 (1H, s).

Working Example 49

Synthesis of 5-(benzoxazol-2-yl)-1-(4-hydroxycyclohexyl)-2-methylbenzimidazole

Working Example 49-1

Synthesis of 2-(2-(4-hydroxycyclohexyl)aminoanilin-5-yl)benzoxazole

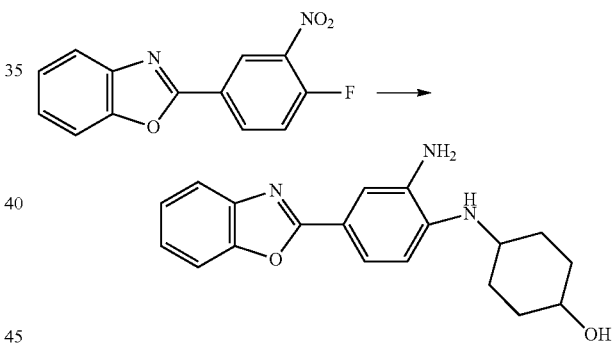

2-(4-Fluoro-3-nitrophenyl)benzoxazole (see Working Example 15-2) (0.60 g, 2.3 mmol) was added to an acetonitrile (20 mL) solution containing triethylamine (0.70 g, 7.0 mmol) and 4-aminocyclohexanol hydrochloride (0.53 g, 2.5 mmol), and this was heated to reflux for 2 hours with stirring. After the reaction was complete, this was cooled to room temperature, and the crystals precipitated by the addition of water were filtered. After the crystals were washed with water, they were dried under reduced pressure with heating to give crystals that were added to a solution of a solvent mixture of methanol/tetrahydrofuran (1:1, 20 mL) including 10% palladium-carbon (50 mg). A hydrogen atmosphere was substituted in the flask, and this was stirred at room temperature for 8 hours. After the reaction was complete, this was filtered through Celite and the filtrate was concentrated. The residue obtained was purified by silica gel column chromatography to yield the title compound (0.50 g, 67% yield) as pale red crystals.

$^1$H-NMR (CDCl$_3$) δ (ppm): 1.18-1.85 (6H, m), 2.07 (2H, d, J=12.9 Hz), 2.20 (2H, d, J=12.9 Hz), 3.33-3.41 (1H, m), 3.70-3.73 (1H, m), 6.71 (1H, d, J=8.4 Hz), 7.25-7.31 (3H, m), 7.51-7.53 (1H, m), 7.63-7.64 (1H, m), 7.68-7.71 (1H, m), 7.74-7.77 (1H, m).

Working Example 49-2

Synthesis of 5-(benzoxazol-2-yl)-1-(4-hydroxycyclohexyl)-2-methylbenzimidazole

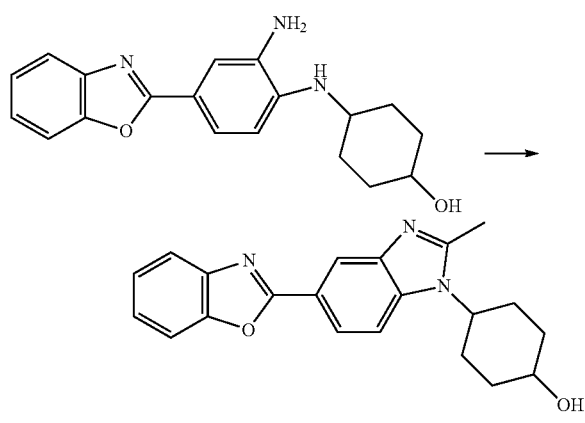

(2-amino-1-(4-hydroxycyclohexyl)aminobenzen-4-yl)benzoxazole (see Working Example 49-1) (0.20 g, 0.62 mmol), methylimidate hydrochloride (0.07 g, 0.68 mmol) and methanol were heated to reflux with stirring for 5 hours. After the reaction was complete, this was cooled to room temperature, saturated aqueous sodium hydrogen carbonate solution was added, and this was extracted with chloroform. The organic layer obtained was dried over anhydrous sodium sulfate, after which it was filtered and concentrated to yield the title compound (0.14 g, 64% yield) as light red crystals.

$^1$H-NMR (CDCl$_3$) δ (ppm): 1.58-2.38 (9H, m), 2.68 (3H, s), 3.86-3.94 (1H, m), 4.26 (1H, tt, J=12.2, 4.1 Hz), 7.31-7.38 (2H, m), 7.56 (1H, d, J=8.6 Hz), 7.59-7.64 (1H, m), 7.73-7.80 (1H, m), 8.15 (1H, dd, J=8.6, 1.6 Hz), 8.55 (1H, d, J=1.6 Hz).

Working Example 50

Synthesis of 5-(benzoxazol-2-yl)-2-methyl-1-n-propylbenzimidazole

Working Example 50-1

Synthesis of 2-(2-n-propylaminoanilin-5-yl)benzoxazole

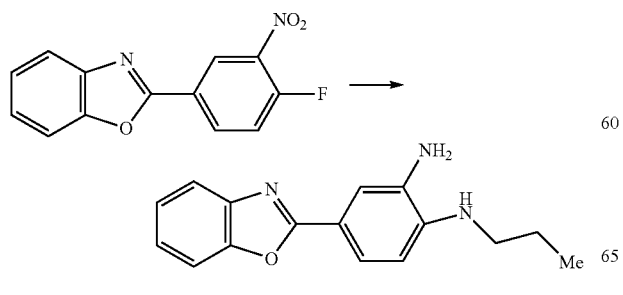

To a suspension of 2-(4-fluoro-3-nitrophenyl)benzoxazole (see Working Example 15-2) (300 mg, 1.16 mmol) in ethanol (5 mL) was added potassium carbonate (176 mg, 1.28 mmol) and aqueous n-propylamine (82.4 mg, 1.39 mmol), and this was heated to reflux for 2.5 hours. After the reaction was complete, this was cooled to room temperature, water was added, and the precipitated crystals were filtered, washed with water and then dried. To a tetrahydrofuran solution (7 mL) of the crystals obtained was added 10% palladium-carbon (100 mg). A hydrogen atmosphere was substituted in the flask, and this was stirred at room temperature for 14 hours. After the reaction was complete, this was filtered through Celite and the filtrate was concentrated. The residue obtained was purified by silica gel column chromatography to yield the title compound (152 mg, 49% yield).

$^1$H-NMR (CDCl$_3$) δ: 1.06 (3H, t, J=7.3 Hz), 1.67-1.77 (2H, m), 3.18 (2H, t, J=7.2 Hz), 6.71 (1H, d, J=8.2 Hz), 7.26-7.33 (2H, m), 7.50-7.79 (4H, m).

Working Example 50-2

Synthesis of 5-(benzoxazol-2-yl)-2-methyl-1-n-propylbenzimidazole

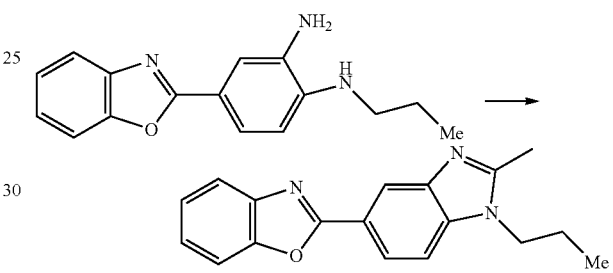

To a solution of 2-(2-n-propylaminoanilin-5-yl)benzoxazole (see Working Example 50-1) (148 mg, 0.554 mmol) in dimethylformamide (3 mL) was added an aqueous solution of acetaldehyde (approx. 90%, 104 μL, 1.66 mmol) and oxone (341 mg, 0.554 mmol), and this was stirred at room temperature for 3 hours. After the reaction was complete, aqueous potassium carbonate solution was added, this was filtered and washed with water. The crystals obtained were purified by silica gel column chromatography to yield the title compound (46.6 mg, 29% yield) as gray crystals.

$^1$H-NMR (CDCl$_3$) δ: 1.01 (3H, t, J=7.4 Hz), 1.82-1.95 (2H, m), 2.65 (3H, s), 4.12 (2H, t, J=7.3 Hz), 7.30-7.43 (3H, m), 7.58-7.62 (1H, m), 7.74-7.78 (1H, m), 8.20 (1H, dd, J=8.6, 1.2 Hz), 8.55 (1H, d, J=1.2 Hz).

Working Example 51

Synthesis of 5-(benzoxazol-2-yl)-1-(2-methoxyethyl)-2-methylbenzimidazole

Working Example 51-1

Synthesis of 2-(2-(2-methoxyethyl)aminoanilin-5-yl)benzoxazole

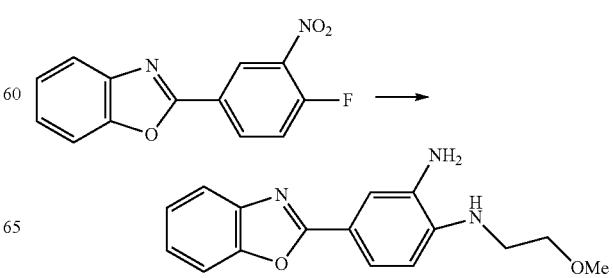

To a suspension of 2-(4-fluoro-3-nitrophenyl)benzoxazole (see Working Example 15-2) (300 mg, 1.16 mmol) in ethanol (5 mL) was added potassium carbonate (176 mg, 1.28 mmol) and 2-methoxyethylamine (105 mg, 1.39 mmol), and this was heated to reflux for 3.5 hours. After the reaction was complete, this was cooled to room temperature, water was added, and the precipitated crystals were filtered, washed with water and then dried. To a tetrahydrofuran solution (7 mL) of the crystals obtained was added 10% palladium-carbon (100 mg). A hydrogen atmosphere was substituted in the flask, and this was stirred at room temperature for 6 hours. After the reaction was complete, this was filtered through Celite and the filtrate was concentrated. The residue obtained was purified by silica gel column chromatography to yield the title compound (102 mg, 31% yield).

$^1$H-NMR (CDCl$_3$) δ: 3.35-3.42 (5H, m), 3.67-3.71 (2H, m), 6.72 (1H, d, J=8.2 Hz), 7.26-7.31 (2H, m), 7.50-7.77 (4H, m).

Working Example 51-2

Synthesis of 5-(benzoxazol-2-yl)-1-(2-methoxyethyl)-2-methylbenzimidazole

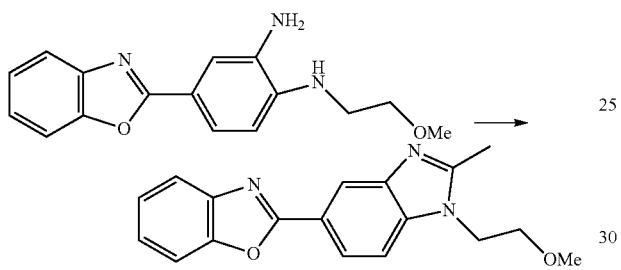

To a solution of 2-(2-(2-methoxyethyl)aminoanilin-5-yl)benzoxazole (see Working Example 51-1) (98 mg, 0.346 mmol) in dimethylformamide (2 mL) was added an aqueous solution of acetaldehyde (approx. 90%, 65.1 μL, 1.66 mmol) and oxone (213 mg, 0.346 mmol), and this was stirred at room temperature for 3 hours. After the reaction was complete, aqueous potassium carbonate solution was added, this was filtered and washed with water. The crystals obtained were purified by silica gel column chromatography to yield the title compound (41.4 mg, 39% yield) as light brown crystals.

$^1$H-NMR (CDCl$_3$) δ: 2.67 (3H, s), 3.29 (3H, s), 3.72 (2H, t, J=5.4 Hz), 4.33 (2H, t, J=5.4 Hz), 7.32-7.44 (3H, m), 7.58-7.63 (1H, m), 7.75-7.78 (1H, m), 8.20 (1H, dd, J=8.5, 1.5 Hz), 8.56 (1H, d, J=1.5 Hz).

Working Example 52

Synthesis of 5-(benzoxazol-2-yl)-2-methyl-1-(2-phenylethyl)benzimidazole

Working Example 52-1

Synthesis of 2-(2-(2-phenylethyl)aminoanilin-5-yl)benzoxazole

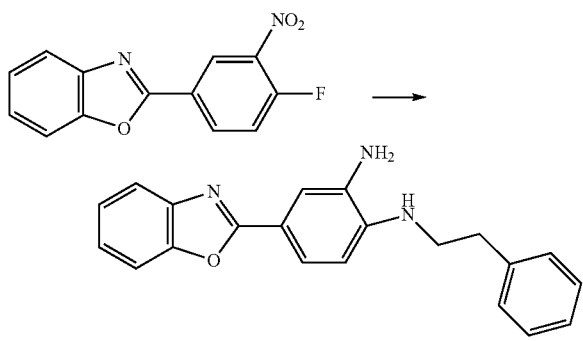

To a suspension of 2-(4-fluoro-3-nitrophenyl)benzoxazole (see Working Example 15-2) (300 mg, 1.16 mmol) in ethanol (5 mL) was added potassium carbonate (176 mg, 1.28 mmol) and 2-phenylethylamine (169 mg, 1.39 mmol), and this was heated to reflux for 4 hours. After the reaction was complete, this was cooled to room temperature, water was added, and the precipitated crystals were filtered, washed with water and then dried. To a tetrahydrofuran solution (5 mL) of the crystals obtained was added 10% palladium-carbon (50 mg). A hydrogen atmosphere was substituted in the flask, and this was stirred at room temperature for 14 hours. After the reaction was complete, this was filtered through Celite and the filtrate was concentrated. The residue obtained was purified by silica gel column chromatography to yield the title compound (143 mg, 37% yield).

$^1$H-NMR (CDCl$_3$) δ: 3.01 (2H, t, J=7.0 Hz), 3.50 (2H, t, J=7.0 Hz), 6.75 (1H, d, J=8.4 Hz), 7.25-7.79 (11H, m).

Working Example 52-2

Synthesis of 5-(benzoxazol-2-yl)-2-methyl-1-(2-phenylethyl)benzimidazole

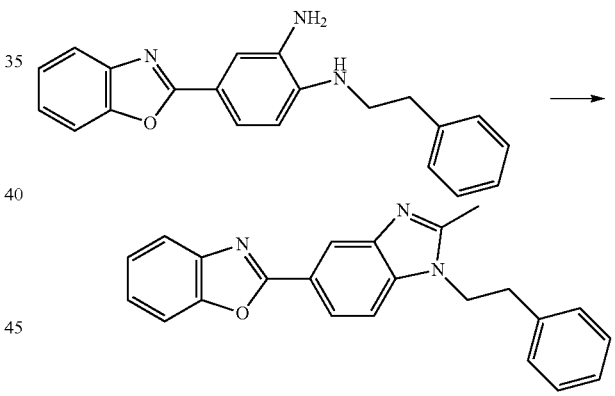

To a methanol (5 mL) solution of 2-(2-(2-phenylethyl)aminoanilin-5-yl)benzoxazole (see Working Example 52-1) (140 mg, 0.425 mmol) was added 1,1,1-trimethoxyethane (61.3 mg, 0.510 mmol), and this was stirred at room temperature for 6 hours. After the reaction was complete, this was concentrated, and the residue obtained was purified by silica gel column chromatography to yield the title compound (98.4 mg, 66% yield) as white crystals.

$^1$H-NMR (CDCl$_3$) δ: 2.22 (3H, s), 3.10 (2H, t, J=6.8 Hz), 4.35 (2H, t, J=6.8 Hz), 6.94-6.98 (2H, m), 7.22-7.37 (6H, m), 7.59-7.62 (1H, m), 7.76-7.79 (1H, m), 8.19 (1H, dd, J=8.5, 1.2 Hz), 8.55 (1H, d, J=1.2 Hz).

Working Example 53

Synthesis of 5-(benzoxazol-2-yl)-2-methyl-1-cyclopropylbenzimidazole

Working Example 53-1

Synthesis of 2-(2-cyclopropylaminoanilin-5-yl)benzoxazole

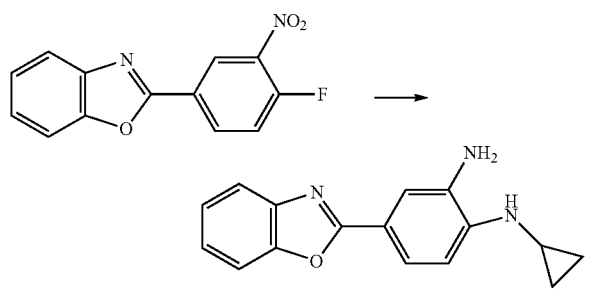

To a suspension of 2-(4-fluoro-3-nitrophenyl)benzoxazole (see Working Example 15-2) (300 mg, 1.16 mmol) in ethanol (5 mL) was added potassium carbonate (176 mg, 1.28 mmol) and cyclopropylamine (99.3 mg, 1.74 mmol), and this was heated to reflux for 7 hours. After the reaction was complete, this was cooled to room temperature, water was added, and the precipitated crystals were filtered, washed with water and then dried. To a tetrahydrofuran solution (5 mL) of the crystals obtained was added 10% palladium-carbon (50 mg). A hydrogen atmosphere was substituted in the flask, and this was stirred at room temperature for 14 hours. After the reaction was complete, this was filtered through Celite and the filtrate was concentrated. The residue obtained was purified by silica gel column chromatography to yield the title compound (141 mg, 46% yield).

$^1$H-NMR (CDCl$_3$) δ: 0.56-0.62 (2H, m), 0.79-0.86 (2H, m), 2.50-2.55 (1H, m), 7.12 (1H, d, J=8.4 Hz), 7.26-7.33 (2H, m), 7.51-7.81 (4H, m).

Working Example 53-2

Synthesis of 5-(benzoxazol-2-yl)-2-methyl-1-cyclopropylbenzimidazole

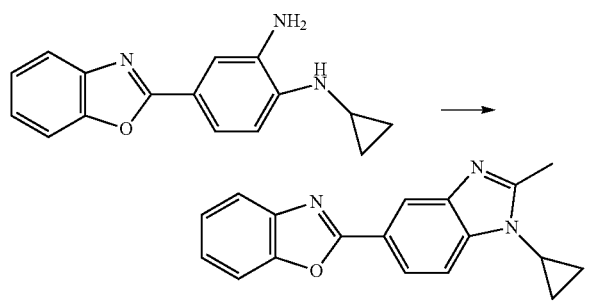

To a methanol (5 mL) solution of 2-(2-cyclopropylaminoanilin-5-yl)benzoxazole (see Working Example 53-1) (140 mg, 0.425 mmol) was added 1,1,1-trimethoxyethane (75 mg, 0.624 mmol), and this was stirred at room temperature for 6 hours. After the reaction was complete, this was concentrated, and the residue obtained was purified by silica gel column chromatography to yield the imidazole (63.5 mg, 42% yield).

$^1$H-NMR (CDCl$_3$) δ: 1.07-1.13 (2H, m), 1.23-1.33 (2H, m), 2.71 (3H, s), 3.22-3.30 (1H, m), 7.32-7.35 (2H, m), 7.58-7.62 (2H, m), 7.75-7.78 (1H, m), 8.19 (1H, dd, J=8.5, 1.2 Hz), 8.52 (1H, s).

Working Example 54

Synthesis of 5-(benzoxazol-2-yl)-2-methyl-1-cyclopropylmethylbenzimidazole

Working Example 54-1

Synthesis of 2-(2-cyclopropylmethylaminoanilin-5-yl)benzoxazole

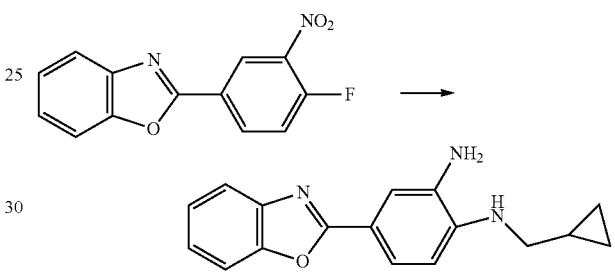

To a suspension of 2-(4-fluoro-3-nitrophenyl)benzoxazole (see Working Example 15-2) (300 mg, 1.16 mmol) in ethanol (5 mL) was added potassium carbonate (176 mg, 1.28 mmol) and cyclopropylmethylamine (176 mg, 1.28 mmol), and this was heated to reflux for 7 hours. After the reaction was complete, this was cooled to room temperature, water was added, and the precipitated crystals were filtered, washed with water and then dried. To a tetrahydrofuran solution (5 mL) of the crystals obtained was added 10% palladium-carbon (50 mg). A hydrogen atmosphere was substituted in the flask, and this was stirred at room temperature for 6 hours. After the reaction was complete, this was filtered through Celite and the filtrate was concentrated. The residue obtained was purified by silica gel column chromatography to yield the title compound (142 mg, 44% yield).

$^1$H-NMR (CDCl$_3$) δ: 0.27-0.32 (2H, m), 0.58-0.64 (2H, m), 1.13-1.23 (1H, m), 3.05 (2H, d, J=7.1 Hz), 6.68 (1H, d, J=8.4 Hz), 7.27-7.32 (2H, m), 7.50-7.77 (4H, m).

Working Example 54-2

Synthesis of 5-(benzoxazol-2-yl)-2-methyl-1-cyclopropylmethylbenzimidazole

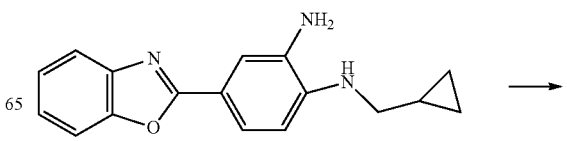

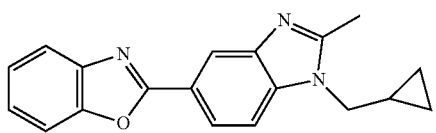

To a methanol (5 mL) solution of 2-(2-cyclopropylmethylaminoanilin-5-yl)benzoxazole (see Working Example 54-1) (140 mg, 0.425 mmol) was added 1,1,1-trimethoxyethane (75 mg, 0.624 mmol), and this was stirred at room temperature for 10 hours. After the reaction was complete, this was concentrated, and the residue obtained was purified by silica gel column chromatography to yield the title compound (81.9 mg, 54% yield) as pink crystals.

$^1$H-NMR (CDCl$_3$) δ: 0.38-0.44 (2H, m), 0.61-0.68 (2H, m), 1.20-1.28 (1H, m), 2.67 (3H, s), 4.05 (2H, d, J=6.6 Hz), 7.30-7.45 (3H, m), 7.57-7.62 (1H, m), 7.75-7.78 (1H, m), 8.20 (1H, dd, J=8.5, 1.2 Hz), 8.56 (1H, d, J=1.2 Hz).

Working Example 55

Synthesis of 5-(benzoxazol-2-yl)-1-(2-(tert-butoxycarbonylamino)ethyl)-2-methylbenzimidazole Working Example 55-1

Synthesis of 2-(tert-butoxycarbonylamino)ethylaminoanilin-5-yl)benzoxazole

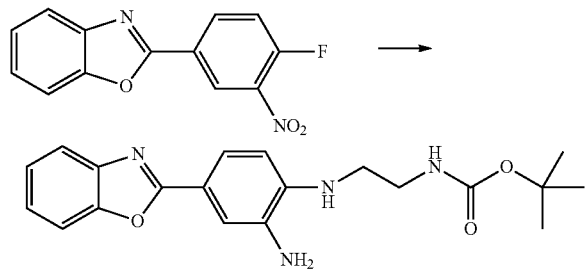

2-(4-Fluoro-3-nitrophenyl)benzoxazole (see Working Example 15-2) (600 mg, 2.32 mmol) was added to an acetonitrile (10 mL) solution containing triethylamine (469 mg, 4.65 mmol) and 2-(tert-butoxycarbonylamino)ethylamine (447 mg, 2.79 mmol), and this was heated to reflux for 5 hours. After the reaction was complete, this was cooled to room temperature, water was added, and the precipitated crystals were filtered, washed with water and then dried. To a tetrahydrofuran solution (5 mL) of the crystals obtained was added 10% palladium-carbon (50 mg). A hydrogen atmosphere was substituted in the flask, and this was stirred at room temperature for 6 hours. After the reaction was complete, this was filtered through Celite and the filtrate was concentrated. The residue obtained was purified by silica gel column chromatography to yield the title compound (550 mg, 64% yield).

$^1$H-NMR (CDCl$_3$) δ: 1.46 (9H, s), 3.34-3.49 (5H, m), 4.48 (1H, br s), 4.87 (1H, br s), 6.67 (1H, d, J=8.4 Hz), 7.26-7.33 (2H, m), 7.50-7.54 (1H, m), 7.61 (1H, d, J=1.8 Hz), 7.68-7.76 (2H, m).

Working Example 55-2

Synthesis of 5-(benzoxazol-2-yl)-1-(2-(tert-butoxycarbonylamino)ethyl)-2-methylbenzimidazole To a methanol (5 mL) solution of 2-(tert-butoxycarbonylamino)ethylaminoanilin-5-yl)benzoxazole (see Working Example 55-1) (200 mg, 0.567 mmol) was added methyl acetimidate hydrochloride (102 mg, 0.851 mmol), and this was heated to reflux for 5 hours. After the reaction was complete, saturated aqueous sodium hydrogen carbonate solution was added, and this was extracted with chloroform. The organic layer obtained was dried over anhydrous sodium sulfate, after which it was filtered and concentrated to yield the title compound (160 mg, 72% yield) as white crystals.

$^1$H-NMR (CDCl$_3$) δ: 1.47 (9H, s), 2.64 (3H, s), 3.53-3.55 (2H, m), 4.33 (2H, t, J=5.4 Hz), 5.12 (1H, s), 7.33-7.36 (2H, m), 7.41 (1H, d, J=8.4 Hz), 7.56-7.59 (1H, m), 7.72-7.77 (1H, m), 8.14 (1H, d, J=8.4 Hz), 8.45 (1H, s).

Working Example 56

Synthesis of 1-(2-aminoethyl)-5-(benzoxazol-2-yl)-2-methylbenzimidazole hydrochloride

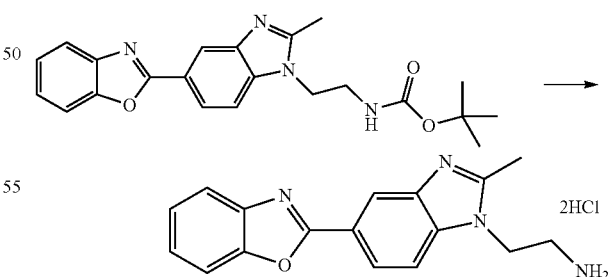

5-(Benzoxazol-2-yl)-1-(2-(tert-butoxycarbonylamino)ethyl)-2-methylbenzimidazole (see Working Example 55-2) (100 mg, 0.255 mmol) was added to a 4N hydrochloric acid solution in dioxane (10 mL), and this was heated to reflux for 5 hours. After the reaction was complete, this was concentrated to dryness to yield the title compound (95 mg, quant.) as white crystals.

¹H-NMR (D₂O) δ: 2.72 (3H, s), 3.40 (2H, t, J=6.8 Hz), 4.54 (2H, t, J=6.8 Hz), 7.21-7.32 (2H, m), 7.43-7.46 (2H, m), 7.68 (1H, d, J=8.9 Hz), 8.06-8.11 (2H, m).

Working Example 57

Synthesis of 5-(benzoxazol-2-yl)-2-methyl-1-(3-phenylpropyl)benzimidazole

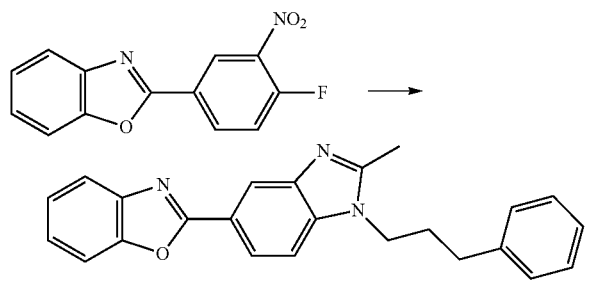

To a suspension of 2-(4-fluoro-3-nitrophenyl)benzoxazole (see Working Example 15-2) (300 mg, 1.16 mmol) in ethanol (5 mL) was added potassium carbonate (176 mg, 1.28 mmol) and 3-phenylpropylamine (189 mg, 1.39 mmol), and this was heated to reflux for 3 hours. After the reaction was complete, this was cooled to room temperature, water was added, and the precipitated crystals were filtered, washed with water and then dried. To a tetrahydrofuran solution (5 mL) of the crystals obtained was added 10% palladium-carbon (50 mg). A hydrogen atmosphere was substituted in the flask, and this was stirred at room temperature for 6 hours. After the reaction was complete, this was filtered through Celite and the filtrate was concentrated. The residue obtained was dissolved in methanol (5 mL), and to this was added 1,1,1-trimethoxyethane (108 mg, 0.896 mmol), and this was heated to reflux for 6 hours. After the reaction was complete, this was concentrated, and the residue obtained was purified by silica gel column chromatography to yield the title compound (58.5 mg, 14% yield) as white crystals.

¹H-NMR (CDCl₃) δ: 2.11-2.22 (2H, m), 2.55 (3H, s), 2.72 (2H, t, J=7.5 Hz), 4.12 (2H, t, J=7.5 Hz), 7.16-7.35 (8H, m), 7.58-7.61 (1H, m), 7.75-7.78 (1H, m), 8.17 (1H, d, J=8.2 Hz), 8.54 (1H, s).

Working Example 58

Synthesis of 5-(benzoxazol-2-yl)-2-(tert-butoxycarbamidomethyl)-1-(tetrahydropyran-4-yl)benzimidazole

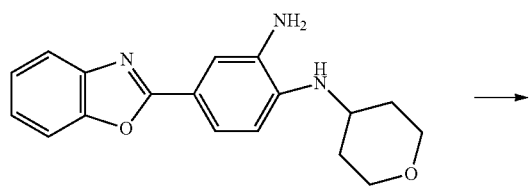

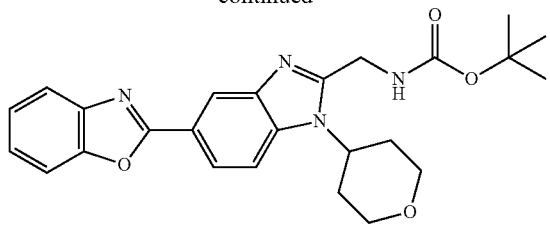

To a solution of 5-(benzoxazol-2-yl)-2-(tetrahydropyran-4-yl)aminoaniline (see Working Example 20-2) (300 mg, 0.97 mmol) in dimethylformamide (5 mL) was added N-Boc-2-aminoacetaldehyde (232 mg, 1.45 mmol) and oxone (388 mg, 0.631 mmol), and this was stirred at room temperature for 3 hours. After the reaction was complete, aqueous potassium carbonate solution was added, this was filtered and washed with water. The crystals obtained were purified by silica gel column chromatography to yield the title compound (130 mg, 30% yield) as pink crystals.

¹H-NMR (CDCl₃) δ: 1.49 (9H, s), 1.83-1.88 (2H, m), 2.53-2.68 (2H, m), 3.57-3.67 (2H, m), 4.16-4.22 (2H, m), 4.70-4.83 (3H, m), 5.59 (1H, br s), 7.33-7.39 (2H, m), 7.59-7.62 (1H, m), 7.71-7.79 (2H, m), 8.21 (1H, dd, J=8.7, 1.5 Hz), 8.60 (1H, d, J=1.5 Hz).

Working Example 59

Synthesis of 5-(5-tert-butylbenzoxazol-2-yl)-2-methyl-1-(tetrahydropyran-4-yl)benzimidazole

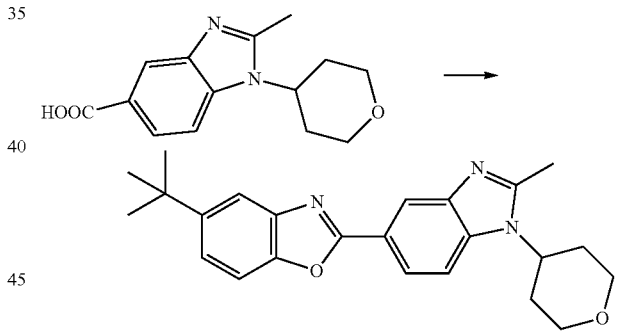

2-methyl-1-(tetrahydropyran-4-yl)benzimidazole-5-carboxylic acid HCl salt (see Working Example 4-3) (250 mg, 0.842 mmol), 2-amino-4-tert-butylphenol (139 mg, 0.842 mmol), DMF (2 mL), chloroform (5 mL) and WSC (178 mg, 0.926 mmol) were stirred for 22 hours. Water was added, and the solid obtained was filtered off, washed with water, and dried to give a solid that was taken up in dioxane (5 mL) to which was added methanesulfonic acid (140 mg, 1.46 mmol), and this was heated to reflux for 18 hours. After the reaction solution was cooled, water and saturated aqueous sodium hydrogen carbonate solution were added, and this was extracted with chloroform. After the organic layer obtained was dried over anhydrous sodium sulfate, it was filtered and concentrated. The residue obtained was purified by silica gel column chromatography to yield the title compound (160 mg, 49% yield) as white crystals.

¹H-NMR (CDCl₃) δ: 1.40 (9H, s), 1.85-1.92 (2H, m), 2.54-2.69 (5H, m), 3.60 (2H, t, J=11.6 Hz), 4.22 (2H, dd, J=11.6, 4.1 Hz), 4.40-4.50 (1H, m), 7.39 (1H, dd, J=8.6, 1.5

Hz), 7.51 (1H, d, J=8.6 Hz), 7.66 (1H, d, J=8.6 Hz), 7.80 (1H, s), 8.16 (1H, d, J=8.6 Hz), 8.54 (1H, s).

Working Example 60

Synthesis of 5-(5-nitrobenzoxazol-2-yl)-2-methyl-1-(tetrahydropyran-4-yl)benzimidazole

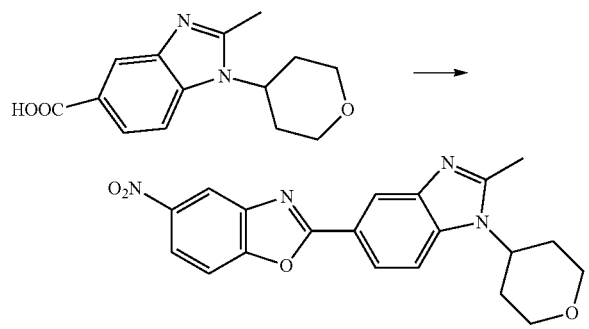

To 2-methyl-1-(tetrahydropyran-4-yl)benzimidazole-5-carboxylic acid HCl salt (see Working Example 4-3) (264 mg, 0.888 mmol) was added thionyl chloride (2 mL), and this was stirred at reflux for 3 hours. After the reaction was complete, concentration at reduced pressure gave a residue that was added to 2-amino-4-nitrophenol (137 mg, 0.888 mmol), triethylamine (449 mg, 4.44 mmol) and tetrahydrofuran (10 mL), and this was stirred at room temperature for 14 hours. After the reaction was complete, this was concentrated, and to a dioxane (5 mL) solution of the residue obtained was added methanesulfonic acid (140 mg, 1.46 mmol), and this was heated to reflux for 18 hours. After the reaction solution was cooled, water and saturated aqueous sodium hydrogen carbonate solution were added, and this was extracted with chloroform. After the organic layer obtained was dried over anhydrous sodium sulfate, it was filtered and concentrated. The residue obtained was purified by silica gel column chromatography to yield the title compound (66 mg, 20% yield) as white crystals.

$^1$H-NMR (CDCl$_3$) δ: 1.91 (2H, d, J=13.0 Hz), 2.59-2.72 (5H, m), 3.61 (3H, t, J=12.0 Hz), 4.21-4.28 (3H, m), 4.42-4.53 (1H, m), 7.70 (2H, d, J=8.7 Hz), 8.18 (1H, d, J=8.6 Hz), 8.30 (1H, d, J=8.7 Hz), 8.56 (1H, s), 8.63 (1H, s).

Working Example 61

Synthesis of 5-(benzoxazol-2-yl)-2-benzyl-1-(tetrahydropyran-4-yl)benzimidazole

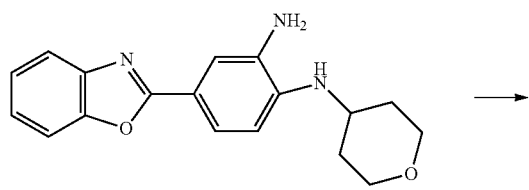

-continued

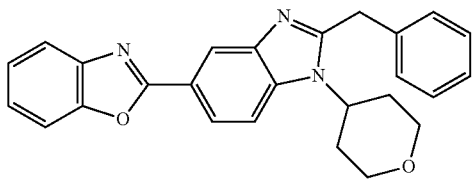

To a solution of 5-(benzoxazol-2-yl)-2-(tetrahydropyran-4-yl)aminoaniline (see Working Example 20-2) (200 mg, 0.646 mmol) in dimethylformamide (3 mL) was added phenylacetaldehyde (101 mg, 0.840 mmol) and oxone (258 mg, 0.420 mmol), and this was stirred at room temperature for 3 hours. After the reaction was complete, aqueous potassium carbonate solution was added, this was filtered and washed with water. The crystals obtained were purified by silica gel column chromatography to yield the title compound (110 mg, 42% yield) as light brown amorphous mass.

$^1$H-NMR (CDCl$_3$) δ: 1.39 (2H, dd, J=12.5, 2.6 Hz), 2.37-2.53 (2H, m), 3.24-3.34 (2H, m), 4.05 (2H, dd, J=11.5, 4.5 Hz), 4.32-4.42 (3H, m), 7.22-7.38 (7H, m), 7.56-7.68 (2H, m), 7.76-7.80 (1H, m), 8.19 (1H, dd, J=8.6, 1.3 Hz), 8.65 (1H, d, J=1.3 Hz).

Working Example 62

Synthesis of 5-(benzoxazol-2-yl)-2-trans-cinnam-1-(tetrahydropyran-4-yl)benzimidazole

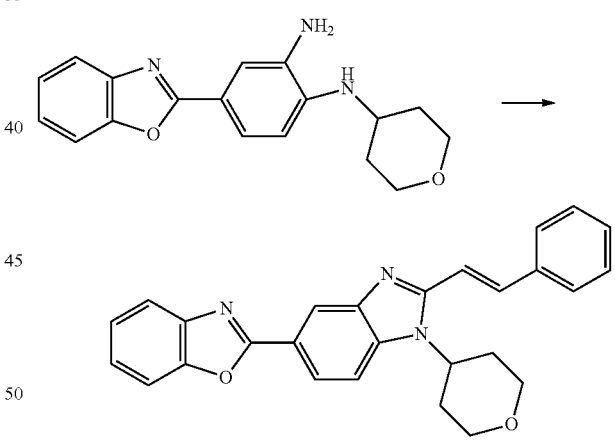

To a solution of 5-(benzoxazol-2-yl)-2-(tetrahydropyran-4-yl)aminoaniline (see Working Example 20-2) (200 mg, 0.646 mmol) in dimethylformamide (3 mL) was added trans-cinnamaldehyde (111 mg, 0.840 mmol) and oxone (258 mg, 0.420 mmol), and this was stirred at room temperature for 3 hours. After the reaction was complete, aqueous potassium carbonate solution was added, this was filtered and washed with water. The crystals obtained were purified by silica gel column chromatography to yield the title compound (97 mg, 36% yield) as pale yellow crystals.

$^1$H-NMR (CDCl$_3$) δ: 1.94-2.01 (2H, m), 2.61-2.77 (2H, m), 3.61-3.71 (2H, m), 4.26 (2H, dd, J=11.6, 4.4 Hz), 4.64-4.75 (1H, m), 7.18 (1H, d, J=15.7 Hz), 7.32-7.48 (5H, m), 7.59-7.72 (4H, m), 7.77-7.80 (1H, m), 8.03 (1H, d, J=15.7 Hz), 8.22 (1H, dd, J=8.6, 1.3 Hz), 8.64 (1H, d, J=1.3 Hz).

Working Example 63

Synthesis of 5-(benzoxazol-2-yl)-2-(furan-2-yl)-1-(tetrahydropyran-4-yl)benzimidazole

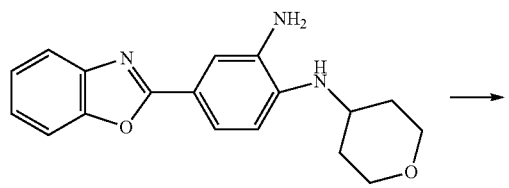

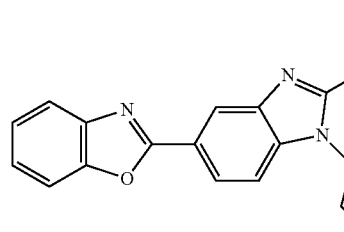

To a solution of 5-(benzoxazol-2-yl)-2-(tetrahydropyran-4-yl)aminoaniline (see Working Example 20-2) (200 mg, 0.646 mmol) in dimethylformamide (2 mL) was added furfural (80.7 mg, 0.840 mmol) and oxone (258 mg, 0.420 mmol), and this was stirred at room temperature for 3 hours. After the reaction was complete, aqueous potassium carbonate solution was added, this was filtered and washed with water. The crystals obtained were purified by silica gel column chromatography to yield the title compound (121 mg, 49% yield) as pale yellow crystals.

$^1$H-NMR (CDCl$_3$) δ: 2.00 (2H, dd, J=12.8, 2.6 Hz), 2.63-2.79 (2H, m), 3.56-3.65 (2H, m), 4.23 (2H, dd, J=11.6, 4.4 Hz), 5.09-5.21 (1H, m), 6.66 (1H, dd, J=3.5, 1.8 Hz), 7.19 (1H, dd, J=3.5, 0.7 Hz), 7.32-7.39 (2H, m), 7.59-7.65 (1H, m), 7.69 (1H, dd, J=1.8, 0.7 Hz), 7.76-7.81 (2H, m), 8.24 (1H, dd, J=8.7, 1.6 Hz), 8.66 (1H, d, J=1.6 Hz).

Working Example 64

Synthesis of 5-(benzoxazol-2-yl)-2-(furan-3-yl)-1-(tetrahydropyran-4-yl)benzimidazole

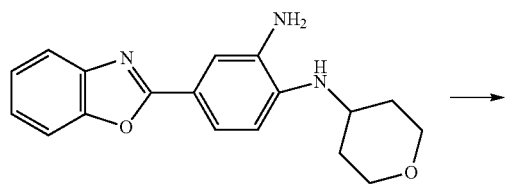

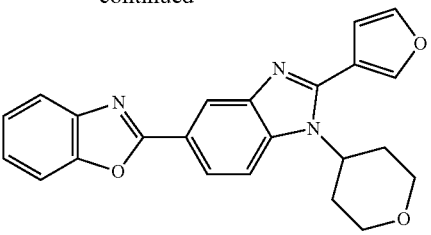

To a solution of 5-(benzoxazol-2-yl)-2-(tetrahydropyran-4-yl)aminoaniline (see Working Example 20-2) (200 mg, 0.646 mmol) in dimethylformamide (2 mL) was added 3-furaldehyde (80.7 mg, 0.840 mmol) and oxone (258 mg, 0.420 mmol), and this was stirred at room temperature for 3 hours. After the reaction was complete, aqueous potassium carbonate solution was added, this was filtered and washed with water. The crystals obtained were purified by silica gel column chromatography to yield the title compound (171 mg, 69% yield) as pale yellow crystals.

$^1$H-NMR (CDCl$_3$) δ: 1.87-1.94 (2H, m), 2.65-2.81 (2H, m), 3.50-3.59 (2H, m), 4.22 (2H, dd, J=11.5, 4.5 Hz), 4.70-4.79 (1H, m), 6.79 (1H, dd, J=1.9, 0.7 Hz), 7.34-7.37 (2H, m), 7.60-7.65 (2H, m), 7.77-7.80 (2H, m), 7.93 (1H, dd, J=1.5, 0.7 Hz), 8.24 (1H, dd, J=8.7, 1.6 Hz), 8.66 (1H, d, J=1.6 Hz).

Working Example 65

Synthesis of 5-(benzoxazol-2-yl)-2-(3-methoxyphenyl)-1-(tetrahydropyran-4-yl)benzimidazole

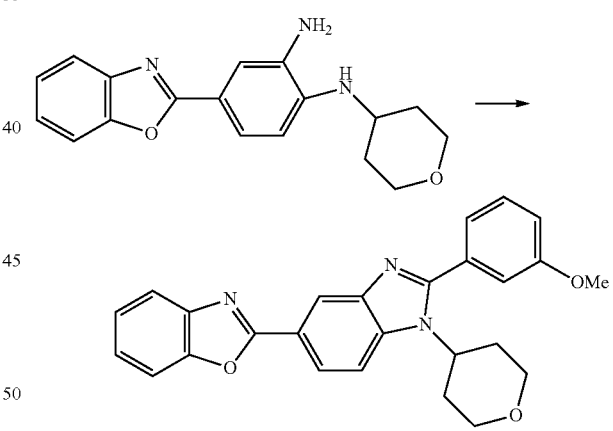

To a solution of 5-(benzoxazol-2-yl)-2-(tetrahydropyran-4-yl)aminoaniline (see Working Example 20-2) (200 mg, 0.646 mmol) in methanol (5 mL) was added ethyl 3-methoxybenzimidate hydrochloride (153 mg, 0.711 mmol), and this was stirred at room temperature for 8 hours. After the reaction was complete, saturated aqueous sodium hydrogen carbonate solution was added, and this was extracted with chloroform. After the organic layer obtained was dried over anhydrous sodium sulfate, it was filtered and concentrated. The crystals obtained were purified by silica gel column chromatography to yield the title compound (216 mg, 79% yield) as light brown crystals.

$^1$H-NMR (DMSO-d$_6$) δ: 1.92-1.98 (2H, m), 2.50-2.57 (2H, m), 3.35-3.45 (5H, m), 3.86 (3H, s), 3.99-4.04 (2H, m), 4.56-

4.67 (1H, m), 7.06-7.57 (6H, m), 7.79-7.84 (2H, m), 8.06 (1H, d, J=8.7 Hz), 8.18 (1H, dd, J=8.7, 1.5 Hz), 8.49 (1H, d, J=1.5 Hz).

Working Example 66

Synthesis of 5-(5-methoxybenzoxazol-2-yl)-2-methyl-1-(tetrahydropyran-4-yl)benzimidazole

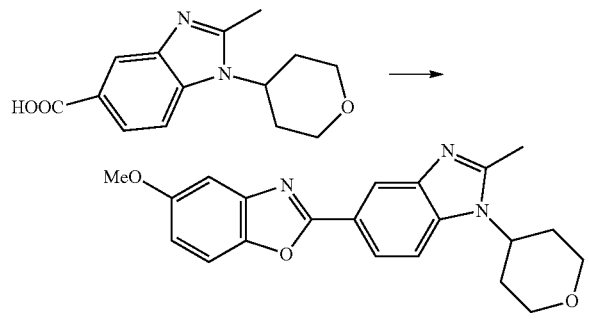

2-methyl-1-(tetrahydropyran-4-yl)benzimidazole-5-carboxylic acid HCl salt (see Working Example 4-3) ((250 mg, 0.842 mmol), 2-amino-3-methoxyphenol (139 mg, 0.842 mmol), DMF (5 mL), and WSC (178 mg, 0.926 mmol) were stirred for 22 hours. Water was added and this was extracted with chloroform. After the organic layer obtained was dried over anhydrous sodium sulfate, it was filtered and concentrated. To a dioxane (5 mL) solution of the solid obtained was added methanesulfonic acid (283 mg, 2.95 mmol), and this was heated to reflux for 18 hours. After the reaction solution was cooled, water and saturated aqueous sodium hydrogen carbonate solution were added, and this was extracted with chloroform. After the organic layer obtained was dried over anhydrous sodium sulfate, it was filtered and concentrated. The residue obtained was purified by silica gel column chromatography to yield the title compound (10 mg, 3.3% yield) as brown crystals.

$^1$H-NMR (CDCl$_3$) δ: 1.86-1.93 (2H, m), 2.55-2.70 (5H, m), 3.56-3.65 (2H, m), 3.88 (3H, s), 4.23 (2H, dd, J=11.8, 4.5 Hz), 4.41-4.50 (1H, m), 6.93 (1H, dd, J=8.7, 2.6 Hz), 7.26-7.28 (1H, m), 7.48 (1H, d, J=8.7 Hz), 7.65 (1H, d, J=8.7 Hz), 8.15 (1H, dd, J=8.6, 1.5 Hz), 8.53 (1H, d, J=1.5 Hz).

Working Example 67

Synthesis of 2-aminomethyl-5-(benzoxazol-2-yl)-1-(tetrahydropyran-4-yl)benzimidazole hydrochloride

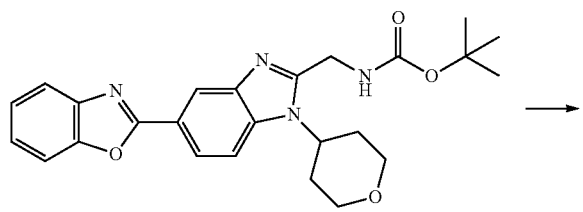

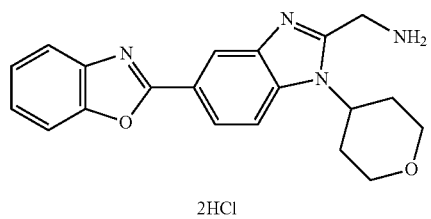

2HCl

To a solution of 5-(benzoxazol-2-yl)-2-(tert-butoxycarbamidomethyl)-1-(tetrahydropyran-4-yl)benzimidazole (see Working Example 58) (116 mg, 0.259 mmol) in dioxane (3 mL) was added a 4N hydrogen chloride solution in dioxane (1 mL), and this was heat to reflux for 2 hours. The reaction solution was cooled to room temperature and filtered, and the crystals obtained were washed with THF, and dried to yield the title compound (101 mg, 93% yield) as white crystals.

$^1$H-NMR (D$_2$O) δ: 1.77-1.84 (2H, m), 2.22-2.38 (2H, m), 3.50-3.62 (2H, m), 4.04 (2H, dd, J=11.5, 3.8 Hz), 4.35-4.46 (3H, m), 7.02-7.13 (2H, m), 7.26-7.31 (2H, m), 7.51 (1H, d, J=8.9 Hz), 7.62 (1H, dd, J=8.9, 1.3 Hz), 7.91 (1H, d, J=1.3 Hz).

Working Example 68

Synthesis of 5-(benzoxazol-2-yl)-2-(2-phenylethyl)-1-(tetrahydropyran-4-yl)benzimidazole

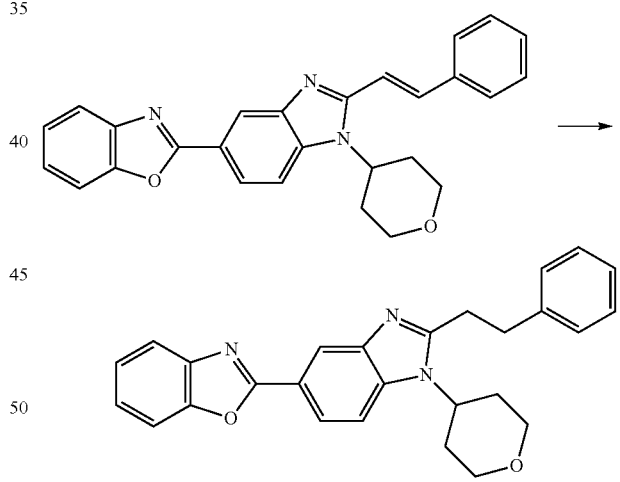

To a solution of 5-(benzoxazol-2-yl)-2-trans-cinnam-1-(tetrahydropyran-4-yl)benzimidazole (see Working Example 62) (80 mg, 0.189 mmol) in tetrahydrofuran (5 mL) was added 10% palladium-carbon (20 mg), a hydrogen atmosphere was substituted in the flask, and this was stirred at room temperature for 17 hours. After the reaction was complete, this was filtered through Celite and the filtrate was concentrated. The residue obtained was purified by silica gel column chromatography to yield the title compound (61.5 mg, 76% yield) as white crystals.

$^1$H-NMR (CDCl$_3$) δ: 1.56 (2H, dd, J=12.5, 2.6 Hz), 2.45-2.61 (2H, m), 3.27 (4H, s), 3.40-3.50 (2H, m), 4.14 (2H, dd,

J=11.6, 4.5 Hz), 4.23-4.35 (1H, m), 7.20-7.38 (7H, m), 7.56-7.67 (2H, m), 7.75-7.81 (1H, m), 8.18 (1H, dd, J=8.6, 1.3 Hz), 8.63 (1H, d, J=1.3 Hz).

Working Example 69

Synthesis of 5-(benzoxazol-2-yl)-2-(2-phenylethynyl)-1-(tetrahydropyran-4-yl)benzimidazole

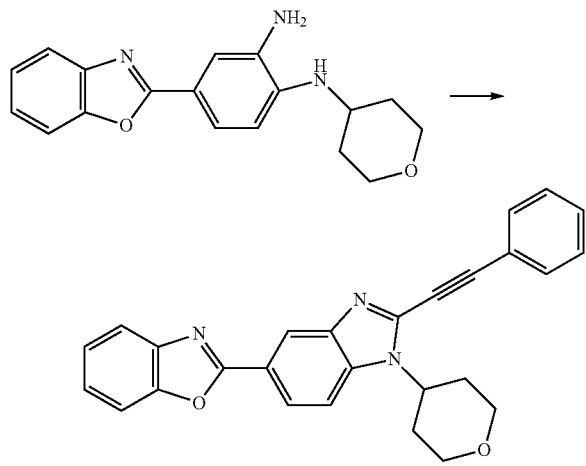

To a solution of 5-(benzoxazol-2-yl)-2-(tetrahydropyran-4-yl)aminoaniline (see Working Example 20-2) (38.0 mg, 0.119 mmol) in dimethylformamide (2 mL) was added phenylpropargylaldehyde (ca. 90%, 22.6 µL, 0.360 mmol) and oxone (73.2 mg, 0.119 mmol), and this was stirred at room temperature for 3 hours. After the reaction was complete, aqueous potassium carbonate solution was added, this was filtered and washed with water. The crystals obtained were purified by silica gel column chromatography to yield the title compound (20.0 mg, 49% yield) as pale yellow crystals.

$^1$H-NMR (CDCl$_3$) δ: 1.98-2.04 (2H, m), 2.68-2.84 (2H, m), 3.60-3.70 (2H, m), 4.26 (2H, dd, J=11.7, 4.5 Hz), 4.85-4.94 (1H, m), 7.33-7.49 (5H, m), 7.59-7.80 (5H, m), 8.29 (1H, dd, J=8.7, 1.5 Hz), 8.65 (1H, d, J=1.5 Hz).

Working Example 70

Synthesis of 5-(5-ethylbenzoxazol-2-yl)-2-methyl-1-(tetrahydropyran-4-yl)benzimidazole

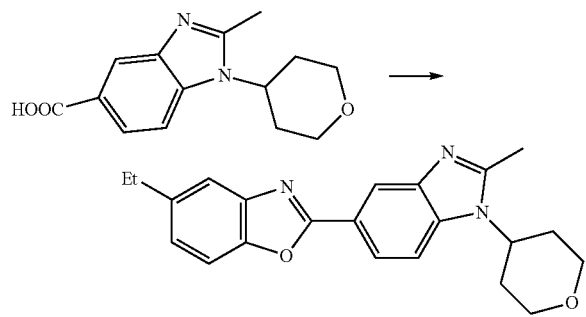

To 2-methyl-1-(tetrahydropyran-4-yl)benzimidazole-5-carboxylic acid HCl salt (see Working Example 4-3) (182 mg, 0.612 mmol) was added thionyl chloride (2 mL), and this was stirred at reflux for 3 hours. After the reaction was complete, concentration at reduced pressure gave a residue that was added to 2-amino-4-ethylphenol (106 mg, 0.612 mmol), triethylamine (309 mg, 3.06 mmol) and tetrahydrofuran (5 mL), and this was stirred at room temperature for 14 hours. After the reaction was complete, this was concentrated, and to a dioxane (5 mL) solution of the residue obtained was added methanesulfonic acid (353 mg, 1.46 mmol), and this was heated to reflux for 18 hours. After the reaction solution was cooled, water and saturated aqueous sodium hydrogen carbonate solution were added, and this was extracted with chloroform. After the organic layer obtained was dried over anhydrous sodium sulfate, it was filtered and concentrated. The residue obtained was purified by silica gel column chromatography to yield the title compound (40 mg, 18% yield) as pale yellow crystals.

$^1$H-NMR (CDCl$_3$) δ: 1.31 (3H, t, J=7.6 Hz), 1.86-1.93 (2H, m), 2.55-2.70 (5H, m), 2.79 (2H, q, J=7.6 Hz), 3.56-3.65 (2H, m), 4.23 (2H, dd, J=11.9, 4.6 Hz), 4.41-4.50 (1H, m), 7.17 (1H, dd, J=8.3, 1.6 Hz), 7.49 (1H, d, J=8.3 Hz), 7.59 (1H, br s), 7.66 (1H, d, J=8.6 Hz), 8.17 (1H, dd, J=8.6, 1.5 Hz), 8.55 (1H, d, J=1.5 Hz).

Working Example 71

Synthesis of 5-(5-trifluoromethylbenzoxazol-2-yl)-2-methyl-1-(tetrahydropyran-4-yl)benzimidazole

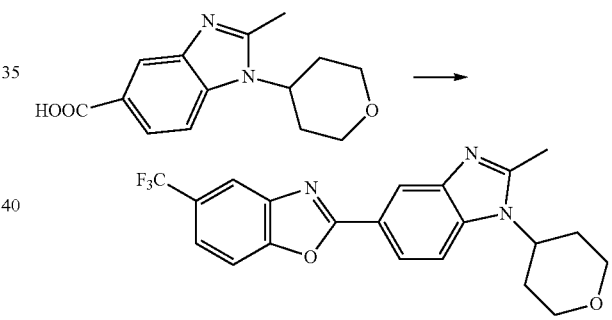

To 2-methyl-1-(tetrahydropyran-4-yl)benzimidazole-5-carboxylic acid HCl salt (see Working Example 4-3) (182 mg, 0.612 mmol) was added thionyl chloride (2 mL), and this was stirred at reflux for 3 hours. After the reaction was complete, concentration at reduced pressure gave a residue that was added to 4-trifluoromethyl-2-aminophenol (132 mg, 0.612 mmol), triethylamine (309 mg, 3.06 mmol) and tetrahydrofuran (5 mL), and this was stirred at room temperature for 14 hours. After the reaction was complete, this was concentrated, and to a dioxane (5 mL) solution of the residue obtained was added methanesulfonic acid (353 mg, 1.46 mmol), and this was heated to reflux for 18 hours. After the reaction solution was cooled, water and saturated aqueous sodium hydrogen carbonate solution were added, and this was extracted with chloroform. After the organic layer obtained was dried over anhydrous sodium sulfate, it was filtered and concentrated. The residue obtained was purified by silica gel column chromatography to yield the title compound (28.8 mg, 12% yield) as white crystals.

$^1$H-NMR (CDCl$_3$) δ: 1.88-1.93 (2H, m), 2.55-2.72 (5H, m), 3.56-3.65 (2H, m), 4.24 (2H, dd, J=11.7, 4.6 Hz), 4.41-

4.53 (1H, m), 7.61 (1H, dd, J=8.6, 1.6 Hz), 7.69 (2H, dd, J=8.6, 2.6 Hz), 8.04 (1H, br s), 8.18 (1H, dd, J=8.6, 1.5 Hz), 8.57 (1H, d, J=1.5 Hz).

Working Example 72

Synthesis of 5-(5-cyclohexylbenzoxazol-2-yl)-2-methyl-1-(tetrahydropyran-4-yl)benzimidazole

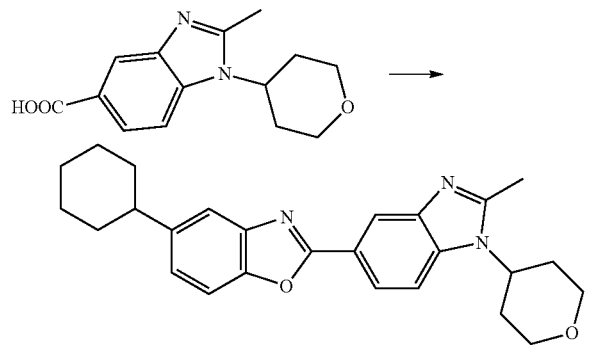

To 2-methyl-1-(tetrahydropyran-4-yl)benzimidazole-5-carboxylic acid HCl salt (see Working Example 4-3) (182 mg, 0.612 mmol) was added thionyl chloride (2 mL), and this was stirred at reflux for 3 hours. After the reaction was complete, concentration at reduced pressure gave a residue that was added to 4-cyclohexyl-2-aminophenol (117 mg, 0.612 mmol), triethylamine (309 mg, 3.06 mmol) and tetrahydrofuran (5 mL), and this was stirred at room temperature for 14 hours. After the reaction was complete, this was concentrated, and to a dioxane (5 mL) solution of the residue obtained was added methanesulfonic acid (353 mg, 1.46 mmol), and this was heated to reflux for 18 hours. After the reaction solution was cooled, water and saturated aqueous sodium hydrogen carbonate solution were added, and this was extracted with chloroform. After the organic layer obtained was dried over anhydrous sodium sulfate, it was filtered and concentrated. The residue obtained was purified by silica gel column chromatography to yield the title compound (125 mg, 49% yield) as white crystals.

$^1$H-NMR (CDCl$_3$) δ:1.18-1.92 (13H, m), 2.56-2.70 (5H, m), 3.56-3.65 (2H, m), 4.23 (2H, dd, J=11.5, 4.5 Hz), 4.41-4.50 (1H, m), 7.19 (1H, dd, J=8.6, 1.6 Hz), 7.49 (1H, d, J=8.6 Hz), 7.60-7.67 (2H, m), 8.16 (1H, dd, J=8.6, 1.6 Hz), 8.54 (1H, d, J=1.6 Hz).

Working Example 73

Synthesis of 5-(5-methoxycarbonylbenzoxazol-2-yl)-2-methyl-1-(tetrahydropyran-4-yl)benzimidazole

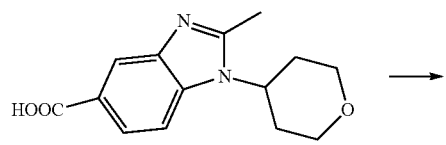

-continued

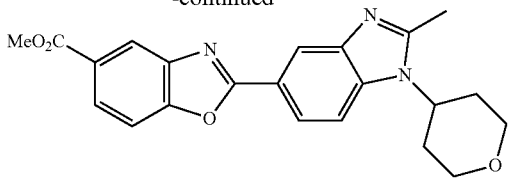

To 2-methyl-1-(tetrahydropyran-4-yl)benzimidazole-5-carboxylic acid HCl salt (see Working Example 4-3) (182 mg, 0.612 mmol) was added thionyl chloride (2 mL), and this was stirred at reflux for 3 hours. After the reaction was complete, concentration at reduced pressure gave a residue that was added to 2-amino-4-methoxycarbonylphenol (117 mg, 0.612 mmol), triethylamine (309 mg, 3.06 mmol) and tetrahydrofuran (5 mL), and this was stirred at room temperature for 14 hours. After the reaction was complete, this was concentrated, and to a dioxane (5 mL) solution of the residue obtained was added methanesulfonic acid (353 mg, 1.46 mmol), and this was heated to reflux for 18 hours. After the reaction solution was cooled, water and saturated aqueous sodium hydrogen carbonate solution were added, and this was extracted with chloroform. After the organic layer obtained was dried over anhydrous sodium sulfate, it was filtered and concentrated. The residue obtained was purified by silica gel column chromatography to yield the title compound (37 mg, 15% yield).

$^1$H-NMR (CDCl$_3$) δ: 1.88-1.94 (2H, m), 2.55-2.72 (5H, m), 3.56-3.65 (2H, m), 3.97 (3H, s), 4.24 (2H, dd, J=11.9, 4.5 Hz), 4.42-4.52 (1H, m), 7.63 (1H, d, J=8.6 Hz), 7.68 (1H, d, J=8.6 Hz), 8.10 (1H, dd, J=8.6, 1.6 Hz), 8.18 (1H, dd, J=8.6, 1.6 Hz), 8.46 (1H, d, J=1.6 Hz), 8.56 (1H, d, J=1.6 Hz).

Working Example 74

Synthesis of 5-(benzoxazol-2-yl)-1-n-butyl-2-methylbenzimidazole

Working Example 74-1

Synthesis of 2-(4-n-butylamino-3-nitrophenyl)benzoxazole

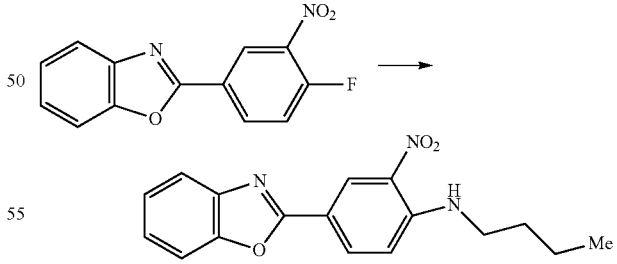

To a suspension of 2-(4-fluoro-3-nitrophenyl)benzoxazole (see Working Example 15-2) (300 mg, 1.16 mmol) in ethanol (5 mL) was added potassium carbonate (321 mg, 2.32 mmol) and butylamine (170 mg, 2.32 mmol), and this was heated to reflux for 4 hours. After the reaction was complete, this was cooled to room temperature, water was added, and after the precipitated crystals were filtered and washed with water, they were dried to yield the title compound (358 mg, 99.1% yield).

¹H-NMR (CDCl₃) δ: 1.02 (3H, t, J=7.3 Hz), 1.45-1.59 (2H, m), 1.72-1.83 (2H, m), 3.40 (2H, td, J=7.0, 5.3 Hz), 7.00 (1H, d, J=9.1 Hz), 7.32-7.36 (2H, m), 7.55-7.59 (1H, m), 7.71-7.75 (1H, m), 8.29 (1H, dd, J=9.1, 2.0 Hz), 8.38 (1H, br s), 9.06 (1H, d, J=2.0 Hz).

Working Example 74-2

2-(2-n-Butylaminoanilin-5-yl)benzoxazole

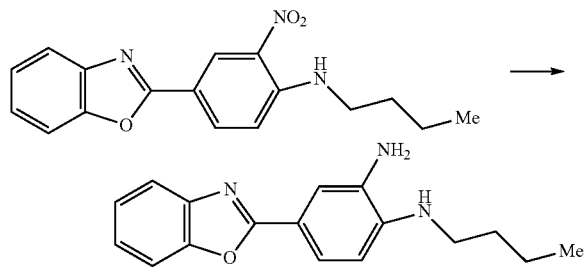

To a tetrahydrofuran solution (5 mL) of 2-(4-n-butylamino-3-nitrophenyl)benzoxazole (see Working Example 74-1) (353 mg, 1.13 mmol) was added 10% palladium-carbon (50 mg), a hydrogen atmosphere was substituted in the flask, and this was stirred at room temperature for 15 hours. After the reaction was complete, this was filtered through Celite and the filtrate was concentrated. The residue obtained was purified by silica gel column chromatography to yield the title compound (305 mg, 96% yield).

¹H-NMR (CDCl₃) δ: 0.99 (3H, t, J=7.3 Hz), 1.42-1.56 (2H, m), 1.64-1.75 (2H, m), 3.21 (2H, t, J=7.1 Hz), 6.71 (1H, d, J=8.4 Hz), 7.23-7.33 (2H, m), 7.50-7.79 (4H, m).

Working Example 74-3

5-(Benzoxazol-2-yl)-1-n-butyl-2-methylbenzimidazole

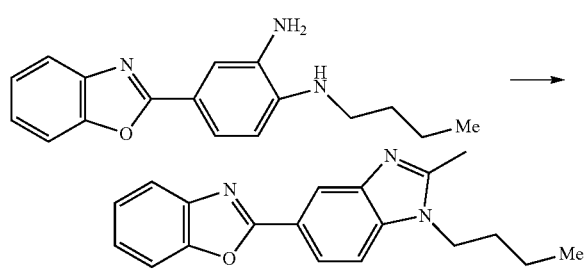

To a methanol (5 mL) solution of 2-(2-n-butylaminoanilin-5-yl)benzoxazole (see Working Example 74-2) (300 mg, 1.07 mmol) was added methyl acetimidate hydrochloride (175 mg, 1.60 mmol), and this was heated to reflux for 3 hours. After the reaction was complete, saturated aqueous sodium hydrogen carbonate solution was added, and this was extracted with chloroform. After the organic layer obtained was dried over anhydrous sodium sulfate, it was filtered and concentrated. The crystals obtained were purified by silica gel column chromatography to yield the title compound (293 mg, 90% yield) as white crystals.

¹H-NMR (CDCl₃) δ: 0.99 (3H, t, J=7.2 Hz), 1.35-1.50 (2H, m), 1.76-1.88 (2H, m), 2.65 (3H, s), 4.14 (2H, t, J=7.3 Hz), 7.27-7.42 (3H, m), 7.59-7.62 (1H, m), 7.75-7.79 (1H, m), 8.20 (1H, d, J=8.2 Hz), 8.56 (1H, s).

Working Example 75

Synthesis of 5-(5-cyanobenzoxazol-2-yl)-2-methyl-1-(tetrahydropyran-4-yl)benzimidazole

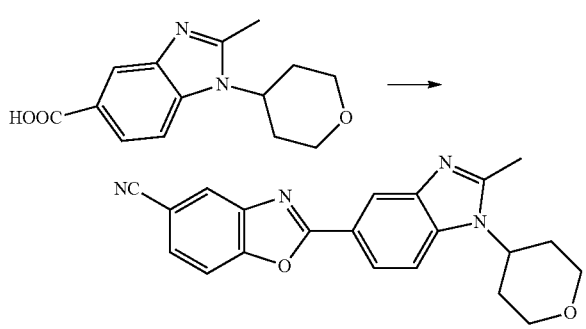

To 2-methyl-1-(tetrahydropyran-4-yl)benzimidazole-5-carboxylic acid HCl salt (see Working Example 4-3) (182 mg, 0.612 mmol) was added thionyl chloride (2 mL), and this was stirred at reflux for 3 hours. After the reaction was complete, concentration at reduced pressure gave a residue that was added to 2-amino-4-cyanophenol (82.1 mg, 0.612 mmol), triethylamine (309 mg, 3.06 mmol) and tetrahydrofuran (5 mL), and this was stirred at room temperature for 14 hours. After the reaction was complete, this was concentrated, and to a dioxane (5 mL) solution of the residue obtained was added methanesulfonic acid (353 mg, 1.46 mmol), and this was heated to reflux for 18 hours. After the reaction solution was cooled, water and saturated aqueous sodium hydrogen carbonate solution were added, and this was extracted with chloroform. After the organic layer obtained was dried over anhydrous sodium sulfate, it was filtered and concentrated. The residue obtained was purified by silica gel column chromatography to yield the title compound (26.1 mg, 12% yield) as pale yellow crystals.

¹H-NMR (CDCl₃) δ: 1.89-1.95 (2H, m), 2.54-2.72 (5H, m), 3.56-3.67 (2H, m), 4.24 (2H, dd, J=11.9, 4.6 Hz), 4.42-4.54 (1H, m), 7.61-7.71 (3H, m), 8.05-8.06 (1H, m), 8.17 (1H, dd, J=8.7, 1.5 Hz), 8.56 (1H, d, J=1.5 Hz).

Working Example 76

Synthesis of 5-(5-trifluoromethoxybenzoxazol-2-yl)-2-methyl-1-(tetrahydropyran-4-yl)benzimidazole

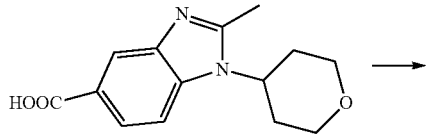

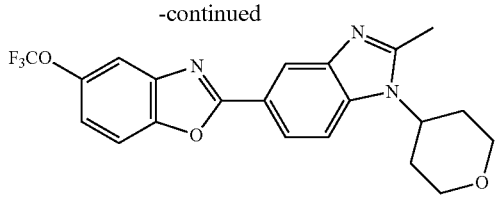

To 2-methyl-1-(tetrahydropyran-4-yl)benzimidazole-5-carboxylic acid HCl salt (see Working Example 4-3) (182 mg, 0.612 mmol) was added thionyl chloride (2 mL), and this was stirred at reflux for 3 hours. After the reaction was complete, concentration at reduced pressure gave a residue that was added to 2-amino-4-trifluoromethoxyphenol (117 mg, 0.612 mmol), triethylamine (309 mg, 3.06 mmol) and tetrahydrofuran (5 mL), and this was stirred at room temperature for 14 hours. After the reaction was complete, this was concentrated, and to a dioxane (5 mL) solution of the residue obtained was added methanesulfonic acid (353 mg, 1.46 mmol), and this was heated to reflux for 18 hours. After the reaction solution was cooled, water and saturated aqueous sodium hydrogen carbonate solution were added, and this was extracted with chloroform. After the organic layer obtained was dried over anhydrous sodium sulfate, it was filtered and concentrated. The residue obtained was purified by silica gel column chromatography to yield the title compound (64 mg, 25% yield) as pink crystals.

$^1$H-NMR (CDCl$_3$) δ: 1.87-1.93 (2H, m), 2.54-2.72 (5H, m), 3.56-3.66 (2H, m), 4.24 (2H, dd, J=11.8, 4.4 Hz), 4.40-4.54 (1H, m), 7.20-7.24 (1H, m), 7.57-7.70 (3H, m), 8.16 (1H, dd, J=8.6, 1.3 Hz), 8.56 (1H, d, J=1.3 Hz).

Working Example 77

Synthesis of 5-(benzoxazol-2-yl)-1-(tetrahydropyran-4-yl)-2-trichloromethylbenzimidazole

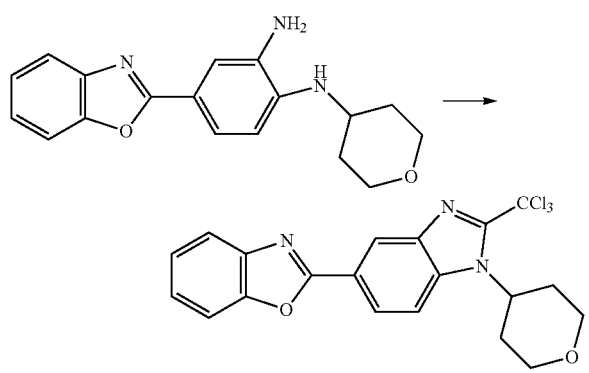

To a solution of 5-(benzoxazol-2-yl)-2-(tetrahydropyran-4-yl)aminoaniline (see Working Example 20-2) (150 mg, 0.485 mmol) in acetic acid (3 mL) was added methyl 2,2,2-trichloroacetimidate hydrochloride (94.1 mg, 0.533 mmol), and this was stirred at room temperature for 4 hours. After the reaction was complete, water was added, and the precipitated crystals were filtered, and after being washed with water were dried to yield the title compound (196 mg, 93% yield) as gray crystals.

$^1$H-NMR (CDCl$_3$) δ: 2.04-2.11 (2H, m), 2.63-2.79 (2H, m), 3.57-3.66 (2H, m), 4.25 (2H, dd, J=11.7, 4.6 Hz), 5.29-5.38 (1H, m), 7.34-7.40 (2H, m), 7.59-7.64 (1H, m), 7.75-7.85 (2H, m), 8.34 (1H, dd, J=8.7, 1.3 Hz), 8.77 (1H, d, J=1.3 Hz).

Working Example 78

Synthesis of 5-(benzoxazol-2-yl)-1-(cyclohexanon-4-yl)-2-methylbenzimidazole

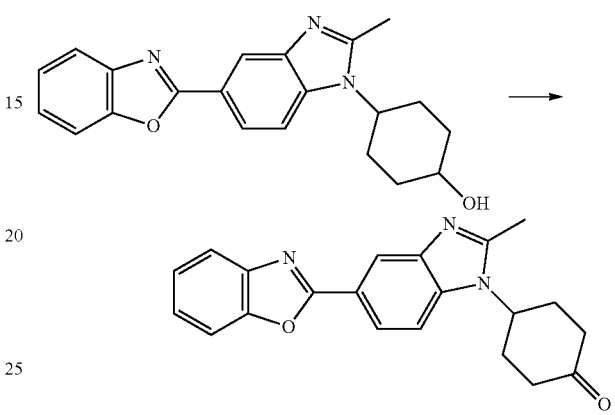

To a solution of 5-(benzoxazol-2-yl)-1-(4-hydroxycyclohexyl)-2-methylbenzimidazole (see Working Example 49-2) (50 mg, 0.14 mmol) in chloroform (3 mL) was added DDQ (35 mg, 0.16 mmol), and this was stirred overnight at room temperature. After the reaction was complete, this was concentrated, and the residue obtained was purified by silica gel column chromatography to yield the title compound (20 mg, 40% yield) as reddish-brown crystals.

$^1$H-NMR (DMSO-d$_6$) δ: 1.73-2.77 (9H, m), 5.03 (1H, br), 7.39-7.42 (2H, m), 7.77-7.81 (2H, m), 8.00-8.15 (2H, m), 8.36 (1H, s).

Working Example 79

Synthesis of 5-(benzoxazol-2-yl)-2-methyl-1-(2-picolyl)benzimidazole

Working Example 79-1

Synthesis of 2-(2-(2-picolyl)aminoanilin-5-yl)benzoxazole

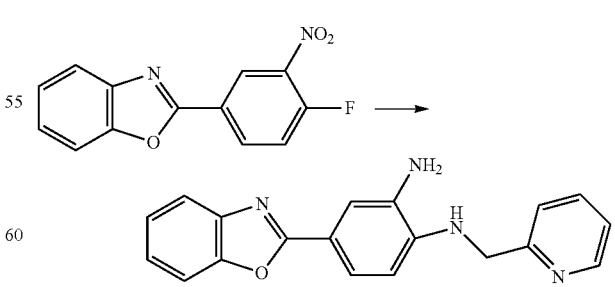

2-(4-Fluoro-3-nitrophenyl)benzoxazole (see Working Example 15-2) (500 mg, 1.9 mmol) was added to an acetonitrile (5 mL) suspension containing 2-picolylamine (520 mg, 4.8 mmol), and this was heated to reflux for 2.5 hours. After the reaction was complete, this was cooled to room temperature, water was added, and the precipitated crystals were filtered, washed with water and then dried. To a tetrahydrofuran solution (7 mL) of the crystals obtained was added 10% palladium-carbon (100 mg). A hydrogen atmosphere was substituted in the flask, and this was stirred at room temperature for 14 hours. After the reaction was complete, this was filtered through Celite and the filtrate was concentrated. The residue obtained was purified by silica gel column chromatography to yield the title compound (480 mg, 78% yield) as a white solid.

$^1$H-NMR (DMSO-$d_6$) δ: 4.50 (2H, d, J=5.8 Hz), 4.97 (2H, s), 6.10 (1H, t, J=5.8 Hz), 6.43 (1H, d, J=8.4 Hz), 7.24-7.37 (5H, m), 7.44 (1H, d, J=2.0 Hz), 7.61-7.65 (2H, m), 7.75 (1H, td, J=7.7, 2.0 Hz), 8.55 (1H, d, J=4.1 Hz).

Working Example 79-2

Synthesis of 5-(benzoxazol-2-yl)-2-methyl-1-(2-picolyl)benzimidazole

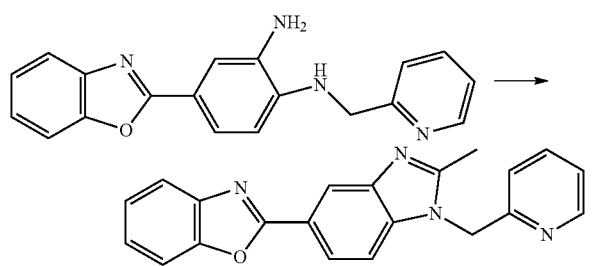

To a methanol (5 mL) solution of 2-(2-(2-picolyl)aminoanilin-5-yl)benzoxazole (see Working Example 79-1) (250 mg, 0.79 mmol) was added methyl acetimidate hydrochloride (100 mg, 0.87 mmol), and this was heated to reflux for 3 hours. After the reaction was complete, saturated aqueous sodium hydrogen carbonate solution was added, and this was extracted with chloroform. The organic layer obtained was dried over anhydrous sodium sulfate, after which it was filtered and concentrated to yield the title compound (250 mg, 93% yield) as white crystals.

$^1$H-NMR (DMSO-$d_6$) δ: 2.62 (3H, s), 5.64 (2H, s), 7.33-7.38 (4H, m), 7.74-7.79 (4H, m), 8.04 (1H, dd, J=8.4, 1.3 Hz), 8.35 (1H, d, J=1.3 Hz), 8.50 (1H, d, J=4.9 Hz).

Working Example 80

Synthesis of 5-(benzoxazol-2-yl)-2-methyl-1-isopropylbenzimidazole

Working Example 80-1

Synthesis of 2-(4-isoproylamino-3-nitrophenyl)benzoxazole

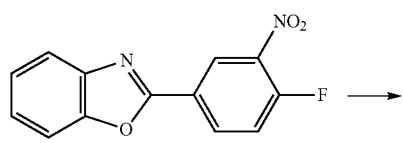

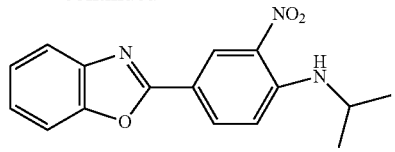

To a suspension of 2-(4-fluoro-3-nitrophenyl)benzoxazole (see Working Example 15-2) (200 mg, 0.774 mmol) in ethanol (5 mL) was added potassium carbonate (214 mg, 1.55 mmol) and isopropylamine (137 mg, 2.32 mmol), and this was heated to reflux for 4 hours. After the reaction was complete, this was cooled to room temperature, water was added, and after the precipitated crystals were filtered and washed with water, they were dried to yield the title compound (227 mg, 99% yield).

$^1$H-NMR (CDCl$_3$) δ: 1.38 (3H, s), 1.41 (3H, s), 3.88-4.01 (1H, m), 7.01 (1H, d, J=9.2 Hz), 7.31-7.39 (2H, m), 7.55-7.59 (1H, m), 7.71-7.75 (1H, m), 8.26-8.36 (2H, m), 9.06 (1H, d, J=2.1 Hz).

Working Example 80-2

Synthesis of 2-(2-isopropylaminoanilin-5-yl)benzoxazole

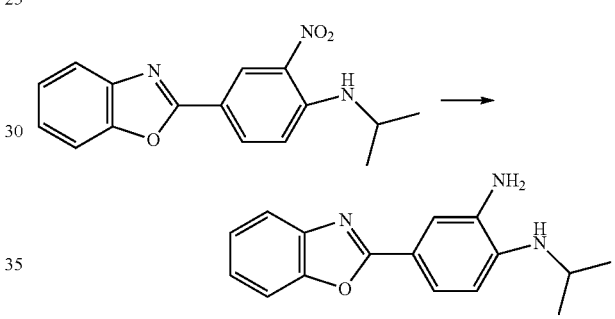

To a tetrahydrofuran solution (5 mL) of 2-(4-isopropylamino-3-nitrophenyl)benzoxazole (see Working Example 80-1) (224 mg, 0.753 mmol) was added 10% palladium-carbon (40 mg), a hydrogen atmosphere was substituted in the flask, and this was stirred at room temperature for 15 hours. After the reaction was complete, this was filtered through Celite and the filtrate was concentrated. The residue obtained was purified by silica gel column chromatography to yield the title compound (184 mg, 91% yield).

$^1$H-NMR (CDCl$_3$) δ: 1.28 (3H, s), 1.31 (3H, s), 3.68-3.78 (1H, m), 6.71 (1H, d, J=8.4 Hz), 7.26-7.33 (2H, m), 7.50-7.78 (4H, m).

Working Example 80-3

Synthesis of 5-(benzoxazol-2-yl)-2-methyl-1-isopropylbenzimidazole

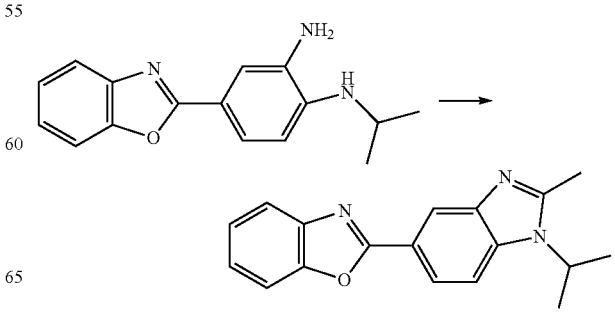

To a methanol (5 mL) solution of 2-(2-isopropylaminoanilin-5-yl)benzoxazole (see Working Example 80-2) (180 mg, 0.673 mmol) was added methyl acetimidate hydrochloride (111 mg, 1.01 mmol), and this was heated to reflux for 2 hours. After the reaction was complete, saturated aqueous sodium hydrogen carbonate solution was added, and this was extracted with ethyl acetate. After the organic layer obtained was dried over anhydrous sodium sulfate, it was filtered and concentrated. The crystals obtained were purified by silica gel column chromatography to yield the title compound (196 mg, quant.) as white crystals.

$^1$H-NMR (CDCl$_3$) δ: 1.67 (3H, s), 1.70 (3H, s), 2.67 (3H, s), 4.66-4.76 (1H, m), 7.30-7.37 (2H, m), 7.58-7.62 (2H, m), 7.74-7.79 (1H, m), 8.16 (1H, dd, J=8.6, 1.5 Hz), 8.55 (1H, d, J=1.5 Hz).

Working Example 81

Synthesis of 5-(benzoxazol-2-yl)-2-methyl-1-neopentylbenzimidazole

Working Example 81-1

Synthesis of 2-(4-neopentylamino-3-nitrophenyl)benzoxazole

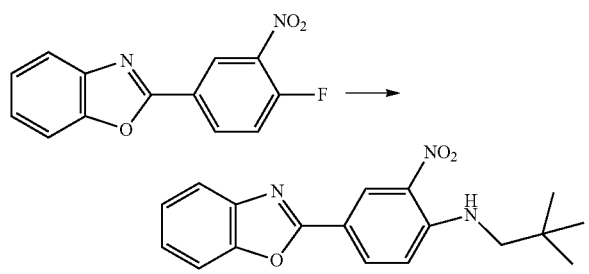

To a suspension of 2-(4-fluoro-3-nitrophenyl)benzoxazole (see Working Example 15-2) (200 mg, 0.774 mmol) in ethanol (5 mL) was added potassium carbonate (214 mg, 1.55 mmol) and neopentylamine (135 mg, 1.55 mmol), and this was heated to reflux for 4 hours. After the reaction was complete, this was cooled to room temperature, water was added, and after the precipitated crystals were filtered and washed with water, they were dried to yield the title compound (245 mg, 97% yield).

$^1$H-NMR (CDCl$_3$) δ: 1.11 (9H, s) 3.19 (2H, d, J=5.1 Hz) 7.02 (1H, d, J=9.1 Hz) 7.33-7.37 (2H m) 7.55-7.59 (1H m) 7.71-7.75 (1H m) 8.28 (1H, dd, J=9.12.0 Hz) 8.60 (1H br s) 9.07 (1H, d, J=2.0 Hz).

Working Example 81-2

Synthesis of 2-(2-neopentylaminoanilin-5-yl)benzoxazole

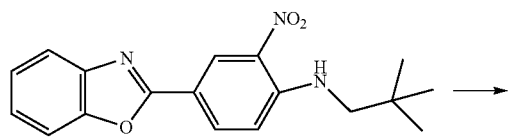

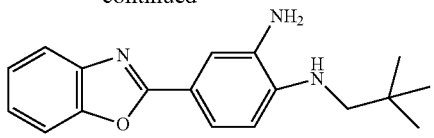

To a tetrahydrofuran solution (5 mL) of 2-(4-neopentylamino-3-nitrophenyl)benzoxazole (see Working Example 81-1) (242 mg, 0.744 mmol) was added 10% palladium-carbon (40 mg), a hydrogen atmosphere was substituted in the flask, and this was stirred at room temperature for 15 hours. After the reaction was complete, this was filtered through Celite and the filtrate was concentrated. The residue obtained was purified by silica gel column chromatography to yield the title compound (196 mg, 89% yield).

$^1$H-NMR (CDCl$_3$) δ: 1.06 (9H, s), 2.98 (2H, s), 6.73 (1H, d, J=8.4 Hz), 7.23-7.33 (2H, m), 7.49-7.79 (4H, m).

Working Example 81-3

Synthesis of 5-(benzoxazol-2-yl)-2-methyl-1-neopentylbenzimidazole

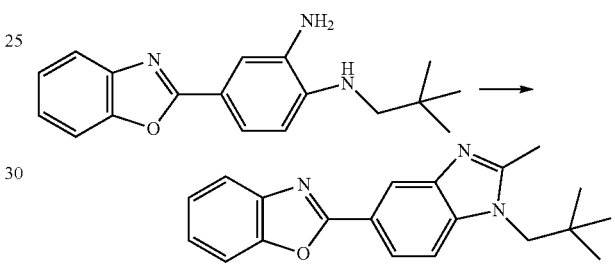

To a methanol (5 mL) solution of 2-(2-neopentylaminoanilin-5-yl)benzoxazole (see Working Example 81-2) (192 mg, 0.650 mmol) was added methyl acetimidate hydrochloride (107 mg, 0.975 mmol), and this was heated to reflux for 2 hours. After the reaction was complete, saturated aqueous sodium hydrogen carbonate solution was added, and this was extracted with ethyl acetate. After the organic layer obtained was dried over anhydrous sodium sulfate, it was filtered and concentrated. The crystals obtained were purified by silica gel column chromatography to yield the title compound (155 mg, 75% yield) as white crystals.

$^1$H-NMR (CDCl$_3$) δ: 1.08 (9H, s), 2.67 (3H, s), 3.97 (2H, s), 7.32-7.37 (2H, m), 7.45 (1H, d, J=8.6 Hz), 7.59-7.62 (1H, m), 7.75-7.79 (1H, m), 8.18 (1H, dd, J=8.6, 1.5 Hz), 8.55 (1H, d, J=1.5 Hz).

Working Example 82

Synthesis of 5-(5-aminobenzoxazol-2-yl)-2-methyl-1-n-propylbenzimidazole

Working Example 82-1

Synthesis of 3-nitro-4-n-propylaminobenzoic acid

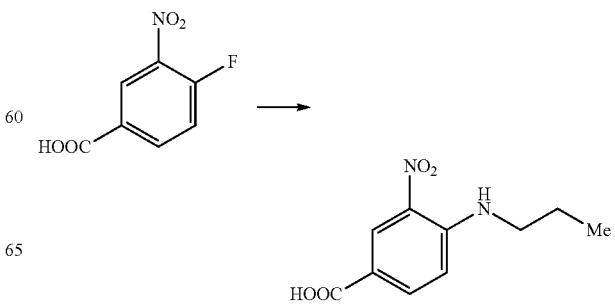

To a suspension of 4-fluoro-3-nitrobenzoic acid (2.0 g, 10.8 mmol) in ethanol (20 mL) was added potassium carbonate (2.34 mg, 16.2 mmol) and propylamine (1.27 g, 21.6 mmol), and this was heated to reflux for 4 hours. After the reaction was complete, this was cooled to room temperature, and water was added, this was adjusted to pH 5 with 10% hydrochloric acid and acetic acid, and after the precipitated crystals were filtered and washed with water, they were dried to yield the title compound (1.94 g, 80% yield).

$^1$H-NMR (CDCl$_3$) δ: 1.08 (3H, t, J=7.4 Hz), 1.74-1.84 (2H, m), 3.32-3.39 (2H, m), 6.90 (1H, d, J=9.1 Hz), 8.09 (1H, dd, J=9.1, 2.0 Hz), 8.45 (1H, br s), 8.97 (1H, d, J=2.0 Hz).

Working Example 82-2

3-Amino-4-n-propylaminobenzoic acid

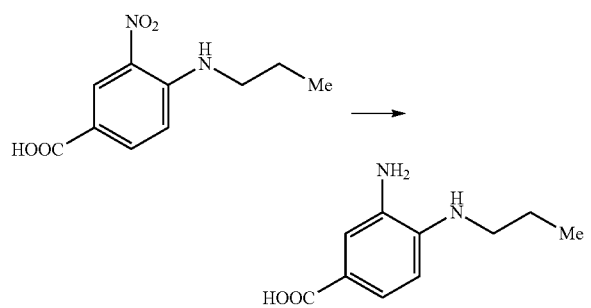

To a tetrahydrofuran solution (20 mL) of 3-nitro-4-n-propylaminobenzoic acid (see Working Example 82-1) (1.94 g, 10.8 mmol) was added 10% palladium-carbon (200 mg), a hydrogen atmosphere was substituted in the flask, and this was stirred at room temperature for 6 hours. After the reaction was finished, this was filtered through Celite, and the filtrate was concentrated to yield the title compound (1.68 g, quant.).

$^1$H-NMR (DMSO-d$_6$) δ: 0.96 (3H, t, J=7.3 Hz), 1.54-1.65 (2H, m), 3.02-3.10 (2H, m), 5.10 (1H, br s), 6.40 (1H, d, J=8.2 Hz), 7.13-7.20 (2H, m).

Working Example 82-3

2-Methyl-1-n-propylbenzimidazole-5-carboxylic acid

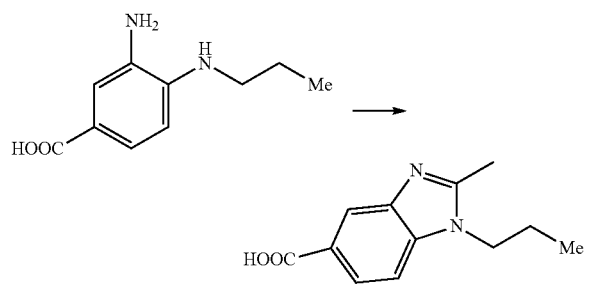

To a methanol (17 mL) solution of 3-amino-4-n-propylaminobenzoic acid (see Working Example 82-2) (1.68 g, 8.65 mmol) was added methyl acetimidate hydrochloride (1.14 g, 10.4 mmol), and this was heated to reflux for 4 hours. After the reaction was complete, this was cooled to room temperature, diethyl ether was added, and this was allowed to stand at room temperature for 10 minutes. The crystals obtained were filtered, and after being washed with diethyl ether, they were dried to yield the title compound (2.20 g, quant.).

$^1$H-NMR (DMSO-d$_6$) δ: 0.94 (3H, t, J=7.3 Hz), 1.76-1.89 (2H, m), 2.86 (3H, s), 4.39 (2H, t, J=7.3 Hz), 8.03-8.11 (2H, m), 8.27 (1H, s).

Working Example 82-4

Synthesis of 5-(5-aminobenzoxazol-2-yl)-2-methyl-1-n-propylbenzimidazole

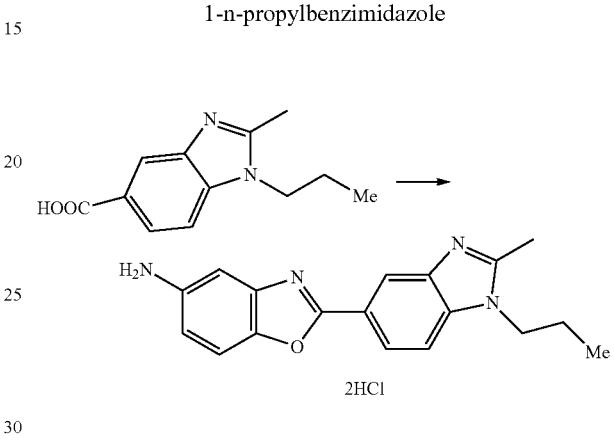

To 2-methyl-1-n-propylbenzimidazole-5-carboxylic acid (see Working Example 82-3) (1.0 g, 3.93 mmol) was added thionyl chloride (8 mL), and this was stirred at reflux for 3 hours. After the reaction was complete, concentration at reduced pressure gave a residue that was added to 2-aminophenol (456 mg, 2.96 mmol), triethylamine (899 mg, 8.88 mmol) and tetrahydrofuran (10 mL), and this was stirred at room temperature for 14 hours. After the reaction was complete, this was concentrated, and to a dioxane (10 mL) solution of the residue obtained was added methanesulfonic acid (1.42 g, 14.8 mmol), and this was heated to reflux for 18 hours. After the reaction solution was cooled, water and saturated aqueous sodium hydrogen carbonate were added, the precipitated crystals were filtered, washed with water and dried. To the residue obtained was added iron powder (400 mg, 7.12 mmol), 10% aqueous acetic acid (20 mL), and ethanol (20 mL), and this was heated to reflux for 2 hours. After the reaction solution was cooled, a 1N aqueous sodium hydroxide solution and chloroform were added, this was filtered through Celite, and the filtrate obtained was extracted. After the organic layer obtained was dried over anhydrous sodium sulfate, it was filtered and concentrated. The residue obtained was purified by silica gel column chromatography, and the oil obtained was dissolved in tetrahydrofuran (3 mL), and to this was added a 1M solution of hydrogen chloride in diethyl ether (1 mL). The precipitated crystals were filtered, and after washing with tetrahydrofuran, they were dried to yield the title compound (168 mg, 25% yield) as light green crystals.

$^1$H-NMR (D$_2$O) δ: 0.85 (3H, t, J=7.4 Hz), 1.73-1.86 (2H, m), 2.72 (3H, s), 4.23 (2H, t, J=7.3 Hz), 7.28 (1H, dd, J=8.6, 2.1 Hz), 7.56 (1H, br s), 7.64 (1H, d, J=8.6 Hz), 7.80 (1H, d, J=8.6 Hz), 8.13 (1H, d, J=8.6 Hz), 8.27 (1H, s).

Working Example 83

Synthesis of 5-(benzoxazol-2-yl)-2-methyl-1-(2-(tetrahydropyran-4-yl)ethyl)benzimidazole Working Example 83-1

Synthesis of 2-(2-(tetrahydropyran-4-yl)ethyl)benzoxazole

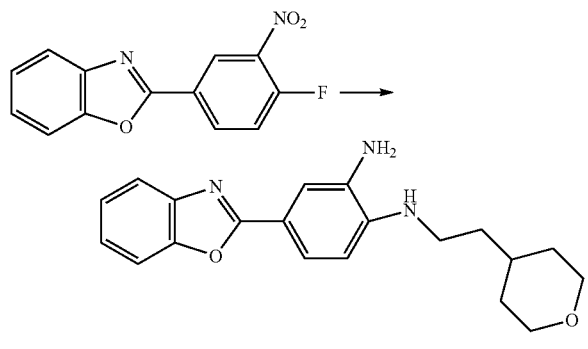

2-(4-Fluoro-3-nitrophenyl)benzoxazole (see Working Example 15-2) (800 mg, 3.1 mmol) was added to an acetonitrile (5 mL) solution containing 2-(tetrahydropyran-4-yl)ethylamine (520 mg, 3.9 mmol) and triethylamine (500 mg, 3.9 mmol), and this was heated to reflux for 3 hours. After the reaction was complete, this was cooled to room temperature, water was added, and the precipitated crystals were filtered, washed with water and then dried. To a tetrahydrofuran solution (20 mL) of the crystals obtained was added 10% palladium-carbon (100 mg). A hydrogen atmosphere was substituted in the flask, and this was stirred overnight at room temperature. After the reaction was complete, this was filtered through Celite and the filtrate was concentrated. The residue obtained was purified by silica gel column chromatography to yield the title compound (450 mg, 43% yield) as a syrup.

$^1$H-NMR (DMSO-$d_6$) δ: 1.07-1.66 (7H, m), 2.95-3.34 (4H, m), 3.85 (2H, dd, J=11.0, 3.5 Hz), 4.91 (2H, br), 5.18 (1H, t, J=5.2 Hz), 6.56 (1H, d, J=8.1 Hz), 7.26-7.43 (5H, m), 7.62-7.67 (2H, m).

Working Example 83-2

Synthesis of 5-(benzoxazol-2-yl)-2-methyl-1-(2-(tetrahydropyran-4-yl)ethyl)benzimidazole

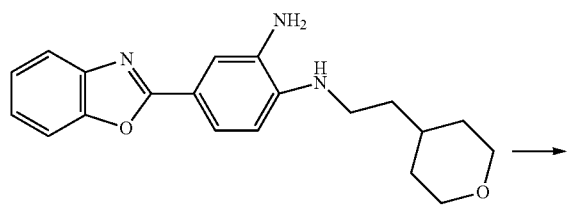

-continued

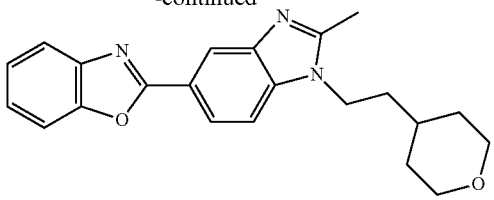

To a methanol (5 mL) solution of 2-(2-(tetrahydropyran-4-yl)ethyl)benzoxazole (see Working Example 83-1) (300 mg, 0.89 mmol) was added methyl acetimidate hydrochloride (220 mg, 1.96 mmol), and this was heated to reflux for 3 hours. After the reaction was complete, saturated aqueous sodium hydrogen carbonate solution was added, and this was extracted with chloroform. The organic layer obtained was dried over anhydrous sodium sulfate, after which it was filtered and concentrated to yield the title compound (190 mg, 59% yield) as white crystals.

$^1$H-NMR (DMSO-$d_6$) δ: 1.21-1.34 (2H, m), 1.60-1.66 (5H, m), 2.60 (3H, s), 3.24-3.40 (2H, m), 3.85 (2H, dd, J=11.4, 3.3 Hz), 4.27 (2H, t, J=7.4 Hz), 7.38-7.42 (2H, m), 7.71-7.82 (3H, m), 8.08 (1H, dd, J=8.5, 1.5 Hz), 8.33 (1H, d, J=1.5 Hz).

Working Example 84

Synthesis of 5-(benzoxazol-2-yl)-2-methyl-1-((tetrahydropyran-4-yl)methyl)benzimidazole Working Example 84-1

Synthesis of 2-((tetrahydropyran-4-yl)methyl)benzoxazole

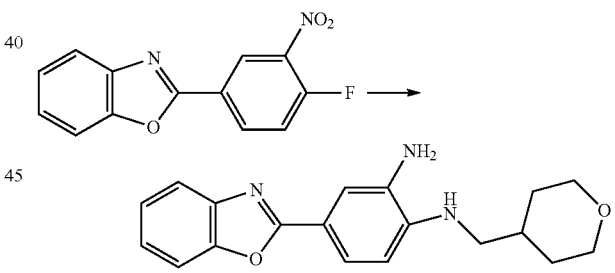

2-(4-Fluoro-3-nitrophenyl)benzoxazole (see Working Example 15-2) (900 mg, 3.5 mmol) was added to an acetonitrile (5 mL) solution containing (tetrahydropyran-4-yl)methylamine (520 mg, 3.9 mmol) and triethylamine (500 mg, 4.3 mmol), and this was heated to reflux for 3 hours. After the reaction was complete, this was cooled to room temperature, water was added, and the precipitated crystals were filtered, washed with water and then dried. To a tetrahydrofuran solution (20 mL) of the crystals obtained was added 10% palladium-carbon (100 mg). A hydrogen atmosphere was substituted in the flask, and this was stirred overnight at room temperature. After the reaction was finished, this was filtered through Celite, and the filtrate was concentrated to yield the title compound (790 mg, 70% yield) as a white solid.

$^1$H-NMR (DMSO-$d_6$) δ: 1.22-1.275 (2H, m), 1.73 (2H, d, J=12.7 Hz), 1.82-1.95 (1H, m), 3.05 (2H, t, J=6.0 Hz), 3.27-3.32 (2H, m), 3.88 (2H, dd, J=11.4, 2.8 Hz), 4.92 (2H, s), 5.27

(1H, t, J=5.4 Hz), 6.57 (1H, d, J=8.9 Hz), 7.26-7.35 (2H, m), 7.39-7.43 (2H, m), 7.60-7.69 (2H, m).

Working Example 84-2

Synthesis of 5-(benzoxazol-2-yl)-2-methyl-1-((tetrahydropyran-4-yl)methyl)benzimidazole

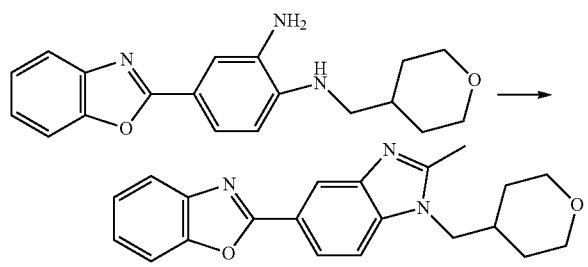

To a methanol (5 mL) solution of 2-((tetrahydropyran-4-yl)methyl)benzoxazole (see Working Example 84-1) (300 mg, 0.93 mmol) was added methyl acetimidate hydrochloride (120 mg, 1.11 mmol), and this was heated to reflux for 3 hours. After the reaction was complete, saturated aqueous sodium hydrogen carbonate solution was added, and this was extracted with chloroform. The organic layer obtained was dried over anhydrous sodium sulfate, after which it was filtered and concentrated to yield the title compound (290 mg, 90% yield) as white crystals.

$^1$H-NMR (DMSO-$d_6$) δ: 1.37-1.41 (4H, m), 2.06-2.12 (1H, m), 2.61 (3H, s), 3.18-3.28 (2H, m), 3.83 (2H, d, J=11.0 Hz), 4.16 (2H, d, J=7.4 Hz), 7.39-7.41 (2H, m), 7.77-7.82 (3H, m), 8.06-8.09 (1H, m), 8.32 (1H, s).

Working Example 85

Synthesis of 5-(benzoxazol-2-yl)-2-methyl-1-(3,3,3-trifluoropropyl)benzimidazole Working Example 85-1

Synthesis of 2-(2-(3,3,3-trifluoropropyl)aminoanilin-5-yl)benzoxazole

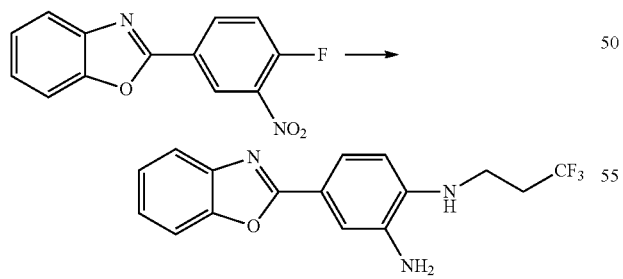

2-(4-Fluoro-3-nitrophenyl)benzoxazole (see Working Example 15-2) (500 mg, 3.5 mmol) was added to an acetonitrile (5 mL) solution containing (tetrahydropyran-4-yl)methylamine (360 mg, 2.4 mmol) and triethylamine (590 mg, 7.3 mmol), and this was heated to reflux for 3 hours. After the reaction was complete, this was cooled to room temperature, water was added, and the precipitated crystals were filtered, washed with water and then dried. To a tetrahydrofuran solution (20 mL) of the crystals obtained was added 10% palladium-carbon (100 mg). A hydrogen atmosphere was substituted in the flask, and this was stirred overnight at room temperature. After the reaction was complete, this was concentrated, and the residue obtained was purified by silica gel column chromatography to yield the title compound (450 mg, 71% yield) as an amorphous mass.

$^1$H-NMR (CDCl$_3$) δ: 1.59 (1H, br s), 2.47-2.55 (2H, m), 3.34 (1H, br s), 3.54 (2H, t, J=6.4 Hz), 4.09 (1H, br s), 6.71 (1H, d, J=8.2 Hz), 7.22-7.35 (2H, m), 7.52-7.56 (1H, m), 7.66-7.72 (2H, m), 7.78 (1H, dd, J=8.2, 2.0 Hz).

Working Example 85-2

Synthesis of 5-(benzoxazol-2-yl)-2-methyl-1-(3,3,3-trifluoropropyl)benzimidazole

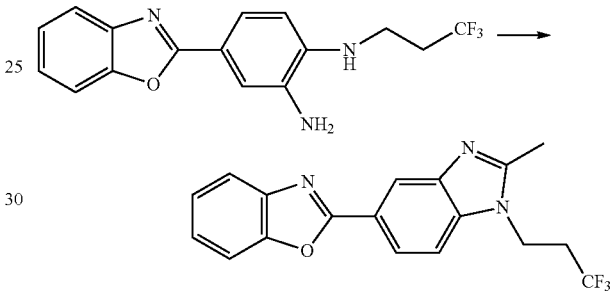

To a methanol (5 mL) solution of 2-(2-(3,3,3-trifluoropropyl)aminoanilin-5-yl)benzoxazole (see Working Example 85-1) (300 mg, 0.93 mmol) was added methyl acetimidate hydrochloride (120 mg, 1.11 mmol), and this was heated to reflux for 3 hours. After the reaction was complete, saturated aqueous sodium hydrogen carbonate solution was added, and this was extracted with chloroform. The organic layer obtained was dried over anhydrous sodium sulfate, after which it was filtered and concentrated to yield the title compound (250 mg, 93% yield) as white crystals.

$^1$H-NMR (DMSO-$d_6$) δ: 2.63 (3H, s), 2.83-3.00 (2H, m), 4.55 (2H, t, J=6.9 Hz), 7.36-7.40 (2H, m), 7.75-7.82 (3H, m), 8.10 (1H, dd, J=8.5, 1.3 Hz), 8.34 (1H, d, J=1.3 Hz).

Working Example 86

Synthesis of 5-(benzoxazol-2-yl)-2-(ethoxycarbonylmethyl)-1-(tetrahydropyran-4-yl)benzimidazole

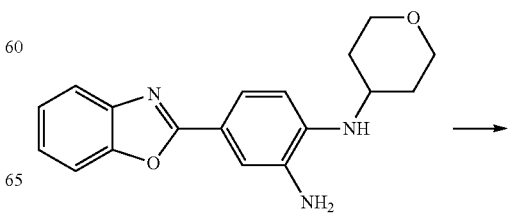

-continued

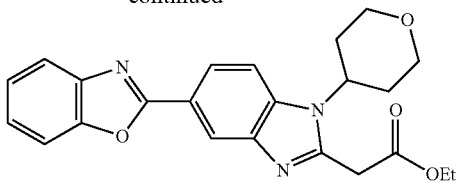

To a solution of 5-(benzoxazol-2-yl)-2-(tetrahydropyran-4-yl)aminoaniline (see Working Example 20-2) (200 mg, 0.646 mmol) in ethanol (5 mL) was added ethyl 3-ethoxy-3-iminopropionate (190 mg, 0.969 mmol), and this was heated to reflux for 2 hours. After the reaction was complete, saturated aqueous sodium hydrogen carbonate solution was added, and this was extracted with ethyl acetate. After the organic layer obtained was dried over anhydrous sodium sulfate, it was filtered and concentrated. The crystals obtained were purified by silica gel column chromatography to yield the title compound (249 mg, 95% yield) as gray crystals.

$^1$H-NMR (CDCl$_3$) δ: 1.30 (3H, t, J=7.1 Hz), 1.92-2.00 (2H, m), 2.58-2.73 (2H, m), 3.53-3.63 (2H, m), 4.12 (2H, s), 4.19-4.27 (4H, m), 4.41-4.54 (1H, m), 7.33-7.37 (2H, m), 7.58-7.66 (1H, m), 7.73-7.80 (2H, m), 8.22 (1H, dd, J=8.6, 1.4 Hz), 8.61 (1H, d, J=1.4 Hz).

Working Example 87

Synthesis of 5-(benzoxazol-2-yl)-2-methyl-1-(1,2,3,4-tetrahydronaphthalen-1-yl)benzimidazole Working Example 87-1

Synthesis of 2-(2-(1,2,3,4-tetrahydronaphthalen-1-yl)aminoanilin-5-yl)benzoxazole

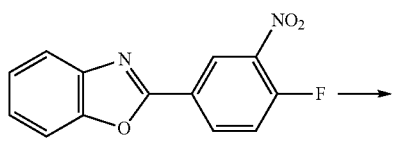

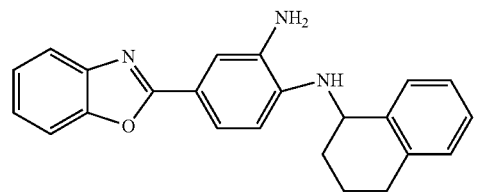

To a suspension of 2-(4-fluoro-3-nitrophenyl)benzoxazole (see Working Example 15-2) (0.50 g, 1.9 mmol) in acetonitrile (10 mL) was added 1-amino-1,2,3,4-tetrahydronaphthalene (0.31 g, 2.1 mmol) and triethylamine (0.29 g, 3.2 mmol), and this was heated to reflux for 6 hours. After the reaction was complete, this was cooled to room temperature, water was added, and the precipitated crystals were filtered, washed with water and then dried. To a solution of the residue obtained in a solvent mixture of methanol/tetrahydrofuran (1:1, 50 mL) was added 10% palladium-carbon (50 mg). A hydrogen atmosphere was substituted in the flask, and this was stirred at room temperature for 3 hours. After the reaction was complete, this was filtered through Celite and the filtrate was concentrated. The residue obtained was purified by silica gel column chromatography to yield the title compound (0.40 g, 84% yield) as a colorless amorphous mass.

$^1$H-NMR (CDCl$_3$) δ: 1.80-2.05 (4H, m), 2.82-2.88 (2H, m), 3.28 (2H, br s), 4.20 (1H, d, J=6.9 Hz), 4.71-4.79 (1H, br m), 6.88 (1H, d, J=8.4 Hz), 7.15-7.39 (6H, m), 7.50-7.53 (1H, m), 7.67-7.70 (2H, m), 7.80 (1H, dd, J=8.4, 2.0 Hz).

Working Example 87-2

Synthesis of 5-(benzoxazol-2-yl)-2-methyl-1-(1,2,3,4-tetrahydronaphthalen-1-yl)benzimidazole

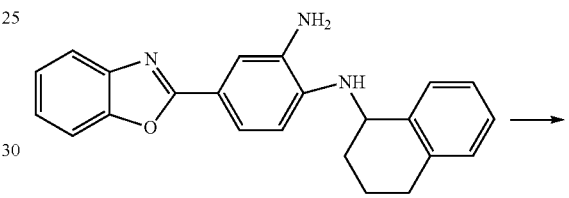

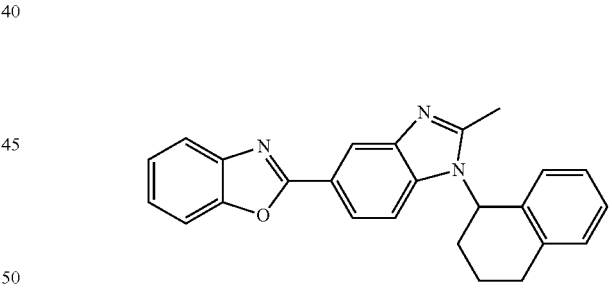

To a methanol (5 mL) solution of 2-(2-(1,2,3,4-tetrahydronaphthalen-1-yl)aminoanilin-5-yl)benzoxazole (see Working Example 87-1) (0.30 g, 0.8 mmol) was added methyl acetimidate hydrochloride (0.10 g, 0.9 mmol), and this was heated to reflux for 3 hours. After the reaction solution was cooled, water was added, and this was extracted with chloroform. After the organic layer obtained was dried over anhydrous sodium sulfate, it was filtered and concentrated. The residue obtained was purified by silica gel column chromatography to yield the title compound (0.15 g, 47% yield) as a colorless amorphous mass.

$^1$H-NMR (CDCl$_3$) δ: 1.90-2.34 (4H, m), 2.64 (3H, s), 2.93-3.16 (2H, m), 5.71 (1H, t, J=8.6 Hz), 6.72 (1H, d, J=7.7

Hz), 6.82-6.90 (1H, br m), 7.01-7.07 (1H, m), 7.24-7.34 (4H, m), 7.56-7.60 (1H, m), 7.72-7.78 (1H, m), 7.96 (1H, d, J=8.5 Hz), 8.57 (1H, t, J=2.3 Hz).

Working Example 88

Synthesis of 5-(benzoxazol-2-yl)-1-(2-hydroxyethyl)-2-methylbenzimidazole

Working Example 88-1

Synthesis of 2-(2-(2-hydroxyethyl)aminoanilin-5-yl)benzoxazole

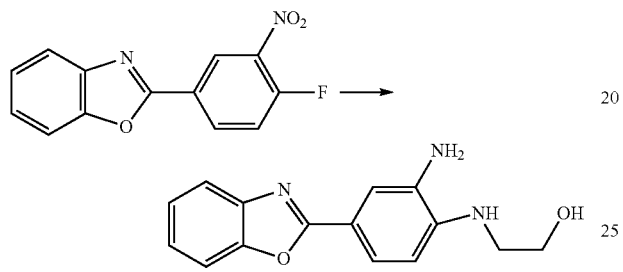

To a suspension of 2-(4-fluoro-3-nitrophenyl)benzoxazole (see Working Example 15-2) (0.50 g, 1.9 mmol) in acetonitrile (10 mL) was added 2-hydroxyethylamine (0.14 g, 2.1 mmol) and triethylamine (0.29 g, 2.4 mmol), and this was heated to reflux for 6 hours. After the reaction was complete, this was cooled to room temperature, water was added, and the precipitated crystals were filtered, washed with water and then dried. To a solution of the residue obtained in a solvent mixture of methanol/tetrahydrofuran=1:1 (50 mL) was added 10% palladium-carbon (50 mg). A hydrogen atmosphere was substituted in the flask, and this was stirred at room temperature for 3 hours. After the reaction was complete, this was filtered through Celite and the filtrate was concentrated. The residue obtained was purified by silica gel column chromatography to yield the title compound (0.36 g, 70% yield) as a pale yellow solid.

$^1$H-NMR (CDCl$_3$) δ: 1.87 (1H, s), 3.41 (4H, br), 3.94 (2H, d, J=4.5 Hz), 4.26 (1H, s), 6.74 (1H, d, J=8.2 Hz), 7.26-7.34 (2H, m), 7.51-7.55 (1H, m), 7.64 (1H, d, J=2.0 Hz), 7.68-7.72 (1H, m), 7.76 (1H, dd, J=8.2, 2.0 Hz).

Working Example 88-2

Synthesis of 5-(benzoxazol-2-yl)-1-(2-hydroxyethyl)-2-methylbenzimidazole

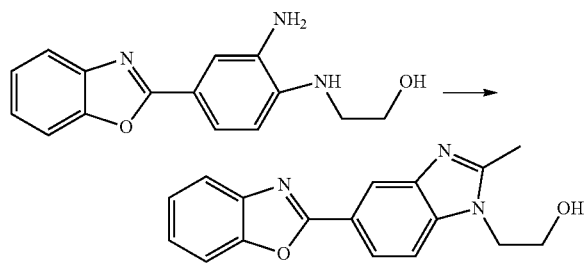

To a methanol (5 mL) solution of 2-(2-(2-hydroxyethyl)aminoanilin-5-yl)benzoxazole (see Working Example 88-1) (0.10 g, 0.4 mmol) was added methyl acetimidate hydrochloride (0.08 g, 0.7 mmol), and this was heated to reflux for 3 hours. After the reaction was complete, water was added, and the precipitated crystals were filtered, and after being washed with water were dried to yield the title compound (0.05 g, 49% yield) as white crystals.

$^1$H-NMR (DMSO-d$_6$) δ: 2.61 (3H, s), 3.75 (2H, q, J=5.3 Hz), 4.31 (2H, t, J=5.3 Hz), 4.99 (1H, t, J=5.3 Hz), 7.38-7.41 (2H, m), 7.73-7.79 (3H, m), 8.07 (1H, dd, J=8.4, 1.5 Hz), 8.32 (1H, d, J=1.5 Hz).

Working Example 89

Synthesis of 5-(benzoxazol-2-yl)-2-diphenylmethyl-2-methylbenzimidazole

Working Example 89-1

Synthesis of 2-(2-diphenylmethylaminoanilin-5-yl)benzoxazole

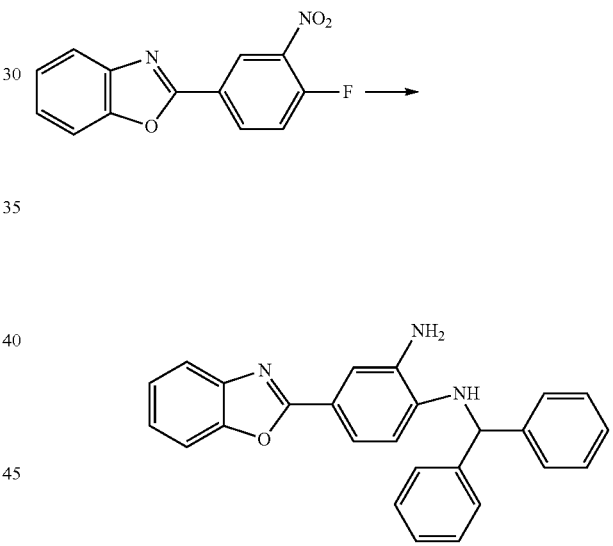

To a suspension of 2-(4-fluoro-3-nitrophenyl)benzoxazole (see Working Example 15-2) (0.50 g, 1.9 mmol) in acetonitrile (10 mL) was added diphenylmethylamine (0.39 g, 2.1 mmol) and triethylamine (0.29 g, 2.4 mmol), and this was heated to reflux for 10 hours. After the reaction was complete, this was cooled to room temperature, water was added, and the precipitated crystals were filtered, washed with water and then dried. To the residue obtained was added iron powder (0.33 g, 5.8 mmol), and aqueous acetic acid (50 mL), and this was heated to reflux for 2 hours. After cooling the reaction solution, filtration through Celite and concentration, the residue obtained was purified by silica gel column chromatography. The oil obtained was dissolved in tetrahydrofuran (3 mL), and to this was added a 1M solution of hydrogen chloride in diethyl ether (1 mL). The precipitated crystals were filtered, and after washing with tetrahydrofuran, they were dried to yield the title compound (0.15 g, 20% yield) as a light brown solid.

$^1$H-NMR (CDCl$_3$) δ: 3.41 (2H, br s), 4.49 (1H, br s), 5.63 (1H, br s), 6.52 (1H, d, J=8.4 Hz), 7.27-7.35 (12H, m), 7.47-7.50 (1H, m), 7.60 (1H, dd, J=8.2, 2.0 Hz), 7.65-7.69 (2H, m).

Working Example 89-2

Synthesis of 5-(benzoxazol-2-yl)-2-diphenylmethyl-2-methylbenzimidazole

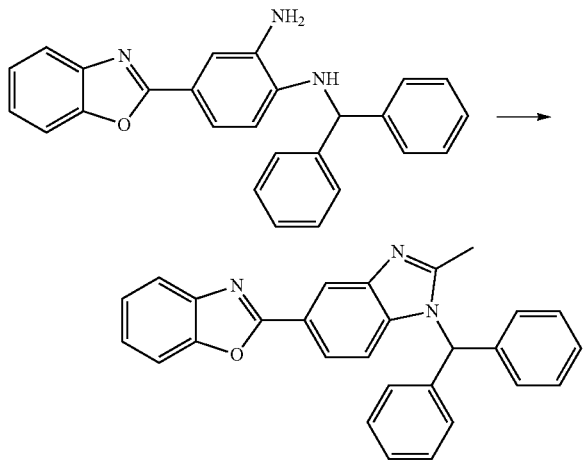

To a methanol (5 mL) solution of 2-(2-diphenylmethylaminoanilin-5-yl)benzoxazole (see Working Example 89-1) (0.10 g, 0.3 mmol) was added methyl acetimidate hydrochloride (0.06 g, 0.5 mmol), and this was heated to reflux for 3 hours. After the reaction solution was cooled, water was added, and this was extracted with chloroform. After the organic layer obtained was dried over anhydrous sodium sulfate, it was filtered and concentrated. The residue obtained was purified by silica gel column chromatography to yield the title compound (0.04 g, 37% yield) as white crystals.

$^1$H-NMR (CDCl$_3$) δ: 2.59 (3H, s), 6.66 (1H, d, J=8.7 Hz), 6.91 (1H, s), 7.14-7.18 (4H, m), 7.29-7.39 (8H, m), 7.54-7.60 (1H, m), 7.72-7.78 (1H, m), 7.91 (1H, dd, J=8.7, 1.6 Hz), 8.56 (1H, d, J=1.2 Hz).

Working Example 90

Synthesis of 5-(benzoxazol-2-yl)-2-(tetrahydrofuran-2-yl)-1-(tetrahydropyran-4-yl)benzimidazole

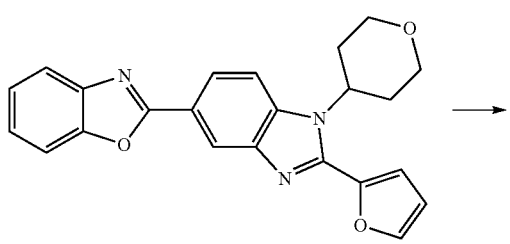

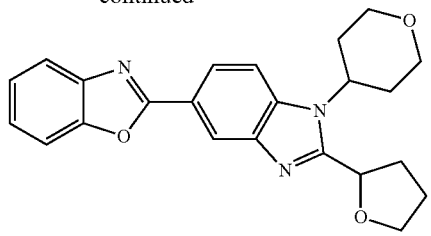

To a solution of 5-(benzoxazol-2-yl)-2-(furan-2-yl)-1-(tetrahydropyran-4-yl)benzimidazole (see Working Example 63) (90 mg, 0.234 mmol) in methanol/ethyl acetate (1:1, 6 mL) was added 10% palladium-carbon (20 mg), a hydrogen atmosphere was substituted in the flask, and this was stirred at room temperature for 20 hours. After the reaction was complete, this was filtered through Celite and the filtrate was concentrated. The residue obtained was purified by silica gel column chromatography to yield the title compound (31.4 mg, 34% yield) as a colorless amorphous mass.

$^1$H-NMR (CDCl$_3$) δ: 1.86-2.45 (5H, m), 2.52-2.76 (2H, m), 2.90-3.02 (1H, m), 3.55-3.67 (2H, m), 3.86-4.00 (2H, m), 4.21 (2H, dd, J=11.6, 4.5 Hz), 4.83-4.96 (1H, m), 5.23 (1H, dd, J=7.1, 6.1 Hz), 7.30-7.38 (2H, m), 7.58-7.62 (1H, m), 7.72-7.80 (2H, m), 8.21 (1H, dd, J=8.7, 1.5 Hz), 8.65 (1H, d, J=1.5 Hz).

Working Example 91

Synthesis of 5-(benzoxazol-2-yl)-2-tert-butoxycarbonylmethyl-1-(tetrahydropyran-4-yl)benzimidazole Working Example 91-1

Synthesis of 2-(2-(tert-butoxycarbonylmethylamino)anilin-5-yl)benzoxazole

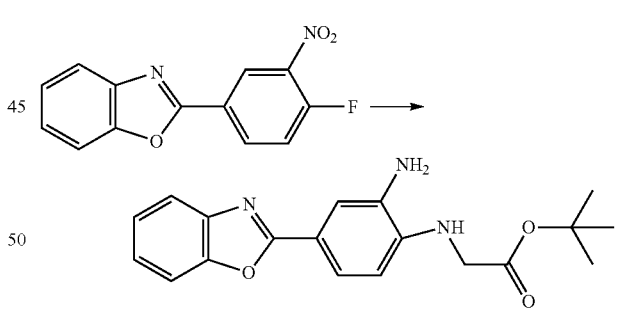

To a suspension of 2-(4-fluoro-3-nitrophenyl)benzoxazole (see Working Example 15-2) (0.77 g, 3.0 mmol) in acetonitrile (10 mL) was added glycine tert-butyl ester hydrochloride (0.60 g, 3.6 mmol) and triethylamine (0.90 g, 9.0 mmol), and this was heated to reflux for 4 hours. After the reaction was complete, this was cooled to room temperature, water was added, and the precipitated crystals were filtered, washed with water and then dried. To a tetrahydrofuran solution (50 mL) of the residue obtained was added 10% palladium-carbon (50 mg). A hydrogen atmosphere was substituted in the flask, and this was stirred overnight at room temperature. After the reaction was complete, this was filtered through Celite and the filtrate was concentrated. The residue obtained was purified by silica gel column chromatography to yield the title compound (0.40 g, 40% yield) as a light orange solid.

$^1$H-NMR (CDCl$_3$) δ: 1.52 (9H, s), 3.72-3.80 (3H, m), 3.90 (2H, s), 6.59 (1H, d, J=8.2 Hz), 7.29-7.31 (2H, m), 7.50-7.52 (1H, m), 7.64 (1H, d, J=1.8 Hz), 7.68-7.77 (2H, m).

Working Example 91-2

Synthesis of 5-(benzoxazol-2-yl)-2-methyl-1-tert-butoxycarbonylmethylbenzimidazole

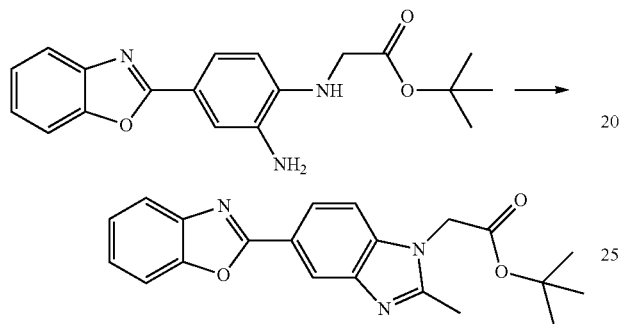

To a solution of 2-(2-(tert-butoxycarbonylmethylamino) anilin-5-yl)benzoxazole (see Working Example 91-1) (120 mg, 0.353 mmol) in dimethylformamide (2 mL) was added an aqueous solution of acetaldehyde (approx. 90%, 66 μL, 1.06 mmol) and oxone (217 mg, 0.353 mmol), and this was stirred at room temperature for 2 hours. After the reaction was complete, aqueous potassium carbonate solution was added, this was filtered and washed with water. The crystals obtained were purified by silica gel column chromatography to yield the title compound (30.7 mg, 24% yield) as white crystals.

$^1$H-NMR (CDCl$_3$) δ: 1.45 (9H, s), 2.63 (3H, s), 4.76 (2H, s), 7.32-7.37 (3H, m), 7.59-7.62 (1H, m), 7.75-7.79 (1H, m), 8.23 (1H, dd, J=8.5, 1.5 Hz), 8.57 (1H, d, J=1.5 Hz).

Working Example 92

Synthesis of 5-(benzoxazol-2-yl)-1-carboxymethyl-2-methylbenzimidazole

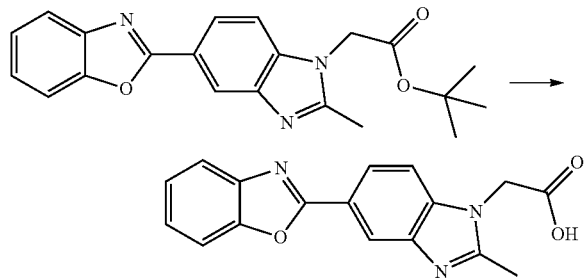

To a solution of 5-(benzoxazol-2-yl)-2-methyl-1-tert-butoxycarbonylmethylbenzimidazole (see Working Example 91-2) (100 mg, 0.275 mmol) in chloroform (3 mL) was added aqueous sodium hydroxide solution (1 M, 0.55 mL, 0.55 mmol). This two-layer solution was homogenized by the addition of methanol, and this was stirred at room temperature for 2 hours. After the reaction was complete, the solution was concentrated, aqueous acetic acid solution was added, and this was stirred at room temperature. The precipitated crystals were filtered, and after washing with water were dried to yield the title compound (76.9 mg, 91% yield) as light yellow crystals.

$^1$H-NMR (DMSO-d$_6$) δ: 2.51 (3H, s), 5.04 (2H, s), 7.38-7.42 (2H, m), 7.67-7.70 (1H, m), 7.77-7.81 (2H, m), 8.04-8.08 (1H, m), 8.32-8.33 (1H, m).

Working Example 93

Synthesis of 5-(benzoxazol-2-yl)-2-methyl-1-(2-(thiomorpholin-1,1-dioxide-4-yl)ethyl)benzimidazole Working Example 93-1

Synthesis of 2-(N-(2-thiomorpholin-1,1-dioxide-4-yl)ethyl)-2-nitroanilin-4-yl)benzoxazole

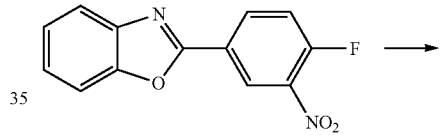

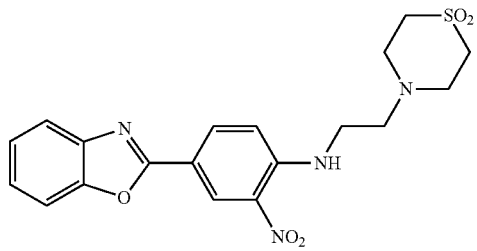

To a suspension of 2-(4-fluoro-3-nitrophenyl)benzoxazole (see Working Example 15-2) (200 mg, 0.774 mmol) in ethanol (5 mL) was added potassium carbonate (214 mg, 1.55 mmol) and 4-(2-aminoethyl)thiomorpholine-1,1-dioxide (166 mg, 0.930 mmol), and this was heated to reflux for 7 hours. After the reaction was complete, this was cooled to room temperature, water was added, and after the precipitated crystals were filtered and washed with water, they were dried to yield the title compound (296 mg, 92% yield).

$^1$H-NMR (CDCl$_3$) δ: 2.96 (2H, t, J=5.9 Hz), 3.15 (8H, s), 3.48 (2H, q, J=5.5 Hz), 6.96 (1H, d, J=8.9 Hz), 7.34-7.39 (2H, m), 7.56-7.60 (1H, m), 7.72-7.75 (1H, m), 8.33 (1H, dd, J=8.9, 2.0 Hz), 8.82 (1H, br s), 9.07 (1H, d, J=2.0 Hz).

Working Example 93-2

Synthesis of 5-(benzoxazol-2-yl)-2-methyl-1-(2-(thiomorpholin-1,1-dioxide-4-yl)ethyl)benzimidazole

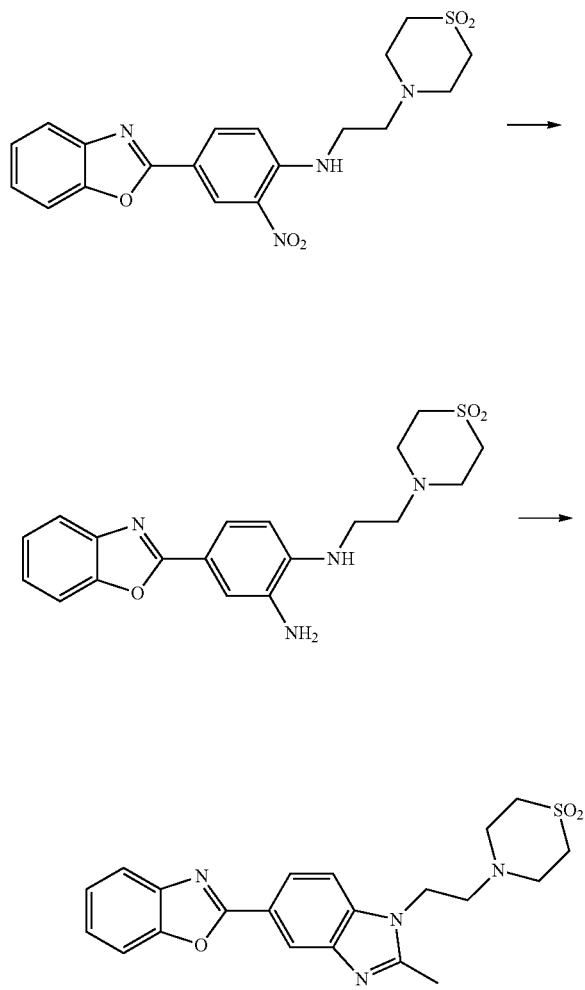

To a solution of 2-(N-(2-thiomorpholin-1,1-dioxide-4-yl) ethyl)-2-nitroanilin-4-yl)benzoxazole (see Working Example 93-1) (290 mg, 0.696 mmol) in tetrahydrofuran (5 mL) was added 10% palladium-carbon (50 mg), a hydrogen atmosphere was substituted in the flask, and this was stirred at room temperature for 17 hours. After the reaction was complete, this was filtered through Celite and the filtrate was concentrated. To a solution of the residue obtained in dimethylformamide (2 mL) was added acetaldehyde (ca. 90%, 131 µL, 2.09 mmol) and oxone (429 mg, 0.696 mmol), and this was stirred at room temperature for 3 hours. After the reaction was complete, aqueous potassium carbonate solution was added, this was filtered, and after washing with water and ethyl acetate, drying yield the title compound (125 mg, 44% yield) as pale yellow crystals.

$^1$H-NMR (DMSO-d$_6$) δ: 2.67 (3H, s), 3.26-3.31 (2H, m), 3.42-3.48 (2H, m), 3.77 (2H, t, J=7.3 Hz), 3.90-3.99 (4H, m), 4.84 (2H, t, J=7.3 Hz), 7.39-7.42 (2H, m), 7.78-7.84 (3H, m), 8.11 (1H, dd, J=8.4, 1.4 Hz), 8.34 (1H, d, J=1.4 Hz).

Working Example 94

Synthesis of 5-(benzoxazol-2-yl)-2-methyl-1-(tetrahydropyran-4-yl)-4-trifluoromethylbenzimidazole Working Example 94-1

Synthesis of 2-(2-fluoro-3-trifluoromethylnitrobenzen-5-yl)benzoxazole

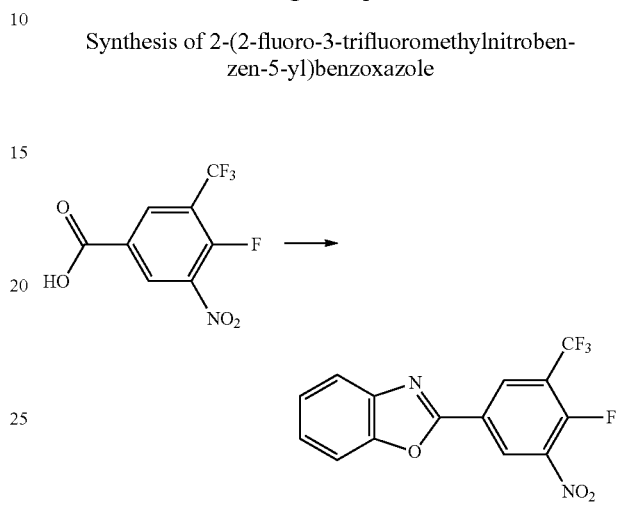

4-Fluoro-3-nitro-5-trifluoromethyl benzoic acid (1.00 g, 4.0 mmol), 2-aminophenol (0.47 g, 4.4 mmol), CHCl$_3$ (20 mL), and WSC (0.83 g, 4.4 mmol) were added together and stirred at room temperature for 1 hour. Water was added, and this was extracted with chloroform/acetone (3:1). After the organic layer obtained was dried over anhydrous sodium sulfate, it was filtered and concentrated. To a dioxane (20 mL) solution of the solid obtained was added methanesulfonic acid (2.28 g, 24 mmol), and this was heated to reflux for 18 hours. After the reaction solution was cooled, water was added, and the precipitated crystals were filtered, and after being washed with water were dried to yield the title compound (0.70 g, 54% yield) as yellowish-brown crystals.

$^1$H-NMR (DMSO-d$_6$) δ: 7.44-7.55 (2H, m), 7.85-7.92 (2H, m), 8.74 (1H, dd, J=6.0, 1.8 Hz), 9.04 (1H, dd, J=6.6, 1.8 Hz).

Working Example 94-2

Synthesis of 2-(2-(tetrahydrofran-4-yl)amino-3-trifluoromethylanilin-5-yl)benzoxazole

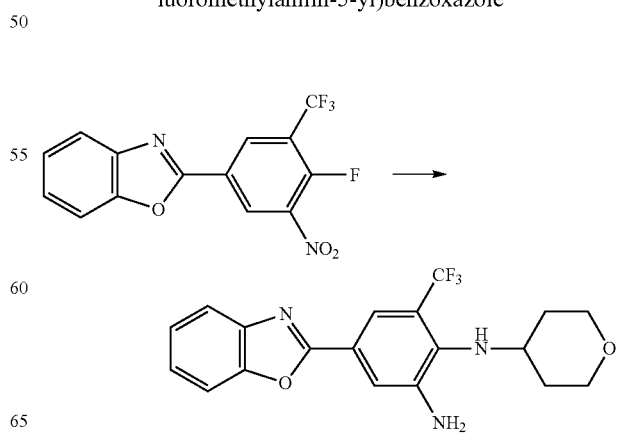

To a suspension of 2-(2-fluoro-3-trifluoromethylnitrobenzen-5-yl)benzoxazole (see Working Example 94-1) (0.40 g, 1.2 mmol) in acetonitrile (8 mL) was added 4-aminotetrahydropyran (0.30 g, 2.9 mmol), and this was heated to reflux for 4 hours. After the reaction was complete, this was cooled to room temperature, water was added, and the precipitated crystals were filtered, washed with water and then dried. To a solution of the crystals obtained in a solvent mixture of methanol/tetrahydrofuran (1:1, 100 mL) was added 10% palladium-carbon (50 mg). A hydrogen atmosphere was substituted in the flask, and this was stirred at room temperature for 2 hours. After the reaction was complete, this was filtered through Celite and the filtrate was concentrated. The residue obtained was purified by silica gel column chromatography to yield the title compound (0.20 g, 43% yield) as white crystals.

$^1$H-NMR (CDCl$_3$) δ: 1.56-1.59 (2H, m), 1.83 (2H, d, J=13.0 Hz), 3.40 (2H, t, J=11.4 Hz), 3.61 (2H, s), 3.98-4.02 (4H, m), 7.33-7.38 (2H, m), 7.54-7.59 (1H, m), 7.75 (2H, t, J=4.3 Hz), 7.89 (1H, s).

Working Example 94-3

Synthesis of 5-(benzoxazol-2-yl)-2-methyl-1-(tetrahydropyran-4-yl)-4-trifluoromethylbenzimidazole

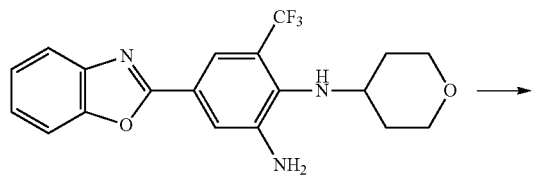

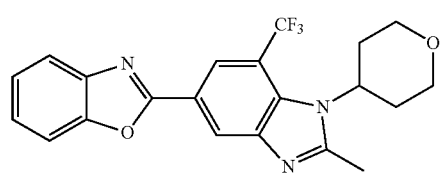

To a solution of 2-(2-(tetrahydropyran-4-yl)amino-3-trifluoromethylanilin-5-yl)benzoxazole (see Working Example 94-2) (0.20 g, 0.5 mmol) in methanol (4 mL) was added methyl acetimidate hydrochloride (0.06 g, 0.6 mmol), and this was heated to reflux for 3 hours. After the reaction solution was cooled, water was added, and the precipitated crystals were filtered, and after being washed with water were dried to yield the title compound (0.17 g, 79% yield) as white crystals.

$^1$H-NMR (CDCl$_3$) δ: 1.96 (2H, dd, J=12.1, 2.1 Hz), 2.40-2.49 (2H, m), 2.88 (3H, s), 3.59 (2H, td, J=11.8, 1.8 Hz), 4.21 (2H, dd, J=11.8, 4.5 Hz), 4.97-5.02 (1H, m), 7.33-7.41 (2H, m), 7.63 (1H, dd, J=6.1, 3.1 Hz), 7.80 (1H, dd, J=5.9, 3.1 Hz), 8.57 (1H, d, J=1.5 Hz), 8.71 (1H, d, J=1.5 Hz).

Working Example 95

Synthesis of 5-(benzoxazol-2-yl)-2-methyl-1-(tetrahydrofuran-2-yl)methylbenzimidazole Working Example 95-1

Synthesis of 2-(2-(tetrahydrofuran-2-yl)methylaminoanilin-5-yl)benzoxazole

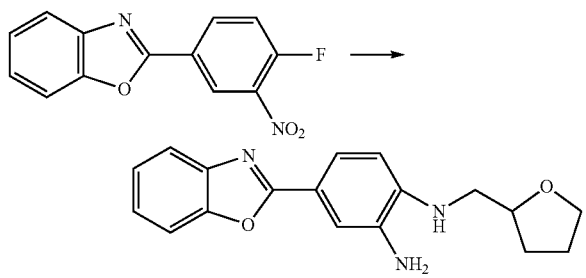

To a suspension of 2-(4-fluoro-3-nitrophenyl)benzoxazole (see Working Example 15-2) (0.40 mg, 1.5 mmol) in acetonitrile (8 mL) was added 2-aminomethyltetrahydrofuran (0.36 g, 3.6 mmol), and this was heated to reflux for 7 hours. After the reaction was complete, this was cooled to room temperature, water was added, and the precipitated crystals were filtered, washed with water and then dried. To a solution of the residue obtained in a solvent mixture of methanol/tetrahydrofuran=1:1 (40 mL) was added 10% palladium-carbon (40 mg). A hydrogen atmosphere was substituted in the flask, and this was stirred at room temperature for 3 hours. After the reaction was complete, this was filtered through Celite and the filtrate was concentrated. The residue obtained was purified by silica gel column chromatography to yield the title compound (0.40 g, 84% yield) as a brown syrup.

$^1$H-NMR (CDCl$_3$) δ: 1.64-1.77 (1H, m), 1.92-2.02 (2H, m), 2.04-2.17 (1H, m), 3.17 (1H, dd, J=12.3, 7.8 Hz), 3.34 (1H, dd, J=12.3, 3.7 Hz), 3.78-3.96 (2H, m), 4.17-4.27 (1H, m), 6.71 (1H, d, J=8.2 Hz), 7.27-7.34 (2H, m), 7.50-7.54 (1H, m), 7.62 (1H, d, J=2.0 Hz), 7.68-7.71 (1H, m), 7.75 (1H, dd, J=8.4, 2.0 Hz).

Working Example 95-2

Synthesis of 5-(benzoxazol-2-yl)-2-methyl-1-(tetrahydrofuran-2-yl)methylbenzimidazole

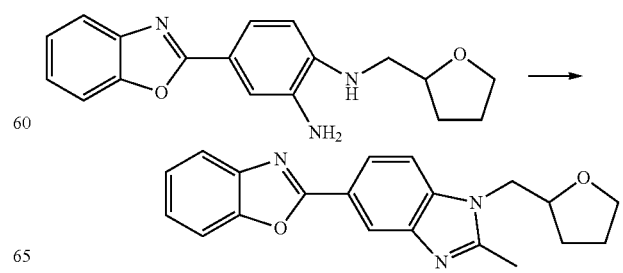

To a solution of 2-(tetrahydrofuran-2-yl)methylaminoanilin-5-yl)benzoxazole (see Working Example 95-1) (0.15 g, 0.4 mmol) in methanol (5 mL) was added methyl acetimidate hydrochloride (0.05 mg, 0.4 mmol), and this was heated to reflux for 3 hours. After the reaction solution was cooled, water was added, and the precipitated crystals were filtered, and after being washed with water were dried to yield the title compound (0.17 g, 79% yield) as white crystals.

$^1$H-NMR (CDCl$_3$) δ: 1.56-2.14 (4H, m), 2.69 (3H, s), 3.77-3.83 (2H, m), 4.18-4.29 (3H, m), 7.30-7.37 (2H, m), 7.46 (1H, d, J=8.6 Hz), 7.58-7.62 (1H, m), 7.75-7.79 (1H, m), 8.20 (1H, dd, J=8.6, 1.5 Hz), 8.55 (1H, d, J=1.5 Hz).

Working Example 96

Synthesis of 5-(benzoxazol-2-yl)-2-methyl-1-(3-(morpholine-4-yl)propyl)benzimidazole

Working Example 96-1

Synthesis of 2-(N-(2-(morpholin-4-yl)-n-propyl)-2-nitroanilin-4-yl)benzoxazole

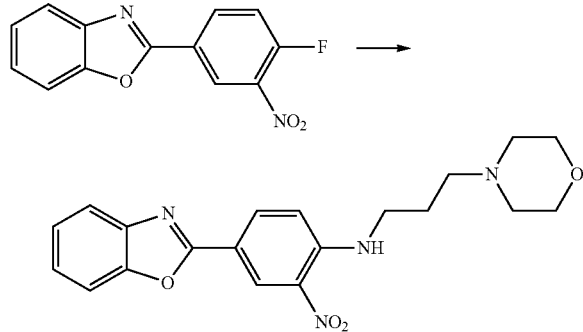

To a suspension of 2-(4-fluoro-3-nitrophenyl)benzoxazole (see Working Example 15-2) (500 mg, 1.94 mmol) in ethanol (10 mL) was added potassium carbonate (535 mg, 3.87 mmol) and N-(3-amino-n-propyl)morpholine (336 mg, 2.33 mmol), and this was heated to reflux for 4 hours. After the reaction was complete, this was cooled to room temperature, water was added, and after the precipitated crystals were filtered and washed with water, they were dried to yield the title compound (670 mg, 90% yield).

$^1$H-NMR (CDCl$_3$) δ: 1.89-1.99 (2H, m), 2.47-2.55 (6H, m), 3.47-3.54 (2H, m), 3.79 (4H, t, J=4.7 Hz), 7.05 (1H, d, J=9.1 Hz), 7.31-7.39 (2H, m), 7.55-7.60 (1H, m), 7.71-7.75 (1H, m), 8.29 (1H, dd, J=9.1, 2.1 Hz), 8.74 (1H, br s), 9.07 (1H, d, J=2.1 Hz).

Working Example 96-2

Synthesis of 2-(2-(3-(morpholin-4-yl)-n-propyl)aminoanilin-4-yl)benzoxazole

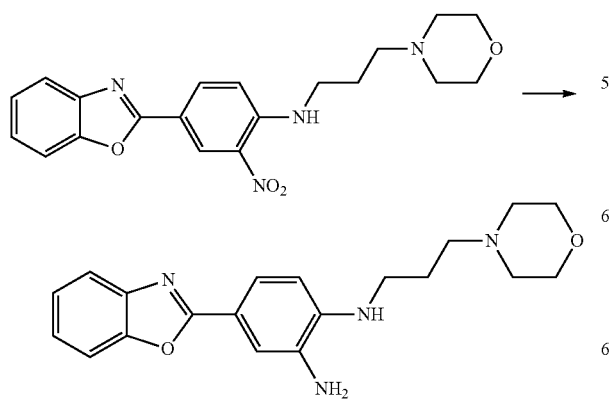

To a solution of 2-(N-(2-(morpholin-4-yl)-n-propyl)-2-nitroanilin-4-yl)benzoxazole (see Working Example 96-1) (665 mg, 1.74 mmol) in tetrahydrofuran (10 mL) was added 10% palladium-carbon (70 mg). A hydrogen atmosphere was then substituted in the flask, and this was stirred at room temperature for 17 hours. After the reaction was finished, this was filtered through Celite, and the filtrate was concentrated to yield the title compound (605 mg, 99% yield).

$^1$H-NMR (CDCl$_3$) δ: 1.85-1.95 (2H, m), 2.49-2.57 (6H, m), 3.31 (2H, t, J=6.2 Hz), 3.38 (1H, br s), 3.77 (4H, t, J=4.7 Hz), 6.68 (1H, d, J=8.4 Hz), 7.26-7.33 (2H, m), 7.50-7.77 (4H, m).

Working Example 96-3

Synthesis of 5-(benzoxazol-2-yl)-2-methyl-1-(3-(morpholin-4-yl)-n-propyl)benzimidazole

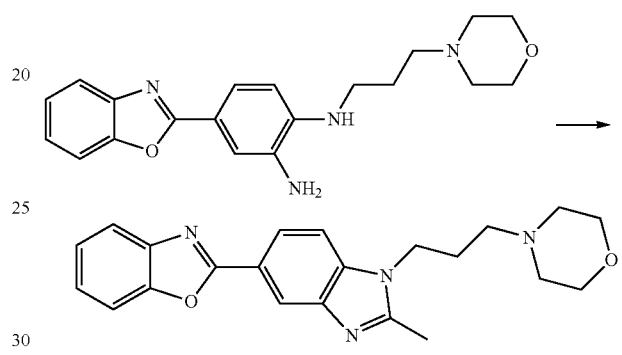

To a solution of 2-(2-(3-(morpholin-4-yl)-n-propyl)aminoanilin-4-yl)benzoxazole (see Working Example 96-1) (300 mg, 0.851 mmol) in methanol (5 mL) was added methyl acetimidate hydrochloride (103 mg, 0.936 mmol), and this was heated to reflux for 3 hours. After the reaction was complete, saturated aqueous sodium hydrogen carbonate solution was added, and this was extracted with ethyl acetate. After the organic layer obtained was dried over anhydrous sodium sulfate, it was filtered and concentrated. To the crystals obtained was added diethyl ether, this was filtered, washed with diethyl ether, and dried to yield the title compound (195 mg, 61% yield) as light brown crystals.

$^1$H-NMR (CDCl$_3$) δ: 1.97-2.06 (2H, m), 2.31 (2H, t, J=6.5 Hz), 2.40 (4H, t, J=4.5 Hz), 2.68 (3H, s), 3.73 (4H, t, J=4.7 Hz), 4.27 (2H, t, J=6.7 Hz), 7.32-7.36 (2H, m), 7.50 (1H, d, J=8.6 Hz), 7.59-7.62 (1H, m), 7.75-7.78 (1H, m), 8.20 (1H, dd, J=8.6, 1.5 Hz), 8.55 (1H, d, J=1.5 Hz).

Working Example 97

Synthesis of 5-(5-carboxylbenzoxazol-2-yl)-2-methyl-1-(tetrahydropyran-4-yl)benzimidazole

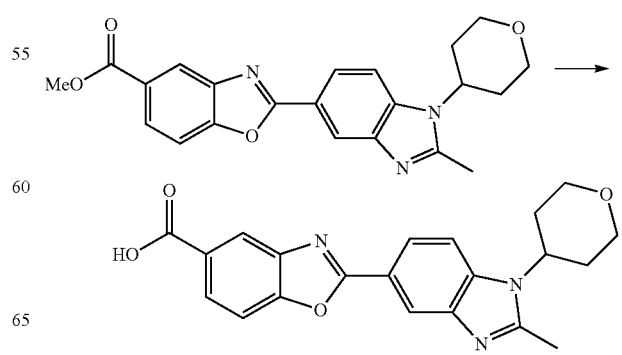

To a solution of 5-(5-methoxycarbonylbenzoxazol-2-yl)-2-methyl-1-(tetrahydropyran-4-yl)benzimidazole (see Working Example 73) (150 mg, 0.383 mmol) in chloroform (3 mL) was added aqueous sodium hydroxide solution (1 M, 0.55 mL, 0.5 mmol). This two-layer solution was homogenized by the addition of methanol, and this was stirred at room temperature for 20 hours. After the reaction was complete, the solution was concentrated, aqueous acetic acid solution was added, and this was stirred at room temperature. The precipitated crystals were filtered, and after washing with water were dried to yield the title compound (145 mg, quant.) as light yellow crystals.

$^1$H-NMR (DMSO-$d_6$) δ: 1.85-1.91 (2H, m), 2.35-2.44 (2H, m), 2.68 (3H, s), 3.58 (2H, t, J=11.0 Hz), 4.06 (2H, dd, J=11.0, 3.8 Hz), 4.61-4.73 (1H, m), 7.87-7.92 (2H, m), 8.01-8.09 (2H, m), 8.29 (1H, d, J=1.4 Hz), 8.35 (1H, d, J=1.4 Hz).

Working Example 98

Synthesis of 5-(5-acetylaminobenzoxazol-2-yl)-2-methyl-1-n-propylbenzimidazole

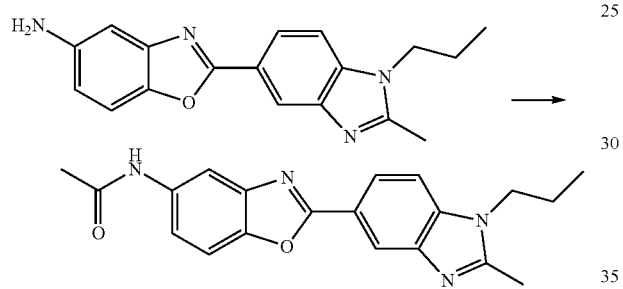

To a solution of 5-(5-aminobenzoxazol-2-yl)-2-methyl-1-n-propylbenzimidazole (see Working Example 82-4) (200 mg, 0.653 mmol) in chloroform (5 mL) was added triethylamine (132 mg, 1.31 mmol) and acetic anhydride (100 mg, 0.979 mmol), and this was stirred at room temperature for 20 hours. After the reaction was complete, the solution was concentrated, the precipitated crystals were filtered, and after washing with water were dried to yield the title compound (176 mg, 77% yield) as pale yellow crystals.

$^1$H-NMR (DMSO-$d_6$) δ: 0.91 (3H, t, J=7.3 Hz), 1.70-1.85 (2H, m), 2.08 (3H, s), 2.60 (3H, s), 4.22 (2H, t, J=7.3 Hz), 7.48 (1H, dd, J=8.7, 2.1 Hz), 7.68-7.76 (2H, m), 8.00-8.10 (2H, m), 8.30 (1H, d, J=1.3 Hz), 10.10 (1H, s).

Working Example 99

Synthesis of 2-methyl-5-(5-n-propylaminocarbonyl-benzoxazol-2-yl)-1-(tetrahydropyran-4-yl)benzimidazole

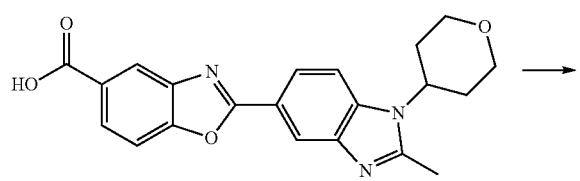

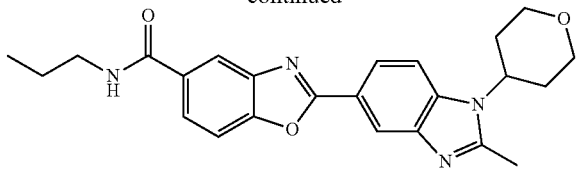

To a solution of 5-(5-carboxylbenzoxazol-2-yl)-2-methyl-1-(tetrahydropyran-4-yl)benzimidazole (see Working Example 97) (133 mg, 0.352 mmol) in chloroform (5 mL) was added propylamine (25 mg, 0.423 mmol) and WSC (81 mg, 0.423 mmol), and this was stirred at room temperature for 22 hours. Saturated aqueous sodium hydrogen carbonate solution was added, and this was extracted with chloroform. After the organic layer obtained was dried over anhydrous sodium sulfate, it was filtered and concentrated. The residue obtained was purified by silica gel column chromatography to yield the title compound (57 mg, 39% yield) as white crystals.

$^1$H-NMR (CDCl$_3$) δ: 1.02 (3H, t, J=7.3 Hz), 1.61-1.73 (2H, m), 1.90 (2H, dd, J=12.9, 2.9 Hz), 2.55-2.69 (2H, m), 2.71 (3H, s), 3.47 (2H, dd, J=13.6, 6.3 Hz), 3.56-3.66 (2H, m), 4.24 (2H, dd, J=11.8, 4.5 Hz), 4.42-4.51 (1H, m), 6.21 (1H, t, J=4.9 Hz), 7.62-7.70 (2H, m), 7.84 (1H, dd, J=8.6, 1.6 Hz), 8.11 (1H, d, J=1.6 Hz), 8.17 (1H, dd, J=8.6, 1.6 Hz), 8.56 (1H, d, J=1.6 Hz).

Working Example 100

Synthesis of 2-(4-acetylaminophenyl)-5-(5-chlorobenzoxazol-2-yl)-1-(tetrahydropyran-4-yl)benzimidazole Working Example 100-1

Synthesis of 5-chloro-2-(2-fluoronitrobenzen-5-yl)benzoxazole

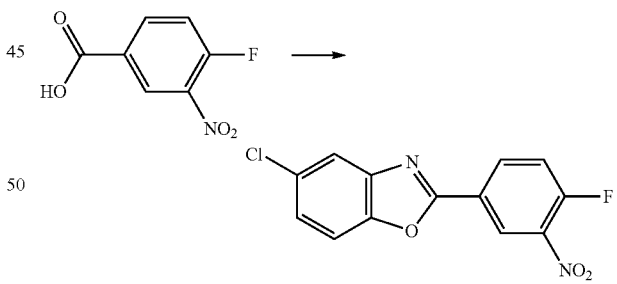

4-Fluoro-3-nitrobenzoic acid (25.0 g, 135 mmol), 2-amino-4-chlorophenol (21.3 g, 149 mmol), CHCl$_3$ (500 mL), and WSC (28.5 g, 149 mmol) were added together and stirred at room temperature for 2 hours. The reaction mass was concentrated, and then the residue was washed with water and ethanol. To a dioxane (500 mL) solution of the solid obtained was added methanesulfonic acid (81.9 g, 811 mmol), and this was heated to reflux for 18 hours. After the reaction solution was cooled, water was added, and the precipitated crystals were filtered, and after being washed with water were dried to yield the title compound (31.0 g, 78% yield) as reddish-brown crystals.

¹H-NMR (DMSO-d₆) δ: 7.54 (1H, d, J=8.4 Hz), 7.84-7.89 (2H, m), 7.99 (1H, s), 8.54-8.59 (1H, m), 8.80 (1H, d, J=8.4 Hz).

Working Example 100-2

Synthesis of 5-chloro-2-(2-(tetrahydropyran-4-yl)aminoanilin-5-yl)benzoxazole

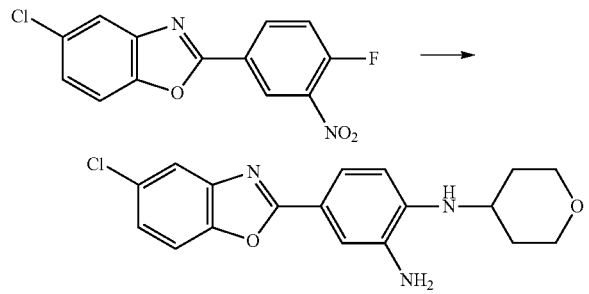

To a suspension of 5-chloro-2-(2-fluoronitrobenzen-5-yl)benzoxazole (see Working Example 100-1) (5.00 g, 17.1 mmol) in acetonitrile (20 mL) was added 4-aminotetrahydropyran (3.81 g, 38.0 mmol), and this was heated to reflux for 3 hours. After the reaction was complete, this was cooled to room temperature, water was added, and the precipitated crystals were filtered, washed with water and then dried. To a solution of the crystals obtained in a solvent mixture of methanol/tetrahydrofuran (1:1, 100 mL) was added 10% palladium-carbon (500 mg). A hydrogen atmosphere was substituted in the flask, and this was stirred at room temperature overnight. After the reaction was complete, this was filtered through Celite, the filtrate was concentrated, and the residue obtained was purified by silica gel column chromatography to yield the title compound (2.86 g, 49% yield) as yellowish-brown crystals.

¹H-NMR (DMSO-d₆) δ: 1.40-1.54 (2H, m), 1.94 (2H, d, J=12.4 Hz), 3.46 (2H, t, J=11.4 Hz), 3.60 (1H, br s), 3.90 (2H, d, J=11.4 Hz), 4.97 (2H, s), 5.12 (1H, d, J=7.6 Hz), 6.67 (1H, d, J=8.3 Hz), 7.33 (1H, dd, J=8.3, 1.9 Hz), 7.38-7.41 (2H, m), 7.68-7.74 (2H, m).

Working Example 100-3

Synthesis of 2-(4-acetylaminophenyl)-5-(5-chlorobenzoxazol-2-yl)-1-(tetrahydropyran-4-yl)benzimidazole

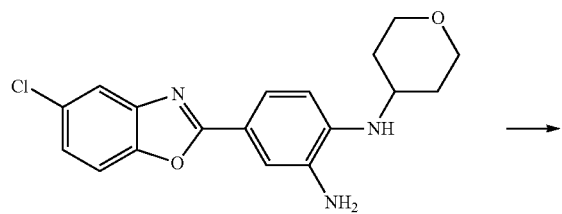

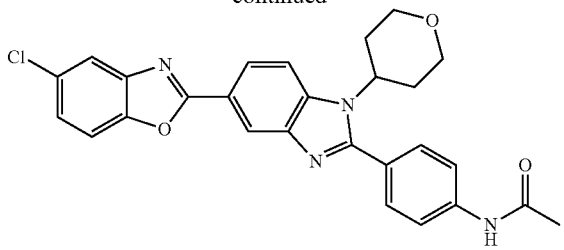

To a solution of 5-chloro-2-(2-(tetrahydropyran-4-yl)aminoanilin-5-yl)benzoxazole (see Working Example 100-2) (250 mg, 0.727 mmol) in dimethylformamide (3 mL) was added 4-formylacetanilide (142 mg, 0.872 mmol) and oxone (313 mg, 0.509 mmol), and this was stirred at room temperature for 2 hours. After the reaction was complete, aqueous potassium carbonate solution was added, this was filtered and washed with water. The crystals obtained were purified by silica gel column chromatography to yield the title compound (261 mg, 74% yield) as white crystals.

¹H-NMR (CDCl₃) δ: 1.86-1.93 (2H, m), 2.25 (3H, s), 2.66-2.80 (2H, m), 3.47 (2H, t, J=11.4 Hz), 4.11-4.20 (2H, m), 4.60-4.69 (1H, m), 7.32 (1H, dd, J=8.7, 2.1 Hz), 7.52-7.83 (7H, m), 8.22 (1H, dd, J=8.7, 1.5 Hz), 8.65 (1H, d, J=1.5 Hz).

Working Example 101

Synthesis of 5-(5-chlorobenzoxazol-2-yl)-2-(4-methoxycarbonylphenyl)-1-(tetrahydropyran-4-yl)benzimidazole

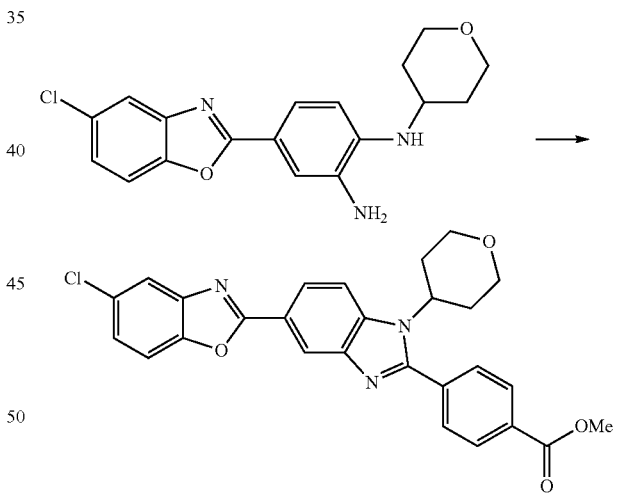

To a solution of 5-chloro-2-(2-(tetrahydropyran-4-yl)aminoanilin-5-yl)benzoxazole (see Working Example 100-2) (250 mg, 0.727 mmol) in dimethylformamide (3 mL) was added methyl 4-formylbenzoate (143 mg, 0.872 mmol) and oxone (313 mg, 0.509 mmol), and this was stirred at room temperature for 2 hours. After the reaction was complete, aqueous potassium carbonate solution was added, this was filtered, and after washing with water and ethyl acetate, drying yield the title compound (239 mg, 67% yield) as pale yellow crystals.

¹H-NMR (CDCl₃) δ: 1.88-1.96 (2H, m), 2.65-2.81 (2H, m), 3.40-3.50 (2H, m), 4.00 (3H, s), 4.13-4.22 (2H, m), 4.55-4.64 (1H, m), 7.33 (1H, dd, J=8.6, 2.1 Hz), 7.54 (1H, d, J=9.1

Hz), 7.74-7.77 (3H, m), 7.84 (1H, d, J=8.7 Hz), 8.23-8.27 (3H, m), 8.68 (1H, d, J=1.3 Hz).

Working Example 102

Synthesis of 2-(4-carboxylphenyl)-5-(5-chlorobenzoxazol-2-yl)-1-(tetrahydropyran-4-yl)benzimidazole

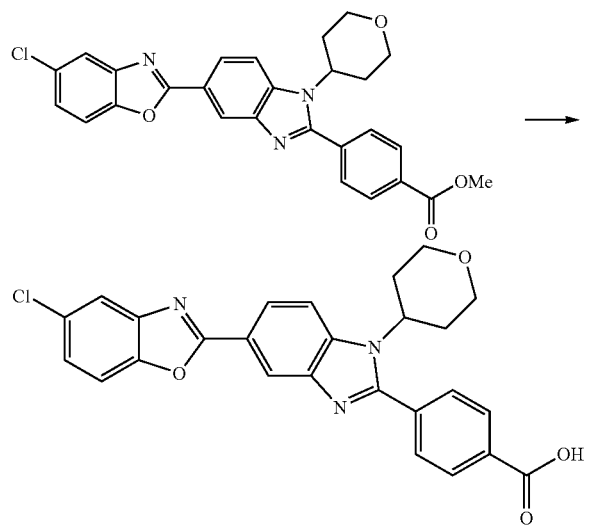

To a solution of 5-(5-chlorobenzoxazol-2-yl)-2-(4-methoxycarbonylphenyl)-1-(tetrahydropyran-4-yl)benzimidazole (see Working Example 101) (220 mg, 0.451 mmol) in chloroform (3 mL) was added aqueous sodium hydroxide solution (1 M, 1 mL, 1 mmol). This two-layer solution was homogenized by the addition of methanol, and this was stirred at room temperature for 3 hours. After the reaction was complete, the solution was concentrated, aqueous acetic acid solution was added, and this was stirred at room temperature. The precipitated crystals were filtered, and after washing with water were dried to yield the title compound (205 mg, 96% yield) as white crystals.

$^1$H-NMR (DMSO-$d_6$) δ: 1.93-2.02 (2H, m), 2.51-2.59 (2H, m), 3.35-3.47 (2H, m), 3.98-4.05 (2H, m), 4.55-4.67 (1H, m), 7.47 (1H, dd, J=8.7, 2.1 Hz), 7.84-7.93 (4H, m), 8.08-8.20 (4H, m), 8.50 (1H, s).

Working Example 103

Synthesis of 5-(5-chlorobenzoxazol-2-yl)-2-(3-methoxycarbonylphenyl)-1-(tetrahydropyran-4-yl)benzimidazole

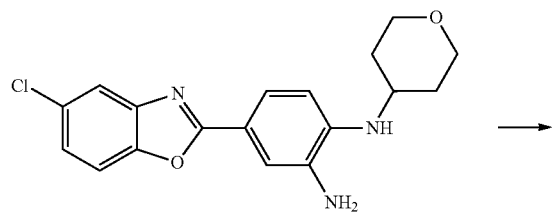

-continued

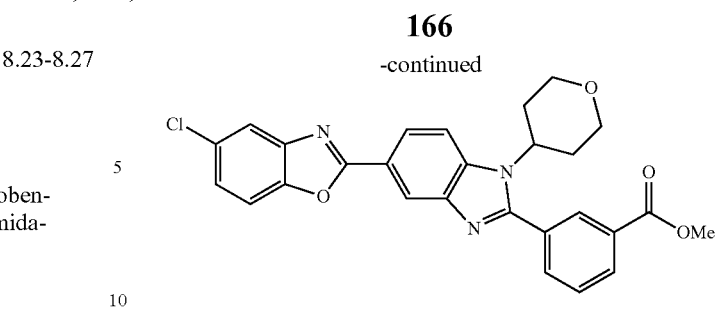

To a solution of 5-chloro-2-(2-(tetrahydropyran-4-yl)aminoanilin-5-yl)benzoxazole (see Working Example 100-2) (250 mg, 0.727 mmol) in dimethylformamide (3 mL) was added methyl 3-formylbenzoate (143 mg, 0.872 mmol) and oxone (313 mg, 0.509 mmol), and this was stirred at room temperature for 2 hours. After the reaction was complete, aqueous potassium carbonate solution was added, this was filtered and washed with water. The crystals obtained were purified by silica gel column chromatography to yield the title compound (220 mg, 62% yield) as yellow crystals.

$^1$H-NMR (CDCl$_3$) δ: 1.91-1.97 (2H, m), 2.66-2.81 (2H, m), 3.41-3.51 (2H, m), 3.97 (3H, s), 4.13-4.21 (2H, m), 4.55-4.64 (1H, m), 7.32 (1H, dd, J=8.6, 2.1 Hz), 7.54 (1H, d, J=8.6 Hz), 7.67 (1H, t, J=7.7 Hz), 7.75-7.91 (3H, m), 8.22-8.27 (2H, m), 8.34 (1H, t, J=1.5 Hz), 8.67 (1H, d, J=1.5 Hz).

Working Example 104

Synthesis of 2-acetylaminomethyl-5-(5-chlorobenzoxazol-2-yl)-1-(tetrahydropyran-4-yl)benzimidazole

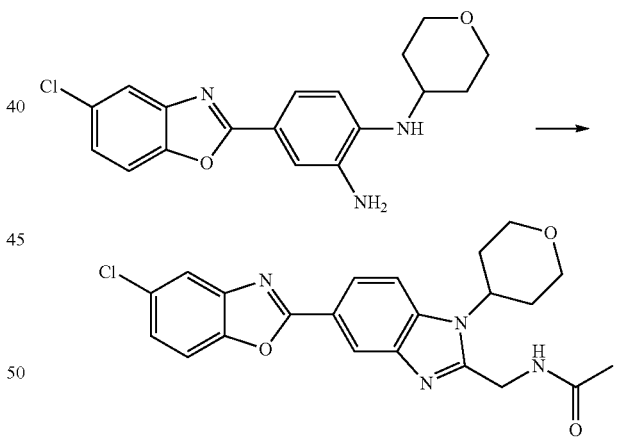

To a solution of 5-chloro-2-(2-(tetrahydropyran-4-yl)aminoanilin-5-yl)benzoxazole (see Working Example 100-2) (250 mg, 0.727 mmol) in ethanol (5 mL) was added ethyl 2-acetylaminoacetimidate hydrochloride (263 mg, 1.45 mmol), and this was heated to reflux for 2 hours. After the reaction was complete, aqueous potassium carbonate solution was added, this was filtered and washed with water. The crystals obtained were purified by silica gel column chromatography to yield the title compound (65.2 mg, 21% yield) as white crystals.

$^1$H-NMR (CDCl$_3$) δ: 1.83-1.91 (2H, m), 2.13 (3H, s), 2.53-2.69 (2H, m), 3.57-3.66 (2H, m), 4.21 (2H, dd, J=11.7, 4.3 Hz), 4.60-4.72 (1H, m), 4.77 (2H, d, J=4.9 Hz), 6.82 (1H, br s), 7.32 (1H, dd, J=8.6, 2.1 Hz), 7.52 (1H, d, J=8.6 Hz), 7.72-7.75 (2H, m), 8.19 (1H, dd, J=8.6, 1.5 Hz), 8.57 (1H, d, J=1.5 Hz).

Working Example 105

Synthesis of 2-(3-carboxylphenyl)-5-(5-chlorobenzoxazol-2-yl)-1-(tetrahydropyran-4-yl)benzimidazole

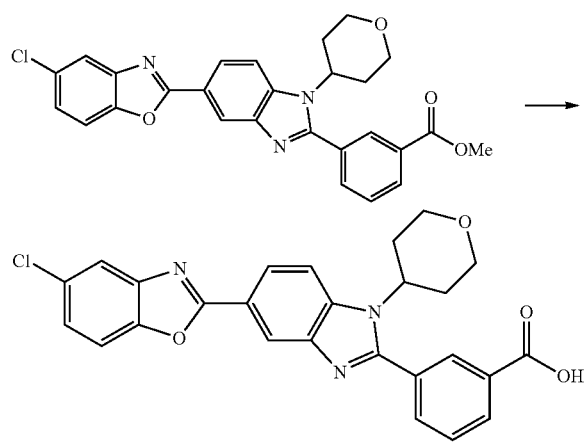

To a solution of 5-(5-chlorobenzoxazol-2-yl)-2-(3-methoxycarbonylphenyl)-1-(tetrahydropyran-4-yl)benzimidazole (see Working Example 103) (280 mg, 0.574 mmol) in chloroform (3 mL) was added 1M aqueous sodium hydroxide solution (1 mL, 1 mmol). This two-layer solution was homogenized by the addition of methanol, and this was stirred at room temperature for 3 hours. After the reaction was complete, the solution was concentrated, aqueous acetic acid solution was added, and this was stirred at room temperature. The precipitated crystals were filtered, and after washing with water were dried to yield the title compound (240 mg, 88% yield) as white crystals.

$^1$H-NMR (DMSO-$d_6$) δ: 1.93-2.01 (2H, m), 2.51-2.59 (2H, m), 3.33-3.45 (2H, m), 3.99-4.06 (2H, m), 4.55-4.67 (1H, m), 7.45-7.49 (1H, m), 7.73-8.00 (4H, m), 8.07-8.19 (3H, m), 8.28 (1H, br s), 8.50 (1H, br s).

Working Example 106

Synthesis of 2-(3-acetylaminophenyl)-5-(5-chlorobenzoxazol-2-yl)-1-(tetrahydropyran-4-yl)benzimidazole

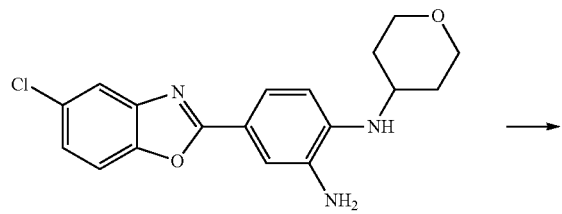

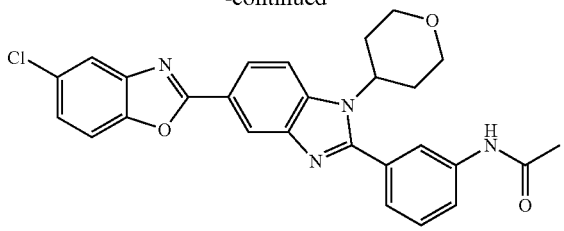

To a solution of 5-chloro-2-(2-(tetrahydropyran-4-yl)aminoanilin-5-yl)benzoxazole (see Working Example 100-2) (250 mg, 0.727 mmol) in dimethylformamide (5 mL) was added 3-acetamidobenzoic acid (130 mg, 0.727 mmol) and WSC (167 mg, 0.872 mmol), and this was stirred at room temperature for 23 hours. Saturated aqueous sodium hydrogen carbonate solution was added, the precipitated crystals were filtered, washed with water and then dried. To a solution of the residue obtained in dioxane (5 mL) was added methanesulfonic acid (2 drops), and this was heated to reflux for 3 hours. After the reaction was complete, saturated aqueous sodium hydrogen carbonate solution was added, the precipitated crystals were filtered, washed with water and then dried. The residue obtained was purified by silica gel column chromatography to yield the title compound (50.5 mg, 14%) as white crystals.

$^1$H-NMR (CDCl$_3$) δ: 1.91-1.98 (2H, m), 2.20 (3H, s), 2.63-2.79 (2H, m), 3.47-3.56 (2H, m), 4.14-4.20 (2H, m), 4.71-4.84 (1H, m), 7.32 (1H, dd, J=8.7, 2.1 Hz), 7.41-7.60 (4H, m), 7.75 (1H, d, J=2.0 Hz), 7.84 (1H, d, J=8.7 Hz), 8.00 (1H, br s), 8.22 (1H, dd, J=8.7, 1.6 Hz), 8.65 (1H, d, J=1.6 Hz).

Working Example 107

Synthesis of 5-(benzoxazol-2-yl)-2-methyl-1-((4-morpholinyl)carbonylmethylbenzimidazole Working Example 107-1

Synthesis of 2-(2-((4-morpholinyl)carbonylmethyl)aminoanilin-5-yl)benzoxazole

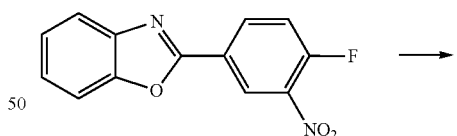

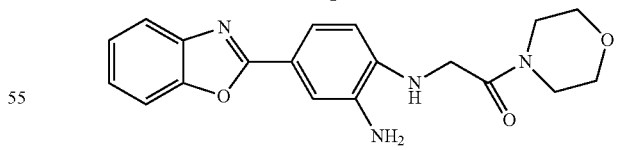

To a suspension of 2-(4-fluoro-3-nitrophenyl)benzoxazole (see Working Example 15-2) (1.20 g, 4.6 mmol) in acetonitrile (24 mL) was added triethylamine (1.17 g, 11.6 mmol) and aminoacetylmorpholine (0.73 g, 5.1 mmol), and this was heated to reflux for 3 h. After the reaction was complete, this was cooled to room temperature, water was added, and the precipitated crystals were filtered, washed with water and then dried. To a solution of the residue obtained in methanol (40 mL) was added 10% palladium-carbon (120 mg). A hydrogen atmosphere was substituted in the flask, and this was stirred at room temperature for 3 hours. After the reaction was complete, this was filtered through Celite and the filtrate was concentrated. The residue obtained was purified by silica gel column chromatography to yield the title compound (1.50 g, 91% yield) as light brown crystals.

$^1$H-NMR (CDCl$_3$) δ: 3.48-3.73 (10H, m), 3.96 (2H, d, J=4.1 Hz), 5.09 (1H, t, J=4.1 Hz), 6.58 (1H, dd, J=8.3, 2.1 Hz), 7.26-7.35 (2H, m), 7.49-7.54 (1H, m), 7.62 (1H, t, J=1.8 Hz), 7.66-7.83 (2H, m).

Working Example 107-2

Synthesis of 5-(benzoxazol-2-yl)-2-methyl-1-(4-morpholinyl)benzimidazole

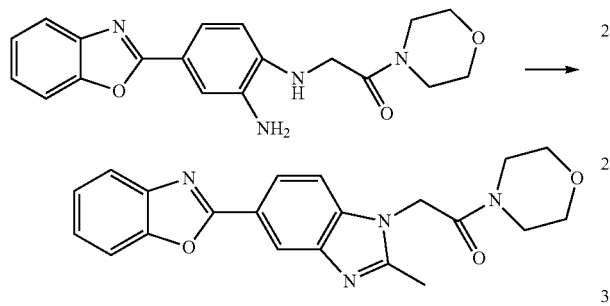

To a solution of 2-(2-((4-morpholinyl)carbonylmethyl)aminoanilin-5-yl)benzoxazole (see Working Example 107-1) (0.08 g, 0.2 mmol) in methanol (2 mL) was added methyl acetimidate hydrochloride (0.03 g, 3 mmol), and this was heated to reflux for 3 hours. After the reaction was complete, the reaction solution was cooled, water was added, and the precipitated crystals were filtered, and after being washed with water were dried to yield the title compound (0.10 g, quant.) as white crystals.

$^1$H-NMR (DMSO-d$_6$) δ: 2.47 (3H, s), 3.39-3.84 (8H, m), 5.34 (2H, s), 7.39-7.41 (2H, m), 7.67 (1H, d, J=8.6 Hz), 7.78-7.80 (2H, m), 8.07 (1H, d, J=8.6 Hz), 8.34 (1H, s).

Working Example 108

Synthesis of 4-oxo-4-(2-(5-(benzoxazol-2-yl)-2-methylbenzimidazol-1-yl)ethyl)aminobutyric acid

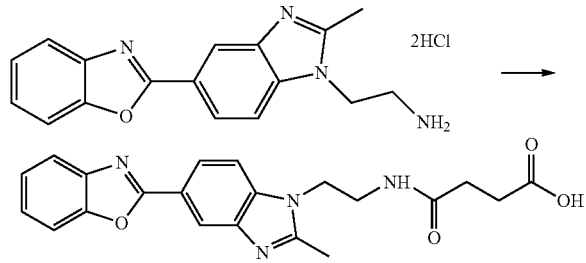

1-(2-Aminoethyl)-5-(benzoxazol-2-yl)-2-methylbenzimidazole hydrochloride (see Working Example 56) (0.20 g, 0.6 mmol), succinic anhydride (0.06 g, 0.6 mmol), triethylamine (0.22 g, 2.2 mmol) and CHCl$_3$ (2 mL) were added together, and after stirring for 1 hour at room temperature this was heated to reflux with stirring for 1 hour. After cooling, water was added and back-extraction was carried out. The aqueous layer obtained was concentrated, and the residue was reslurried in methanol. After the precipitated crystals were filtered, they were dried to yield the title compound (0.13 g, 69% yield) as white crystals.

$^1$H-NMR (DMSO-d$_6$) δ: 2.22 (2H, t, J=6.8 Hz), 2.36 (2H, t, J=6.8 Hz), 2.57 (3H, s), 3.41-3.45 (2H, m), 4.29 (2H, t, J=5.9 Hz), 7.39-7.43 (2H, m), 7.68 (1H, d, J=8.6 Hz), 7.78-7.80 (2H, m), 8.07-8.11 (2H, m), 8.33 (1H, s).

Working Example 109

Synthesis of 5-(benzoxazol-2-yl)-2-methyl-1-(2-trifluoroacetylaminoethyl)benzimidazole

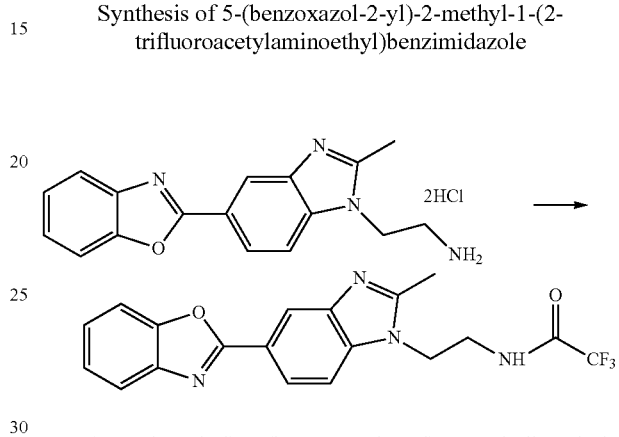

1-(2-Aminoethyl)-5-(benzoxazol-2-yl)-2-methylbenzimidazole hydrochloride (see Working Example 56) (0.20 g, 0.6 mmol), trifluoroacetic anhydride (0.17 g, 0.8 mmol), triethylamine (0.22 g, 2.2 mmol) and CHCl$_3$ (2 mL) were added together, and stirred for 1 hour at room temperature. After cooling, chloroform and water were added and extraction was carried out. After the organic layer obtained was dried over anhydrous sodium sulfate, it was filtered and concentrated. The solid obtained was separated by filtration and dried to yield the title compound (0.08 g, 34% yield) as white crystals.

$^1$H-NMR (DMSO-d$_6$) δ: 2.58 (3H, s), 3.58-3.63 (2H, m), 4.42 (2H, t, J=5.6 Hz), 7.41 (2H, dd, J=5.4, 3.8 Hz), 7.69 (1H, d, J=8.4 Hz), 7.78-7.80 (2H, m), 8.07-8.09 (1H, m), 8.33 (1H, s), 9.66 (1H, br).

Working Example 110

3-(2-(5-(benzoxazol-2-yl)-2-methylbenzimidazol-1-yl)ethyl)-1-methylthiourea

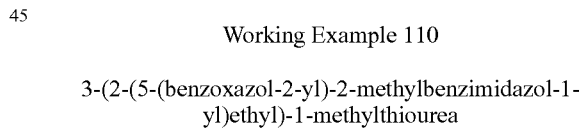

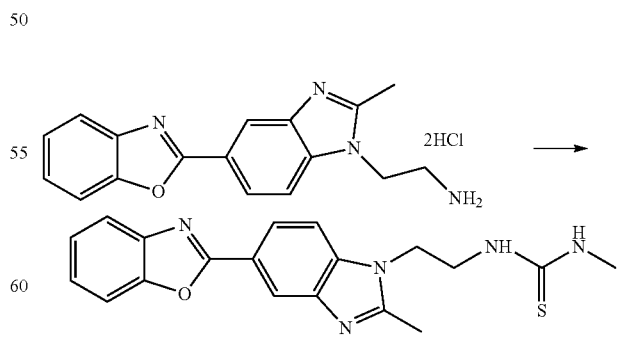

1-(2-Aminoethyl)-5-(benzoxazol-2-yl)-2-methylbenzimidazole hydrochloride (see Working Example 56) (0.20 g, 0.6 mmol), methyl isothiocyanate (0.17 g, 0.6 mmol), triethylamine (0.13 g, 13 mmol) and THF (2 mL) were added together, and stirred for 1 hour at room temperature. After cooling, chloroform and water were added and extraction was carried out. After the organic layer obtained was dried over anhydrous sodium sulfate, it was filtered and concentrated. The solid obtained was separated by filtration and dried to yield the title compound (0.08 g, 40% yield) as white crystals.

$^1$H-NMR (DMSO-$d_6$) δ: 2.50-2.62 (6H, m), 2.76 (1H, br s), 3.79-3.81 (2H, m), 4.43 (2H, t, J=5.5 Hz), 7.39-7.42 (2H, m), 7.54 (1H, br s), 7.74-7.79 (3H, m), 8.07 (1H, dd, J=8.5, 1.4 Hz), 8.33 (1H, d, J=1.4 Hz).

Working Example 111

Synthesis of 5-(benzoxazol-2-yl)-1-(tetrahydropyran-4-yl)-2-(tetrahydropyran-4-yl)methylbenzimidazole

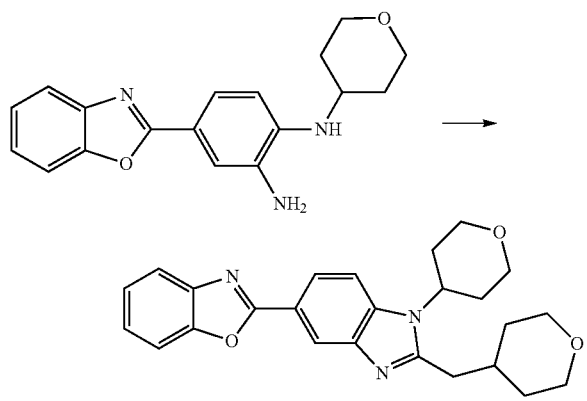

To a solution of 5-(benzoxazol-2-yl)-2-(tetrahydropyran-4-yl)aminoaniline (see Working Example 20-2) (250 mg, 0.808 mmol) in dimethylformamide (3 mL) was added (4-tetrahydropyranyl)acetaldehyde (114 mg, 0.889 mmol) and oxone (323 mg, 0.525 mmol), and this was stirred at room temperature for 2 hours. After the reaction was complete, aqueous potassium carbonate solution was added, this was filtered and washed with water. The crystals obtained were purified by silica gel column chromatography to yield the title compound (197 mg, 58% yield) as light brown crystals.

$^1$H-NMR (CDCl$_3$) δ: 1.41-1.89 (6H, m), 2.20-2.32 (1H, m), 2.60-2.76 (2H, m), 2.90 (2H, d, J=7.3 Hz), 3.45 (2H, td, J=11.7, 1.9 Hz), 3.61 (2H, t, J=11.3 Hz), 4.00 (2H, dd, J=11.1, 3.5 Hz), 4.25 (2H, dd, J=11.8, 4.2 Hz), 4.41-4.54 (1H, m), 7.33-7.36 (2H, m), 7.57-7.80 (3H, m), 8.19 (1H, dd, J=8.7, 1.6 Hz), 8.59 (1H, d, J=1.6 Hz).

Working Example 112

Synthesis of 5-(benzoxazol-2-yl)-2-methyl-1-(tetrahydropyran-4-yl)-6-chlorobenzimidazole Working Example 112-1

Synthesis of 2-(4-chloro-2-fluoronitrobenzen-5-yl)benzoxazole

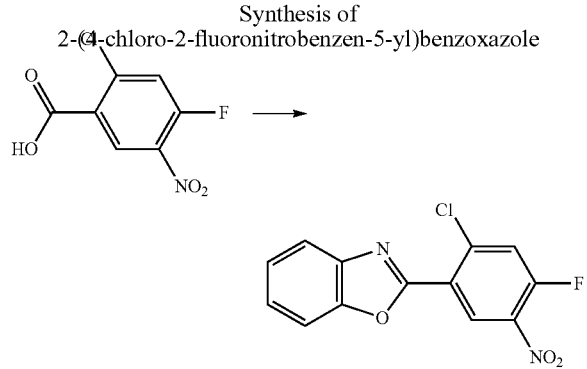

2-Chloro-4-fluoro-5-nitrobenzoic acid (4.00 g, 18.2 mmol), 2-aminophenol (2.09 g, 20.1 mmol), CHCl$_3$ (80 mL), and WSC (3.84 g, 20.0 mmol) were added together and stirred at room temperature for 2 hours. Water was added, and this was extracted with chloroform/acetone (3:1). After the organic layer obtained was dried over anhydrous sodium sulfate, it was filtered and concentrated. To a toluene (80 mL) solution of the solid obtained was added p-toluenesulfonic acid monohydrate (0.18 g, 1.8 mmol), and this was heated to reflux for 40 hours. After the reaction solution was concentrated, water was added, and the precipitated crystals were filtered, and after being washed with water were dried to yield the title compound (1.40 g, 26% yield) as yellowish-brown crystals.

$^1$H-NMR (DMSO-$d_6$) δ: 7.44-7.56 (2H, m), 7.85-7.92 (2H, m), 8.21 (1H, d, J=11.0 Hz), 8.87 (1H, d, J=7.9 Hz).

Working Example 112-2

Synthesis of 2-(4-chloro-2-(tetrahydropyran-4-yl)aminonitrobenzen-5-yl)benzoxazole

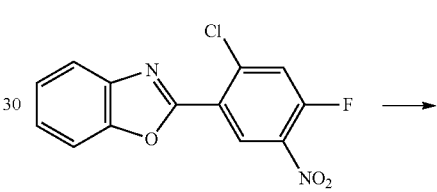

To a suspension of 2-(4-chloro-2-fluoronitrobenzen-5-yl)benzoxazole (see Working Example 112-1) (0.38 g, 1.3 mmol) in acetonitrile (8 mL) was added 4-aminotetrahydropyran (0.30 g, 2.9 mmol), and this was heated to reflux for 2 hours. After the reaction was complete, this was cooled to room temperature, water was added, and the precipitated crystals were filtered. The crystals obtained were purified by silica gel column chromatography to yield the title compound (0.10 g, 21% yield) as brown crystals.

$^1$H-NMR (CDCl$_3$) δ: 1.66-1.81 (2H, m), 2.10-2.17 (2H, m), 3.57-3.66 (2H, m), 3.76-3.81 (1H, m), 4.07 (2H, dt, J=12.1, 3.8 Hz), 7.05 (1H, s), 7.35-7.42 (2H, m), 7.56-7.67 (1H, m), 7.78-7.84 (1H, m), 8.28 (1H, d, J=7.3 Hz), 9.09 (1H, t, J=2.9 Hz).

Working Example 112-3

Synthesis of 2-(4-chloro-2-(tetrahydropyran-4-yl)aminoanilin-5-yl)benzoxazole

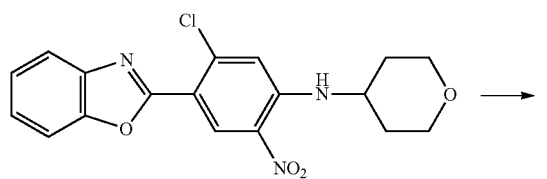

To 2-(4-chloro-2-(tetrahydropyran-4-yl)aminonitrobenzen-5-yl)benzoxazole (see Working Example 112-2) (0.10 g, 0.8 mmol) was added iron powder (0.33 g, 5.8 mmol) and acetic acid (50 mL), and this was heated to reflux for 2 hours. After the reaction solution cooled, this was filtered through Celite and concentrated, and the residue obtained was purified by silica gel column chromatography to yield the title compound (0.06 g, 65% yield) as a reddish-brown solid.

$^1$H-NMR (CDCl$_3$) δ: 1.50-1.64 (2H, m), 2.04-2.11 (2H, m), 3.31 (2H, br), 3.61 (2H, t, J=11.4 Hz), 3.95-4.08 (3H, m), 6.72 (1H, s), 7.26-7.36 (2H, m), 7.53-7.59 (2H, m), 7.74-7.81 (1H, m).

Working Example 112-4

Synthesis of 5-(benzoxazol-2-yl)-2-methyl-1-(tetrahydropyran-4-yl)-6-chlorobenzimidazole

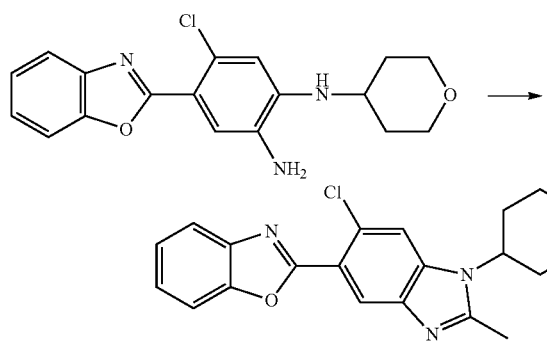

To a solution of 2-(4-chloro-2-(tetrahydropyran-4-yl)aminoanilin-5-yl)benzoxazole (see Working Example 112-3) (0.04 g, 0.2 mmol) in methanol (1.2 mL) was added methyl acetimidate hydrochloride (0.06 g, 0.6 mmol), and this was heated to reflux for 3 hours. After the reaction solution was cooled, water was added, and the precipitated crystals were filtered, and after being washed with water were dried to yield the title compound (0.03 g, 79% yield) as a yellowish-brown solid.

$^1$H-NMR (CDCl$_3$) δ: 1.92-1.97 (2H, m), 2.50-2.66 (2H, m), 2.78 (3H, s), 3.61 (2H, t, J=11.5 Hz), 4.25 (2H, dd, J=11.5, 4.7 Hz), 4.42-4.45 (1H, m), 7.36-7.43 (2H, m), 7.62-7.65 (1H, m), 7.79 (1H, s), 7.84-7.88 (1H, m), 8.47 (1H, s).

Working Example 113

Synthesis of 5-(benzoxazol-2-yl)-1-(4-methoxycarbonylphenylmethyl)-2-methylbenzimidazole

Working Example 113-1

Synthesis of 2-(2-(4-methoxycarbonylphenylmethyl)aminonitrobenzen-5-yl)benzoxazole

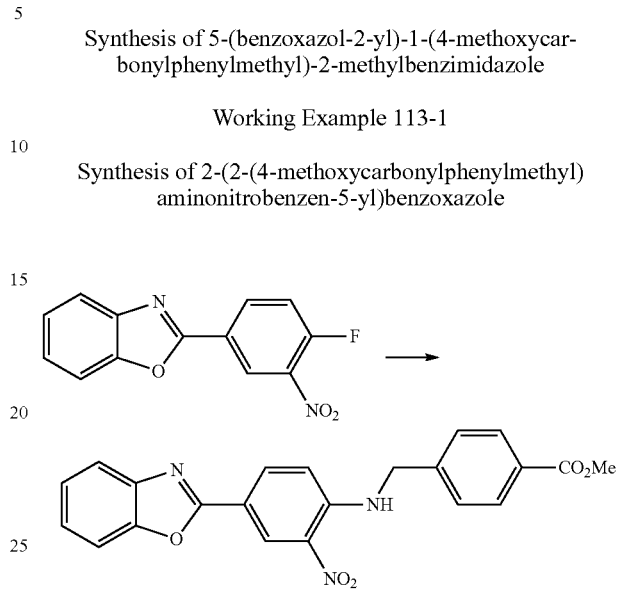

To a suspension of 2-(4-fluoro-3-nitrophenyl)benzoxazole (see Working Example 15-2) (250 mg, 0.968 mmol) in acetonitrile (5 mL) was added triethylamine (245 mg, 2.42 mmol) and 4-carbomethoxybenzylamine hydrochloride (215 mg, 1.07 mmol), and this was heated to reflux for 2 hours. After the reaction was complete, this was cooled to room temperature, water was added, and after the precipitated crystals were filtered and washed with water, they were dried to yield the title compound (372 mg, 95% yield).

$^1$H-NMR (DMSO-d$_6$) δ: 3.84 (3H, s), 4.84 (2H, d, J=6.3 Hz), 7.07 (1H, d, J=9.2 Hz), 7.35-7.42 (2H, m), 7.54 (2H, d, J=8.2 Hz), 7.72-7.78 (2H, m), 7.95 (2H, d, J=8.2 Hz), 8.15 (1H, dd, J=9.1, 2.1 Hz), 8.85 (1H, d, J=2.1 Hz), 9.20 (1H, t, J=6.3 Hz).

Working Example 113-2

Synthesis of 2-(2-(4-methoxycarbonylphenylmethyl)aminoanilin-5-yl)benzoxazole

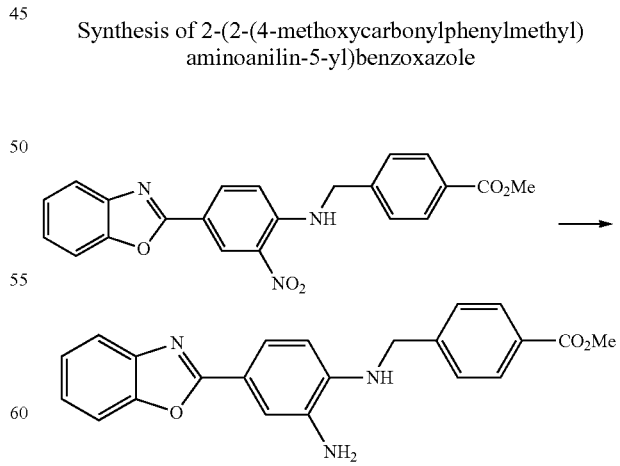

To 2-(2-(4-methoxycarbonylphenylmethyl)aminonitrobenzen-5-yl)benzoxazole (see Working Example 113-2) (367 mg, 0.910 mmol) was added iron powder (102 mg, 1.82 mmol), 10% aqueous acetic acid (5 mL) and methanol (7 mL), and this was heated to reflux for 16 hours. After the reaction solution was cooled, saturated aqueous sodium hydrogen carbonate solution and chloroform were added, this was filtered through Celite, and the filtrate obtained was extracted. After the organic layer obtained was dried over anhydrous sodium sulfate, it was filtered and concentrated. The residue obtained was purified by silica gel column chromatography to yield the title compound (61.8 mg, 18% yield).

$^1$H-NMR (CDCl$_3$) δ: 3.92 (3H, s), 4.50 (2H, s), 6.65 (1H, d, J=8.2 Hz), 7.26-7.32 (2H, m), 7.45-7.53 (3H, m), 7.67-7.73 (3H, m), 8.04 (2H, d, J=8.2 Hz).

Working Example 113-3

Synthesis of 5-(benzoxazol-2-yl)-1-(4-methoxycarbonylphenylmethyl)-2-methylbenzimidazole

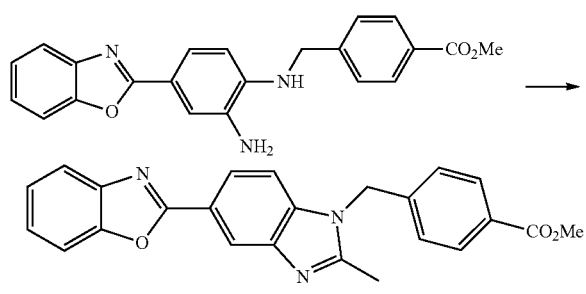

To a solution of 2-(2-(4-methoxycarbonylphenylmethyl)aminoanilin-5-yl)benzoxazole (see Working Example 113-2) (59.0 mg, 0.159 mmol) in methanol (3 mL) was added methyl acetimidate hydrochloride (19 mg, 0.174 mmol), and this was heated to reflux for 1.5 hours. After the reaction was complete, saturated aqueous sodium hydrogen carbonate solution was added, and this was stirred for several minutes at room temperature. The crystals obtained were filtered, and after being washed with water, they were dried to yield the title compound (62.2 mg, 98% yield) as yellow crystals.

$^1$H-NMR (DMSO-d$_6$) δ: 2.56 (3H, s), 3.83 (3H, s), 5.67 (2H, s), 7.28 (2H, d, J=8.2 Hz), 7.38-7.42 5(2H, m), 7.70 (1H, d, J=8.5 Hz), 7.77-7.81 (2H, m), 7.94 (2H, d, J=8.2 Hz), 8.07 (1H, dd, J=8.5, 1.6 Hz), 8.38 (1H, s).

Working Example 114

Synthesis of 5-(benzoxazol-2-yl)-1-(4-carboxyphenylmethyl)-2-methylbenzimidazole

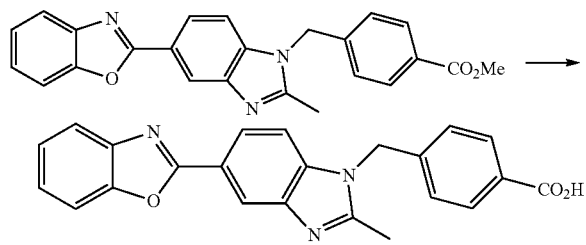

To a solution of 5-(benzoxazol-2-yl)-1-(4-methoxycarbonylphenylmethyl)-2-methylbenzimidazole (see Working Example 113-3) (55 mg, 0.138 mmol) in chloroform (3 mL) was added aqueous sodium hydroxide solution (1 M, 0.6 mL, 0.6 mmol). This two-layer solution was homogenized by the addition of methanol, and this was stirred at room temperature for 20 hours. After the reaction was complete, the solution was concentrated, aqueous acetic acid solution was added, and this was stirred at room temperature. The precipitated crystals were filtered, and after washing with water were dried to yield the title compound (45.9 mg, 87% yield) as yellow crystals.

$^1$H-NMR (DMSO-d$_6$) δ: 2.57 (3H, s), 5.66 (2H, s), 7.24 (2H, d, J=8.2 Hz), 7.38-7.42 (2H, m), 7.70 (1H, d, J=8.5 Hz), 7.77-7.81 (2H, m), 7.91 (2H, d, J=8.2 Hz), 8.07 (1H, dd, J=8.5, 1.6 Hz), 8.38 (1H, s).

Working Example 115

Synthesis of 5-(1-benzoxazol-2-yl)-1-(1-butanol-2-yl)-2-methylbenzimidazole

Working Example 115-1

Synthesis of 2-(2-(1-n-butanol-2-yl)aminonitrobenzen-5-yl)benzoxazole

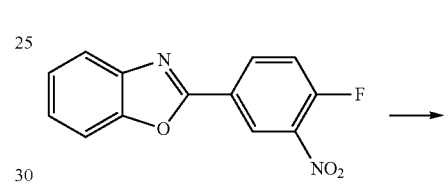

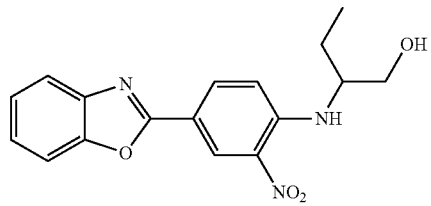

To a suspension of 2-(4-fluoro-3-nitrophenyl)benzoxazole (see Working Example 15-2) (250 mg, 1.94 mmol) in acetonitrile (5 mL) was added potassium carbonate (268 mg, 1.94 mmol) and 2-amino-1-n-butanol (95.4 mg, 1.07 mmol), and this was heated to reflux for 4 hours. After the reaction was complete, this was cooled to room temperature, water was added, and after the precipitated crystals were filtered and washed with water, they were dried to yield the title compound (298 mg, 94% yield).

$^1$H-NMR (CDCl$_3$) δ: 1.06 (3H, t, J=7.4 Hz), 1.65-1.90 (2H, m), 2.00-2.04 (1H, m), 3.75-3.90 (3H, m), 7.10 (1H, d, J=9.1 Hz), 7.33-7.37 (2H, m), 7.54-7.59 (1H, m), 7.70-7.76 (1H, m), 8.25 (1H, dd, J=9.1, 2.1 Hz), 8.47 (1H, d, J=7.1 Hz), 9.04 (1H, d, J=2.1 Hz).

Working Example 115-2

Synthesis of 5-(1-benzoxazol-2-yl)-1-(1-n-butanol-2-yl)-2-methylbenzimidazole

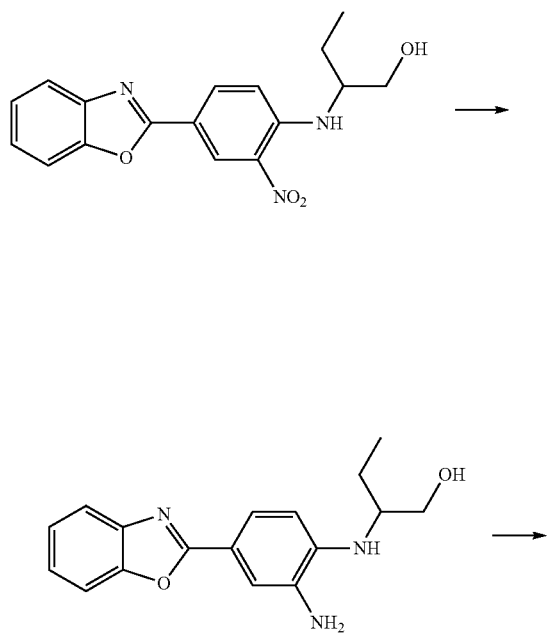

To a solution of 2-(2-(1-n-butanol-2-yl)aminonitrobenzen-5-yl)benzoxazole (see Working Example 115-1) (295 mg, 0.901 mmol) in ethanol/ethyl acetate (1:1, 6 mL) was added 10% palladium-carbon (50 mg). A hydrogen atmosphere was then substituted in the flask, and this was stirred at room temperature for 19 hours. After the reaction was complete, this was filtered through Celite, and the filtrate was concentrated. To a solution of the residue obtained in ethanol (5 mL) was added ethyl acetimidate hydrochloride (133 mg, 1.08 mmol), and this was heated to reflux for 2 hours. After the reaction was complete, saturated aqueous sodium hydrogen carbonate solution was added, and this was stirred for several minutes at room temperature. The crystals obtained were filtered, and after being washed with water, they were dried to yield the title compound (232 mg, 72% yield) as white crystals.

$^1$H-NMR (CDCl$_3$) δ: 0.84 (3H, t, J=7.4 Hz), 1.93-2.20 (2H, m), 2.61 (3H, s), 3.96-4.02 (1H, m), 4.32-4.49 (2H, m), 7.29-7.44 (4H, m), 7.65-7.68 (1H, m), 7.73 (1H, dd, J=8.7, 1.6 Hz), 7.87 (1H, d, J=1.5 Hz).

Working Example 116

Synthesis of 5-(1-benzoxazol-2-yl)-1-(2-n-propanol-1-yl)-2-methylbenzimidazole

Working Example 116-1

Synthesis of 2-(2-(2-n-propanol-1-yl)aminonitrobenzen-5-yl)benzoxazole

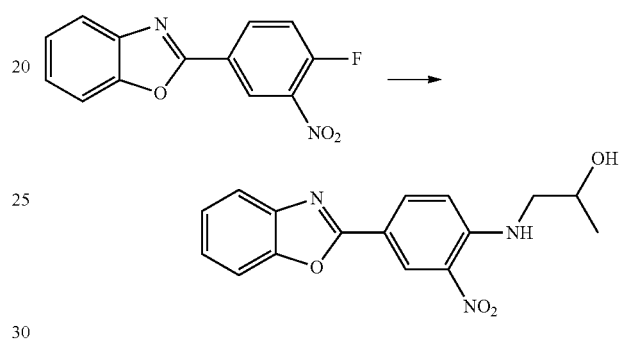

To a suspension of 2-(4-fluoro-3-nitrophenyl)benzoxazole (see Working Example 15-2) (250 mg, 1.94 mmol) in acetonitrile (5 mL) was added potassium carbonate (268 mg, 1.94 mmol) and 1-amino-2-n-propanol (80.4 mg, 1.07 mmol), and this was heated to reflux for 4 hours. After the reaction was complete, this was cooled to room temperature, water was added, and after the precipitated crystals were filtered and washed with water, they were dried to yield the title compound (284 mg, 94% yield).

$^1$H-NMR (DMSO-d$_6$) δ: 1.18 (3H, d, J=6.1 Hz), 3.26-3.34 (1H, m), 3.48-3.56 (1H, m), 3.88-3.99 (1H, m), 5.13 (1H, d, J=4.9 Hz), 7.33 (1H, d, J=9.2 Hz), 7.38-7.42 (2H, m), 7.74-7.79 (2H, m), 8.23 (1H, dd, J=9.1, 1.8 Hz), 8.68 (1H, t, J=5.4 Hz), 8.82 (1H, d, J=2.1 Hz).

Working Example 116-2

Synthesis of 5-(1-benzoxazol-2-yl)-1-(2-n-propanol-1-yl)-2-methylbenzimidazole

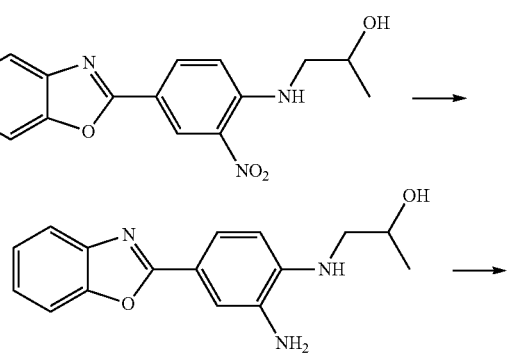

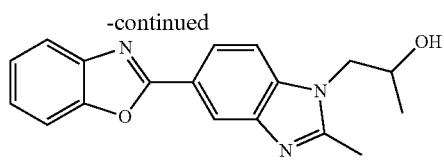

To a solution of 2-(2-(2-n-propanol-1-yl)aminonitrobenzen-5-yl)benzoxazole (see Working Example 116-1) (280 mg, 0.894 mmol) in ethanol/ethyl acetate (1:1, 6 mL) was added 10% palladium-carbon (50 mg). A hydrogen atmosphere was then substituted in the flask, and this was stirred at room temperature for 19 hours. After the reaction was complete, this was filtered through Celite, and the filtrate was concentrated. To a solution of the residue obtained in ethanol (5 mL) was added ethyl acetimidate hydrochloride (133 mg, 1.08 mmol), and this was heated to reflux for 2 hours. After the reaction was complete, saturated aqueous sodium hydrogen carbonate solution was added, and this was stirred for several minutes at room temperature. The crystals obtained were filtered, and after being washed with water, they were dried to yield the title compound (254 mg, 92% yield) as white crystals.

$^1$H-NMR (CDCl$_3$) δ: 1.48 (3H, d, J=6.3 Hz), 2.64 (3H, s), 3.90-4.15 (2H, m), 4.45-4.52 (1H, m), 5.63 (1H, br s), 7.29-7.41 (4H, m), 7.66-7.79 (3H, m).

Working Example 117

Synthesis of 5-(benzoxazol-2-yl)-1-(3-methoxycarbonylphenylmethyl)-2-methylbenzimidazole Working Example 117-1

Synthesis of 2-(2-(3-methoxycarbonylphenylmethyl)aminonitrobenzen-5-yl)benzoxazole

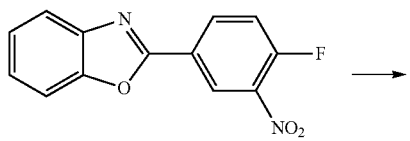

To a suspension of 2-(4-fluoro-3-nitrophenyl)benzoxazole (see Working Example 15-2) (250 mg, 0.968 mmol) in acetonitrile (5 mL) was added triethylamine (245 mg, 2.42 mmol) and 3-carbomethoxybenzylamine hydrochloride (215 mg, 1.07 mmol), and this was heated to reflux for 2 hours. After the reaction was complete, this was cooled to room temperature, water was added, and after the precipitated crystals were filtered and washed with water, they were dried to yield the title compound (365 mg, 94% yield).

$^1$H-NMR (DMSO-d$_6$) δ: 3.85 (3H, s), 4.82 (2H, d, J=6.3 Hz), 7.14 (1H, d, J=9.1 Hz), 7.37-7.40 (2H, m), 7.52 (1H, t, J=7.8 Hz), 7.68-7.77 (3H, m), 7.87 (1H, d, J=7.8 Hz), 8.03 (1H, s), 8.15 (1H, dd, J=9.1, 2.1 Hz), 8.84 (1H, d, J=2.1 Hz), 9.21 (1H, t, J=6.5 Hz).

Working Example 117-2

Synthesis of 5-(benzoxazol-2-yl)-1-(3-methoxycarbonylphenylmethyl)-2-methylbenzimidazole

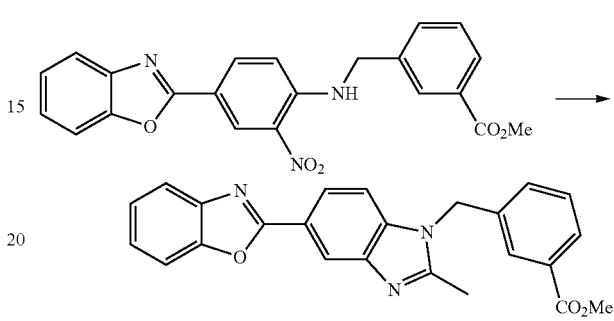

To 2-(2-(3-methoxycarbonylphenylmethyl)aminonitrobenzen-5-yl)benzoxazole (see Working Example 117-1) (220 mg, 0.545 mmol) was added iron powder (91.4 mg, 1.64 mmol) and acetic acid (5 mL), and this was heated to reflux for 12 hours. After the reaction solution was cooled, it was concentrated. The residue obtained was purified by silica gel column chromatography to yield the title compound (139 mg, 64% yield) as white crystals.

$^1$H-NMR (CDCl$_3$) δ: 2.63 (3H, s), 3.91 (3H, s), 5.42 (2H, s), 7.18 (1H, d, J=7.8 Hz), 7.32-7.44 (4H, m), 7.59-7.62 (1H, m), 7.75-7.79 (1H, m), 7.89 (1H, s), 7.99 (1H, d, J=7.8 Hz), 8.19 (1H, dd, J=8.6, 1.5 Hz), 8.62 (1H, d, J=1.5 Hz).

Working Example 118

Synthesis of 5-(1-benzoxazol-2-yl)-1-(1-acetoxy-2-phenylethan-2-yl)-2-methylbenzimidazole Working Example 118-1

Synthesis of 2-(2-(2-phenyl-1-ethanol-2-yl)aminonitrobenzen-5-yl)benzoxazole

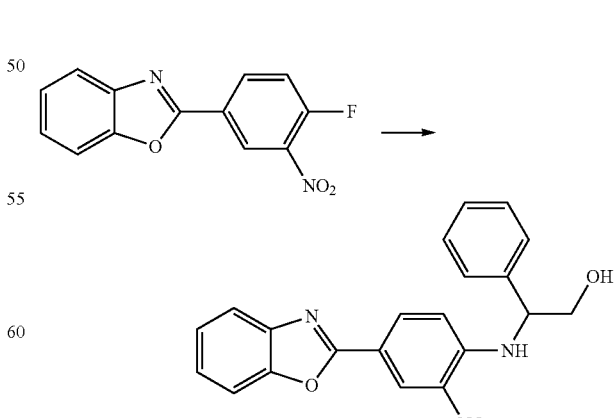

To a suspension of 2-(4-fluoro-3-nitrophenyl)benzoxazole (see Working Example 15-2) (250 mg, 0.968 mmol) in acetonitrile (5 mL) was added potassium carbonate (268 mg, 1.94 mmol) and 2-phenylglycinol (146 mg, 1.07 mmol), and this was heated to reflux for 2 hours. After the reaction was complete, this was cooled to room temperature, water was added, and after the precipitated crystals were filtered and washed with water, they were dried to yield the title compound (343 mg, 94% yield).

$^1$H-NMR (CDCl$_3$) δ: 1.93 (1H, br s), 3.95-4.13 (2H, m), 4.82 (1H, dd, J=10.4, 5.9 Hz), 6.77 (1H, d, J=9.1 Hz), 7.29-7.44 (7H, m), 7.51-7.56 (1H, m), 7.68-7.72 (1H, m), 8.12 (1H, dd, J=9.1, 2.1 Hz), 9.06-9.12 (2H, m).

Working Example 118-2

Synthesis of 5-(1-benzoxazol-2-yl)-1-(1-acetoxy-2-phenylethan-2-yl)-2-methylbenzimidazole

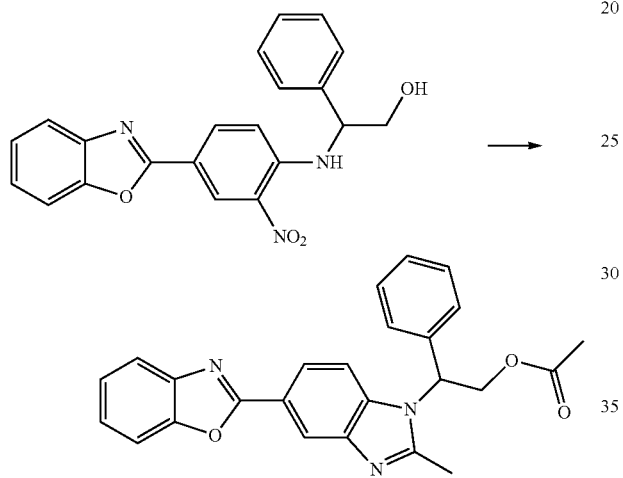

To 2-(2-(2-phenyl-1-ethanol-2-yl)aminonitrobenzen-5-yl) benzoxazole (see Working Example 118-1) (340 mg, 0.545 mmol) was added iron powder (152 mg, 2.72 mmol) and acetic acid (5 mL), and this was heated to reflux for 12 hours. After the reaction solution was cooled, it was concentrated. The residue obtained was purified by silica gel column chromatography to yield the title compound (214 mg, 57% yield) as a colorless amorphous mass.

$^1$H-NMR (CDCl$_3$) δ: 1.96 (3H, s), 2.66 (3H, s), 4.91 (1H, dd, J=11.5, 9.4 Hz), 5.08 (1H, dd, J=11.5, 5.0 Hz), 5.95 (1H, dd, J=9.4, 5.0 Hz), 7.11 (1H, d, J=8.6 Hz), 7.23-7.26 (2H, m), 7.30-7.43 (5H, m), 7.57-7.61 (1H, m), 7.74-7.77 (1H, m), 8.04 (1H, dd, J=8.6, 1.5 Hz), 8.58 (1H, d, J=1.5 Hz).

Working Example 119

Synthesis of 5-(benzoxazol-2-yl)-1-(3-carboxyphenylmethyl)-2-methylbenzimidazole

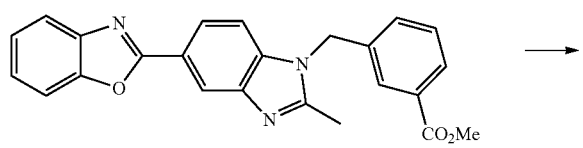

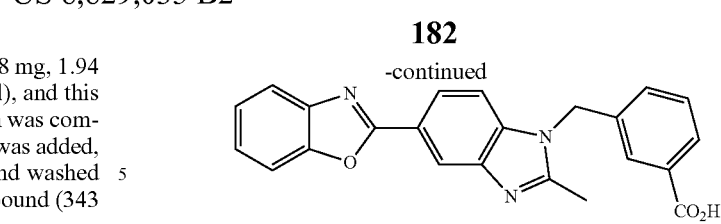

To a solution of 5-(benzoxazol-2-yl)-1-(3-methoxycarbonylphenylmethyl)-2-methylbenzimidazole (see Working Example 117-2) (125 mg, 0.315 mmol) in chloroform (3 mL) was added aqueous sodium hydroxide solution (1 M, 1 mL, 1 mmol). This two-layer solution was homogenized by the addition of methanol, and this was stirred at room temperature for 20 hours. After the reaction was complete, the solution was concentrated, aqueous acetic acid solution was added, and this was stirred at room temperature. The precipitated crystals were filtered, and after washing with water were dried to yield the title compound (120 mg, 99% yield) as white crystals.

$^1$H-NMR (DMSO-d$_6$) δ: 2.57 (3H, s), 5.65 (2H, s), 7.34-7.50 (4H, m), 7.72-7.87 (5H, m), 8.07 (1H, dd, J=8.4, 1.4 Hz), 8.38 (1H, d, J=1.4 Hz).

Working Example 120

Synthesis of 5-(1-benzoxazol-2-yl)-1-(2-phenyletha-nol-2-yl)-2-methylbenzimidazole

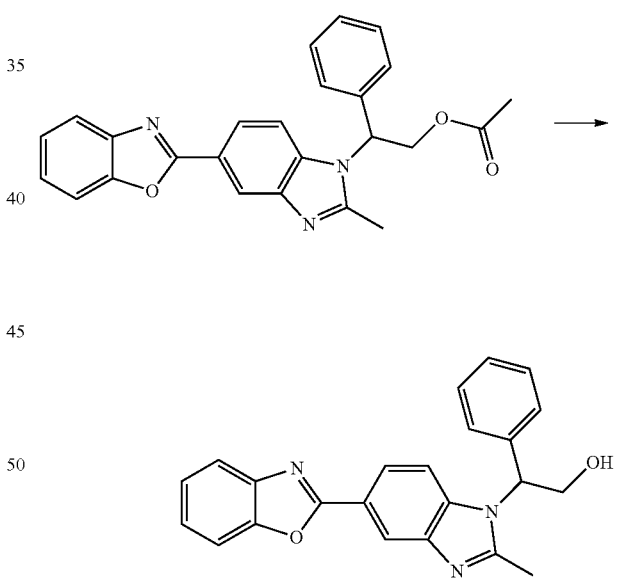

To a solution of 5-(1-benzoxazol-2-yl)-1-(1-acetoxy-2-phenylethan-2-yl)-2-methylbenzimidazole (see Working Example 118-2) (200 mg, 0.486 mmol) in methanol (5 mL) was added aqueous sodium hydroxide solution (1 M, 1.5 mL, 1.5 mmol). After the reaction was complete, the solution was concentrated, water was added, and this was stirred at room temperature. The precipitated crystals were filtered, and after washing with water were dried to yield the title compound (158 mg, 88% yield) as white crystals.

$^1$H-NMR (CDCl$_3$) δ: 2.67 (3H, s), 4.67 (1H, dd, J=12.0, 4.0 Hz), 4.80 (1H, dd, J=12.0, 9.4 Hz), 5.76 (1H, dd, J=9.4, 4.0

Hz), 6.95 (1H, d, J=8.6 Hz), 7.20-7.24 (2H, m), 7.28-7.39 (6H, m), 7.55 (1H, dd, J=8.6, 1.4 Hz), 7.60-7.65 (1H, m), 7.79 (1H, d, J=1.4 Hz).

Working Example 121

Synthesis of 5-(benzoxazol-2-yl)-2-methyl-1-(2-tert-butoxycarbonyl-n-propyl)benzimidazole Working Example 121-1

Synthesis of 2-(2-tert-butoxycarbonyl-n-propy-lamino)anilin-5-yl)benzoxazole

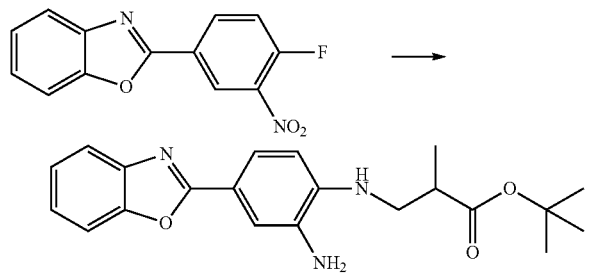

To a suspension of 2-(4-fluoro-3-nitrophenyl)benzoxazole (see Working Example 15-2) (0.50 g, 1.9 mmol) in acetonitrile (10 mL) was added 2-tert-butoxycarbonyl-1-propy-lamine (0.32 g, 2.0 mmol) and triethylamine (0.22 g, 2.2 mmol), and this was heated to reflux for 2 hours. After the reaction was complete, this was cooled to room temperature, water was added, and the precipitated crystals were filtered, washed with water and then dried. To a solution of the residue obtained in tetrahydrofuran (50 mL) was added 10% palladium-carbon (50 mg). A hydrogen atmosphere was substituted in the flask, and this was stirred at room temperature for 3 hours. After the reaction was complete, this was filtered through Celite, and the filtrate was concentrated. The residue obtained was purified by silica gel column chromatography to yield the title compound (0.62 g, 83% yield) as a light brown solid.

$^1$H-NMR (CDCl$_3$) δ: 1.25 (3H, d, J=7.1 Hz), 1.46 (9H, s), 2.68-2.82 (1H, m), 3.24-3.49 (4H, m), 4.31 (1H, br), 6.71 (1H, d, J=8.4 Hz), 7.24-7.31 (2H, m), 7.48-7.55 (1H, m), 7.62 (1H, d, J=2.0 Hz), 7.64-7.77 (2H, m).

Working Example 121-2

Synthesis of 5-(benzoxazol-2-yl)-2-methyl-1-(2-tert-butoxycarbonyl-n-propyl)benzimidazole

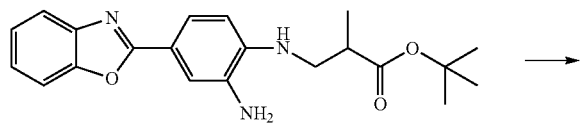

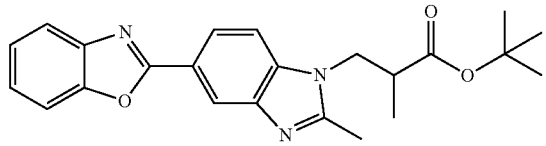

To a solution of 2-(2-tert-butoxycarbonyl-n-propylamino) anilin-5-yl)benzoxazole (see Working Example 121-1) (0.62 g, 1.7 mmol) in THF (20 mL) was added methyl acetimidate hydrochloride (0.37 g, 3.4 mmol), and this was heated to reflux for 3 hours. After the reaction solution was cooled, water was added, and the precipitated crystals were filtered, and after being washed with water were dried to yield the title compound (0.61 g, 92% yield) as a yellowish-brown solid.

$^1$H-NMR (CDCl$_3$) δ: 1.23 (3H, d, J=7.1 Hz), 1.30 (9H, s), 2.67 (3H, s), 2.91-3.08 (1H, m), 4.09 (1H, dd, J=14.7, 7.1 Hz), 4.46 (1H, dd, J=14.7, 8.3 Hz), 7.27 (1H, s), 7.32-7.37 (1H, m), 7.45 (1H, d, J=8.4 Hz), 7.57-7.62 (1H, m), 7.75-7.79 (1H, m), 8.20 (1H, dd, J=8.4, 1.2 Hz), 8.55 (1H, s).

Working Example 122

Synthesis of 5-(benzoxazol-2-yl)-2-methyl-1-(2-carboxy-n-propyl)benzimidazole

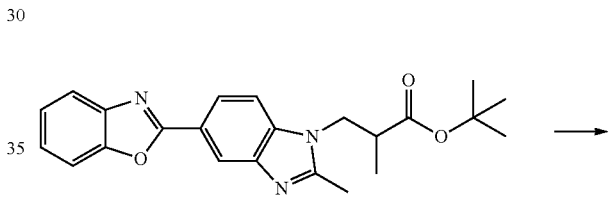

5-(Benzoxazol-2-yl)-2-methyl-1-(2-tert-butoxycarbonyl-n-propyl)benzimidazole (see Working Example 121-2) (0.4 g, 1.0 mmol) and THF/water=2:1 (40 mL) were charged, and lithium hydroxide (0.043 g, 1.0 mmol) was added at room temperature, and this was heated and stirred for 5 hours. After being kept cool, the liquid was brought to approximately pH 5 with dilute hydrochloric acid (1 M), the crystals obtained were filtered off and washed with distilled water, and then were dried with heating under reduced pressure to yield the title compound (0.29 g, 83% yield) as white crystals.

$^1$H-NMR (DMSO-d$_6$) δ: 1.15 (3H, d, J=6.9 Hz), 2.61 (3H, s), 2.97-3.06 (1H, m), 4.28 (1H, dd, J=14.8, 6.8 Hz), 4.49 (1H, dd, J=14.8, 8.6 Hz), 7.39-7.42 (2H, m), 7.77-7.80 (3H, m), 8.08 (1H, dd, J=8.6, 1.3 Hz), 8.33 (1H, d, J=1.3 Hz).

Working Example 123

Synthesis of 5-(5-chlorobenzoxazol-2-yl)-2-(4-n-propylaminocarbonylphenyl)-1-(tetrahydropyran-4-yl)benzimidazole

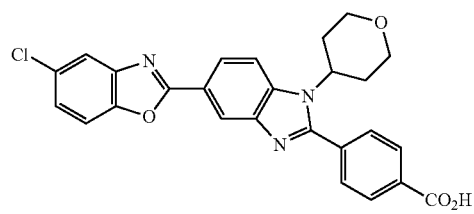

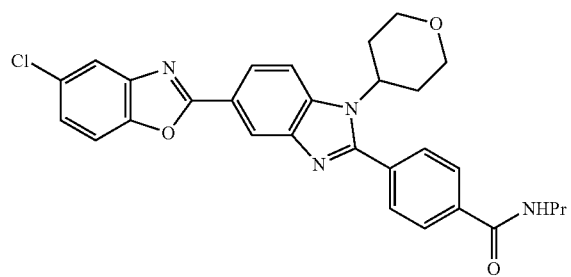

To 2-(4-carboxylphenyl)-5-(5-chlorobenzoxazol-2-yl)-1-(tetrahydropyran-4-yl)benzimidazole (see Working Example 102) (150 mg, 0.317 mmol) was added thionyl chloride (3 mL), and this was heated to reflux for 2 hours. After the reaction was complete, this was cooled to room temperature and concentrated. To a suspension of the residue obtained in tetrahydrofuran (3 mL) was added propylamine (56.2 mg, 0.951 mmol), and this was stirred at room temperature for 2 hours. After the reaction was complete, water was added and this was extracted with chloroform. The organic layer obtained was dried over anhydrous sodium sulfate, filtered, and concentrated to give crude crystals that were purified by silica gel column chromatography to yield the title compound (81.3 mg, 50% yield) as colorless crystals.

$^1$H-NMR (CDCl$_3$) δ: 1.01 (3H, t, J=7.4 Hz), 1.61-1.74 (2H, m), 1.89-1.96 (2H, m), 2.65-2.81 (2H, m), 3.42-3.51 (4H, m), 4.18 (2H, dd, J=11.7, 4.3 Hz), 4.57-4.66 (1H, m), 6.37 (1H, br s), 7.33 (1H, dd, J=8.7, 2.1 Hz), 7.54 (1H, d, J=8.6 Hz), 7.66 (1H, t, J=7.7 Hz), 7.74-7.78 (2H, m), 7.84 (1H, d, J=8.9 Hz), 7.99 (1H, dt, J=7.7, 1.5 Hz), 8.10 (1H, s), 8.25 (1H, dd, J=8.7, 1.6 Hz), 8.67 (1H, d, J=1.6 Hz).

Working Example 124

Synthesis of 5-(benzoxazol-2-yl)-2-(4-methoxyphenyl)-1-(tetrahydropyran-4-yl)benzimidazole

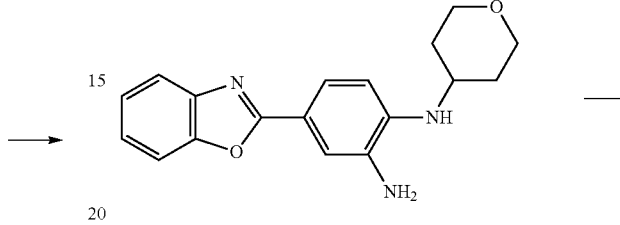

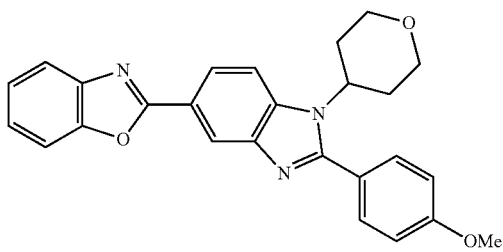

To a solution of 5-(benzoxazol-2-yl)-2-(tetrahydropyran-4-yl)aminoaniline (see Working Example 20-2) (150 mg, 0.485 mmol) in dimethylformamide (3 mL) was added p-anisaldehyde (79.2 mg, 0.582 mmol) and oxone (179 mg, 0.291 mmol), and this was stirred at room temperature for 2 hours. After the reaction was complete, aqueous potassium carbonate solution was added, and after this was filtered and washed with water, drying yielded the title compound (184 mg, 89% yield) as pale yellow crystals.

$^1$H-NMR (CDCl$_3$) δ: 1.87-1.93 (2H, m), 2.70-2.79 (2H, m), 3.43-3.51 (2H, m), 3.92 (3H, s), 4.18 (2H, dd, J=11.7, 4.6 Hz), 4.60-4.69 (1H, m), 7.07-7.11 (2H, m), 7.34-7.39 (2H, m), 7.58-7.64 (3H, m), 7.77-7.82 (2H, m), 8.24 (1H, dd, J=8.7, 1.6 Hz), 8.67 (1H, d, J=1.6 Hz).

Working Example 125

Synthesis of 5-(benzoxazol-2-yl)-2-(2-methoxyphenyl)-1-(tetrahydropyran-4-yl)benzimidazole

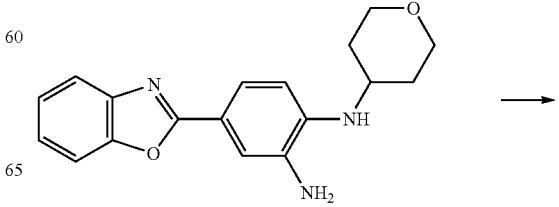

-continued

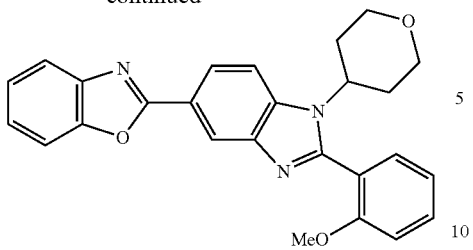

To a solution of 5-(benzoxazol-2-yl)-2-(tetrahydropyran-4-yl)aminoaniline (see Working Example 20-2) (150 mg, 0.485 mmol) in dimethylformamide (3 mL) was added o-anisaldehyde (79.2 mg, 0.582 mmol) and oxone (179 mg, 0.291 mmol), and this was stirred at room temperature for 2 hours. After the reaction was complete, aqueous potassium carbonate solution was added, and after this was filtered and washed with water, drying yielded the title compound (170 mg, 82% yield) as pale yellow crystals.

$^1$H-NMR (CDCl$_3$) δ: 2.02 (2H, br s), 2.63 (2H, br s), 3.36-3.46 (2H, m), 3.82 (3H, s), 4.13-4.30 (3H, m), 7.07 (1H, d, J=8.4 Hz), 7.15 (1H, t, J=7.5 Hz), 7.32-7.39 (2H, m), 7.52-7.64 (3H, m), 7.77-7.82 (2H, m), 8.25 (1H, dd, J=8.6, 1.6 Hz), 8.68 (1H, d, J=1.6 Hz).

Working Example 126

Synthesis of 5-(benzoxazol-2-yl)-2-(2-chlorophenyl)-1-(tetrahydropyran-4-yl)benzimidazole

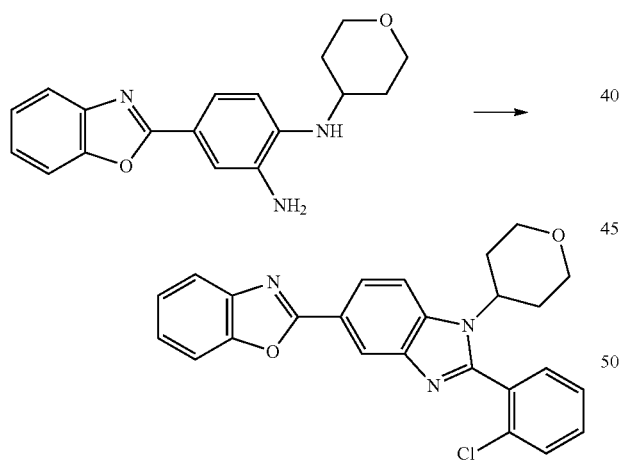

To a solution of 5-(benzoxazol-2-yl)-2-(tetrahydropyran-4-yl)aminoaniline (see Working Example 20-2) (150 mg, 0.485 mmol) in dimethylformamide (3 mL) was added o-chlorobenzaldehyde (81.8 mg, 0.582 mmol) and oxone (179 mg, 0.291 mmol), and this was stirred at room temperature for 2 hours. After the reaction was complete, aqueous potassium carbonate solution was added, and after this was filtered and washed with water, drying yielded the title compound (200 mg, 96% yield) as colorless crystals.

$^1$H-NMR (CDCl$_3$) δ: 1.69-1.73 (1H, m), 2.15-2.20 (1H, m), 2.51-2.75 (2H, m), 3.32-3.49 (2H, m), 4.07-4.21 (3H, m), 7.33-7.65 (7H, m), 7.78-7.84 (2H, m), 8.29 (1H, dd, J=8.6, 1.6 Hz), 8.71 (1H, d, J=1.6 Hz).

Working Example 127

Synthesis of 5-(benzoxazol-2-yl)-2-(3-chlorophenyl)-1-(tetrahydropyran-4-yl)benzimidazole

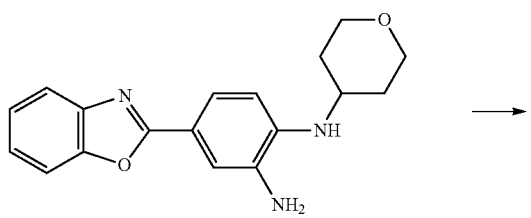

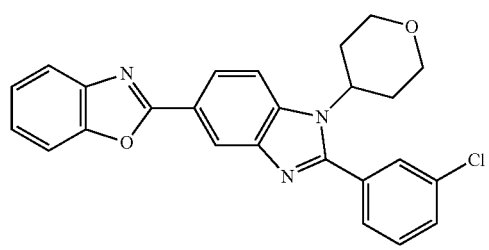

To a solution of 5-(benzoxazol-2-yl)-2-(tetrahydropyran-4-yl)aminoaniline (see Working Example 20-2) (150 mg, 0.485 mmol) in dimethylformamide (3 mL) was added m-chlorobenzaldehyde (81.8 mg, 0.582 mmol) and oxone (179 mg, 0.291 mmol), and this was stirred at room temperature for 2 hours. After the reaction was complete, aqueous potassium carbonate solution was added, and after this was filtered and washed with water, drying yielded the title compound (196 mg, 94% yield) as colorless crystals.

$^1$H-NMR (CDCl$_3$) δ: 1.91 (2H, dd, J=12.9, 3.3 Hz), 2.66-2.81 (2H, m), 3.43-3.53 (2H, m), 4.19 (2H, dd, J=11.8, 4.4 Hz), 4.53-4.65 (1H, m), 7.33-7.39 (2H, m), 7.49-7.86 (7H, m), 8.28 (1H, dd, J=8.7, 1.6 Hz), 8.70 (1H, d, J=1.6 Hz).

Working Example 128

Synthesis of 5-(benzoxazol-2-yl)-2-(4-chlorophenyl)-1-(tetrahydropyran-4-yl)benzimidazole

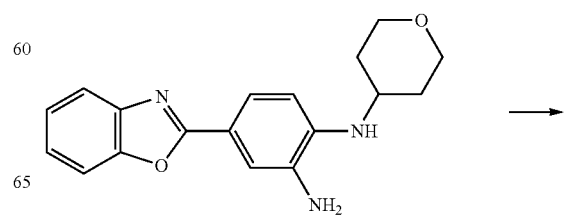

-continued

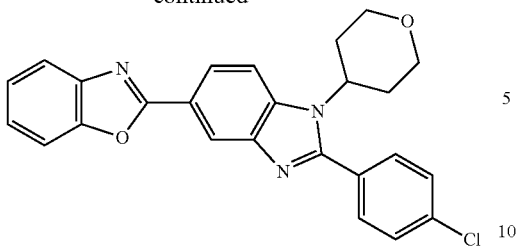

To a solution of 5-(benzoxazol-2-yl)-2-(tetrahydropyran-4-yl)aminoaniline (see Working Example 20-2) (150 mg, 0.485 mmol) in dimethylformamide (3 mL) was added p-chlorobenzaldehyde (81.8 mg, 0.582 mmol) and oxone (179 mg, 0.291 mmol), and this was stirred at room temperature for 2 hours. After the reaction was complete, aqueous potassium carbonate solution was added, and after this was filtered and washed with water, drying yielded the title compound (188 mg, 90% yield) as colorless crystals.

$^1$H-NMR (CDCl$_3$) δ: 1.90 (2H, dd, J=13.0, 3.3 Hz), 2.65-2.81 (2H, m), 3.42-3.52 (2H, m), 4.18 (2H, dd, J=11.7, 4.6 Hz), 4.51-4.64 (1H, m), 7.33-7.41 (2H, m), 7.55-7.64 (5H, m), 7.77-7.84 (2H, m), 8.27 (1H, dd, J=8.7, 1.6 Hz), 8.69 (1H, d, J=1.6 Hz).

Working Example 129

Synthesis of 5-(benzoxazol-2-yl)-1-(2-(piperidin-1-yl)ethyl)-1-(tetrahydropyran-4-yl)benzimidazole Working Example 129-1

Synthesis of N-(2-(piperidin-1-yl)ethyl)-4-(benzoxazol-2-yl)-2-nitroaniline

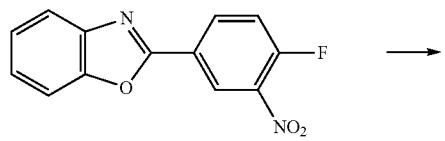

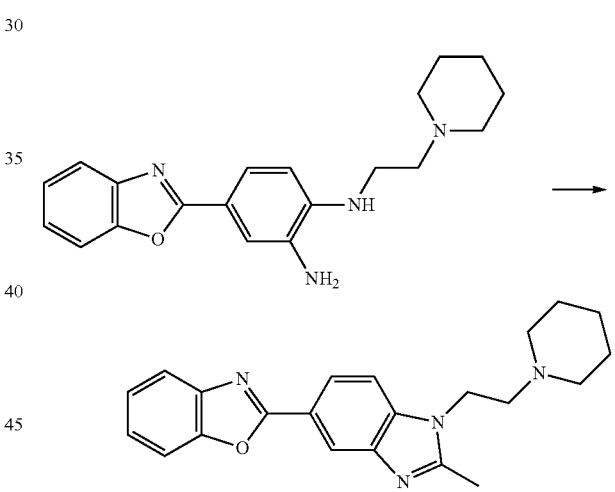

To a suspension of 2-(4-fluoro-3-nitrophenyl)benzoxazole (see Working Example 15-2) (200 mg, 0.775 mmol) in acetonitrile (5 mL) was added potassium carbonate (214 mg, 1.55 mmol) and 1-(2-aminoethyl)piperidine (119 mg, 0.93 mmol), and this was heated to reflux for 3 hours. After the reaction was complete, this was cooled to room temperature, water was added, and after the precipitated crystals were filtered and washed with water, they were dried to yield the title compound (266 mg, 94% yield) as yellow crystals.

$^1$H-NMR (CDCl$_3$) δ: 1.45-1.69 (6H, m), 2.48 (4H, t, J=4.9 Hz), 2.70 (2H, t, J=6.2 Hz), 3.44 (2H, dd, J=10.8, 6.2 Hz), 6.97 (1H, d, J=9.1 Hz), 7.28-7.37 (2H, m), 7.54-7.58 (1H, m), 7.71-7.76 (1H, m), 8.29 (1H, dd, J=9.0, 2.1 Hz), 8.92 (1H, br s), 9.07 (1H, d, J=2.1 Hz).

Working Example 129-2

Synthesis of 5-(benzoxazol-2-yl)-1-(2-(piperidin-1-yl)ethyl)-1-(tetrahydropyran-4-yl)benzimidazole

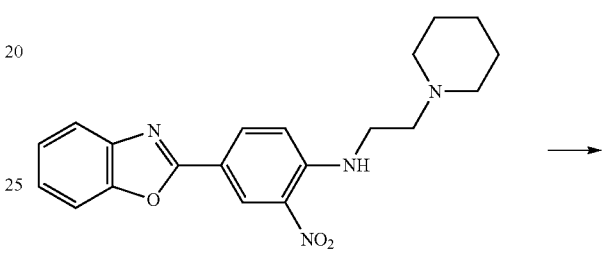

To a solution of N-(2-(piperidin-1-yl)ethyl)-4-(benzoxazol-2-yl)-2-nitroaniline (263 mg, 0.718 mmol) in ethanol/ethyl acetate (1:1, 6 mL) was added 10% palladium-carbon (30 mg). A hydrogen atmosphere was then substituted in the flask, and this was stirred at room temperature for 16 hours. After the reaction was complete, this was filtered through Celite, and the filtrate was concentrated. To a solution of the residue obtained in ethanol (5 mL) was added ethyl acetimidate hydrochloride (103 mg, 0.825 mmol), and this was heated to reflux for 2 hours. After the reaction was complete, saturated aqueous sodium hydrogen carbonate solution was added, and this was stirred for several minutes at room temperature. The crystals obtained were filtered, and after being washed with diethyl ether, they were dried to yield the title compound (141 mg, 54% yield).

$^1$H-NMR (CDCl$_3$) δ: 1.44-1.62 (6H, m), 2.43-2.47 (4H, m), 2.67 (2H, t, J=6.8 Hz), 2.68 (3H, s), 4.24 (2H, t, J=6.8 Hz), 7.32-7.36 (2H, m), 7.42 (1H, d, J=8.6 Hz), 7.57-7.80 (2H, m), 8.20 (1H, dd, J=8.6, 1.5 Hz), 8.55 (1H, d, J=1.5 Hz).

Working Example 130

Synthesis of 5-(benzoxazol-2-yl)-1-(2-dimethylaminoethyl)-1-(tetrahydropyran-4-yl)benzimidazole Working Example 130-1

Synthesis of N-(2-dimethylaminoethyl)-4-(benzoxazol-2-yl)-2-nitroaniline

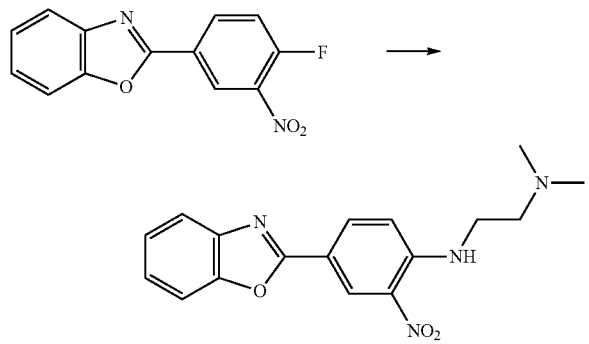

To a suspension of 2-(4-fluoro-3-nitrophenyl)benzoxazole (see Working Example 15-2) (200 mg, 0.775 mmol) in acetonitrile (5 mL) was added potassium carbonate (214 mg, 1.55 mmol) and N,N-dimethylethylenediamine (82 mg, 0.93 mmol), and this was heated to reflux for 3 hours. After the reaction was complete, this was cooled to room temperature, water was added, and after the precipitated crystals were filtered and washed with water, they were dried to yield the title compound (240 mg, 95% yield) as orange crystals.

$^1$H-NMR (CDCl$_3$) δ: 2.34 (6H, s), 2.68 (2H, t, J=6.1 Hz), 3.44 (2H, dd, J=10.9, 6.1 Hz), 6.98 (1H, d, J=9.1 Hz), 7.32-7.38 (2H, m), 7.55-7.59 (1H, m), 7.71-7.75 (1H, m), 8.30 (1H, dd, J=9.1, 2.0 Hz), 8.72 (1H, br s), 9.07 (1H, d, J=2.0 Hz).

Working Example 130-2

Synthesis of 5-(benzoxazol-2-yl)-1-(2-dimethylaminoethyl)-1-(tetrahydropyran-4-yl)benzimidazole

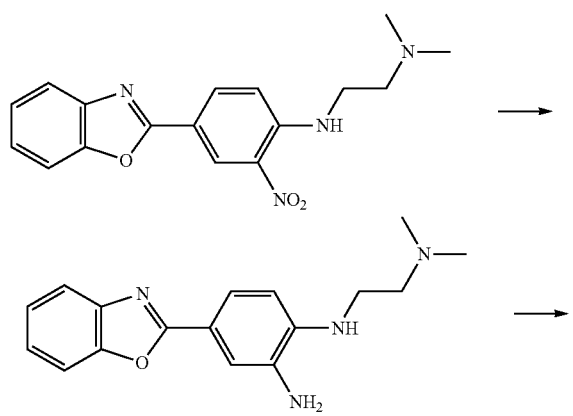

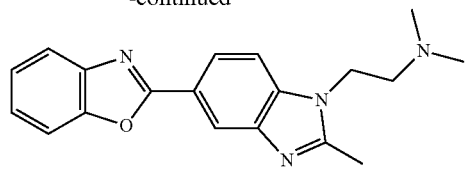

To a solution of N-(2-dimethylaminoethyl)-4-(benzoxazol-2-yl)-2-nitroaniline (236 mg, 0.723 mmol) in ethanol/ethyl acetate (1:1, 6 mL) was added 10% palladium-carbon (30 mg). A hydrogen atmosphere was then substituted in the flask, and this was stirred at room temperature for 16 hours. After the reaction was complete, this was filtered through Celite, and the filtrate was concentrated. To a solution of the residue obtained in ethanol (5 mL) was added ethyl acetimidate hydrochloride (103 mg, 0.825 mmol), and this was heated to reflux for 2 hours. After the reaction was complete, saturated aqueous sodium hydrogen carbonate solution was added, and this was stirred for several minutes at room temperature. The crystals obtained were filtered, and after being washed with diethyl ether, they were dried to yield the title compound (83.4 mg, 36% yield) as colorless crystals.

$^1$H-NMR (CDCl$_3$) δ: 2.33 (6H, s), 2.67 (2H, t, J=7.1 Hz), 2.68 (3H, s), 4.23 (2H, t, J=7.1 Hz), 7.32-7.36 (2H, m), 7.42 (1H, d, J=8.4 Hz), 7.59-7.62 (1H, m), 7.75-7.79 (1H, m), 8.21 (1H, dd, J=8.4, 1.5 Hz), 8.56 (1H, d, J=1.5 Hz).

Working Example 131

Synthesis of 5-(benzoxazol-2-yl)-1-(2-(methylthio)ethyl)-2-methylbenzimidazole

Working Example 131-1

Synthesis of N-(2-(methylthio)ethyl)-4-(benzoxazol-2-yl)-2-nitroaniline

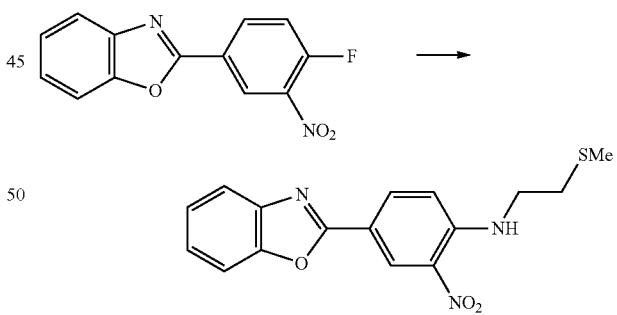

To a suspension of 2-(4-fluoro-3-nitrophenyl)benzoxazole (see Working Example 15-2) (300 mg, 1.16 mmol) in acetonitrile (5 mL) was added potassium carbonate (321 mg, 1.55 mmol) and 2-(methylthio)ethylamine (127 mg, 1.39 mmol), and this was heated to reflux for 3 hours. After the reaction was complete, this was cooled to room temperature, water was added, and after the precipitated crystals were filtered and washed with water, they were dried to yield the title compound (373 mg, 98% yield) as red crystals.

$^1$H-NMR (CDCl$_3$) δ: 2.20 (3H, s), 2.89 (2H, t, J=6.7 Hz), 3.61-3.68 (2H, m), 7.01 (1H, d, J=9.1 Hz), 7.31-7.38 (2H, m), 7.56-7.59 (1H, m), 7.72-7.75 (1H, m), 8.32 (1H, dd, J=9.1, 2.0 Hz), 8.61 (1H, br s), 9.08 (1H, d, J=2.0 Hz).

Working Example 131-2

Synthesis of 5-(benzoxazol-2-yl)-1-(2-(methylthio)ethyl)-2-methylbenzimidazole

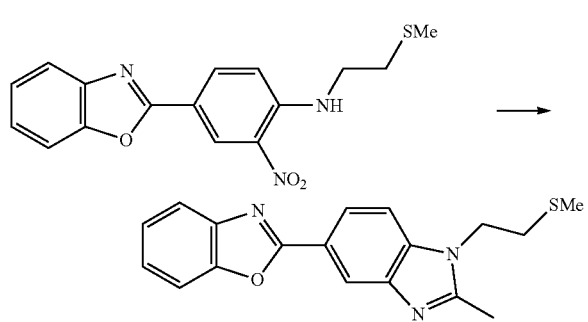

To N-(2-(methylthio)ethyl)-4-(benzoxazol-2-yl)-2-nitroaniline (370 mg, 1.12 mmol) was added iron powder (188 mg, 3.37 mmol) and acetic acid (5 mL), and this was heated to reflux for 10 hours. After the reaction solution was cooled, it was concentrated. The residue obtained was purified by silica gel column chromatography to yield the title compound (305 mg, 84% yield) as pink crystals.

$^1$H-NMR (CDCl$_3$) δ: 2.08 (3H, s), 2.72 (3H, s), 2.93 (2H, t, J=7.1 Hz), 4.38 (2H, t, J=7.1 Hz), 7.32-7.36 (2H, m), 7.43 (1H, d, J=8.6 Hz), 7.59-7.63 (1H, m), 7.74-7.79 (1H, m), 8.23 (1H, dd, J=8.6, 1.5 Hz), 8.57 (1H, d, J=1.5 Hz).

Working Example 132

Synthesis of 5-(benzoxazol-2-yl)-1-(2-(methylsulfonyl)ethyl)-2-methylbenzimidazole

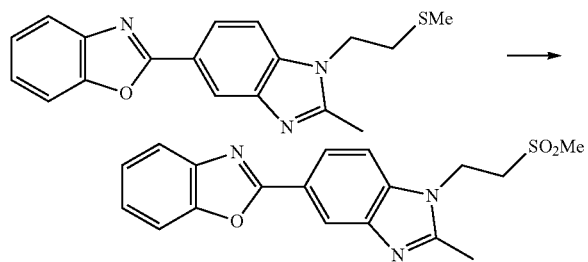

To a solution of 5-(benzoxazol-2-yl)-1-(2-(methylthio)ethyl)-2-methylbenzimidazole (see Working Example 131) (135 mg, 0.417 mmol) in chloroform (3 mL) was added m-chloroperbenzoic acid (166 mg, 0.96 mmol), and this was stirred at room temperature for 5 hours. After the reaction was complete, saturated aqueous sodium hydrogen carbonate solution was added, and this was extracted with chloroform. The organic layer obtained was dried over anhydrous sodium sulfate, filtered, and concentrated to give crude crystals that were purified by silica gel column chromatography to yield the title compound (113 mg, 76% yield) as light pink crystals.

$^1$H-NMR (CDCl$_3$) δ: 2.74 (3H, s), 2.80 (3H, s), 3.52 (2H, t, J=6.9 Hz), 4.73 (2H, t, J=6.9 Hz), 7.34-7.39 (2H, m), 7.47 (1H, d, J=8.4 Hz), 7.59-7.63 (1H, m), 7.76-7.79 (1H, m), 8.26 (1H, dd, J=8.5, 1.4 Hz), 8.58 (1H, d, J=1.3 Hz).

Working Example 133

Synthesis of 5-(benzoxazol-2-yl)-2-(2-(methylthio)ethyl)-1-(tetrahydropyran-4-yl)benzimidazole

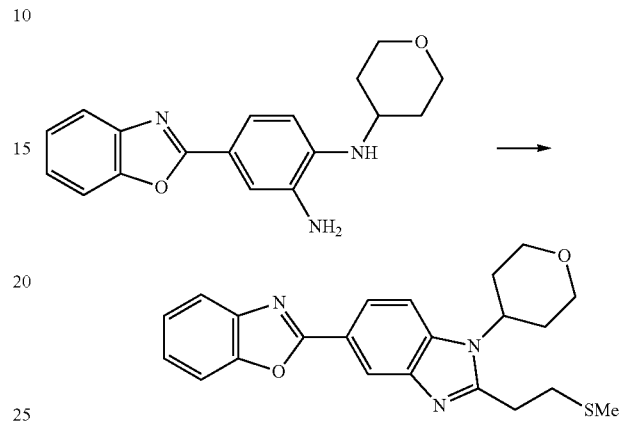

To a solution of 5-(benzoxazol-2-yl)-2-(tetrahydropyran-4-yl)aminoaniline (see Working Example 20-2) (200 mg, 0.646 mmol) in tetrahydrofuran (5 mL) was added 3-(methylthio)propionyl chloride (98.5 mg, 0.711 mmol) and triethylamine (131 mg, 1.29 mmol), and this was stirred at room temperature for 7 hours. After the reaction was complete, water was added and this was extracted with ethyl acetate. After the organic layer obtained was dried over anhydrous sodium sulfate, it was filtered and concentrated. To a solution of the residue obtained in dioxane (5 mL) was added methanesulfonic acid (0.5 mL), and this was heated to reflux for 3 hours. After the reaction was complete, 1M aqueous sodium hydroxide solution was added, and this was extracted with ethyl acetate. The organic layer obtained was dried over anhydrous sodium sulfate, filtered, and concentrated to give crude crystals that were purified by silica gel column chromatography to yield the title compound (170 mg, 67% yield) as colorless crystals.

$^1$H-NMR (CDCl$_3$) δ: 1.91 (2H, dd, J=13.0, 3.3 Hz), 2.20 (3H, s), 2.59-2.75 (2H, m), 3.07-3.13 (2H, m), 3.21-3.29 (2H, m), 3.61 (2H, td, J=12.0, 1.8 Hz), 4.24 (2H, dd, J=11.7, 4.5 Hz), 4.46-4.55 (1H, m), 7.31-7.38 (2H, m), 7.57-7.63 (1H, m), 7.70 (1H, dd, J=8.7, 0.5 Hz), 7.74-7.81 (1H, m), 8.20 (1H, dd, J=8.7, 1.6 Hz), 8.60 (1H, dd, J=1.6, 0.5 Hz).

Working Example 134

Synthesis of 5-(benzoxazol-2-yl)-2-(2-(methylsulfonyl)ethyl)-1-(tetrahydropyran-4-yl)benzimidazole

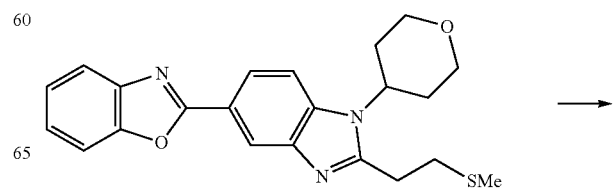

-continued

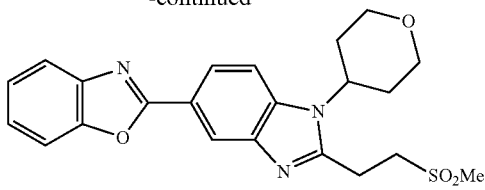

To a solution of 5-(benzoxazol-2-yl)-2-(2-(methylthio)ethyl)-1-(tetrahydropyran-4-yl)benzimidazole (see Working Example 133) (130 mg, 0.33 mmol) in chloroform (3 mL) was added m-chloroperbenzoic acid (205 mg, 0.83 mmol), and this was stirred at room temperature for 6 hours. After the reaction was complete, saturated aqueous sodium hydrogen carbonate solution was added, and this was extracted with chloroform. The organic layer obtained was dried over anhydrous sodium sulfate, filtered, and concentrated to give crude crystals that were purified by silica gel column chromatography to yield the title compound (105 mg, 75% yield) as yellow crystals.

$^1$H-NMR (CDCl$_3$) δ: 1.86-1.94 (2H, m), 2.56-2.72 (2H, m), 3.05 (3H, s), 3.48 (2H, t, J=7.5 Hz), 3.61 (2H, t, J=11.5 Hz), 3.86 (2H, t, J=7.5 Hz), 4.19-4.26 (2H, m), 4.47-4.56 (1H, m), 7.33-7.38 (2H, m), 7.58-7.79 (3H, m), 8.21 (1H, dd, J=8.7, 1.6 Hz), 8.57 (1H, s).

Working Example 135

Synthesis of 5-(5-chlorobenzoxazol-2-yl)-1-n-propylbenzimidazole

Working Example 135-1

Synthesis of 5-(5-chlorobenzoxazol-2-yl)-2-n-propylaminoaniline

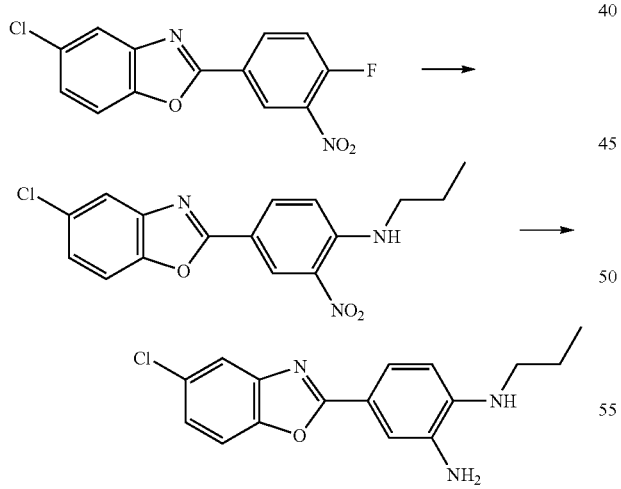

To a suspension of 5-chloro-2-(2-fluoronitrobenzen-5-yl)benzoxazole (see Working Example 100-1) (1.5 g, 5.13 mmol) in acetonitrile (10 mL) was added triethylamine (779 mg, 7.70 mmol) and propylamine (364 mg, 6.16 mmol), and this was heated to reflux for 4 hours. After the reaction was complete, this was cooled to room temperature, water was added, and the precipitated crystals were filtered, washed with water and then dried. To a solution of the crystals obtained in ethanol/tetrahydrofuran (1:2, 15 mL) was added 10% palladium-carbon (200 mg). A hydrogen atmosphere was substituted in the flask, and this was stirred at room temperature for 18 hours. After the reaction was finished, this was filtered through Celite, and the filtrate was concentrated to yield the title compound (1.5 g, 97% yield) as orange crystals.

$^1$H-NMR (CDCl$_3$) δ: 1.05 (3H, t, J=7.5 Hz), 1.67-1.80 (2H, m), 3.18 (2H, t, J=7.1 Hz), 6.70 (1H, d, J=8.5 Hz), 7.23 (1H, dd, J=8.5, 1.9 Hz), 7.41 (1H, d, J=8.8 Hz), 7.59-7.65 (2H, m), 7.73 (1H, dd, J=8.5, 1.9 Hz).

Working Example 135-2

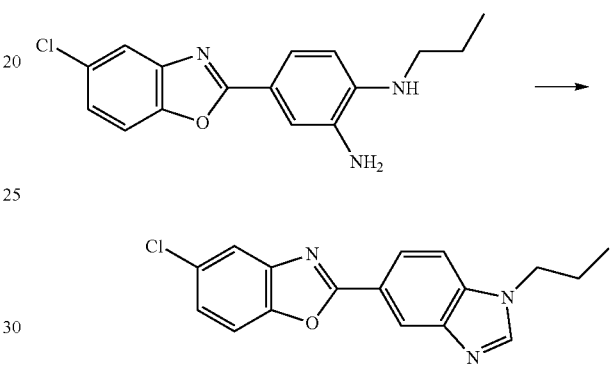

To a solution of 5-(5-chlorobenzoxazol-2-yl)-2-n-propylaminoaniline (see Working Example 135-1) (300 mg, 0.994 mmol) in triethyl orthoformate (5 mL) was added p-toluenesulfonic acid (10 mg), and this was stirred at 100° C. for 2 hours. After the reaction was complete, saturated aqueous sodium hydrogen carbonate solution was added, and this was extracted with chloroform. The organic layer obtained was dried over anhydrous sodium sulfate, filtered, and concentrated to give crude crystals that were washed with diethyl ether to yield the title compound (146 mg, 47% yield) as pale yellow crystals.

$^1$H-NMR (DMSO-d$_6$) δ: 0.87 (3H, t, J=7.3 Hz), 1.79-1.92 (2H, m), 4.29 (2H, t, J=7.1 Hz), 7.45 (1H, dd, J=8.8, 2.2 Hz), 7.82-7.91 (3H, m), 8.13 (1H, dd, J=8.4, 1.5 Hz), 8.45-8.46 (2H, m).

Working Example 136

Synthesis of 5-(5-chlorobenzoxazol-2-yl)-1-(tetrahydropyran-4-yl)benzimidazole

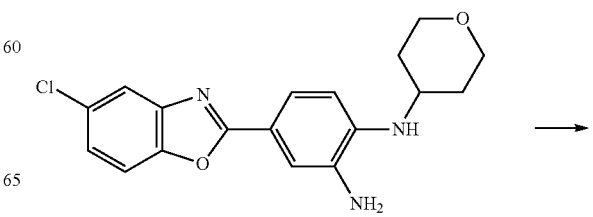

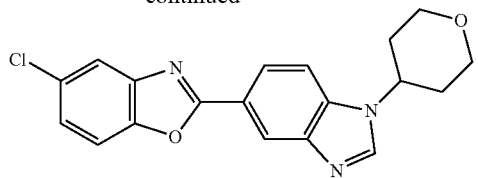

To a solution of 5-chloro-2-(2-(tetrahydropyran-4-yl)aminoanilin-5-yl)benzoxazole (see Working Example 100-2) (300 mg, 0.873 mmol) in triethyl orthoformate (5 mL) was added p-toluenesulfonic acid (10 mg), and this was stirred at 100° C. for 2 hours. After the reaction was complete, saturated aqueous sodium hydrogen carbonate solution was added, and this was extracted with chloroform. The organic layer obtained was dried over anhydrous sodium sulfate, filtered, and concentrated to give crude crystals that were washed with diethyl ether and ethyl acetate to yield the title compound (200 mg, 65% yield) as brown crystals.

$^1$H-NMR (DMSO-$d_6$) δ: 2.02-2.22 (4H, m), 3.58 (2H, td, J=11.5, 2.2 Hz), 4.04 (2H, dd, J=11.5, 3.1 Hz), 4.71-4.83 (1H, m), 7.45 (1H, dd, J=8.7, 2.1 Hz), 7.83 (1H, d, J=8.6 Hz), 7.90 (1H, d, J=2.1 Hz), 7.97 (1H, d, J=8.6 Hz), 8.14 (1H, dd, J=8.6, 1.6 Hz), 8.47 (1H, d, J=1.5 Hz), 8.60 (1H, s).

Working Example 137

Synthesis of 5-(5-chlorobenzoxazol-2-yl)-2-methyl-1-n-propylbenzimidazole

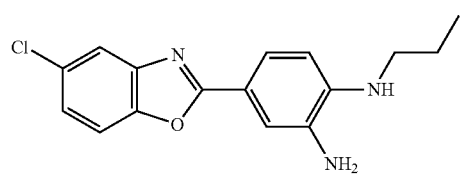

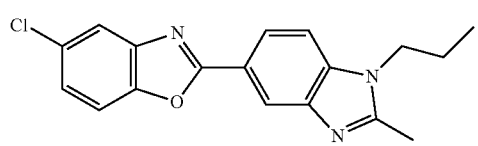

To a solution of 5-(5-chlorobenzoxazol-2-yl)-2-n-propylaminoaniline (see Working Example 135-1) (200 mg, 0.663 mmol) in ethanol (5 mL) was added methyl acetimidate hydrochloride (123 mg, 0.995 mmol), and this was heated to reflux for 5 hours. After the reaction was complete, saturated aqueous sodium hydrogen carbonate solution was added, and this was extracted with chloroform. The organic layer obtained was dried over anhydrous sodium sulfate, filtered, and concentrated to give crude crystals that were washed with diethyl ether to yield the title compound (155 mg, 72% yield) as green crystals.

$^1$H-NMR (DMSO-$d_6$) δ: 0.90 (3H, t, J=7.4 Hz), 1.71-1.81 (2H, m), 2.60 (3H, s), 4.22 (2H, t, J=7.3 Hz), 7.44 (1H, dd, J=8.6, 2.1 Hz), 7.76 (1H, d, J=8.6 Hz), 7.82 (1H, d, J=8.7 Hz), 7.89 (1H, d, J=2.1 Hz), 8.06 (1H, dd, J=8.5, 1.6 Hz), 8.32 (1H, d, J=1.2 Hz).

Working Example 138

Synthesis of 5-(5-chlorobenzoxazol-2-yl)-2-methyl-1-(3,3,3-trifluoropropyl)benzimidazole Working Example 138-1

Synthesis of 5-chloro-2-(2-(3,3,3-trifluoropropyl)aminoanilin-5-yl)benzoxazole

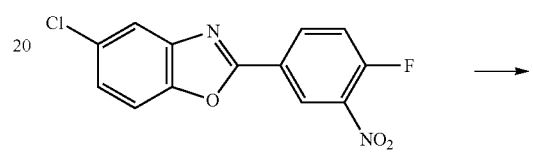

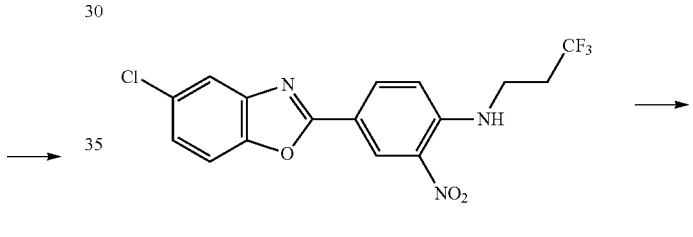

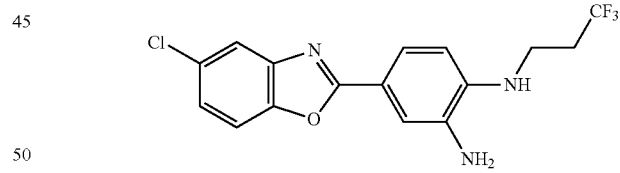

To a suspension of 5-chloro-2-(2-fluoronitrobenzen-5-yl)benzoxazole (see Working Example 100-1) (815 mg, 2.79 mmol) in acetonitrile (10 mL) was added triethylamine (847 mg, 8.37 mmol) and 3,3,3-trifluoropropylamine hydrochloride (500 mg, 3.34 mmol), and this was heated to reflux for 4 hours. After the reaction was complete, this was cooled to room temperature, water was added, and the precipitated crystals were filtered, washed with water and then dried. To a solution of the crystals obtained in ethanol/tetrahydrofuran (1:2, 15 mL) was added 10% palladium-carbon (100 mg). A hydrogen atmosphere was substituted in the flask, and this was stirred at room temperature for 18 hours. After the reaction was finished, this was filtered through Celite, and the filtrate was concentrated to yield the title compound (993 mg, 100% yield) as orange crystals.

$^1$H-NMR (CDCl$_3$) δ: 2.45-2.57 (2H, m), 3.54 (2H, t, J=7.0 Hz), 6.70 (1H, d, J=8.4 Hz), 7.25 (1H, dd, J=8.7, 1.9 Hz), 7.43 (1H, dd, J=8.6, 0.5 Hz), 7.62-7.66 (2H, m), 7.76 (1H, dd, J=8.4, 2.0 Hz).

Working Example 138-2

Synthesis of 5-(5-chlorobenzoxazol-2-yl)-2-methyl-1-(3,3,3-trifluoropropyl)benzimidazole

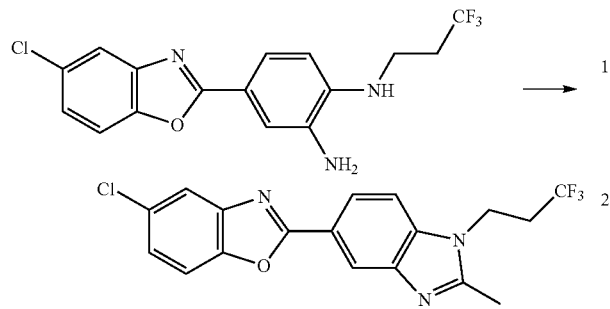

To a solution of 5-chloro-2-(2-(3,3,3-trifluoropropyl)aminoanilin-5-yl)benzoxazole (see Working Example 138-1) (200 mg, 0.562 mmol) in ethanol (5 mL) was added ethyl acetimidate hydrochloride (104 mg, 0.843 mmol), and this was heated to reflux for 5 hours. After the reaction was complete, saturated aqueous sodium hydrogen carbonate solution was added, and this was extracted with chloroform. The organic layer obtained was dried over anhydrous sodium sulfate, filtered, and concentrated to give crude crystals that were washed with diethyl ether to yield the title compound (170 mg, 80% yield) as light green crystals.

$^1$H-NMR (DMSO-d$_6$) δ: 2.63 (3H, s), 2.82-3.00 (2H, m), 4.55 (2H, t, J=6.9 Hz), 7.45 (1H, dd, J=8.7, 2.1 Hz), 7.77 (1H, d, J=8.4 Hz), 7.83 (1H, d, J=8.7 Hz), 7.90 (1H, d, J=2.1 Hz), 8.09 (1H, dd, J=8.5, 1.6 Hz), 8.33 (1H, d, J=1.6 Hz).

Working Example 139

Synthesis of 5-(5-chlorobenzoxazol-2-yl)-1-(3,3,3-trifluoropropyl)benzimidazole

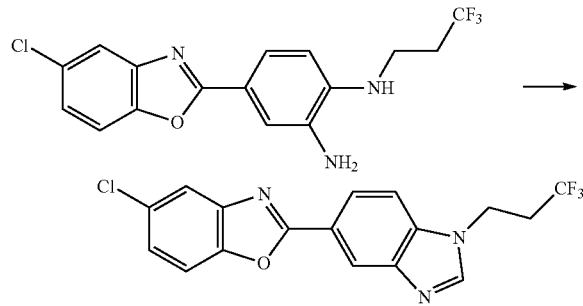

To a solution of 5-chloro-2-(2-(3,3,3-trifluoropropyl)aminoanilin-5-yl)benzoxazole (see Working Example 138-1) (200 mg, 0.562 mmol) in triethyl orthoformate (5 mL) was added p-toluenesulfonic acid (10 mg), and this was stirred at 100° C. for 4 hours. After the reaction was complete, saturated aqueous sodium hydrogen carbonate solution was added, and this was extracted with chloroform. The organic layer obtained was dried over anhydrous sodium sulfate, filtered, and concentrated to give crude crystals that were washed with diethyl ether and ethyl acetate to yield the title compound (127 mg, 62% yield) as light yellow crystals.

$^1$H-NMR (DMSO-d$_6$) δ: 2.91-3.09 (2H, m), 4.63 (2H, t, J=6.8 Hz), 7.46 (1H, dd, J=8.6, 1.3 Hz), 7.84 (1H, d, J=8.7 Hz), 7.91-7.94 (2H, m), 8.16 (1H, d, J=8.4 Hz), 8.47-8.50 (2H, m).

Working Example 140

Synthesis of 5-(benzimidazol-2-yl)-2-methyl-1-(tetrahydropyran-4-yl)benzimidazole

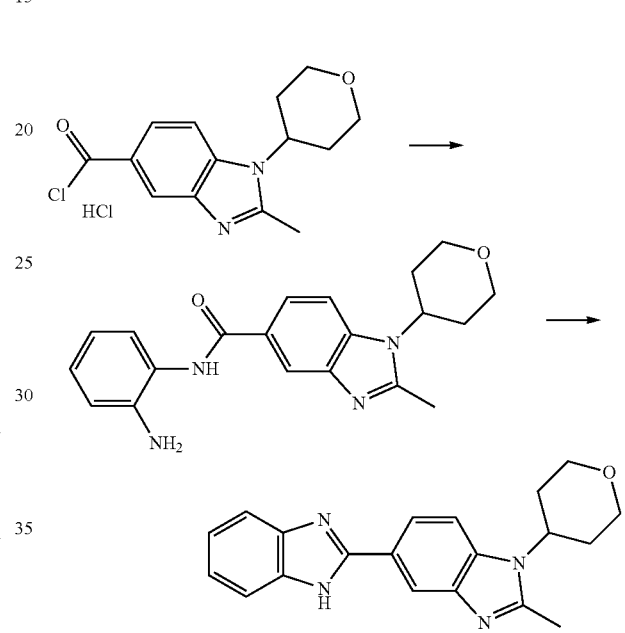

To a suspension of 2-methyl-1-(tetrahydropyran-4-yl)benzimidazole-5-carboxylic acid HCl salt (see Working Example 4-3) (500 mg, 1.86 mmol) in toluene (10 mL) was added thionyl chloride (3 mL), and this was stirred at reflux for 1.5 hours. This was then concentrated at reduced pressure to obtain 2-methyl-1-(tetrahydropyran-4-yl)benzimidazole-5-carboxylic acid HCl salt chloride, to a solution of which (533 mg, 1.69 mmol) in tetrahydrofuran (10 mL) was added phenylenediamine (183 mg, 1.69 mmol) and triethylamine (512 mg, 5.07 mmol), and this was stirred at room temperature for 7 hours. After the reaction was complete, water was added and this was extracted with chloroform. After the organic layer obtained was dried over anhydrous sodium sulfate, it was filtered and concentrated. To a solution of the residue obtained in dioxane (5 mL) was added methanesulfonic acid (0.5 mL), and this was heated to reflux for 24 hours. After the reaction was complete, 1M aqueous sodium hydroxide solution was added, and this was extracted with chloroform. The organic layer obtained was dried over anhydrous sodium sulfate, filtered, and concentrated to give crude crystals that were washed with ethyl acetate to yield the title compound (300 mg, 54% yield).

$^1$H-NMR (DMSO-d$_6$) δ: 1.86 (2H, dd, J=12.3, 2.7 Hz), 2.36-2.45 (2H, m), 2.65 (3H, s), 3.53-3.62 (2H, m), 4.03-4.08 (2H, m), 4.58-4.69 (1H, m), 7.15-7.21 (2H, m), 7.49-7.67 (2H, m), 7.81 (1H, d, J=8.4 Hz), 8.06 (1H, dd, J=8.6, 1.6 Hz), 8.33 (1H, d, J=1.5 Hz), 12.82 (1H, br s).

Test Example 1

Preparation of Cells for Compound Evaluation

The forward primer 5'-tccagtatttgagaaaaggagccaggagtctccat-3' and the reverse primer 5'-ggaggcttcctcttccttgcttcccggtcttttcg-3' were prepared as the PCR primers according to the sequence information for the NXF gene genome sequence (Accession Nos. AB054577 and NC_000085), and the PCR method was used to isolate from approximately 5 kbp upstream from the translated region of the NXF gene promoter portion to the vicinity of the transcription start site. For this, 1 µg of mouse genomic DNA (Takara) was used as the template, and the 2-step PCR reaction was carried out for 35 cycles, the conditions for which were 95° C./1 m in the denaturing step, and 68° C./8 m in the annealing and extension steps, to obtain the PCR product. The NXF promoter fragment was inserted into the SmaI site of the pGL3 Basic vector (Promega) in the upstream of luciferase gene to prepare a reporter plasmid that would express the luciferase enzyme driven by the NXF promoter.

PC12 cells (available from the ATCC) were cultured using RPMI medium (GIBCO-BRL) with 5% FCS (GIBCO-BR) and 15% horse serum (GIBCO-BRL) added, and 1 mM in sodium pyruvate (GIBCO-BRL), at 37° C. in the presence of 5% $CO_2$. After transfection in $10^6$ of these PC12 cells for 2 days with 12 µg of the above-described reporter plasmid and 1 µg of pRC/RSV vector (Invitrogen) using the Lipofectamine 2000 reagent (Invitrogen), the medium was exchanged for fresh medium containing 40 mg/L of geneticin sulfate (GIBCO), and this was cultured continuously. Culturing was continued for approximately 1 month with medium exchange of the cultured medium containing 40 mg/L of geneticin sulfate (GIBCO) every several days, with the result that multiple colonies of the obtained cells were picked up. Among these, one of the colonies that induced luciferase activity in the presence of 40 ng/mL of NGF (Wako Pure Chemicals) was selected and used for the cells to evaluate the activity of the compounds below.

(Compound Activity Evaluations)

These cells were set up in 96-well plates with 80% confluence, and the luciferase reporter assay was conducted using the Promega Steady Glo luciferase assay kit. The procedure was carried out overnight (approx. 16 hours) using culture medium containing the compound, and the Steady Glo substrate solution was added to the cells in half-diluted in PBS after removal of all remaining medium containing the compound. After this was allowed to stand for 30 minutes, the respective quantity of light produced was measured with a luminometer (Envision Perkin Elmer).

The activity of the compounds for evaluation was measured as the potentiation of the activity of 200 ng/mL of NGF. For the experiment control wells, the negative control well had medium containing only a final concentration of 0.1% DMSO, the positive control well had medium containing a saturation concentration of NGF. In addition, a test well was set up containing 0.1% DMSO with 200 ng/mL of NGF added corresponding to a 0 compound concentration. When its luciferase activity was taken as a standard, the relative luciferase activity could be calculated for the test wells to which the compound solution (dissolved in DMSO and prepared to have a final DMSO concentration of 0.1%) had been added in addition to the 200 ng/mL of NGF, to find the potentiation of the activity of 200 ng/mL of NGF due to that compound.

The experimental results for the potentiation of NGF activity are described in the table below.

+: Showed relatively weak potentiation (potentiation only exhibited at 10 µM)
++: Showed potentiation
+++: Showed particularly strong potentiation (2-fold or greater potentiation of the activity of 200 ng/mL of NGF at 1 µM)

TABLE 1

| compound | Activity |
| --- | --- |
| Syn. Ex. 1 | +++ |
| Syn. Ex. 2 | +++ |
| Syn. Ex. 3 | ++ |
| Ex. 1 | + |
| Ex. 2 | +++ |
| Ex. 3 | +++ |
| Ex. 4 | +++ |
| Ex. 6 | ++ |
| Ex. 7 | +++ |
| Ex. 8 | +++ |
| Ex. 9 | ++ |
| Ex. 11 | ++ |
| Ex. 12 | +++ |
| Ex. 14 | + |
| Ex. 15 | + |
| Ex. 16 | ++ |
| Ex. 17 | ++ |
| Ex. 18 | +++ |
| Ex. 19 | ++ |
| Ex. 20 | +++ |
| Ex. 21 | ++ |
| Ex. 22 | +++ |
| Ex. 23 | ++ |
| Ex. 24 | ++ |
| Ex. 25 | ++ |
| Ex. 26 | ++ |
| Ex. 27 | ++ |
| Ex. 28 | +++ |
| Ex. 29 | ++ |
| Ex. 30 | ++ |
| Ex. 31 | ++ |
| Ex. 32 | ++ |
| Ex. 33 | ++ |
| Ex. 34 | +++ |
| Ex. 35 | ++ |
| Ex. 36 | +++ |
| Ex. 37 | ++ |
| Ex. 38 | ++ |
| Ex. 39 | +++ |
| Ex. 40 | +++ |
| Ex. 41 | +++ |
| Ex. 42 | +++ |
| Ex. 43 | +++ |
| Ex. 44 | ++ |

Test Example 2

A middle cerebral artery occlusion/reperfusion model was prepared by taking 8-week male C57BL/6J mice after 12 days convention rearing, and ligating the left and external common carotid arteries, then recanalizing them after the middle cerebral artery had been occluded for a period of 90 minutes. In this model, the compounds were administered at 3, 24, and 48 hours after occlusion as 30 mg/kg via the caudate vein. The animals were decapitated 3 days after the occlusion/reperfusion, the skulls were cut open from the cerebellar side and the brain was extracted. The extracted brains were fixed with Bouin's solution (pH 3.5-4.0). Coronal slices were taken from the fixed brains, and after sectioning these underwent dehydration, permeation, and then were embedded in paraffin. Thin slices were taken at 4 sites in the vicinity of Bregma 1.95 mm, Bregma 1.0 mm, Bregma −1.40 mm, and Bregma −3.8 mm. The slices were made with a thickness of approximately 6 μm, and HE staining was done. The infarct volumes were then calculated as shown below.

Optical microscope: digital images were taken using an optical microscope (object lens×1) that was fitted with a camera (MCD-350, Olympus). The digital images taken were pasted into single page mounts (New Laser) in PhotoShop 2.0. Based on the images pasted into the page mounts, the infarct areas (S, mm$^2$), lateral (left) infarct areas (mm$^2$) and lateral (right) non-infarct areas (MR, mm$^2$) were measured using an image analysis system (Win ROOF v. 5.6, Mitani), and the non-infarct areas for the left-side infarcts (ML, mm$^2$) [lateral (left) infarct area (mm$^2$)−infarct area (mm$^2$)] were calculated.

Using the equations below, the infarct volumes (SV, mm$^3$), non-infarct volumes for the left-side infarcts (MLV, mm$^3$), and the lateral (right) non-infarct volumes (MRV, mm$^3$) were calculated.

Calculation method for the vicinity of Bregma 1.95 mm $$SV = 1/3\Sigma(S_1 + S_2 + S_1^{1/2} \times S_2^{1/2})$$

$$MLV = 1/3\Sigma(ML_1 + ML_2 + ML_1^{1/2} \times ML_2^{1/2})$$

$$MRV = 1/3\Sigma(MR_1 + MR_2 + MR_1^{1/2} \times MR_2^{1/2})$$

Calculation method for the vicinities of Bregma 1.0 mm, −1.40 mm, and −3.8 mm $$SV = 2/3\Sigma(S_n + S_{n+1} + S_n^{1/2} \times S_{n+1}^{1/2})$$

$$MLV = 2/3\Sigma(ML_n + ML_{n+1} + ML_n^{1/2} \times ML_{n+1}^{1/2})$$

$$MRV = 2/3\Sigma(MR_n + MR_{n+1} + MR_n^{1/2} \times MR_{n+1}^{1/2}) \ (n=1,2,3,4)$$

The test results for the compound from Working Example 12 are shown in FIG. 2. In this manner, reductions in the infarct volumes were confirmed for the drug administration group.

Test Example 3

The preventative effect of the compounds on the prolongation of latency of the motor nerve conduction velocity (MNCV) were studied in the sciatic nerves of rats with streptozotocin-induced diabetes.

The groups were structured as a non-diabetes control group, a diabetes control group, and a drug administration group. After 8 days of convention rearing, the 8-week male Slc:Wistar rats in the respective groups were given 2 mL/kg of pH 4.5, 0.75 mmol/L citrate buffer solution (non-diabetes control group), or 2 mL/kg of a solution prepared from 20 mg/L of streptozotocin (chemical name: N-(methylnitroso-carbamoyl)-α-D-glucosamine; manufacturer: SIGMA) in 0.75 mmol/L citrate buffer solution (diabetes control group and drug administration group), single administration in the caudate vein. After 4 more weeks of rearing, the animals in the non-diabetes control group and the diabetes control group were given 5 mL/kg of water for injection, while the animals in the drug administration group were given 5 mL/kg of a drug solution prepared from 10 mg/mL of the drug in water for injection. Administration for all groups was orally once per day for 4 weeks. MNCV measurements were carried out 3 times for each group. The first measurement point was the day before administration of the streptozotocin solution or pH 4.5, 0.75 mmol/L citrate buffer solution for the respective groups, the second measurement point was 4 weeks after the administration of the streptozotocin solution or pH 4.5, 0.75 mmol/L citrate buffer solution for the respective groups, and the third measurement point was the day after completion of the 4 weeks of administration of the water for injection or compound solution for the respective groups.

The test results (motor nerve conduction velocity) for the compound from Working Example 12 are shown in FIG. 2 (in the Figure, STZ represents streptozotocin). In this manner, recovery of motor nerve conduction velocity was observed in the drug administration group when compared to the solvent administration control group.

Test Example 4

In the same manner as for Test Example 1, Table 2 shows the potentiation effect on NGF activity as evaluated for the compounds of the working examples. The results are shown in Table 2.

+: Showed relatively weak potentiation (potentiation only exhibited at 10 μM)

++: Showed potentiation

+++: Showed particularly strong potentiation (2-fold or greater potentiation of the activity of 200 ng/mL of NGF at 1 μM)

TABLE 2

| compound | Activity |
| --- | --- |
| Syn. Ex. 7 | +++ |
| Ex. 50 | +++ |
| Ex. 51 | +++ |
| Ex. 52 | ++ |
| Ex. 53 | ++ |
| Ex. 54 | +++ |
| Ex. 55 | ++ |
| Ex. 56 | ++ |
| Ex. 57 | +++ |
| Ex. 58 | ++ |
| Ex. 59 | +++ |
| Ex. 60 | ++ |
| Ex. 61 | ++ |
| Ex. 62 | ++ |
| Ex. 63 | +++ |
| Ex. 64 | ++ |
| Ex. 65 | +++ |
| Ex. 66 | ++ |
| Ex. 67 | + |
| Ex. 68 | ++ |
| Ex. 69 | ++ |
| Ex. 71 | +++ |
| Ex. 72 | ++ |
| Ex. 73 | +++ |
| Ex. 74 | +++ |
| Ex. 75 | ++ |
| Ex. 76 | ++ |
| Ex. 77 | + |
| Ex. 78 | ++ |
| Ex. 79 | ++ |
| Ex. 80 | +++ |
| Ex. 81 | +++ |
| Ex. 82 | +++ |
| Ex. 83 | ++ |
| Ex. 84 | ++ |
| Ex. 85 | +++ |
| Ex. 86 | ++ |
| Ex. 87 | ++ |
| Ex. 88 | +++ |
| Ex. 89 | ++ |
| Ex. 90 | ++ |
| Ex. 92 | ++ |
| Ex. 93 | +++ |
| Ex. 94 | ++ |
| Ex. 95 | +++ |
| Ex. 96 | ++ |
| Ex. 97 | ++ |
| Ex. 98 | +++ |
| Ex. 99 | ++ |

TABLE 2-continued

| compound | Activity |
|---|---|
| Ex. 100 | +++ |
| Ex. 101 | +++ |
| Ex. 102 | +++ |
| Ex. 103 | +++ |
| Ex. 104 | ++ |
| Ex. 105 | +++ |

```
                        SEQUENCE LISTING

<160> NUMBER OF SEQ ID NOS: 2

<210> SEQ ID NO 1
<211> LENGTH: 35
<212> TYPE: DNA
<213> ORGANISM: Artificial
<220> FEATURE:
<223> OTHER INFORMATION: forward primer

<400> SEQUENCE: 1
tccagtattt gagaaaagga gccaggagtc tccat                              35

<210> SEQ ID NO 2
<211> LENGTH: 35
<212> TYPE: DNA
<213> ORGANISM: Artificial
<220> FEATURE:
<223> OTHER INFORMATION: reverse primer

<400> SEQUENCE: 2
ggaggcttcc tcttccttgc ttcccggtct tttcg                              35
```

TABLE 2-continued

| compound | Activity |
|---|---|
| Ex. 106 | +++ |
| Ex. 107 | + |
| Ex. 108 | ++ |
| Ex. 109 | ++ |
| Ex. 110 | +++ |
| Ex. 111 | ++ |
| Ex. 112 | ++ |
| Ex. 113 | ++ |
| Ex. 114 | ++ |
| Ex. 115 | +++ |
| Ex. 116 | +++ |
| Ex. 117 | ++ |
| Ex. 118 | ++ |
| Ex. 120 | ++ |
| Ex. 121 | ++ |
| Ex. 123 | +++ |
| Ex. 124 | +++ |
| Ex. 125 | +++ |
| Ex. 126 | ++ |
| Ex. 127 | +++ |
| Ex. 128 | +++ |
| Ex. 129 | +++ |
| Ex. 130 | ++ |
| Ex. 131 | +++ |
| Ex. 132 | ++ |
| Ex. 133 | ++ |
| Ex. 134 | ++ |
| Ex. 135 | ++ |
| Ex. 136 | +++ |
| Ex. 139 | +++ |
| Ex. 140 | +++ |

INDUSTRIAL APPLICABILITY

The compounds of the present invention are effective for the treatment or prevention of diseases that are associated with neurotrophic factor activity.

Free text sequence table

Sequence No. 1 is the forward primer.

Sequence No. 2 is the reverse primer.

What is claimed is:

1. A compound depicted by formula (I), or a pharmaceutically acceptable salt or solvate thereof:

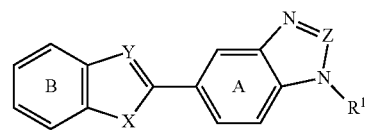

(I)

wherein $R^1$ represents:
(1) a $C_{3-6}$ alkyl group;
(2) a $C_{1-6}$ alkyl group substituted with one or more substituent groups selected from the group consisting of:
  (a) a halogen atom,
  (b) a $R^a$—O—,
  (c) a $R^a$—O—CO—,
  (d) a $R^a$—O—CO—NR$^a$—,
  (e) a $R^a$—O—CO—$C_2H_4$—CO—NH—
  (f) a $R^a$—S—,
  (g) a $R^a$—SO$_2$,
  (h) a $R^a$—CO—O—,
  (i) a $R^a$—CO—NR$^a$—,
  (j) a $R^a$—NR$^a$—,
  (k) a $R^a$—NR$^a$—CS—NR$^a$—,
  (l) a 5- to 6-membered ring group,
  (m) a carboxy group,
  (n) a hydroxy group,
  (o) an amino group, (p) a heterocyclic-carbonyl group, or
(q) a HO—CO—C$_2$H$_4$—CO—NH—
  wherein each R$^a$ is the same or different, and represents an optionally halogen-substituted C$_{1-6}$ alkyl group;
(3) an optionally substituted C$_{2-6}$ alkenyl group,
(4) an optionally substituted C$_{2-6}$ alkynyl group,
(5) a C$_{6-14}$ aryl group substituted with one or more substituents selected from the group consisting of a halogen atom and C$_{1-4}$ alkoxy group;
(6) an optionally substituted 5- to 6-membered aromatic heterocyclic group,
(7) an optionally substituted C$_{3-10}$ non-aromatic cyclic hydrocarbon group, or
(8) an optionally substituted a 5- to 6-membered non-aromatic heterocyclic group;
X represents O, S or N—R$^3$,
  wherein R$^3$ represents hydrogen atom or R$^a$—O—CO—, wherein R$^a$ is a C1-6 alkyl group;
Y represents CH or N;
Z represents N or a C—R$^2$,
  wherein R$^2$ represents:
    (1) an optionally substituted C$_{1-6}$ alkyl group,
    (2) an optionally substituted C$_{2-6}$ alkenyl group,
    (3) an optionally substituted C$_{2-6}$ alkynyl group,
    (4) an optionally substituted C$_{6-14}$ aryl group,
    (5) an optionally substituted 5- to 6-membered aromatic heterocyclic group,
    (6) an optionally substituted C$_{3-10}$ non-aromatic cyclic hydrocarbon group, or
    (7) an optionally substituted a 5- to 6-membered non-aromatic heterocyclic group;
ring A represents an optionally substituted benzene ring; and
ring B represents an optionally substituted benzene ring.

2. A compound according to claim 1, or the pharmaceutically acceptable salt or solvate thereof, wherein:
R$^1$ represents:
(1) a C$_{3-6}$ alkyl group;
(2) a C$_{1-6}$ alkyl group substituted with one or more substituent groups selected from the group consisting of:
  (a) a halogen atom,
  (b) a R$^a$—O—,
  (c) a R$^a$—O—CO—,
  (d) a R$^a$—O—CO—NR$^a$—,
  (e) a R$^a$—O—CO—C$_2$H$_4$—CO—NH—
  (f) a R$^a$—S—,
  (g) a R$^a$—SO$_2$—,
  (h) a R$^a$—CO—O—,
  (i) a R$^a$—CO—NR$^a$—,
  (j) a R$^a$—NR$^a$—,
  (k) a R$^a$—NR$^a$—CS—NR$^a$—,
  (l) a 5- to 6-membered ring group,
  (m) a carboxy group,
  (n) a hydroxy group,
  (o) an amino group,
  (p) a heterocyclic-carbonyl group, or
  (q) a HO—CO—C$_2$H$_4$—CO—NH—
    wherein each R$^a$ is the same or different, and represents an optionally halogen-substituted C$_{1-6}$ alkyl group;
(3) a C$_{3-10}$ non-aromatic cyclic hydrocarbon group or a 5- to 6-membered non-aromatic heterocyclic group, each of said groups is optionally substituted with one or more substituent groups selected from the group consisting of:
  (a) an oxo group, and
  (b) a C$_{1-4}$ alkoxycarbonyl group; or
(4) a C$_{6-14}$ aryl group substituted with one or more substituents selected from the group consisting of a halogen atom and C$_{1-4}$ alkoxy group;
X represents NH, O, or S;
Y represents CH or N;
Z represents N or a C—R$^2$,
  wherein R$^2$ represents:
    (1) a C$_{1-6}$ alkyl group, a C$_{2-6}$ alkenyl group or a C$_{2-6}$ alkynyl group, wherein each of said groups is optionally substituted with one or more substituent groups selected from the group consisting of:
      (a) a halogen atom,
      (b) a R$^b$—O—,
      (c) a R$^b$—O—CO—,
      (d) a R$^b$—O—CO—NR$^b$—,
      (e) a R$^b$—S—,
      (f) a R$^b$—SO$_2$—,
      (g) a R$^b$—CO—O—,
      (h) a R$^b$—CO—NR$^b$—,
      (i) a R$^b$—NR$^b$—,
      (j) a R$^b$—CO—NR$^b$—R$^b$—S(O)$_n$—,
      (k) a phenyl group,
      (l) a 5- to 6-membered saturated heterocyclic group,
      (m) a hydroxy group, and
      (n) an amino group,
        wherein each R$^b$ is the same or different, and represents a hydrogen atom or C$_{1-6}$ alkyl group optionally substituted with one or more halogens, and n represents an integer from 0 to 2; or
    (2) a C$_{5-6}$ non-aromatic cyclic hydrocarbon group or a 5- to 6-membered non-aromatic heterocyclic group, wherein each of said groups is optionally substituted with one or more substituent groups selected from the group consisting of:
      (a) a halogen atom,
      (b) a R$^c$—O—,
      (c) a R$^c$—O—CO—, and
      (d) a R$^c$—CO—NR$^c$—,
        wherein each R$^c$ is the same or different, and represents a hydrogen atom or C$_{1-6}$ alkyl group;
ring A represents a benzene ring optionally substituted with one or more substituent groups selected from the group consisting of:
(a) a halogen atom,
(b) a hydroxy group,
(c) a carboxy group,
(d) a cyano group,
(e) a sulfamoyl group,
(f) a monoalkylamide group,
(g) a dialkylamide group,
(h) an alkyl group optionally substituted with a halogen atom,
(i) a nitro group, and
(j) an aryloxy group; and
ring B represents a benzene ring optionally substituted with one or more substituent groups selected from the group consisting of:
(a) a halogen atom,
(b) a hydroxy group,
(c) a carboxy group,
(d) a cyano group,
(e) a sulfamoyl group,
(f) a monoalkylamide group,
(g) a dialkylamide group,
(h) an amide group,
(i) an ester group,
(j) an alkyl group optionally substituted with a halogen atom,
(k) a nitro group, and
(l) an aryloxy group.

3. The compound according to claim 2, wherein Z is C—R², and Y is N, or the pharmaceutically acceptable salt or solvate thereof.

4. The compound according to claim 2, wherein R¹ is the 5- to 6-membered non-aromatic heterocyclic group, or the pharmaceutically acceptable salt or solvate thereof.

5. The compound according to claim 2, wherein R² is the $C_{1-6}$ alkyl group, or the pharmaceutically acceptable salt or solvate thereof.

6. The compound according to claim 2, wherein Z is C—R², Y is N, R¹ is the 5- to 6-membered non-aromatic heterocyclic group, and R² is the $C_{1-6}$ alkyl group, or the pharmaceutically acceptable salt or solvate thereof.

7. The compound according to claim 1, which is a compound of the following formula, or a pharmaceutically acceptable salt or solvate thereof:

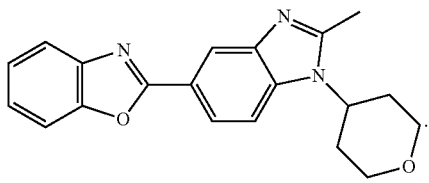 [SMILES: Cc1nc2cc(-c3nc4ccccc4o3)ccc2n1C1CCOCC1]

8. A pharmaceutical composition comprising:
   the compound of claim 7, or the pharmaceutically acceptable salt or solvate thereof; and
   a pharmaceutically acceptable carrier.

9. The pharmaceutical composition according to claim 8, wherein the compound is in an amount effective for the treatment of cerebral ischemic disease or diabetic neuropathy.

10. The compound according to claim 1, which is a compound of the following formula, or a pharmaceutically acceptable salt or solvate thereof:

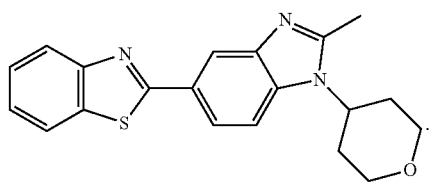 [SMILES: Cc1nc2cc(-c3nc4ccccc4s3)ccc2n1C1CCOCC1]

11. The compound according to claim 1, which is a compound of the following formula, or a pharmaceutically acceptable salt or solvate thereof:

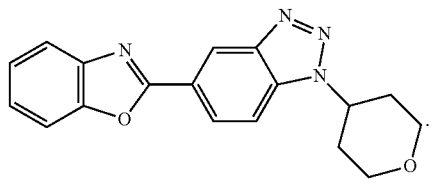 [SMILES: c1ccc2oc(-c3ccc4c(c3)nnn4C3CCOCC3)nc2c1]

12. The compound according to claim 1, which is a compound of the following formula, or a pharmaceutically acceptable salt or solvate thereof:

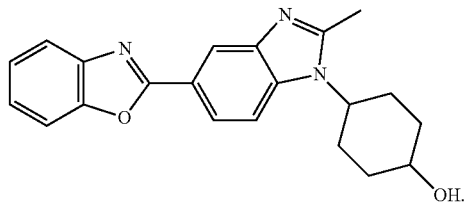 [SMILES: Cc1nc2cc(-c3nc4ccccc4o3)ccc2n1C1CCC(O)CC1]

* * * * *